US008512987B2

(12) United States Patent
Nagai et al.

(10) Patent No.: US 8,512,987 B2
(45) Date of Patent: Aug. 20, 2013

(54) METHOD OF PRODUCING L-AMINO ACID

(75) Inventors: Yuri Nagai, Kawasaki (JP); Kazuyuki Hayashi, Kawasaki (JP); Takuji Ueda, Kawasaki (JP); Yoshihiro Usuda, Kawasaki (JP); Kazuhiko Matsui, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 424 days.

(21) Appl. No.: 12/545,966

(22) Filed: Aug. 24, 2009

(65) Prior Publication Data

US 2010/0047878 A1 Feb. 25, 2010

Related U.S. Application Data

(63) Continuation of application No. PCT/JP2008/053020, filed on Feb. 22, 2008.

(30) Foreign Application Priority Data

Feb. 22, 2007 (JP) ................................ 2007-041724

(51) Int. Cl.
*C12P 13/24* (2006.01)

(52) U.S. Cl.
USPC ...... 435/107; 435/115; 435/252.33; 435/190; 536/23.1

(58) Field of Classification Search
None
See application file for complete search history.

(56) References Cited

U.S. PATENT DOCUMENTS

| | | | | |
|---|---|---|---|---|
| 5,175,107 | A | 12/1992 | Debabov et al. | |
| 5,661,012 | A | 8/1997 | Sano et al. | |
| 688,671 | A | 11/1997 | Sugimoto et al. | |
| 5,688,671 | A | 11/1997 | Sugimoto et al. | |
| 5,827,698 | A | 10/1998 | Kikuchi et al. | |
| 5,830,716 | A | 11/1998 | Kojima et al. | |
| 5,932,453 | A | 8/1999 | Kikuchi et al. | |
| 6,040,160 | A | 3/2000 | Kojima et al. | |
| 6,132,999 | A | 10/2000 | Debabov et al. | |
| 6,303,348 | B1 | 10/2001 | Livshits et al. | |
| 6,319,696 | B1 | 11/2001 | Kishino et al. | |
| 6,911,332 | B2 | 6/2005 | Usuda et al. | |
| 7,026,149 | B2 | 4/2006 | Usuda et al. | |
| 7,029,893 | B2 | 4/2006 | Usuda et al. | |
| 7,060,475 | B2 | 6/2006 | Usuda et al. | |
| 7,090,998 | B2 | 8/2006 | Ishikawa et al. | |
| 7,186,531 | B2 | 3/2007 | Akhverdian et al. | |
| 7,192,748 | B2 | 3/2007 | Usuda et al. | |
| 7,220,570 | B2 | 5/2007 | Usuda et al. | |
| 7,306,933 | B2 | 12/2007 | Van Dien et al. | |
| 7,468,262 | B2 | 12/2008 | Usuda et al. | |
| 7,547,531 | B2 | 6/2009 | Kataoka et al. | |
| 7,575,905 | B2 * | 8/2009 | Rieping et al. | 435/106 |
| 2002/0110876 | A1 | 8/2002 | Miyata et al. | |
| 2002/0155556 | A1 | 10/2002 | Imaizumi et al. | |
| 2002/0160461 | A1 | 10/2002 | Nakai et al. | |
| 2004/0132165 | A1 | 7/2004 | Akhverdian et al. | |
| 2004/0265956 | A1 | 12/2004 | Takikawa et al. | |
| 2005/0233308 | A1 | 10/2005 | Nishi et al. | |
| 2005/0239177 | A1 | 10/2005 | Livshits et al. | |
| 2006/0003424 | A1 | 1/2006 | Asakura et al. | |
| 2006/0019355 | A1 | 1/2006 | Ueda et al. | |
| 2006/0088919 | A1 | 4/2006 | Rybak et al. | |
| 2006/0216796 | A1 | 9/2006 | Hashiguchi et al. | |
| 2006/0234356 | A1 | 10/2006 | Usuda et al. | |
| 2006/0234357 | A1 | 10/2006 | Usuda et al. | |
| 2007/0004014 | A1 | 1/2007 | Tsuji et al. | |
| 2007/0249017 | A1 | 10/2007 | Usuda et al. | |
| 2009/0068712 | A1 | 3/2009 | Terashita et al. | |
| 2009/0087887 | A1 | 4/2009 | Kataoka et al. | |
| 2009/0093029 | A1 * | 4/2009 | Usuda et al. | 435/108 |
| 2009/0098621 | A1 | 4/2009 | Rybak et al. | |
| 2009/0104659 | A1 | 4/2009 | Smirnov et al. | |
| 2009/0104667 | A1 | 4/2009 | Asakura et al. | |
| 2009/0148915 | A1 | 6/2009 | Van Dien et al. | |
| 2009/0203090 | A1 | 8/2009 | Ptitsyn et al. | |
| 2009/0317876 | A1 * | 12/2009 | Rybak et al. | 435/107 |

FOREIGN PATENT DOCUMENTS

| | | |
|---|---|---|
| EP | 1715055 | 10/2006 |
| EP | 1715056 | 10/2006 |
| JP | 2005-261433 | 9/2005 |
| WO | WO 01/53459 | 7/2001 |
| WO | WO01/53459 | 7/2001 |
| WO | WO 2008/002053 | 1/2008 |
| WO | WO2008/002053 | 1/2008 |
| WO | WO 2008/072761 | 6/2008 |
| WO | WO2008/072761 | 6/2008 |
| WO | WO2008/081959 | 7/2008 |
| WO | WO 2008/081959 | 7/2008 |
| WO | WO 2008/107277 | 9/2008 |
| WO | WO2008/107277 | 9/2008 |

OTHER PUBLICATIONS

Luers et al. (Yeast, vol. 14, pp. 759-771, 1998).*

Deutscher et al. (J. of Bacteriology, vol. 166, No. 3, pp. 829-836, 1986).*

Forage et al. (J. of Bacteriology, Feb. 1982, vol. 149, No. 2, pp. 413-419).*

Brinen, L. S., et al., "Crystal Structure of a Zinc-Containing Glycerol Dehydrogenase (TM0423) from *Thermotoga martima* at 1.5 Å Resolution," Proteins: Structure, Function and Genectics 2002;50:371-374.

Cameron, D. C., et al., "Metabolic Engineering of Propanediol Pathways," Biotechnol. 1998;14:116-125.

Daniel, R., et al., "Biochemical and Molecular Characterization of the Oxidative Branch of Glycerol Utilization by *Citrobacter freundii*," J. Bacteriol. 1995;177(15):4392-4401.

(Continued)

*Primary Examiner* — Hope Robinson

(74) *Attorney, Agent, or Firm* — Shelly Guest Cermak; Cermak Nakajima LLP

(57) ABSTRACT

An L-amino acid is produced by culturing a microorganism belonging to the family Enterobacteriaceae having an L-amino acid-producing ability and modified so that glycerol dehydrogenase and dihydroxyacetone kinase activities are increased, in a medium containing glycerol as a carbon source to produce and accumulate an L-amino acid in the medium or cells, and collecting the L-amino acid from the medium or the cells.

13 Claims, No Drawings

(56) References Cited

OTHER PUBLICATIONS

González-Pajuelo, M., et al., "Microbial Conversion of Glycerol to 1,3-Propanediol: Physiological Comparison of a Natural Producer, *Clostridium butyric* VPI 3266, and an Engineered Strain, *Clostridium acetobutylicum* DGI (pSPD5)," Applied Environmen. Microbiol. 2006;72(1):96-101.

Jin, R. Z., et al., "Experimental Evolution of a Novel Pathway for Glycerol," J. Mol. Evol. 1983;19:429-436.

Kelley, J. J., et al., "D-1-Amino-2-propanol:$NAD^+$ Oxidoreductase," J. Biol. Chem. 1984;259(4):2124-2129.

Luers, F., et al., "Glycerol conversion to 1,3-propanediol by *Clostridium pasteurianum*: cloning and expression of the gene encoding 1,3-propanediol dehydrogenase," FEMS Microbiol. Lett. 1997;154:337-345.

Seifert, C., et al., "Identification and expression of the genes and purification and characterization of the gene products involved in reactivation of coenzyme $B_{12}$-dependent glycerol dehydratase of *Citrobacter freundii*," Eur. J. Biochem. 2001;268:2369-2378.

Tang, C.-T., et al., "Purification and Properties of a Nicotinamide Adenine Dinucleotide-Linked Dehydrogenase that Serves an *Escherichia coli* Mutant for Glycerol Catabolism," J. Bacteriol. 1979;140(1):182-187.

Tang, J. C.-T., et al., "Immunochemical Properties of $NAD^+$-Linked Glycerol Dehydrogenases from *Escherichia coli* and *Klebsiella pneumonia*," J. Bacteriol. 1982;152(3):1169-1174.

Truniger, V., et al., "Mapping and Cloning of *gldA*, the Structural Gene of the *Escherichia coil* Glycerol Dehydrogenase," J. Bacteriol. 1994;176(6):1796-1800.

International Preliminary Report on Patentability for PCT Patent App. No. PCT/JP2008/053020 (Nov. 19, 2009).

Joyce, A. R., et al., "Experimental and Computational Assessment of Conditionally Essential Genes in *Escherichia coil*" J. Bacteriol. 2006;188(23):8259-8271.

Molin, M., et al., "Dihydroxyacetone detoxification in *Saccharomyces cerevisiae* involves formaldehyde dissimilation" Mol. Microbiol. 2006;60(4):925-938.

St. Martin, E. J., "Kinase Replacement by a Dehydrogenase for *Escherichia coil* Glycerol Utilization" J. Bacteriol. 1977;131(3):1026-1028.

Usuda, Y., "Recent topics on microbial production and metabolism of amino acids" Report of the Research Committee of Essential Amino Acids (Japan), 2005, No. 174, pp. 26-30.

Altaras, N. E., et al., "Metabolic Engineering of a 1,2-Propanediol Pathway in *Escherichia coli*," Applied Environmen. Microbiol. 1999;65(3):1180-1185.

Cameron, D. C., et al., "Metabolic Engineering of Propanediol Pathways" Biotechnol. 19984; 14:116-125.

Daniel R., et al., "Biochemical and Molecular Characterization of the Oxidative Branch of Glycerol Utilization by *Citrobacter freundii*, " J. Bacteriol. 1995;177(15):4392-4401.

Gonzalez-Pajuelo, M., et al, "Microbial Conversion of Glycerol to 1,3-Propanediol: Physiological Comparison of a Natural Producer, *Clostridium butyricum* VPI 3266, and an Engineered Strain, *Clostridium acetobutylicum* DGI (pSPD5)," Applied Environmen. Microbiol. 2006;72(1):96-101.

Kelley, J. J., et al, "D-1-Amino-2-propanol:$NAD^+$Oxidoreductase," J. Biol. Chem. 1984;259(4):2124-2129.

Luers, F., et al., "Glycerol conversion to 1,3-propanediol by *Clostridium pasteuriemum*: cloning and expression of the gene encoding 1,3-propanediol dehydrogenase," FEMS Microbiol. Lett. 1997;154:337-345.

Seifert, C., et al., "Identification and expression of the genes and purification and characterization of the gene products involved in reactivation of coenzyme $B_{12}$ -dependent glycerol dehydratase of *Citrobacter freundii*, " Eur. J. Biochem. 2001;268:2369-2378.

Tang, C.-T., et al., "Purification and Properties of a Nicotinamide Adenine Dinucleotide-Linked Dehydrogenase that Serves an *Escherichia coil* Mutant for Glycerol Catabolism," J. Bacteriol. 1979;140(1):182-187.

Truniger, V,, at al., "Ma ping and Cloning ofgldA, the Structural Gene of the Ida coli Glycerol Dehydrogenase," J. Bacteriol. 1994.176 6 :1796-1800.

Brinen, L. S., et al., "Crystal Structure of a Zinc-Containing Glycerol Dehydrogenase (TM0423) from *Thermotoga maritima* at 1.5 ÅResolution," Proteins: Structure, Function and Genectics 2002;50:371-374.

Jin, R. Z., et al., "Experimental Evolution of a Novel Pathway for Glycerol *Dissimilation in Escherichia coli*," J. Mol. Evol. 1983;19:429-436.

Tang, J. C.-T., et al., "Immunochemical Properties of $NAD^+$-Linked Glycerol Dehydrogenases from *Escherichia coli* and *Klebsiella pneumoniae*," J. Bacteriol. 1982;152(3):1169-1174.

* cited by examiner

SEQUENCE LISTING

```
<160> NUMBER OF SEQ ID NOS: 94

<210> SEQ ID NO 1
<211> LENGTH: 1104
<212> TYPE: DNA
<213> ORGANISM: Escherichia coli
<220> FEATURE:
<221> NAME/KEY: CDS
<222> LOCATION: (1)..(1104)

<400> SEQUENCE: 1

atg gac cgc att att caa tca ccg ggt aaa tac atc cag ggc gct gat       48
Met Asp Arg Ile Ile Gln Ser Pro Gly Lys Tyr Ile Gln Gly Ala Asp
1               5                   10                  15

gtg att aat cgt ctg ggc gaa tac ctg aag ccg ctg gca gaa cgc tgg       96
Val Ile Asn Arg Leu Gly Glu Tyr Leu Lys Pro Leu Ala Glu Arg Trp
            20                  25                  30

tta gtg gtg ggt gac aaa ttt gtt tta ggt ttt gct caa tcc act gtc      144
Leu Val Val Gly Asp Lys Phe Val Leu Gly Phe Ala Gln Ser Thr Val
        35                  40                  45

gag aaa agc ttt aaa gat gct gga ctg gta gta gaa att gcg ccg ttt      192
Glu Lys Ser Phe Lys Asp Ala Gly Leu Val Val Glu Ile Ala Pro Phe
    50                  55                  60

ggc ggt gaa tgt tcg caa aat gag atc gac cgt ctg cgt ggc atc gcg      240
Gly Gly Glu Cys Ser Gln Asn Glu Ile Asp Arg Leu Arg Gly Ile Ala
65                  70                  75                  80

gag act gcg cag tgt ggc gca att ctc ggt atc ggt ggc gga aaa acc      288
Glu Thr Ala Gln Cys Gly Ala Ile Leu Gly Ile Gly Gly Gly Lys Thr
                85                  90                  95

ctc gat act gcc aaa gca ctg gca cat ttc atg ggt gtt ccg gta gcg      336
Leu Asp Thr Ala Lys Ala Leu Ala His Phe Met Gly Val Pro Val Ala
            100                 105                 110

atc gca ccg act atc gcc tct acc gat gca ccg tgc agc gca ttg tct      384
Ile Ala Pro Thr Ile Ala Ser Thr Asp Ala Pro Cys Ser Ala Leu Ser
        115                 120                 125

gtt atc tac acc gat gag ggt gag ttt gac cgc tat ctg ctg ttg cca      432
Val Ile Tyr Thr Asp Glu Gly Glu Phe Asp Arg Tyr Leu Leu Leu Pro
    130                 135                 140

aat aac ccg aat atg gtc att gtc gac acc aaa atc gtc gct ggc gca      480
Asn Asn Pro Asn Met Val Ile Val Asp Thr Lys Ile Val Ala Gly Ala
145                 150                 155                 160

cct gca cgt ctg tta gcg gcg ggt atc ggc gat gcg ctg gca acc tgg      528
Pro Ala Arg Leu Leu Ala Ala Gly Ile Gly Asp Ala Leu Ala Thr Trp
                165                 170                 175

ttt gaa gcg cgt gcc tgc tct cgt agc ggc gcg acc acc atg gcg ggc      576
Phe Glu Ala Arg Ala Cys Ser Arg Ser Gly Ala Thr Thr Met Ala Gly
            180                 185                 190

ggc aag tgc acc cag gct gcg ctg gca ctg gct gaa ctg tgc tac aac      624
Gly Lys Cys Thr Gln Ala Ala Leu Ala Leu Ala Glu Leu Cys Tyr Asn
        195                 200                 205

acc ctg ctg gaa gaa ggc gaa aaa gcg atg ctt gct gcc gaa cag cat      672
Thr Leu Leu Glu Glu Gly Glu Lys Ala Met Leu Ala Ala Glu Gln His
    210                 215                 220

gta gtg act ccg gcg ctg gag cgc gtg att gaa gcg aac acc tat ttg      720
Val Val Thr Pro Ala Leu Glu Arg Val Ile Glu Ala Asn Thr Tyr Leu
225                 230                 235                 240

agc ggt gtt ggt ttt gaa agt ggt ggt ctg gct gcg gcg cac gca gtg      768
Ser Gly Val Gly Phe Glu Ser Gly Gly Leu Ala Ala Ala His Ala Val
                245                 250                 255

cat aac ggc ctg acc gct atc ccg gac gcg cat cac tat tat cac ggt      816
```

```
His Asn Gly Leu Thr Ala Ile Pro Asp Ala His His Tyr Tyr His Gly
            260                 265                 270

gaa aaa gtg gca ttc ggt acg ctg acg cag ctg gtt ctg gaa aat gcg      864
Glu Lys Val Ala Phe Gly Thr Leu Thr Gln Leu Val Leu Glu Asn Ala
        275                 280                 285

ccg gtg gag gaa atc gaa acc gta gct gcc ctt agc cat gcg gta ggt      912
Pro Val Glu Glu Ile Glu Thr Val Ala Ala Leu Ser His Ala Val Gly
    290                 295                 300

ttg cca ata act ctc gct caa ctg gat att aaa gaa gat gtc ccg gcg      960
Leu Pro Ile Thr Leu Ala Gln Leu Asp Ile Lys Glu Asp Val Pro Ala
305                 310                 315                 320

aaa atg cga att gtg gca gaa gcg gca tgt gca gaa ggt gaa acc att     1008
Lys Met Arg Ile Val Ala Glu Ala Ala Cys Ala Glu Gly Glu Thr Ile
                325                 330                 335

cac aac atg cct ggc ggc gcg acg cca gat cag gtt tac gcc gct ctg     1056
His Asn Met Pro Gly Gly Ala Thr Pro Asp Gln Val Tyr Ala Ala Leu
            340                 345                 350

ctg gta gcc gac cag tac ggt cag cgt ttc ctg caa gag tgg gaa taa     1104
Leu Val Ala Asp Gln Tyr Gly Gln Arg Phe Leu Gln Glu Trp Glu
        355                 360                 365


<210> SEQ ID NO 2
<211> LENGTH: 367
<212> TYPE: PRT
<213> ORGANISM: Escherichia coli

<400> SEQUENCE: 2

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Glu Gly Glu Phe Asp Arg Tyr Leu Leu Leu Pro
    130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Leu Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240
```

```
Ser Gly Val Gly Phe Glu Ser Gly Gly Leu Ala Ala Ala His Ala Val
                245                 250                 255

His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
        275                 280                 285

Pro Val Glu Glu Ile Glu Thr Val Ala Ala Leu Ser His Ala Val Gly
    290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
            340                 345                 350

Leu Val Ala Asp Gln Tyr Gly Gln Arg Phe Leu Gln Glu Trp Glu
        355                 360                 365


<210> SEQ ID NO 3
<211> LENGTH: 1755
<212> TYPE: DNA
<213> ORGANISM: Saccharomyces cerevisiae
<220> FEATURE:
<221> NAME/KEY: CDS
<222> LOCATION: (1)..(1755)

<400> SEQUENCE: 3

atg tcc gct aaa tcg ttt gaa gtc aca gat cca gtc aat tca agt ctc       48
Met Ser Ala Lys Ser Phe Glu Val Thr Asp Pro Val Asn Ser Ser Leu
1               5                   10                  15

aaa ggg ttt gcc ctt gct aac ccc tcc att acg ctg gtc cct gaa gaa       96
Lys Gly Phe Ala Leu Ala Asn Pro Ser Ile Thr Leu Val Pro Glu Glu
            20                  25                  30

aaa att ctc ttc aga aag acc gat tcc gac aag atc gca tta att tct      144
Lys Ile Leu Phe Arg Lys Thr Asp Ser Asp Lys Ile Ala Leu Ile Ser
        35                  40                  45

ggt ggt ggt agt gga cat gaa cct aca cac gcc ggt ttc att ggt aag      192
Gly Gly Gly Ser Gly His Glu Pro Thr His Ala Gly Phe Ile Gly Lys
    50                  55                  60

ggt atg ttg agt ggc gcc gtg gtt ggc gaa att ttt gca tcc cct tca      240
Gly Met Leu Ser Gly Ala Val Val Gly Glu Ile Phe Ala Ser Pro Ser
65                  70                  75                  80

aca aaa cag att tta aat gca atc cgt tta gtc aat gaa aat gcg tct      288
Thr Lys Gln Ile Leu Asn Ala Ile Arg Leu Val Asn Glu Asn Ala Ser
                85                  90                  95

ggc gtt tta ttg att gtg aag aac tac aca ggt gat gtt ttg cat ttt      336
Gly Val Leu Leu Ile Val Lys Asn Tyr Thr Gly Asp Val Leu His Phe
            100                 105                 110

ggt ctg tcc gct gag aga gca aga gcc ttg ggt att aac tgc cgc gtt      384
Gly Leu Ser Ala Glu Arg Ala Arg Ala Leu Gly Ile Asn Cys Arg Val
        115                 120                 125

gct gtc ata ggt gat gat gtt gca gtt ggc aga gaa aag ggt ggt atg      432
Ala Val Ile Gly Asp Asp Val Ala Val Gly Arg Glu Lys Gly Gly Met
    130                 135                 140

gtt ggt aga aga gca ttg gca ggt acc gtt ttg gtt cat aag att gta      480
Val Gly Arg Arg Ala Leu Ala Gly Thr Val Leu Val His Lys Ile Val
145                 150                 155                 160

ggt gcc ttc gca gaa gaa tat tct agt aag tat ggc tta gac ggt aca      528
Gly Ala Phe Ala Glu Glu Tyr Ser Ser Lys Tyr Gly Leu Asp Gly Thr
                165                 170                 175

gct aaa gtg gct aaa att atc aac gac aat ttg gtg acc att gga tct      576
```

```
Ala Lys Val Ala Lys Ile Ile Asn Asp Asn Leu Val Thr Ile Gly Ser
            180                 185                 190

tct tta gac cat tgt aaa gtt cct ggc agg aaa ttc gaa agt gaa tta      624
Ser Leu Asp His Cys Lys Val Pro Gly Arg Lys Phe Glu Ser Glu Leu
        195                 200                 205

aac gaa aaa caa atg gaa ttg ggt atg ggt att cat aac gaa cct ggt      672
Asn Glu Lys Gln Met Glu Leu Gly Met Gly Ile His Asn Glu Pro Gly
    210                 215                 220

gtg aaa gtt tta gac cct att cct tct acc gaa gac ttg atc tcc aag      720
Val Lys Val Leu Asp Pro Ile Pro Ser Thr Glu Asp Leu Ile Ser Lys
225                 230                 235                 240

tat atg cta cca aaa cta ttg gat cca aac gat aag gat aga gct ttt      768
Tyr Met Leu Pro Lys Leu Leu Asp Pro Asn Asp Lys Asp Arg Ala Phe
                245                 250                 255

gta aag ttt gat gaa gat gat gaa gtt gtc ttg tta gtt aac aat ctc      816
Val Lys Phe Asp Glu Asp Asp Glu Val Val Leu Leu Val Asn Asn Leu
            260                 265                 270

ggc ggt gtt tct aat ttt gtt att agt tct atc act tcc aaa act acg      864
Gly Gly Val Ser Asn Phe Val Ile Ser Ser Ile Thr Ser Lys Thr Thr
        275                 280                 285

gat ttc tta aag gaa aat tac aac ata acc ccg gtt caa aca att gct      912
Asp Phe Leu Lys Glu Asn Tyr Asn Ile Thr Pro Val Gln Thr Ile Ala
    290                 295                 300

ggc aca ttg atg acc tcc ttc aat ggt aat ggg ttc agt atc aca tta      960
Gly Thr Leu Met Thr Ser Phe Asn Gly Asn Gly Phe Ser Ile Thr Leu
305                 310                 315                 320

cta aac gcc act aag gct aca aag gct ttg caa tct gat ttt gag gag     1008
Leu Asn Ala Thr Lys Ala Thr Lys Ala Leu Gln Ser Asp Phe Glu Glu
                325                 330                 335

atc aaa tca gta cta gac ttg ttg aac gca ttt acg aac gca ccg ggc     1056
Ile Lys Ser Val Leu Asp Leu Leu Asn Ala Phe Thr Asn Ala Pro Gly
            340                 345                 350

tgg cca att gca gat ttt gaa aag act tct gcc cca tct gtt aac gat     1104
Trp Pro Ile Ala Asp Phe Glu Lys Thr Ser Ala Pro Ser Val Asn Asp
        355                 360                 365

gac ttg tta cat aat gaa gta aca gca aag gcc gtc ggt acc tat gac     1152
Asp Leu Leu His Asn Glu Val Thr Ala Lys Ala Val Gly Thr Tyr Asp
    370                 375                 380

ttt gac aag ttt gct gag tgg atg aag agt ggt gct gaa caa gtt atc     1200
Phe Asp Lys Phe Ala Glu Trp Met Lys Ser Gly Ala Glu Gln Val Ile
385                 390                 395                 400

aag agc gaa ccg cac att acg gaa cta gac aat caa gtt ggt gat ggt     1248
Lys Ser Glu Pro His Ile Thr Glu Leu Asp Asn Gln Val Gly Asp Gly
                405                 410                 415

gat tgt ggt tac act tta gtg gca gga gtt aaa ggc atc acc gaa aac     1296
Asp Cys Gly Tyr Thr Leu Val Ala Gly Val Lys Gly Ile Thr Glu Asn
            420                 425                 430

ctt gac aag ctg tcg aag gac tca tta tct cag gcg gtt gcc caa att     1344
Leu Asp Lys Leu Ser Lys Asp Ser Leu Ser Gln Ala Val Ala Gln Ile
        435                 440                 445

tca gat ttc att gaa ggc tca atg gga ggt act tct ggt ggt tta tat     1392
Ser Asp Phe Ile Glu Gly Ser Met Gly Gly Thr Ser Gly Gly Leu Tyr
    450                 455                 460

tct att ctt ttg tcg ggt ttt tca cac gga tta att cag gtt tgt aaa     1440
Ser Ile Leu Leu Ser Gly Phe Ser His Gly Leu Ile Gln Val Cys Lys
465                 470                 475                 480

tca aag gat gaa ccc gtc act aag gaa att gtg gct aag tca ctc gga     1488
Ser Lys Asp Glu Pro Val Thr Lys Glu Ile Val Ala Lys Ser Leu Gly
                485                 490                 495

att gca ttg gat act tta tac aaa tat aca aag gca agg aag gga tca     1536
```

```
Ile Ala Leu Asp Thr Leu Tyr Lys Tyr Thr Lys Ala Arg Lys Gly Ser
            500                 505                 510

tcc acc atg att gat gct tta gaa cca ttc gtt aaa gaa ttt act gca     1584
Ser Thr Met Ile Asp Ala Leu Glu Pro Phe Val Lys Glu Phe Thr Ala
        515                 520                 525

tct aag gat ttc aat aag gcg gta aaa gct gca gag gaa ggt gct aaa     1632
Ser Lys Asp Phe Asn Lys Ala Val Lys Ala Ala Glu Glu Gly Ala Lys
    530                 535                 540

tcc act gct aca ttc gag gcc aaa ttt ggc aga gct tcg tat gtc ggc     1680
Ser Thr Ala Thr Phe Glu Ala Lys Phe Gly Arg Ala Ser Tyr Val Gly
545                 550                 555                 560

gat tca tct caa gta gaa gat cct ggt gca gta ggc cta tgt gag ttt     1728
Asp Ser Ser Gln Val Glu Asp Pro Gly Ala Val Gly Leu Cys Glu Phe
                565                 570                 575

ttg aag ggg gtt caa agc gcc ttg taa                                 1755
Leu Lys Gly Val Gln Ser Ala Leu
            580


<210> SEQ ID NO 4
<211> LENGTH: 584
<212> TYPE: PRT
<213> ORGANISM: Saccharomyces cerevisiae

<400> SEQUENCE: 4

Met Ser Ala Lys Ser Phe Glu Val Thr Asp Pro Val Asn Ser Ser Leu
1               5                   10                  15

Lys Gly Phe Ala Leu Ala Asn Pro Ser Ile Thr Leu Val Pro Glu Glu
            20                  25                  30

Lys Ile Leu Phe Arg Lys Thr Asp Ser Asp Lys Ile Ala Leu Ile Ser
        35                  40                  45

Gly Gly Gly Ser Gly His Glu Pro Thr His Ala Gly Phe Ile Gly Lys
    50                  55                  60

Gly Met Leu Ser Gly Ala Val Val Gly Glu Ile Phe Ala Ser Pro Ser
65                  70                  75                  80

Thr Lys Gln Ile Leu Asn Ala Ile Arg Leu Val Asn Glu Asn Ala Ser
                85                  90                  95

Gly Val Leu Leu Ile Val Lys Asn Tyr Thr Gly Asp Val Leu His Phe
            100                 105                 110

Gly Leu Ser Ala Glu Arg Ala Arg Ala Leu Gly Ile Asn Cys Arg Val
        115                 120                 125

Ala Val Ile Gly Asp Asp Val Ala Val Gly Arg Glu Lys Gly Gly Met
    130                 135                 140

Val Gly Arg Arg Ala Leu Ala Gly Thr Val Leu Val His Lys Ile Val
145                 150                 155                 160

Gly Ala Phe Ala Glu Glu Tyr Ser Ser Lys Tyr Gly Leu Asp Gly Thr
                165                 170                 175

Ala Lys Val Ala Lys Ile Ile Asn Asp Asn Leu Val Thr Ile Gly Ser
            180                 185                 190

Ser Leu Asp His Cys Lys Val Pro Gly Arg Lys Phe Glu Ser Glu Leu
        195                 200                 205

Asn Glu Lys Gln Met Glu Leu Gly Met Gly Ile His Asn Glu Pro Gly
    210                 215                 220

Val Lys Val Leu Asp Pro Ile Pro Ser Thr Glu Asp Leu Ile Ser Lys
225                 230                 235                 240

Tyr Met Leu Pro Lys Leu Leu Asp Pro Asn Asp Lys Asp Arg Ala Phe
                245                 250                 255

Val Lys Phe Asp Glu Asp Asp Glu Val Val Leu Leu Val Asn Asn Leu
```

```
            260                 265                 270

Gly Gly Val Ser Asn Phe Val Ile Ser Ser Ile Thr Ser Lys Thr Thr
        275                 280                 285

Asp Phe Leu Lys Glu Asn Tyr Asn Ile Thr Pro Val Gln Thr Ile Ala
    290                 295                 300

Gly Thr Leu Met Thr Ser Phe Asn Gly Asn Gly Phe Ser Ile Thr Leu
305                 310                 315                 320

Leu Asn Ala Thr Lys Ala Thr Lys Ala Leu Gln Ser Asp Phe Glu Glu
                325                 330                 335

Ile Lys Ser Val Leu Asp Leu Leu Asn Ala Phe Thr Asn Ala Pro Gly
            340                 345                 350

Trp Pro Ile Ala Asp Phe Glu Lys Thr Ser Ala Pro Ser Val Asn Asp
        355                 360                 365

Asp Leu Leu His Asn Glu Val Thr Ala Lys Ala Val Gly Thr Tyr Asp
    370                 375                 380

Phe Asp Lys Phe Ala Glu Trp Met Lys Ser Gly Ala Glu Gln Val Ile
385                 390                 395                 400

Lys Ser Glu Pro His Ile Thr Glu Leu Asp Asn Gln Val Gly Asp Gly
                405                 410                 415

Asp Cys Gly Tyr Thr Leu Val Ala Gly Val Lys Gly Ile Thr Glu Asn
            420                 425                 430

Leu Asp Lys Leu Ser Lys Asp Ser Leu Ser Gln Ala Val Ala Gln Ile
        435                 440                 445

Ser Asp Phe Ile Glu Gly Ser Met Gly Gly Thr Ser Gly Gly Leu Tyr
    450                 455                 460

Ser Ile Leu Leu Ser Gly Phe Ser His Gly Leu Ile Gln Val Cys Lys
465                 470                 475                 480

Ser Lys Asp Glu Pro Val Thr Lys Glu Ile Val Ala Lys Ser Leu Gly
                485                 490                 495

Ile Ala Leu Asp Thr Leu Tyr Lys Tyr Thr Lys Ala Arg Lys Gly Ser
            500                 505                 510

Ser Thr Met Ile Asp Ala Leu Glu Pro Phe Val Lys Glu Phe Thr Ala
        515                 520                 525

Ser Lys Asp Phe Asn Lys Ala Val Lys Ala Ala Glu Glu Gly Ala Lys
    530                 535                 540

Ser Thr Ala Thr Phe Glu Ala Lys Phe Gly Arg Ala Ser Tyr Val Gly
545                 550                 555                 560

Asp Ser Ser Gln Val Glu Asp Pro Gly Ala Val Gly Leu Cys Glu Phe
                565                 570                 575

Leu Lys Gly Val Gln Ser Ala Leu
            580


<210> SEQ ID NO 5
<211> LENGTH: 1695
<212> TYPE: DNA
<213> ORGANISM: Agrobacterium tumefaciens
<220> FEATURE:
<221> NAME/KEY: CDS
<222> LOCATION: (1)..(1695)

<400> SEQUENCE: 5

atg aag aag ctc atc aac gat cca tcc acc gtt gtc cgg gac atg ctg       48
Met Lys Lys Leu Ile Asn Asp Pro Ser Thr Val Val Arg Asp Met Leu
1               5                   10                  15

gag ggc atc gtg gcg ctc agc ccc gaa acc att ctg ctt cag gat gag       96
Glu Gly Ile Val Ala Leu Ser Pro Glu Thr Ile Leu Leu Gln Asp Glu
            20                  25                  30
```

```
aac gtg gtc ata agg tcc ggc ctg cct gaa gcg gaa aag cgc aag gtt      144
Asn Val Val Ile Arg Ser Gly Leu Pro Glu Ala Glu Lys Arg Lys Val
        35                  40                  45

gca gtg ctt tcg ggc ggt ggc agc gga cat gag ccg gcc cac gcc ggt      192
Ala Val Leu Ser Gly Gly Gly Ser Gly His Glu Pro Ala His Ala Gly
    50                  55                  60

tat gtc ggc acg ggc atg ttg acg gtt gcg gtg gcg ggc gat gtc ttc      240
Tyr Val Gly Thr Gly Met Leu Thr Val Ala Val Ala Gly Asp Val Phe
65                  70                  75                  80

act tcg ccg agc acc gac gcg gtt ctc gcc ggc atc agg gcc gcg gcc      288
Thr Ser Pro Ser Thr Asp Ala Val Leu Ala Gly Ile Arg Ala Ala Ala
                85                  90                  95

ggc cct gcc ggt gcg ctg gtc atc gtc aag aac tat acc ggc gac cgg      336
Gly Pro Ala Gly Ala Leu Val Ile Val Lys Asn Tyr Thr Gly Asp Arg
            100                 105                 110

ctg aat ttc ggc ttg gcg gcg gag ctg gcg agg gcc gaa gga atc cct      384
Leu Asn Phe Gly Leu Ala Ala Glu Leu Ala Arg Ala Glu Gly Ile Pro
        115                 120                 125

gtc gag atc gtt gtc gtc gcc gac gac gtt gcc ttg aag gat acg gtt      432
Val Glu Ile Val Val Val Ala Asp Asp Val Ala Leu Lys Asp Thr Val
    130                 135                 140

ccc gcc gag cgc cgc cgc ggg att gcg ggg acg gtg ctc gtg cac aag      480
Pro Ala Glu Arg Arg Arg Gly Ile Ala Gly Thr Val Leu Val His Lys
145                 150                 155                 160

ctc gcg ggg gcc gca gcg gaa aag ggc ctt cct ctt caa gag gtg gcc      528
Leu Ala Gly Ala Ala Ala Glu Lys Gly Leu Pro Leu Gln Glu Val Ala
                165                 170                 175

cgc atc gcc cgg gac gct gcc gcc aag cta tct tcc atg ggt gtc tcg      576
Arg Ile Ala Arg Asp Ala Ala Ala Lys Leu Ser Ser Met Gly Val Ser
            180                 185                 190

ctg gga tcc tgc acg ctg ccg gct gtc ggc aag ccg ggc ttc gtg ctt      624
Leu Gly Ser Cys Thr Leu Pro Ala Val Gly Lys Pro Gly Phe Val Leu
        195                 200                 205

ggc gag acc gaa atc gaa gtc ggg ctc ggt atc cat ggc gag cag ggc      672
Gly Glu Thr Glu Ile Glu Val Gly Leu Gly Ile His Gly Glu Gln Gly
    210                 215                 220

gtg cag cgg atg ccc att gcc tcg gct gac gcg ctc gtg cag ctg gtg      720
Val Gln Arg Met Pro Ile Ala Ser Ala Asp Ala Leu Val Gln Leu Val
225                 230                 235                 240

atc gaa acg atc gaa gcc gac ggc aag ctc gcc ggc ggc aat cgc gtc      768
Ile Glu Thr Ile Glu Ala Asp Gly Lys Leu Ala Gly Gly Asn Arg Val
                245                 250                 255

gct ctg ctg gtc aac ggc ctg ggg gca acg ccg ccg atg gaa ctc gcc      816
Ala Leu Leu Val Asn Gly Leu Gly Ala Thr Pro Pro Met Glu Leu Ala
            260                 265                 270

atc gtc gca cgg tcg gca gtc gcg cgg ctg gag gcg aaa ggc atc gtc      864
Ile Val Ala Arg Ser Ala Val Ala Arg Leu Glu Ala Lys Gly Ile Val
        275                 280                 285

gtg gaa cgt gcc tgg gcc ggc acc ttc ctt tca gcc ctc gat atg ccc      912
Val Glu Arg Ala Trp Ala Gly Thr Phe Leu Ser Ala Leu Asp Met Pro
    290                 295                 300

ggg ttt tcg ttg tcg gtc atg cag gtt gac gac gca gcg ctc agc ctc      960
Gly Phe Ser Leu Ser Val Met Gln Val Asp Asp Ala Ala Leu Ser Leu
305                 310                 315                 320

atc gac gcg cca acc gag gct ggc gca tgg ccg cgc ggc ggt gcg gtg     1008
Ile Asp Ala Pro Thr Glu Ala Gly Ala Trp Pro Arg Gly Gly Ala Val
                325                 330                 335

aac cgc aag cgg gtt ctg cct tcg gca aac gcc gaa aag acc gtg gtt     1056
Asn Arg Lys Arg Val Leu Pro Ser Ala Asn Ala Glu Lys Thr Val Val
            340                 345                 350
```

```
gcg aca aac aag atg acg gcg gcc ggc gag cgg ctt cgt tcg ggc gcg     1104
Ala Thr Asn Lys Met Thr Ala Ala Gly Glu Arg Leu Arg Ser Gly Ala
        355                 360                 365

gaa cgg tcc gcg aga gcc ctg atc gct gcg gag ccc agg ctg acg caa     1152
Glu Arg Ser Ala Arg Ala Leu Ile Ala Ala Glu Pro Arg Leu Thr Gln
    370                 375                 380

ctc gat agc gtt gca ggt gac ggc gac ctc ggc gcc agc atg gtg cgt     1200
Leu Asp Ser Val Ala Gly Asp Gly Asp Leu Gly Ala Ser Met Val Arg
385                 390                 395                 400

ggc ggc gag gcg atc ctt gcg ctg ccg aaa gag agt ttc ggc gac gtc     1248
Gly Gly Glu Ala Ile Leu Ala Leu Pro Lys Glu Ser Phe Gly Asp Val
                405                 410                 415

tcc gat gga ttg atg gcg atg gcc aat gcg atg cgc aag gcc atc ggc     1296
Ser Asp Gly Leu Met Ala Met Ala Asn Ala Met Arg Lys Ala Ile Gly
            420                 425                 430

gga agc tcg ggg ccg ttc tat gcg aca ggc ctc atg cgc gct tcg cga     1344
Gly Ser Ser Gly Pro Phe Tyr Ala Thr Gly Leu Met Arg Ala Ser Arg
        435                 440                 445

cag ctg gca ggg atc gat gag cca gcg gcc cag cag atg gcg gaa gca     1392
Gln Leu Ala Gly Ile Asp Glu Pro Ala Ala Gln Gln Met Ala Glu Ala
    450                 455                 460

ttc gtg gcg gct gtt gcg gcg gtc tcg gaa ctt ggc ggt gcg aaa ccg     1440
Phe Val Ala Ala Val Ala Ala Val Ser Glu Leu Gly Gly Ala Lys Pro
465                 470                 475                 480

ggc gat cgc acg atg atc gat gcg ctt tat ccg gca gcg aaa acc ttc     1488
Gly Asp Arg Thr Met Ile Asp Ala Leu Tyr Pro Ala Ala Lys Thr Phe
                485                 490                 495

agg gac aag ctt gtg aca ggc gct tcg gca gaa gaa gcc tgg caa tcc     1536
Arg Asp Lys Leu Val Thr Gly Ala Ser Ala Glu Glu Ala Trp Gln Ser
            500                 505                 510

gcg gtg gcg gcg ggc gag gtg ggc gca gag gcg aca gcg tcc atg aag     1584
Ala Val Ala Ala Gly Glu Val Gly Ala Glu Ala Thr Ala Ser Met Lys
        515                 520                 525

cca cgg ctc ggg cgc gca agt tac ctc ggt gag cgg gcc gtc ggc cat     1632
Pro Arg Leu Gly Arg Ala Ser Tyr Leu Gly Glu Arg Ala Val Gly His
    530                 535                 540

ccc gat ggg ggc gcg gtc gcc gtt ggc atc tgg ctc aaa gct atc gag     1680
Pro Asp Gly Gly Ala Val Ala Val Gly Ile Trp Leu Lys Ala Ile Glu
545                 550                 555                 560

gct gcg atc tcg tga                                                 1695
Ala Ala Ile Ser


<210> SEQ ID NO 6
<211> LENGTH: 564
<212> TYPE: PRT
<213> ORGANISM: Agrobacterium tumefaciens

<400> SEQUENCE: 6

Met Lys Lys Leu Ile Asn Asp Pro Ser Thr Val Val Arg Asp Met Leu
1               5                   10                  15

Glu Gly Ile Val Ala Leu Ser Pro Glu Thr Ile Leu Leu Gln Asp Glu
            20                  25                  30

Asn Val Val Ile Arg Ser Gly Leu Pro Glu Ala Glu Lys Arg Lys Val
        35                  40                  45

Ala Val Leu Ser Gly Gly Gly Ser Gly His Glu Pro Ala His Ala Gly
    50                  55                  60

Tyr Val Gly Thr Gly Met Leu Thr Val Ala Val Ala Gly Asp Val Phe
65                  70                  75                  80

Thr Ser Pro Ser Thr Asp Ala Val Leu Ala Gly Ile Arg Ala Ala Ala
```

```
                85                  90                  95

Gly Pro Ala Gly Ala Leu Val Ile Val Lys Asn Tyr Thr Gly Asp Arg
            100                 105                 110

Leu Asn Phe Gly Leu Ala Ala Glu Leu Ala Arg Ala Glu Gly Ile Pro
        115                 120                 125

Val Glu Ile Val Val Val Ala Asp Asp Val Ala Leu Lys Asp Thr Val
    130                 135                 140

Pro Ala Glu Arg Arg Arg Gly Ile Ala Gly Thr Val Leu Val His Lys
145                 150                 155                 160

Leu Ala Gly Ala Ala Ala Glu Lys Gly Leu Pro Leu Gln Glu Val Ala
                165                 170                 175

Arg Ile Ala Arg Asp Ala Ala Ala Lys Leu Ser Ser Met Gly Val Ser
            180                 185                 190

Leu Gly Ser Cys Thr Leu Pro Ala Val Gly Lys Pro Gly Phe Val Leu
        195                 200                 205

Gly Glu Thr Glu Ile Glu Val Gly Leu Gly Ile His Gly Glu Gln Gly
    210                 215                 220

Val Gln Arg Met Pro Ile Ala Ser Ala Asp Ala Leu Val Gln Leu Val
225                 230                 235                 240

Ile Glu Thr Ile Glu Ala Asp Gly Lys Leu Ala Gly Gly Asn Arg Val
                245                 250                 255

Ala Leu Leu Val Asn Gly Leu Gly Ala Thr Pro Pro Met Glu Leu Ala
            260                 265                 270

Ile Val Ala Arg Ser Ala Val Ala Arg Leu Glu Ala Lys Gly Ile Val
        275                 280                 285

Val Glu Arg Ala Trp Ala Gly Thr Phe Leu Ser Ala Leu Asp Met Pro
    290                 295                 300

Gly Phe Ser Leu Ser Val Met Gln Val Asp Asp Ala Ala Leu Ser Leu
305                 310                 315                 320

Ile Asp Ala Pro Thr Glu Ala Gly Ala Trp Pro Arg Gly Gly Ala Val
                325                 330                 335

Asn Arg Lys Arg Val Leu Pro Ser Ala Asn Ala Glu Lys Thr Val Val
            340                 345                 350

Ala Thr Asn Lys Met Thr Ala Ala Gly Glu Arg Leu Arg Ser Gly Ala
        355                 360                 365

Glu Arg Ser Ala Arg Ala Leu Ile Ala Ala Glu Pro Arg Leu Thr Gln
    370                 375                 380

Leu Asp Ser Val Ala Gly Asp Gly Asp Leu Gly Ala Ser Met Val Arg
385                 390                 395                 400

Gly Gly Glu Ala Ile Leu Ala Leu Pro Lys Glu Ser Phe Gly Asp Val
                405                 410                 415

Ser Asp Gly Leu Met Ala Met Ala Asn Ala Met Arg Lys Ala Ile Gly
            420                 425                 430

Gly Ser Ser Gly Pro Phe Tyr Ala Thr Gly Leu Met Arg Ala Ser Arg
        435                 440                 445

Gln Leu Ala Gly Ile Asp Glu Pro Ala Ala Gln Gln Met Ala Glu Ala
    450                 455                 460

Phe Val Ala Ala Val Ala Ala Val Ser Glu Leu Gly Gly Ala Lys Pro
465                 470                 475                 480

Gly Asp Arg Thr Met Ile Asp Ala Leu Tyr Pro Ala Ala Lys Thr Phe
                485                 490                 495

Arg Asp Lys Leu Val Thr Gly Ala Ser Ala Glu Glu Ala Trp Gln Ser
            500                 505                 510
```

```
Ala Val Ala Ala Gly Glu Val Gly Ala Glu Ala Thr Ala Ser Met Lys
        515                 520                 525

Pro Arg Leu Gly Arg Ala Ser Tyr Leu Gly Glu Arg Ala Val Gly His
    530                 535                 540

Pro Asp Gly Gly Ala Val Ala Val Gly Ile Trp Leu Lys Ala Ile Glu
545                 550                 555                 560

Ala Ala Ile Ser


<210> SEQ ID NO 7
<211> LENGTH: 1659
<212> TYPE: DNA
<213> ORGANISM: Citrobacter freundii
<220> FEATURE:
<221> NAME/KEY: CDS
<222> LOCATION: (1)..(1659)

<400> SEQUENCE: 7

atg tct caa ttc ttt ttt aac caa cgc acc cat ctt gtg agc gac gtc       48
Met Ser Gln Phe Phe Phe Asn Gln Arg Thr His Leu Val Ser Asp Val
1               5                   10                  15

atc gac ggg gcg att atc gcc agc cca tgg aat aac ctg gcg cgt ctg       96
Ile Asp Gly Ala Ile Ile Ala Ser Pro Trp Asn Asn Leu Ala Arg Leu
            20                  25                  30

gaa agc gat ccg gcc att cgc atc gtg gtc cgt cgt gac ctt aat aaa      144
Glu Ser Asp Pro Ala Ile Arg Ile Val Val Arg Arg Asp Leu Asn Lys
        35                  40                  45

aat aac gta gcg gtc att tcc ggc ggc ggt tcg gga cac gaa ccc gcg      192
Asn Asn Val Ala Val Ile Ser Gly Gly Gly Ser Gly His Glu Pro Ala
    50                  55                  60

cac gtt ggg ttt atc ggt aaa ggc atg cta acc gct gcg gtc tgc ggc      240
His Val Gly Phe Ile Gly Lys Gly Met Leu Thr Ala Ala Val Cys Gly
65                  70                  75                  80

gac gtt ttc gcc tcc ccg agc gtg gat gct gta ctg acc gcg att cag      288
Asp Val Phe Ala Ser Pro Ser Val Asp Ala Val Leu Thr Ala Ile Gln
                85                  90                  95

gcg gtg acc ggt gag gct ggc tgt ttg ttg att gtg aaa aac tac acc      336
Ala Val Thr Gly Glu Ala Gly Cys Leu Leu Ile Val Lys Asn Tyr Thr
            100                 105                 110

ggt gac cgt ctt aat ttc ggt ctc gcc gcc gag aag gcg cgt cgc ctt      384
Gly Asp Arg Leu Asn Phe Gly Leu Ala Ala Glu Lys Ala Arg Arg Leu
        115                 120                 125

ggc tat aac gtt gaa atg ctg att gtc ggc gac gac atc tcc ctg ccg      432
Gly Tyr Asn Val Glu Met Leu Ile Val Gly Asp Asp Ile Ser Leu Pro
    130                 135                 140

gat aac aaa cac cca cgt ggc att gcg gga act atc ctg gtg cat aaa      480
Asp Asn Lys His Pro Arg Gly Ile Ala Gly Thr Ile Leu Val His Lys
145                 150                 155                 160

atc gca ggc tat ttt gcc gaa cgc ggc tat aac ctc gcc acc gtc ctg      528
Ile Ala Gly Tyr Phe Ala Glu Arg Gly Tyr Asn Leu Ala Thr Val Leu
                165                 170                 175

cgt gaa gcg cag tac gca gcc agc aac acc ttt agc ctg ggc gta gcg      576
Arg Glu Ala Gln Tyr Ala Ala Ser Asn Thr Phe Ser Leu Gly Val Ala
            180                 185                 190

ctt tcc agc tgt cat ctg ccg caa gaa acc gac gca gcc cct cgt cat      624
Leu Ser Ser Cys His Leu Pro Gln Glu Thr Asp Ala Ala Pro Arg His
        195                 200                 205

cat ccg ggt cat gcg gag ctg ggt atg gga att cac ggc gaa cca ggc      672
His Pro Gly His Ala Glu Leu Gly Met Gly Ile His Gly Glu Pro Gly
    210                 215                 220

gca tcg gtt atc gac acc caa aac agt gcg caa gtg gta aac ctg atg      720
Ala Ser Val Ile Asp Thr Gln Asn Ser Ala Gln Val Val Asn Leu Met
```

```
225                 230                 235                 240

gtg gat aaa ctg ctg gcc gcc ctg cct gaa acc ggt cgt ctg gcg gtg       768
Val Asp Lys Leu Leu Ala Ala Leu Pro Glu Thr Gly Arg Leu Ala Val
                245                 250                 255

atg att aat aat ctt ggc ggc gtt tcc gtg gcc gaa atg gcc atc atc       816
Met Ile Asn Asn Leu Gly Gly Val Ser Val Ala Glu Met Ala Ile Ile
            260                 265                 270

acc cgc gaa ctc gcc agc agc ccg ctg cac tcg cgt atc gac tgg cta       864
Thr Arg Glu Leu Ala Ser Ser Pro Leu His Ser Arg Ile Asp Trp Leu
        275                 280                 285

att ggc ccg gcc tcg ctg gtc acc gcg ctg gat atg aaa ggc ttc tca       912
Ile Gly Pro Ala Ser Leu Val Thr Ala Leu Asp Met Lys Gly Phe Ser
    290                 295                 300

ctg acg gcc atc gtg ctg gaa gag agc atc gaa aaa gca ctg ctc acc       960
Leu Thr Ala Ile Val Leu Glu Glu Ser Ile Glu Lys Ala Leu Leu Thr
305                 310                 315                 320

gaa gtg gaa acc agc aac tgg ccg acg ccg gtc cca ccg cgt gaa atc      1008
Glu Val Glu Thr Ser Asn Trp Pro Thr Pro Val Pro Pro Arg Glu Ile
                325                 330                 335

acc tgc gta gtg tca tct cac gct agc gcc cgc gtg gaa ttc cag cct      1056
Thr Cys Val Val Ser Ser His Ala Ser Ala Arg Val Glu Phe Gln Pro
            340                 345                 350

tcg gca aac gcc ctg gtg gcc ggg att gtg gag ctg gtc acc gca acc      1104
Ser Ala Asn Ala Leu Val Ala Gly Ile Val Glu Leu Val Thr Ala Thr
        355                 360                 365

ctt tcc gat ctg gag act cat ctg aat gcg ctg gac gcc aaa gtc ggc      1152
Leu Ser Asp Leu Glu Thr His Leu Asn Ala Leu Asp Ala Lys Val Gly
    370                 375                 380

gat ggc gat acc ggt tcg acc ttt gcc gcc gcg gcg cgt gaa att gcc      1200
Asp Gly Asp Thr Gly Ser Thr Phe Ala Ala Ala Ala Arg Glu Ile Ala
385                 390                 395                 400

agc ctg ctg cat cgc cag cag ctg ccg ctg aat aac ctt gcc acg ctg      1248
Ser Leu Leu His Arg Gln Gln Leu Pro Leu Asn Asn Leu Ala Thr Leu
                405                 410                 415

ttc gcg ctg att ggc gaa cgt ctg acc gtg gtg atg ggc ggt tcc agc      1296
Phe Ala Leu Ile Gly Glu Arg Leu Thr Val Val Met Gly Gly Ser Ser
            420                 425                 430

ggt gtg ctg atg tca atc ttc ttt acc gcc gcc ggg cag aaa ctg gaa      1344
Gly Val Leu Met Ser Ile Phe Phe Thr Ala Ala Gly Gln Lys Leu Glu
        435                 440                 445

cag ggc gct aac gtt gtc gaa gcg cta aat acg ggg ctg gcg cag atg      1392
Gln Gly Ala Asn Val Val Glu Ala Leu Asn Thr Gly Leu Ala Gln Met
    450                 455                 460

aag ttc tac ggc ggc gca gac gaa ggc gat cgc acg atg att gat gcg      1440
Lys Phe Tyr Gly Gly Ala Asp Glu Gly Asp Arg Thr Met Ile Asp Ala
465                 470                 475                 480

ctg caa ccg gcc ctg acc tcg ctg ctc gca cag ccg aaa aat ctg cag      1488
Leu Gln Pro Ala Leu Thr Ser Leu Leu Ala Gln Pro Lys Asn Leu Gln
                485                 490                 495

gcc gca ttc gac gcc gcg caa gcg gga gcc gaa cga acc tgt ttg tcg      1536
Ala Ala Phe Asp Ala Ala Gln Ala Gly Ala Glu Arg Thr Cys Leu Ser
            500                 505                 510

agc aaa gcc aat gcg ggt cgc gca tcg tat ctg agc agc gaa agc ctg      1584
Ser Lys Ala Asn Ala Gly Arg Ala Ser Tyr Leu Ser Ser Glu Ser Leu
        515                 520                 525

ctc gga aat atg gac ccc ggc gcg cag cgc cta gcg atg gtg ttt aaa      1632
Leu Gly Asn Met Asp Pro Gly Ala Gln Arg Leu Ala Met Val Phe Lys
    530                 535                 540

gcg cta gcg gag agt gag ctg ggc taa                                  1659
Ala Leu Ala Glu Ser Glu Leu Gly
```

545 550

<210> SEQ ID NO 8
<211> LENGTH: 552
<212> TYPE: PRT
<213> ORGANISM: Citrobacter freundii

<400> SEQUENCE: 8

Met Ser Gln Phe Phe Phe Asn Gln Arg Thr His Leu Val Ser Asp Val
1 5 10 15

Ile Asp Gly Ala Ile Ile Ala Ser Pro Trp Asn Asn Leu Ala Arg Leu
20 25 30

Glu Ser Asp Pro Ala Ile Arg Ile Val Val Arg Arg Asp Leu Asn Lys
35 40 45

Asn Asn Val Ala Val Ile Ser Gly Gly Gly Ser Gly His Glu Pro Ala
50 55 60

His Val Gly Phe Ile Gly Lys Gly Met Leu Thr Ala Ala Val Cys Gly
65 70 75 80

Asp Val Phe Ala Ser Pro Ser Val Asp Ala Val Leu Thr Ala Ile Gln
85 90 95

Ala Val Thr Gly Glu Ala Gly Cys Leu Leu Ile Val Lys Asn Tyr Thr
100 105 110

Gly Asp Arg Leu Asn Phe Gly Leu Ala Ala Glu Lys Ala Arg Arg Leu
115 120 125

Gly Tyr Asn Val Glu Met Leu Ile Val Gly Asp Asp Ile Ser Leu Pro
130 135 140

Asp Asn Lys His Pro Arg Gly Ile Ala Gly Thr Ile Leu Val His Lys
145 150 155 160

Ile Ala Gly Tyr Phe Ala Glu Arg Gly Tyr Asn Leu Ala Thr Val Leu
165 170 175

Arg Glu Ala Gln Tyr Ala Ala Ser Asn Thr Phe Ser Leu Gly Val Ala
180 185 190

Leu Ser Ser Cys His Leu Pro Gln Glu Thr Asp Ala Ala Pro Arg His
195 200 205

His Pro Gly His Ala Glu Leu Gly Met Gly Ile His Gly Glu Pro Gly
210 215 220

Ala Ser Val Ile Asp Thr Gln Asn Ser Ala Gln Val Val Asn Leu Met
225 230 235 240

Val Asp Lys Leu Leu Ala Ala Leu Pro Glu Thr Gly Arg Leu Ala Val
245 250 255

Met Ile Asn Asn Leu Gly Gly Val Ser Val Ala Glu Met Ala Ile Ile
260 265 270

Thr Arg Glu Leu Ala Ser Ser Pro Leu His Ser Arg Ile Asp Trp Leu
275 280 285

Ile Gly Pro Ala Ser Leu Val Thr Ala Leu Asp Met Lys Gly Phe Ser
290 295 300

Leu Thr Ala Ile Val Leu Glu Glu Ser Ile Glu Lys Ala Leu Leu Thr
305 310 315 320

Glu Val Glu Thr Ser Asn Trp Pro Thr Pro Val Pro Pro Arg Glu Ile
325 330 335

Thr Cys Val Val Ser Ser His Ala Ser Ala Arg Val Glu Phe Gln Pro
340 345 350

Ser Ala Asn Ala Leu Val Ala Gly Ile Val Glu Leu Val Thr Ala Thr
355 360 365

Leu Ser Asp Leu Glu Thr His Leu Asn Ala Leu Asp Ala Lys Val Gly

```
    370                 375                 380

Asp Gly Asp Thr Gly Ser Thr Phe Ala Ala Ala Ala Arg Glu Ile Ala
385                 390                 395                 400

Ser Leu Leu His Arg Gln Gln Leu Pro Leu Asn Asn Leu Ala Thr Leu
                405                 410                 415

Phe Ala Leu Ile Gly Glu Arg Leu Thr Val Val Met Gly Gly Ser Ser
            420                 425                 430

Gly Val Leu Met Ser Ile Phe Phe Thr Ala Ala Gly Gln Lys Leu Glu
        435                 440                 445

Gln Gly Ala Asn Val Val Glu Ala Leu Asn Thr Gly Leu Ala Gln Met
    450                 455                 460

Lys Phe Tyr Gly Gly Ala Asp Glu Gly Asp Arg Thr Met Ile Asp Ala
465                 470                 475                 480

Leu Gln Pro Ala Leu Thr Ser Leu Leu Ala Gln Pro Lys Asn Leu Gln
                485                 490                 495

Ala Ala Phe Asp Ala Ala Gln Ala Gly Ala Glu Arg Thr Cys Leu Ser
            500                 505                 510

Ser Lys Ala Asn Ala Gly Arg Ala Ser Tyr Leu Ser Ser Glu Ser Leu
        515                 520                 525

Leu Gly Asn Met Asp Pro Gly Ala Gln Arg Leu Ala Met Val Phe Lys
    530                 535                 540

Ala Leu Ala Glu Ser Glu Leu Gly
545                 550
```

<210> SEQ ID NO 9
<211> LENGTH: 1740
<212> TYPE: DNA
<213> ORGANISM: Artificial sequence
<220> FEATURE:
<223> OTHER INFORMATION: attR-cat-attL-PtacM-SD-spacer

<400> SEQUENCE: 9

```
tctagacgct caagttagta taaaaaagct gaacgagaaa cgtaaaatga tataaatatc     60

aatatattaa attagatttt gcataaaaaa cagactacat aatactgtaa aacacaacat    120

atgcagtcac tatgaatcaa ctacttagat ggtattagtg acctgtaaca gactgcagtg    180

gtcgaaaaaa aaagcccgca ctgtcaggtg cgggcttttt tctgtgttaa gcttcgacga    240

atttctgcca ttcatccgct tattatcact tattcaggcg tagcaccagg cgtttaaggg    300

caccaataac tgccttaaaa aaattacgcc ccgccctgcc actcatcgca gtactgttgt    360

aattcattaa gcattctgcc gacatggaag ccatcacaga cggcatgatg aacctgaatc    420

gccagcggca tcagcacctt gtcgccttgc gtataatatt tgcccatggt gaaaacgggg    480

gcgaagaagt tgtccatatt ggccacgttt aaatcaaaac tggtgaaact cacccaggga    540

ttggctgaga cgaaaaacat attctcaata aaccctttag ggaaataggc caggttttca    600

ccgtaacacg ccacatcttg cgaatatatg tgtagaaact gccggaaatc gtcgtggtat    660

tcactccaga gcgatgaaaa cgtttcagtt tgctcatgga aaacggtgta acaagggtga    720

acactatccc atatcaccag ctcaccgtct ttcattgcca tacggaattc cggatgagca    780

ttcatcaggc gggcaagaat gtgaataaag gccggataaa acttgtgctt atttttcttt    840

acggtcttta aaaaggccgt aatatccagc tgaacggtct ggttataggt acattgagca    900

actgactgaa atgcctcaaa atgttcttta cgatgccatt gggatatatc aacggtggta    960

tatccagtga ttttttctc cattttagct tccttagctc ctgaaaatct cggatccggc   1020

caagctagct tggctctagc tagagcgccc ggttgacgct gctagtgtta cctagcgatt   1080
```

```
tgtatcttac tgcatgttac ttcatgttgt caatacctgt ttttcgtgcg acttatcagg   1140

ctgtctactt atccggagat ccacaggacg ggtgtggtcg ccatgatcgc gtagtcgata   1200

gtggctccaa gtagcgaagc gagcaggact gggcggcggc caaagcggtc ggacagtgct   1260

ccgagaacgg gtgcgcatag aaattgcatc aacgcatata gcgctagcag cacgccatag   1320

tgactggcga tgctgtcgga atggacgata tcccgcaaga ggcccggcag taccggcata   1380

accaagccta tgcctacagc atccagggtg acggtgccga ggatgacgat gagcgcattg   1440

ttagatttca tacacggtgc ctgactgcgt tagcaattta actgtgataa actaccgcat   1500

taaagcttat cgatgataag ctgtcaaaca tgagaattcg aaatcaaata atgattttat   1560

tttgactgat agtgacctgt tcgttgcaac aaattgataa gcaatgcttt tttataatgc   1620

caacttagta taaaaaagca ggcttcaaga tctctcccca tccccctgtt cacaattaat   1680

catcggctcg tataatgtgt ggaattgtga gcggataaca atttcacaca ggagactgcc   1740
```

<210> SEQ ID NO 10
<211> LENGTH: 80
<212> TYPE: DNA
<213> ORGANISM: Artificial sequence
<220> FEATURE:
<223> OTHER INFORMATION: PtacM
<220> FEATURE:
<221> NAME/KEY: promoter
<222> LOCATION: (1)..(80)
<223> OTHER INFORMATION: PtacM

<400> SEQUENCE: 10

```
ctccccatcc ccctgttcac aattaatcat cggctcgtat aatgtgtgga attgtgagcg     60

gataacaatt tcacacagga                                                  80
```

<210> SEQ ID NO 11
<211> LENGTH: 2844
<212> TYPE: DNA
<213> ORGANISM: Artificial sequence
<220> FEATURE:
<223> OTHER INFORMATION: PtacMgldA::Cm

<400> SEQUENCE: 11

```
tctagacgct caagttagta taaaaaagct gaacgagaaa cgtaaaatga tataaatatc     60

aatatattaa attagatttt gcataaaaaa cagactacat aatactgtaa aacacaacat    120

atgcagtcac tatgaatcaa ctacttagat ggtattagtg acctgtaaca gactgcagtg    180

gtcgaaaaaa aaagcccgca ctgtcaggtg cgggcttttt tctgtgttaa gcttcgacga    240

atttctgcca ttcatccgct tattatcact tattcaggcg tagcaccagg cgtttaaggg    300

caccaataac tgccttaaaa aaattacgcc ccgccctgcc actcatcgca gtactgttgt    360

aattcattaa gcattctgcc gacatggaag ccatcacaga cggcatgatg aacctgaatc    420

gccagcggca tcagcacctt gtcgccttgc gtataatatt tgcccatggt gaaaacgggg    480

gcgaagaagt tgtccatatt ggccacgttt aaatcaaaac tggtgaaact cacccaggga    540

ttggctgaga cgaaaaacat attctcaata aaccctttag ggaaataggc caggttttca    600

ccgtaacacg ccacatcttg cgaatatatg tgtagaaact gccggaaatc gtcgtggtat    660

tcactccaga gcgatgaaaa cgtttcagtt tgctcatgga aaacggtgta acaagggtga    720

acactatccc atatcaccag ctcaccgtct ttcattgcca tacggaattc cggatgagca    780

ttcatcaggc gggcaagaat gtgaataaag gccggataaa acttgtgctt atttttcttt    840

acggtcttta aaaaggccgt aatatccagc tgaacggtct ggttataggt acattgagca    900
```

```
actgactgaa atgcctcaaa atgttcttta cgatgccatt gggatatatc aacggtggta    960
tatccagtga ttttttctc cattttagct tccttagctc ctgaaaatct cggatccggc    1020
caagctagct tggctctagc tagagcgccc ggttgacgct gctagtgtta cctagcgatt   1080
tgtatcttac tgcatgttac ttcatgttgt caatacctgt tttcgtgcg acttatcagg    1140
ctgtctactt atccggagat ccacaggacg ggtgtggtcg ccatgatcgc gtagtcgata   1200
gtggctccaa gtagcgaagc gagcaggact gggcggcggc caaagcggtc ggacagtgct   1260
ccgagaacgg gtgcgcatag aaattgcatc aacgcatata gcgctagcag cacgccatag   1320
tgactggcga tgctgtcgga atggacgata tcccgcaaga ggcccggcag taccggcata   1380
accaagccta tgcctacagc atccagggtg acggtgccga ggatgacgat gagcgcattg   1440
ttagatttca tacacggtgc ctgactgcgt tagcaattta actgtgataa actaccgcat   1500
taaagcttat cgatgataag ctgtcaaaca tgagaattcg aaatcaaata atgattttat   1560
tttgactgat agtgacctgt tcgttgcaac aaattgataa gcaatgcttt tttataatgc   1620
caacttagta taaaaaagca ggcttcaaga tctctcccca tccccctgtt cacaattaat   1680
catcggctcg tataatgtgt ggaattgtga gcggataaca atttcacaca ggagactgcc   1740
atggaccgca ttattcaatc accgggtaaa tacatccagg gcgctgatgt gattaatcgt   1800
ctgggcgaat acctgaagcc gctggcagaa cgctggttag tggtgggtga caaatttgtt   1860
ttaggttttg ctcaatccac tgtcgagaaa agctttaaag atgctggact ggtagtagaa   1920
attgcgccgt ttggcggtga atgttcgcaa aatgagatcg accgtctgcg tggcatcgcg   1980
gagactgcgc agtgtggcgc aattctcggt atcggtggcg gaaaaaccct cgatactgcc   2040
aaagcactgg cacatttcat gggtgttccg gtagcgatcg caccgactat cgcctctacc   2100
gatgcaccgt gcagcgcatt gtctgttatc tacaccgatg agggtgagtt tgaccgctat   2160
ctgctgttgc caaataaccc gaatatggtc attgtcgaca ccaaaatcgt cgctggcgca   2220
cctgcacgtc tgttagcggc gggtatcggc gatgcgctgg caacctggtt tgaagcgcgt   2280
gcctgctctc gtagcggcgc gaccaccatg gcgggcggca agtgcaccca ggctgcgctg   2340
gcactggctg aactgtgcta caacaccctg ctggaagaag gcgaaaaagc gatgcttgct   2400
gccgaacagc atgtagtgac tccggcgctg gagcgcgtga ttgaagcgaa cacctatttg   2460
agcggtgttg gttttgaaag tggtggtctg gctgcggcgc acgcagtgca taacggcctg   2520
accgctatcc cggacgcgca tcactattat cacggtgaaa aagtggcatt cggtacgctg   2580
acgcagctgg ttctggaaaa tgcgccggtg gaggaaatcg aaaccgtagc tgcccttagc   2640
catgcggtag gtttgccaat aactctcgct caactggata ttaaagaaga tgtcccggcg   2700
aaaatgcgaa ttgtggcaga agcggcatgt gcagaaggtg aaaccattca caacatgcct   2760
ggcggcgcga cgccagatca ggtttacgcc gctctgctgg tagccgacca gtacggtcag   2820
cgtttcctgc aagagtggga ataa                                          2844
```

```
<210> SEQ ID NO 12
<211> LENGTH: 77
<212> TYPE: DNA
<213> ORGANISM: Artificial sequence
<220> FEATURE:
<223> OTHER INFORMATION: atL-ptac-gldA

<400> SEQUENCE: 12

acatcagcgc cctggatgta tttacccggt gattgaataa tgcggtccat ggcagtctcc     60

tgtgtgaaat tgttatc                                                    77
```

<210> SEQ ID NO 13
<211> LENGTH: 77
<212> TYPE: DNA
<213> ORGANISM: Artificial sequence
<220> FEATURE:
<223> OTHER INFORMATION: atL-Ptac-fsaB1

<400> SEQUENCE: 13

```
aacgccgcct ctgccgacgc tatcgccagc ctgctgcaac atgaactgga actgtaaatc     60

tagacgctca agttagt                                                    77
```

<210> SEQ ID NO 14
<211> LENGTH: 50
<212> TYPE: DNA
<213> ORGANISM: Artificial sequence
<220> FEATURE:
<223> OTHER INFORMATION: pMW-dak1F

<400> SEQUENCE: 14

```
tgattacgcc aagcttagga ggttaaatgt ccgctaaatc gtttgaagtc                50
```

<210> SEQ ID NO 15
<211> LENGTH: 52
<212> TYPE: DNA
<213> ORGANISM: Artificial sequence
<220> FEATURE:
<223> OTHER INFORMATION: pMW-dak1R

<400> SEQUENCE: 15

```
atcctctaga gtcgacgcgg ccgctactta caaggcgctt tgaacccccct tc            52
```

<210> SEQ ID NO 16
<211> LENGTH: 846
<212> TYPE: DNA
<213> ORGANISM: Escherichia coli
<220> FEATURE:
<221> NAME/KEY: CDS
<222> LOCATION: (1)..(846)

<400> SEQUENCE: 16

```
atg agt caa aca tca acc ttg aaa ggc cag tgc att gct gaa ttc ctc       48
Met Ser Gln Thr Ser Thr Leu Lys Gly Gln Cys Ile Ala Glu Phe Leu
1               5                   10                  15

ggt acc ggg ttg ttg att ttc ttc ggt gtg ggt tgc gtt gca gca cta       96
Gly Thr Gly Leu Leu Ile Phe Phe Gly Val Gly Cys Val Ala Ala Leu
            20                  25                  30

aaa gtc gct ggt gcg tct ttt ggt cag tgg gaa atc agt gtc att tgg      144
Lys Val Ala Gly Ala Ser Phe Gly Gln Trp Glu Ile Ser Val Ile Trp
        35                  40                  45

gga ctg ggg gtg gca atg gcc atc tac ctg acc gca ggg gtt tcc ggc      192
Gly Leu Gly Val Ala Met Ala Ile Tyr Leu Thr Ala Gly Val Ser Gly
    50                  55                  60

gcg cat ctt aat ccc gct gtt acc att gca ttg tgg ctg ttt gcc tgt      240
Ala His Leu Asn Pro Ala Val Thr Ile Ala Leu Trp Leu Phe Ala Cys
65                  70                  75                  80

ttc gac aag cgc aaa gtt att cct ttt atc gtt tca caa gtt gcc ggc      288
Phe Asp Lys Arg Lys Val Ile Pro Phe Ile Val Ser Gln Val Ala Gly
                85                  90                  95

gct ttc tgt gct gcg gct tta gtt tac ggg ctt tac tac aat tta ttt      336
Ala Phe Cys Ala Ala Ala Leu Val Tyr Gly Leu Tyr Tyr Asn Leu Phe
            100                 105                 110

ttc gac ttc gag cag act cat cac att gtt cgc ggc agc gtt gaa agt      384
Phe Asp Phe Glu Gln Thr His His Ile Val Arg Gly Ser Val Glu Ser
```

```
        115                 120                 125

gtt gat ctg gct ggc act ttc tct act tac cct aat cct cat atc aat      432
Val Asp Leu Ala Gly Thr Phe Ser Thr Tyr Pro Asn Pro His Ile Asn
    130                 135                 140

ttt gtg cag gct ttc gca gtt gag atg gtg att acc gct att ctg atg      480
Phe Val Gln Ala Phe Ala Val Glu Met Val Ile Thr Ala Ile Leu Met
145                 150                 155                 160

ggg ctg atc ctg gcg tta acg gac gat ggc aac ggt gta cca cgc ggc      528
Gly Leu Ile Leu Ala Leu Thr Asp Asp Gly Asn Gly Val Pro Arg Gly
                165                 170                 175

cct ttg gct ccc ttg ctg att ggt cta ctg att gcg gtc att ggc gca      576
Pro Leu Ala Pro Leu Leu Ile Gly Leu Leu Ile Ala Val Ile Gly Ala
            180                 185                 190

tct atg ggc cca ttg aca ggt ttt gcc atg aac cca gcg cgt gac ttc      624
Ser Met Gly Pro Leu Thr Gly Phe Ala Met Asn Pro Ala Arg Asp Phe
        195                 200                 205

ggt ccg aaa gtc ttt gcc tgg ctg gcg ggc tgg ggc aat gtc gcc ttt      672
Gly Pro Lys Val Phe Ala Trp Leu Ala Gly Trp Gly Asn Val Ala Phe
    210                 215                 220

acc ggc ggc aga gac att cct tac ttc ctg gtg ccg ctt ttc ggc cct      720
Thr Gly Gly Arg Asp Ile Pro Tyr Phe Leu Val Pro Leu Phe Gly Pro
225                 230                 235                 240

atc gtt ggc gcg att gta ggt gca ttt gcc tac cgc aaa ctg att ggt      768
Ile Val Gly Ala Ile Val Gly Ala Phe Ala Tyr Arg Lys Leu Ile Gly
                245                 250                 255

cgc cat ttg cct tgc gat atc tgt gtt gtg gaa gaa aag gaa acc aca      816
Arg His Leu Pro Cys Asp Ile Cys Val Val Glu Glu Lys Glu Thr Thr
            260                 265                 270

act cct tca gaa caa aaa gct tcg ctg taa                              846
Thr Pro Ser Glu Gln Lys Ala Ser Leu
        275                 280


<210> SEQ ID NO 17
<211> LENGTH: 281
<212> TYPE: PRT
<213> ORGANISM: Escherichia coli

<400> SEQUENCE: 17

Met Ser Gln Thr Ser Thr Leu Lys Gly Gln Cys Ile Ala Glu Phe Leu
1               5                   10                  15

Gly Thr Gly Leu Leu Ile Phe Phe Gly Val Gly Cys Val Ala Ala Leu
            20                  25                  30

Lys Val Ala Gly Ala Ser Phe Gly Gln Trp Glu Ile Ser Val Ile Trp
        35                  40                  45

Gly Leu Gly Val Ala Met Ala Ile Tyr Leu Thr Ala Gly Val Ser Gly
    50                  55                  60

Ala His Leu Asn Pro Ala Val Thr Ile Ala Leu Trp Leu Phe Ala Cys
65                  70                  75                  80

Phe Asp Lys Arg Lys Val Ile Pro Phe Ile Val Ser Gln Val Ala Gly
                85                  90                  95

Ala Phe Cys Ala Ala Ala Leu Val Tyr Gly Leu Tyr Tyr Asn Leu Phe
            100                 105                 110

Phe Asp Phe Glu Gln Thr His His Ile Val Arg Gly Ser Val Glu Ser
        115                 120                 125

Val Asp Leu Ala Gly Thr Phe Ser Thr Tyr Pro Asn Pro His Ile Asn
    130                 135                 140

Phe Val Gln Ala Phe Ala Val Glu Met Val Ile Thr Ala Ile Leu Met
145                 150                 155                 160
```

```
Gly Leu Ile Leu Ala Leu Thr Asp Asp Gly Asn Gly Val Pro Arg Gly
                165                 170                 175

Pro Leu Ala Pro Leu Leu Ile Gly Leu Leu Ile Ala Val Ile Gly Ala
            180                 185                 190

Ser Met Gly Pro Leu Thr Gly Phe Ala Met Asn Pro Ala Arg Asp Phe
        195                 200                 205

Gly Pro Lys Val Phe Ala Trp Leu Ala Gly Trp Gly Asn Val Ala Phe
    210                 215                 220

Thr Gly Gly Arg Asp Ile Pro Tyr Phe Leu Val Pro Leu Phe Gly Pro
225                 230                 235                 240

Ile Val Gly Ala Ile Val Gly Ala Phe Ala Tyr Arg Lys Leu Ile Gly
                245                 250                 255

Arg His Leu Pro Cys Asp Ile Cys Val Val Glu Glu Lys Glu Thr Thr
            260                 265                 270

Thr Pro Ser Glu Gln Lys Ala Ser Leu
        275                 280


<210> SEQ ID NO 18
<211> LENGTH: 768
<212> TYPE: DNA
<213> ORGANISM: Escherichia coli
<220> FEATURE:
<221> NAME/KEY: CDS
<222> LOCATION: (1)..(768)

<400> SEQUENCE: 18

atg cga cat cct tta gtg atg ggt aac tgg aaa ctg aac ggc agc cgc       48
Met Arg His Pro Leu Val Met Gly Asn Trp Lys Leu Asn Gly Ser Arg
1               5                   10                  15

cac atg gtt cac gag ctg gtt tct aac ctg cgt aaa gag ctg gca ggt       96
His Met Val His Glu Leu Val Ser Asn Leu Arg Lys Glu Leu Ala Gly
            20                  25                  30

gtt gct ggc tgt gcg gtt gca atc gca cca ccg gaa atg tat atc gat      144
Val Ala Gly Cys Ala Val Ala Ile Ala Pro Pro Glu Met Tyr Ile Asp
        35                  40                  45

atg gcg aag cgc gaa gct gaa ggc agc cac atc atg ctg ggt gcg caa      192
Met Ala Lys Arg Glu Ala Glu Gly Ser His Ile Met Leu Gly Ala Gln
    50                  55                  60

aac gtg gac ctg aac ctg tcc ggc gca ttc acc ggt gaa acc tct gct      240
Asn Val Asp Leu Asn Leu Ser Gly Ala Phe Thr Gly Glu Thr Ser Ala
65                  70                  75                  80

gct atg ctg aaa gac atc ggc gca cag tac atc atc atc ggt cac tct      288
Ala Met Leu Lys Asp Ile Gly Ala Gln Tyr Ile Ile Ile Gly His Ser
                85                  90                  95

gaa cgt cgt act tac cac aaa gaa tct gac gaa ctg atc gcg aaa aaa      336
Glu Arg Arg Thr Tyr His Lys Glu Ser Asp Glu Leu Ile Ala Lys Lys
            100                 105                 110

ttc gcg gtg ctg aaa gag cag ggc ctg act ccg gtt ctg tgc atc ggt      384
Phe Ala Val Leu Lys Glu Gln Gly Leu Thr Pro Val Leu Cys Ile Gly
        115                 120                 125

gaa acc gaa gct gaa aat gaa gcg ggc aaa act gaa gaa gtt tgc gca      432
Glu Thr Glu Ala Glu Asn Glu Ala Gly Lys Thr Glu Glu Val Cys Ala
    130                 135                 140

cgt cag atc gac gcg gta ctg aaa act cag ggt gct gcg gca ttc gaa      480
Arg Gln Ile Asp Ala Val Leu Lys Thr Gln Gly Ala Ala Ala Phe Glu
145                 150                 155                 160

ggt gcg gtt atc gct tac gaa cct gta tgg gca atc ggt act ggc aaa      528
Gly Ala Val Ile Ala Tyr Glu Pro Val Trp Ala Ile Gly Thr Gly Lys
                165                 170                 175

tct gca act ccg gct cag gca cag gct gtt cac aaa ttc atc cgt gac      576
```

```
Ser Ala Thr Pro Ala Gln Ala Gln Ala Val His Lys Phe Ile Arg Asp
            180                 185                 190

cac atc gct aaa gtt gac gct aac atc gct gaa caa gtg atc att cag      624
His Ile Ala Lys Val Asp Ala Asn Ile Ala Glu Gln Val Ile Ile Gln
        195                 200                 205

tac ggc ggc tct gta aac gcg tct aac gct gca gaa ctg ttt gct cag      672
Tyr Gly Gly Ser Val Asn Ala Ser Asn Ala Ala Glu Leu Phe Ala Gln
    210                 215                 220

ccg gat atc gac ggc gcg ctg gtt ggt ggt gct tct ctg aaa gct gac      720
Pro Asp Ile Asp Gly Ala Leu Val Gly Gly Ala Ser Leu Lys Ala Asp
225                 230                 235                 240

gcc ttc gca gta atc gtt aaa gct gca gaa gcg gct aaa cag gct taa      768
Ala Phe Ala Val Ile Val Lys Ala Ala Glu Ala Ala Lys Gln Ala
                245                 250                 255


<210> SEQ ID NO 19
<211> LENGTH: 255
<212> TYPE: PRT
<213> ORGANISM: Escherichia coli

<400> SEQUENCE: 19

Met Arg His Pro Leu Val Met Gly Asn Trp Lys Leu Asn Gly Ser Arg
1               5                   10                  15

His Met Val His Glu Leu Val Ser Asn Leu Arg Lys Glu Leu Ala Gly
            20                  25                  30

Val Ala Gly Cys Ala Val Ala Ile Ala Pro Pro Glu Met Tyr Ile Asp
        35                  40                  45

Met Ala Lys Arg Glu Ala Glu Gly Ser His Ile Met Leu Gly Ala Gln
    50                  55                  60

Asn Val Asp Leu Asn Leu Ser Gly Ala Phe Thr Gly Glu Thr Ser Ala
65                  70                  75                  80

Ala Met Leu Lys Asp Ile Gly Ala Gln Tyr Ile Ile Ile Gly His Ser
                85                  90                  95

Glu Arg Arg Thr Tyr His Lys Glu Ser Asp Glu Leu Ile Ala Lys Lys
            100                 105                 110

Phe Ala Val Leu Lys Glu Gln Gly Leu Thr Pro Val Leu Cys Ile Gly
        115                 120                 125

Glu Thr Glu Ala Glu Asn Glu Ala Gly Lys Thr Glu Glu Val Cys Ala
    130                 135                 140

Arg Gln Ile Asp Ala Val Leu Lys Thr Gln Gly Ala Ala Ala Phe Glu
145                 150                 155                 160

Gly Ala Val Ile Ala Tyr Glu Pro Val Trp Ala Ile Gly Thr Gly Lys
                165                 170                 175

Ser Ala Thr Pro Ala Gln Ala Gln Ala Val His Lys Phe Ile Arg Asp
            180                 185                 190

His Ile Ala Lys Val Asp Ala Asn Ile Ala Glu Gln Val Ile Ile Gln
        195                 200                 205

Tyr Gly Gly Ser Val Asn Ala Ser Asn Ala Ala Glu Leu Phe Ala Gln
    210                 215                 220

Pro Asp Ile Asp Gly Ala Leu Val Gly Gly Ala Ser Leu Lys Ala Asp
225                 230                 235                 240

Ala Phe Ala Val Ile Val Lys Ala Ala Glu Ala Ala Lys Gln Ala
                245                 250                 255


<210> SEQ ID NO 20
<211> LENGTH: 1080
<212> TYPE: DNA
<213> ORGANISM: Escherichia coli
```

```
<220> FEATURE:
<221> NAME/KEY: CDS
<222> LOCATION: (1)..(1080)

<400> SEQUENCE: 20

atg tct aag att ttt gat ttc gta aaa cct ggc gta atc act ggt gat       48
Met Ser Lys Ile Phe Asp Phe Val Lys Pro Gly Val Ile Thr Gly Asp
1               5                   10                  15

gac gta cag aaa gtt ttc cag gta gca aaa gaa aac aac ttc gca ctg       96
Asp Val Gln Lys Val Phe Gln Val Ala Lys Glu Asn Asn Phe Ala Leu
            20                  25                  30

cca gca gta aac tgc gtc ggt act gac tcc atc aac gcc gta ctg gaa      144
Pro Ala Val Asn Cys Val Gly Thr Asp Ser Ile Asn Ala Val Leu Glu
        35                  40                  45

acc gct gct aaa gtt aaa gcg ccg gtt atc gtt cag ttc tcc aac ggt      192
Thr Ala Ala Lys Val Lys Ala Pro Val Ile Val Gln Phe Ser Asn Gly
    50                  55                  60

ggt gct tcc ttt atc gct ggt aaa ggc gtg aaa tct gac gtt ccg cag      240
Gly Ala Ser Phe Ile Ala Gly Lys Gly Val Lys Ser Asp Val Pro Gln
65                  70                  75                  80

ggt gct gct atc ctg ggc gcg atc tct ggt gcg cat cac gtt cac cag      288
Gly Ala Ala Ile Leu Gly Ala Ile Ser Gly Ala His His Val His Gln
                85                  90                  95

atg gct gaa cat tat ggt gtt ccg gtt atc ctg cac act gac cac tgc      336
Met Ala Glu His Tyr Gly Val Pro Val Ile Leu His Thr Asp His Cys
            100                 105                 110

gcg aag aaa ctg ctg ccg tgg atc gac ggt ctg ttg gac gcg ggt gaa      384
Ala Lys Lys Leu Leu Pro Trp Ile Asp Gly Leu Leu Asp Ala Gly Glu
        115                 120                 125

aaa cac ttc gca gct acc ggt aag ccg ctg ttc tct tct cac atg atc      432
Lys His Phe Ala Ala Thr Gly Lys Pro Leu Phe Ser Ser His Met Ile
    130                 135                 140

gac ctg tct gaa gaa tct ctg caa gag aac atc gaa atc tgc tct aaa      480
Asp Leu Ser Glu Glu Ser Leu Gln Glu Asn Ile Glu Ile Cys Ser Lys
145                 150                 155                 160

tac ctg gag cgc atg tcc aaa atc ggc atg act ctg gaa atc gaa ctg      528
Tyr Leu Glu Arg Met Ser Lys Ile Gly Met Thr Leu Glu Ile Glu Leu
                165                 170                 175

ggt tgc acc ggt ggt gaa gaa gac ggc gtg gac aac agc cac atg gac      576
Gly Cys Thr Gly Gly Glu Glu Asp Gly Val Asp Asn Ser His Met Asp
            180                 185                 190

gct tct gca ctg tac acc cag ccg gaa gac gtt gat tac gca tac acc      624
Ala Ser Ala Leu Tyr Thr Gln Pro Glu Asp Val Asp Tyr Ala Tyr Thr
        195                 200                 205

gaa ctg agc aaa atc agc ccg cgt ttc acc atc gca gcg tcc ttc ggt      672
Glu Leu Ser Lys Ile Ser Pro Arg Phe Thr Ile Ala Ala Ser Phe Gly
    210                 215                 220

aac gta cac ggt gtt tac aag ccg ggt aac gtg gtt ctg act ccg acc      720
Asn Val His Gly Val Tyr Lys Pro Gly Asn Val Val Leu Thr Pro Thr
225                 230                 235                 240

atc ctg cgt gat tct cag gaa tat gtt tcc aag aaa cac aac ctg ccg      768
Ile Leu Arg Asp Ser Gln Glu Tyr Val Ser Lys Lys His Asn Leu Pro
                245                 250                 255

cac aac agc ctg aac ttc gta ttc cac ggt ggt tcc ggt tct act gct      816
His Asn Ser Leu Asn Phe Val Phe His Gly Gly Ser Gly Ser Thr Ala
            260                 265                 270

cag gaa atc aaa gac tcc gta agc tac ggc gta gta aaa atg aac atc      864
Gln Glu Ile Lys Asp Ser Val Ser Tyr Gly Val Val Lys Met Asn Ile
        275                 280                 285

gat acc gat acc caa tgg gca acc tgg gaa ggc gtt ctg aac tac tac      912
Asp Thr Asp Thr Gln Trp Ala Thr Trp Glu Gly Val Leu Asn Tyr Tyr
```

```
    290                 295                 300

aaa gcg aac gaa gct tat ctg cag ggt cag ctg ggt aac ccg aaa ggc      960
Lys Ala Asn Glu Ala Tyr Leu Gln Gly Gln Leu Gly Asn Pro Lys Gly
305                 310                 315                 320

gaa gat cag ccg aac aag aaa tac tac gat ccg cgc gta tgg ctg cgt     1008
Glu Asp Gln Pro Asn Lys Lys Tyr Tyr Asp Pro Arg Val Trp Leu Arg
                325                 330                 335

gcc ggt cag act tcg atg atc gct cgt ctg gag aaa gca ttc cag gaa     1056
Ala Gly Gln Thr Ser Met Ile Ala Arg Leu Glu Lys Ala Phe Gln Glu
            340                 345                 350

ctg aac gcg atc gac gtt ctg taa                                     1080
Leu Asn Ala Ile Asp Val Leu
        355


<210> SEQ ID NO 21
<211> LENGTH: 359
<212> TYPE: PRT
<213> ORGANISM: Escherichia coli

<400> SEQUENCE: 21

Met Ser Lys Ile Phe Asp Phe Val Lys Pro Gly Val Ile Thr Gly Asp
1               5                   10                  15

Asp Val Gln Lys Val Phe Gln Val Ala Lys Glu Asn Asn Phe Ala Leu
            20                  25                  30

Pro Ala Val Asn Cys Val Gly Thr Asp Ser Ile Asn Ala Val Leu Glu
        35                  40                  45

Thr Ala Ala Lys Val Lys Ala Pro Val Ile Val Gln Phe Ser Asn Gly
    50                  55                  60

Gly Ala Ser Phe Ile Ala Gly Lys Gly Val Lys Ser Asp Val Pro Gln
65                  70                  75                  80

Gly Ala Ala Ile Leu Gly Ala Ile Ser Gly Ala His His Val His Gln
                85                  90                  95

Met Ala Glu His Tyr Gly Val Pro Val Ile Leu His Thr Asp His Cys
            100                 105                 110

Ala Lys Lys Leu Leu Pro Trp Ile Asp Gly Leu Leu Asp Ala Gly Glu
        115                 120                 125

Lys His Phe Ala Ala Thr Gly Lys Pro Leu Phe Ser Ser His Met Ile
    130                 135                 140

Asp Leu Ser Glu Glu Ser Leu Gln Glu Asn Ile Glu Ile Cys Ser Lys
145                 150                 155                 160

Tyr Leu Glu Arg Met Ser Lys Ile Gly Met Thr Leu Glu Ile Glu Leu
                165                 170                 175

Gly Cys Thr Gly Gly Glu Glu Asp Gly Val Asp Asn Ser His Met Asp
            180                 185                 190

Ala Ser Ala Leu Tyr Thr Gln Pro Glu Asp Val Asp Tyr Ala Tyr Thr
        195                 200                 205

Glu Leu Ser Lys Ile Ser Pro Arg Phe Thr Ile Ala Ala Ser Phe Gly
    210                 215                 220

Asn Val His Gly Val Tyr Lys Pro Gly Asn Val Val Leu Thr Pro Thr
225                 230                 235                 240

Ile Leu Arg Asp Ser Gln Glu Tyr Val Ser Lys Lys His Asn Leu Pro
                245                 250                 255

His Asn Ser Leu Asn Phe Val Phe His Gly Gly Ser Gly Ser Thr Ala
            260                 265                 270

Gln Glu Ile Lys Asp Ser Val Ser Tyr Gly Val Val Lys Met Asn Ile
        275                 280                 285
```

```
Asp Thr Asp Thr Gln Trp Ala Thr Trp Glu Gly Val Leu Asn Tyr Tyr
    290                 295                 300

Lys Ala Asn Glu Ala Tyr Leu Gln Gly Gln Leu Gly Asn Pro Lys Gly
305                 310                 315                 320

Glu Asp Gln Pro Asn Lys Lys Tyr Tyr Asp Pro Arg Val Trp Leu Arg
                325                 330                 335

Ala Gly Gln Thr Ser Met Ile Ala Arg Leu Glu Lys Ala Phe Gln Glu
            340                 345                 350

Leu Asn Ala Ile Asp Val Leu
        355


<210> SEQ ID NO 22
<211> LENGTH: 1011
<212> TYPE: DNA
<213> ORGANISM: Escherichia coli
<220> FEATURE:
<221> NAME/KEY: CDS
<222> LOCATION: (1)..(1011)

<400> SEQUENCE: 22

atg aga cga gaa ctt gcc atc gaa ttt tcc cgc gtc acc gaa tca gcg      48
Met Arg Arg Glu Leu Ala Ile Glu Phe Ser Arg Val Thr Glu Ser Ala
1               5                   10                  15

gcg ctg gct ggc tac aaa tgg tta gga cgc ggc gat aaa aac acc gcg      96
Ala Leu Ala Gly Tyr Lys Trp Leu Gly Arg Gly Asp Lys Asn Thr Ala
            20                  25                  30

gac ggc gcg gcg gta aac gcc atg cgt att atg ctc aac cag gtc aac     144
Asp Gly Ala Ala Val Asn Ala Met Arg Ile Met Leu Asn Gln Val Asn
        35                  40                  45

att gac ggc acc atc gtc att ggt gaa ggt gaa atc gac gaa gca ccg     192
Ile Asp Gly Thr Ile Val Ile Gly Glu Gly Glu Ile Asp Glu Ala Pro
    50                  55                  60

atg ctc tac att ggt gaa aaa gtc ggt act ggt cgc ggc gac gcg gta     240
Met Leu Tyr Ile Gly Glu Lys Val Gly Thr Gly Arg Gly Asp Ala Val
65                  70                  75                  80

gat att gct gtt gat ccg att gaa ggc acg cgc atg acg gcg atg ggc     288
Asp Ile Ala Val Asp Pro Ile Glu Gly Thr Arg Met Thr Ala Met Gly
                85                  90                  95

cag gct aac gcg ctg gcg gtg ctg gca gta ggc gat aaa ggc tgc ttc     336
Gln Ala Asn Ala Leu Ala Val Leu Ala Val Gly Asp Lys Gly Cys Phe
            100                 105                 110

ctc aat gcg ccg gat atg tat atg gag aag ctg att gtc ggg ccg gga     384
Leu Asn Ala Pro Asp Met Tyr Met Glu Lys Leu Ile Val Gly Pro Gly
        115                 120                 125

gcc aaa ggc acc att gat ctg aac ctg ccg ctg gcg gat aac ctg cgc     432
Ala Lys Gly Thr Ile Asp Leu Asn Leu Pro Leu Ala Asp Asn Leu Arg
    130                 135                 140

aat gta gcg gcg gcg ctc ggc aaa ccg ttg agc gaa ctg acg gta acg     480
Asn Val Ala Ala Ala Leu Gly Lys Pro Leu Ser Glu Leu Thr Val Thr
145                 150                 155                 160

att ctg gct aaa cca cgc cac gat gcc gtt atc gct gaa atg cag caa     528
Ile Leu Ala Lys Pro Arg His Asp Ala Val Ile Ala Glu Met Gln Gln
                165                 170                 175

ctc ggc gta cgc gta ttt gct att ccg gac ggc gac gtt gcg gcc tca     576
Leu Gly Val Arg Val Phe Ala Ile Pro Asp Gly Asp Val Ala Ala Ser
            180                 185                 190

att ctc acc tgt atg cca gac agc gaa gtt gac gtg ctg tac ggt att     624
Ile Leu Thr Cys Met Pro Asp Ser Glu Val Asp Val Leu Tyr Gly Ile
        195                 200                 205

ggt ggc gcg ccg gaa ggc gta gtt tct gcg gcg gtg atc cgc gca tta     672
Gly Gly Ala Pro Glu Gly Val Val Ser Ala Ala Val Ile Arg Ala Leu
```

```
    210                 215                 220

gat ggc gac atg aac ggt cgt ctg ctg gcg cgt cat gac gtc aaa ggc      720
Asp Gly Asp Met Asn Gly Arg Leu Leu Ala Arg His Asp Val Lys Gly
225                 230                 235                 240

gac aac gaa gag aat cgt cgc att ggc gag cag gag ctg gca cgc tgc      768
Asp Asn Glu Glu Asn Arg Arg Ile Gly Glu Gln Glu Leu Ala Arg Cys
                245                 250                 255

aaa gcg atg ggc atc gaa gcc ggt aaa gta ttg cgc ctg ggc gat atg      816
Lys Ala Met Gly Ile Glu Ala Gly Lys Val Leu Arg Leu Gly Asp Met
            260                 265                 270

gcg cgc agc gat aac gtc atc ttc tct gcc acc ggt att acc aaa ggc      864
Ala Arg Ser Asp Asn Val Ile Phe Ser Ala Thr Gly Ile Thr Lys Gly
        275                 280                 285

gat ctg ctg gaa ggc att agc cgc aaa ggc aat atc gcg act acc gaa      912
Asp Leu Leu Glu Gly Ile Ser Arg Lys Gly Asn Ile Ala Thr Thr Glu
    290                 295                 300

acg ctg ctg atc cgc ggc aag tca cgc acc att cgc cgc att cag tcc      960
Thr Leu Leu Ile Arg Gly Lys Ser Arg Thr Ile Arg Arg Ile Gln Ser
305                 310                 315                 320

atc cac tat ctg gat cgc aaa gac ccg gaa atg cag gtg cac atc ctc     1008
Ile His Tyr Leu Asp Arg Lys Asp Pro Glu Met Gln Val His Ile Leu
                325                 330                 335

tga                                                                 1011


<210> SEQ ID NO 23
<211> LENGTH: 336
<212> TYPE: PRT
<213> ORGANISM: Escherichia coli

<400> SEQUENCE: 23

Met Arg Arg Glu Leu Ala Ile Glu Phe Ser Arg Val Thr Glu Ser Ala
1               5                   10                  15

Ala Leu Ala Gly Tyr Lys Trp Leu Gly Arg Gly Asp Lys Asn Thr Ala
            20                  25                  30

Asp Gly Ala Ala Val Asn Ala Met Arg Ile Met Leu Asn Gln Val Asn
        35                  40                  45

Ile Asp Gly Thr Ile Val Ile Gly Glu Gly Glu Ile Asp Glu Ala Pro
    50                  55                  60

Met Leu Tyr Ile Gly Glu Lys Val Gly Thr Gly Arg Gly Asp Ala Val
65                  70                  75                  80

Asp Ile Ala Val Asp Pro Ile Glu Gly Thr Arg Met Thr Ala Met Gly
                85                  90                  95

Gln Ala Asn Ala Leu Ala Val Leu Ala Val Gly Asp Lys Gly Cys Phe
            100                 105                 110

Leu Asn Ala Pro Asp Met Tyr Met Glu Lys Leu Ile Val Gly Pro Gly
        115                 120                 125

Ala Lys Gly Thr Ile Asp Leu Asn Leu Pro Leu Ala Asp Asn Leu Arg
    130                 135                 140

Asn Val Ala Ala Ala Leu Gly Lys Pro Leu Ser Glu Leu Thr Val Thr
145                 150                 155                 160

Ile Leu Ala Lys Pro Arg His Asp Ala Val Ile Ala Glu Met Gln Gln
                165                 170                 175

Leu Gly Val Arg Val Phe Ala Ile Pro Asp Gly Asp Val Ala Ala Ser
            180                 185                 190

Ile Leu Thr Cys Met Pro Asp Ser Glu Val Asp Val Leu Tyr Gly Ile
        195                 200                 205

Gly Gly Ala Pro Glu Gly Val Val Ser Ala Ala Val Ile Arg Ala Leu
```

```
    210                 215                 220

Asp Gly Asp Met Asn Gly Arg Leu Leu Ala Arg His Asp Val Lys Gly
225                 230                 235                 240

Asp Asn Glu Glu Asn Arg Arg Ile Gly Glu Gln Glu Leu Ala Arg Cys
                245                 250                 255

Lys Ala Met Gly Ile Glu Ala Gly Lys Val Leu Arg Leu Gly Asp Met
            260                 265                 270

Ala Arg Ser Asp Asn Val Ile Phe Ser Ala Thr Gly Ile Thr Lys Gly
        275                 280                 285

Asp Leu Leu Glu Gly Ile Ser Arg Lys Gly Asn Ile Ala Thr Thr Glu
    290                 295                 300

Thr Leu Leu Ile Arg Gly Lys Ser Arg Thr Ile Arg Arg Ile Gln Ser
305                 310                 315                 320

Ile His Tyr Leu Asp Arg Lys Asp Pro Glu Met Gln Val His Ile Leu
                325                 330                 335


<210> SEQ ID NO 24
<211> LENGTH: 1509
<212> TYPE: DNA
<213> ORGANISM: Escherichia coli
<220> FEATURE:
<221> NAME/KEY: CDS
<222> LOCATION: (1)..(1509)

<400> SEQUENCE: 24

atg act gaa aaa aaa tat atc gtt gcg ctc gac cag ggc acc acc agc       48
Met Thr Glu Lys Lys Tyr Ile Val Ala Leu Asp Gln Gly Thr Thr Ser
1               5                   10                  15

tcc cgc gcg gtc gta atg gat cac gat gcc aat atc att agc gtg tcg       96
Ser Arg Ala Val Val Met Asp His Asp Ala Asn Ile Ile Ser Val Ser
            20                  25                  30

cag cgc gaa ttt gag caa atc tac cca aaa cca ggt tgg gta gaa cac      144
Gln Arg Glu Phe Glu Gln Ile Tyr Pro Lys Pro Gly Trp Val Glu His
        35                  40                  45

gac cca atg gaa atc tgg gcc acc caa agc tcc acg ctg gta gaa gtg      192
Asp Pro Met Glu Ile Trp Ala Thr Gln Ser Ser Thr Leu Val Glu Val
    50                  55                  60

ctg gcg aaa gcc gat atc agt tcc gat caa att gca gct atc ggt att      240
Leu Ala Lys Ala Asp Ile Ser Ser Asp Gln Ile Ala Ala Ile Gly Ile
65                  70                  75                  80

acg aac cag cgt gaa acc act att gtc tgg gaa aaa gaa acc ggc aag      288
Thr Asn Gln Arg Glu Thr Thr Ile Val Trp Glu Lys Glu Thr Gly Lys
                85                  90                  95

cct atc tat aac gcc att gtc tgg cag tgc cgt cgt acc gca gaa atc      336
Pro Ile Tyr Asn Ala Ile Val Trp Gln Cys Arg Arg Thr Ala Glu Ile
            100                 105                 110

tgc gag cat tta aaa cgt gac ggt tta gaa gat tat atc cgc agc aat      384
Cys Glu His Leu Lys Arg Asp Gly Leu Glu Asp Tyr Ile Arg Ser Asn
        115                 120                 125

acc ggt ctg gtg att gac ccg tac ttt tct ggc acc aaa gtg aag tgg      432
Thr Gly Leu Val Ile Asp Pro Tyr Phe Ser Gly Thr Lys Val Lys Trp
    130                 135                 140

atc ctc gac cat gtg gaa ggc tct cgc gag cgt gca cgt cgt ggt gaa      480
Ile Leu Asp His Val Glu Gly Ser Arg Glu Arg Ala Arg Arg Gly Glu
145                 150                 155                 160

ttg ctg ttt ggt acg gtt gat acg tgg ctt atc tgg aaa atg act cag      528
Leu Leu Phe Gly Thr Val Asp Thr Trp Leu Ile Trp Lys Met Thr Gln
                165                 170                 175

ggc cgt gtc cat gtg acc gat tac acc aac gcc tct cgt acc atg ttg      576
Gly Arg Val His Val Thr Asp Tyr Thr Asn Ala Ser Arg Thr Met Leu
```

```
            180                 185                 190

ttc aac atc cat acc ctg gac tgg gac gac aaa atg ctg gaa gtg ctg       624
Phe Asn Ile His Thr Leu Asp Trp Asp Asp Lys Met Leu Glu Val Leu
        195                 200                 205

gat att ccg cgc gag atg ctg cca gaa gtg cgt cgt tct tcc gaa gta       672
Asp Ile Pro Arg Glu Met Leu Pro Glu Val Arg Arg Ser Ser Glu Val
    210                 215                 220

tac ggt cag act aac att ggc ggc aaa ggc ggc acg cgt att cca atc       720
Tyr Gly Gln Thr Asn Ile Gly Gly Lys Gly Gly Thr Arg Ile Pro Ile
225                 230                 235                 240

tcc ggg atc gcc ggt gac cag cag gcc gcg ctg ttt ggt cag ttg tgc       768
Ser Gly Ile Ala Gly Asp Gln Gln Ala Ala Leu Phe Gly Gln Leu Cys
                245                 250                 255

gtg aaa gaa ggg atg gcg aag aac acc tat ggc act ggc tgc ttt atg       816
Val Lys Glu Gly Met Ala Lys Asn Thr Tyr Gly Thr Gly Cys Phe Met
            260                 265                 270

ctg atg aac act ggc gag aaa gcg gtg aaa tca gaa aac ggc ctg ctg       864
Leu Met Asn Thr Gly Glu Lys Ala Val Lys Ser Glu Asn Gly Leu Leu
        275                 280                 285

acc acc atc gcc tgc ggc ccg act ggc gaa gtg aac tat gcg ttg gaa       912
Thr Thr Ile Ala Cys Gly Pro Thr Gly Glu Val Asn Tyr Ala Leu Glu
    290                 295                 300

ggt gcg gtg ttt atg gca ggc gca tcc att cag tgg ctg cgc gat gaa       960
Gly Ala Val Phe Met Ala Gly Ala Ser Ile Gln Trp Leu Arg Asp Glu
305                 310                 315                 320

atg aag ttg att aac gac gcc tac gat tcc gaa tat ttc gcc acc aaa      1008
Met Lys Leu Ile Asn Asp Ala Tyr Asp Ser Glu Tyr Phe Ala Thr Lys
                325                 330                 335

gtg caa aac acc aat ggt gtg tat gtg gtt ccg gca ttt acc ggg ctg      1056
Val Gln Asn Thr Asn Gly Val Tyr Val Val Pro Ala Phe Thr Gly Leu
            340                 345                 350

ggt gcg ccg tac tgg gac ccg tat gcg cgc ggg gcg att ttc ggt ctg      1104
Gly Ala Pro Tyr Trp Asp Pro Tyr Ala Arg Gly Ala Ile Phe Gly Leu
        355                 360                 365

act cgt ggg gtg aac gct aac cac att ata cgc gcg acg ctg gag tct      1152
Thr Arg Gly Val Asn Ala Asn His Ile Ile Arg Ala Thr Leu Glu Ser
    370                 375                 380

att gct tat cag acg cgt gac gtg ctg gaa gcg atg cag gcc gac tct      1200
Ile Ala Tyr Gln Thr Arg Asp Val Leu Glu Ala Met Gln Ala Asp Ser
385                 390                 395                 400

ggt atc cgt ctg cac gcc ctg cgc gtg gat ggt ggc gca gta gca aac      1248
Gly Ile Arg Leu His Ala Leu Arg Val Asp Gly Gly Ala Val Ala Asn
                405                 410                 415

aat ttc ctg atg cag ttc cag tcc gat att ctc ggc acc cgc gtt gag      1296
Asn Phe Leu Met Gln Phe Gln Ser Asp Ile Leu Gly Thr Arg Val Glu
            420                 425                 430

cgc ccg gaa gtg cgc gaa gtc acc gca ttg ggt gcg gcc tat ctc gca      1344
Arg Pro Glu Val Arg Glu Val Thr Ala Leu Gly Ala Ala Tyr Leu Ala
        435                 440                 445

ggc ctg gcg gtt ggc ttc tgg cag aac ctc gac gag ctg caa gag aaa      1392
Gly Leu Ala Val Gly Phe Trp Gln Asn Leu Asp Glu Leu Gln Glu Lys
    450                 455                 460

gcg gtg att gag cgc gag ttc cgt cca ggc atc gaa acc act gag cgt      1440
Ala Val Ile Glu Arg Glu Phe Arg Pro Gly Ile Glu Thr Thr Glu Arg
465                 470                 475                 480

aat tac cgt tac gca ggc tgg aaa aaa gcg gtt aaa cgc gcg atg gcg      1488
Asn Tyr Arg Tyr Ala Gly Trp Lys Lys Ala Val Lys Arg Ala Met Ala
                485                 490                 495

tgg gaa gaa cac gac gaa taa                                          1509
Trp Glu Glu His Asp Glu
```

500

<210> SEQ ID NO 25
<211> LENGTH: 502
<212> TYPE: PRT
<213> ORGANISM: Escherichia coli

<400> SEQUENCE: 25

```
Met Thr Glu Lys Lys Tyr Ile Val Ala Leu Asp Gln Gly Thr Thr Ser
1               5                   10                  15

Ser Arg Ala Val Val Met Asp His Asp Ala Asn Ile Ile Ser Val Ser
            20                  25                  30

Gln Arg Glu Phe Glu Gln Ile Tyr Pro Lys Pro Gly Trp Val Glu His
        35                  40                  45

Asp Pro Met Glu Ile Trp Ala Thr Gln Ser Ser Thr Leu Val Glu Val
    50                  55                  60

Leu Ala Lys Ala Asp Ile Ser Ser Asp Gln Ile Ala Ala Ile Gly Ile
65                  70                  75                  80

Thr Asn Gln Arg Glu Thr Thr Ile Val Trp Glu Lys Glu Thr Gly Lys
                85                  90                  95

Pro Ile Tyr Asn Ala Ile Val Trp Gln Cys Arg Arg Thr Ala Glu Ile
            100                 105                 110

Cys Glu His Leu Lys Arg Asp Gly Leu Glu Asp Tyr Ile Arg Ser Asn
        115                 120                 125

Thr Gly Leu Val Ile Asp Pro Tyr Phe Ser Gly Thr Lys Val Lys Trp
    130                 135                 140

Ile Leu Asp His Val Glu Gly Ser Arg Glu Arg Ala Arg Arg Gly Glu
145                 150                 155                 160

Leu Leu Phe Gly Thr Val Asp Thr Trp Leu Ile Trp Lys Met Thr Gln
                165                 170                 175

Gly Arg Val His Val Thr Asp Tyr Thr Asn Ala Ser Arg Thr Met Leu
            180                 185                 190

Phe Asn Ile His Thr Leu Asp Trp Asp Asp Lys Met Leu Glu Val Leu
        195                 200                 205

Asp Ile Pro Arg Glu Met Leu Pro Glu Val Arg Arg Ser Ser Glu Val
    210                 215                 220

Tyr Gly Gln Thr Asn Ile Gly Gly Lys Gly Gly Thr Arg Ile Pro Ile
225                 230                 235                 240

Ser Gly Ile Ala Gly Asp Gln Gln Ala Ala Leu Phe Gly Gln Leu Cys
                245                 250                 255

Val Lys Glu Gly Met Ala Lys Asn Thr Tyr Gly Thr Gly Cys Phe Met
            260                 265                 270

Leu Met Asn Thr Gly Glu Lys Ala Val Lys Ser Glu Asn Gly Leu Leu
        275                 280                 285

Thr Thr Ile Ala Cys Gly Pro Thr Gly Glu Val Asn Tyr Ala Leu Glu
    290                 295                 300

Gly Ala Val Phe Met Ala Gly Ala Ser Ile Gln Trp Leu Arg Asp Glu
305                 310                 315                 320

Met Lys Leu Ile Asn Asp Ala Tyr Asp Ser Glu Tyr Phe Ala Thr Lys
                325                 330                 335

Val Gln Asn Thr Asn Gly Val Tyr Val Val Pro Ala Phe Thr Gly Leu
            340                 345                 350

Gly Ala Pro Tyr Trp Asp Pro Tyr Ala Arg Gly Ala Ile Phe Gly Leu
        355                 360                 365

Thr Arg Gly Val Asn Ala Asn His Ile Ile Arg Ala Thr Leu Glu Ser
```

```
    370                 375                 380

Ile Ala Tyr Gln Thr Arg Asp Val Leu Glu Ala Met Gln Ala Asp Ser
385                 390                 395                 400

Gly Ile Arg Leu His Ala Leu Arg Val Asp Gly Gly Ala Val Ala Asn
                405                 410                 415

Asn Phe Leu Met Gln Phe Gln Ser Asp Ile Leu Gly Thr Arg Val Glu
            420                 425                 430

Arg Pro Glu Val Arg Glu Val Thr Ala Leu Gly Ala Ala Tyr Leu Ala
        435                 440                 445

Gly Leu Ala Val Gly Phe Trp Gln Asn Leu Asp Glu Leu Gln Glu Lys
    450                 455                 460

Ala Val Ile Glu Arg Glu Phe Arg Pro Gly Ile Glu Thr Thr Glu Arg
465                 470                 475                 480

Asn Tyr Arg Tyr Ala Gly Trp Lys Lys Ala Val Lys Arg Ala Met Ala
                485                 490                 495

Trp Glu Glu His Asp Glu
            500


<210> SEQ ID NO 26
<211> LENGTH: 1629
<212> TYPE: DNA
<213> ORGANISM: Escherichia coli
<220> FEATURE:
<221> NAME/KEY: CDS
<222> LOCATION: (1)..(1629)

<400> SEQUENCE: 26

atg aaa act cgc gac tcg caa tca agt gac gtg att atc att ggc ggc       48
Met Lys Thr Arg Asp Ser Gln Ser Ser Asp Val Ile Ile Ile Gly Gly
1               5                   10                  15

ggc gca acg gga gcc ggg att gcc cgc gac tgt gcc ctg cgc ggg ctg       96
Gly Ala Thr Gly Ala Gly Ile Ala Arg Asp Cys Ala Leu Arg Gly Leu
            20                  25                  30

cgc gtg att ttg gtt gag cgc cac gac atc gca acc ggt gcc acc ggg      144
Arg Val Ile Leu Val Glu Arg His Asp Ile Ala Thr Gly Ala Thr Gly
        35                  40                  45

cgt aac cac ggc ctg ctg cac agc ggt gcg cgc tat gcg gta acc gat      192
Arg Asn His Gly Leu Leu His Ser Gly Ala Arg Tyr Ala Val Thr Asp
    50                  55                  60

gcg gaa tcg gcc cgc gaa tgc att agt gaa aac cag atc ctg aaa cgc      240
Ala Glu Ser Ala Arg Glu Cys Ile Ser Glu Asn Gln Ile Leu Lys Arg
65                  70                  75                  80

att gca cgt cac tgc gtt gaa cca acc aac ggc ctg ttt atc acc ctg      288
Ile Ala Arg His Cys Val Glu Pro Thr Asn Gly Leu Phe Ile Thr Leu
                85                  90                  95

ccg gaa gat gac ctc tcc ttc cag gcc act ttt att cgc gcc tgc gaa      336
Pro Glu Asp Asp Leu Ser Phe Gln Ala Thr Phe Ile Arg Ala Cys Glu
            100                 105                 110

gaa gca ggg atc agc gca gaa gct ata gac ccg cag caa gcg cgc att      384
Glu Ala Gly Ile Ser Ala Glu Ala Ile Asp Pro Gln Gln Ala Arg Ile
        115                 120                 125

atc gaa cct gcc gtt aac ccg gca ctg att ggc gcg gtg aaa gtt ccg      432
Ile Glu Pro Ala Val Asn Pro Ala Leu Ile Gly Ala Val Lys Val Pro
    130                 135                 140

gat ggc acc gtt gat cca ttt cgt ctg acc gca gca aac atg ctg gat      480
Asp Gly Thr Val Asp Pro Phe Arg Leu Thr Ala Ala Asn Met Leu Asp
145                 150                 155                 160

gcc aaa gaa cac ggt gcc gtt atc ctt acc gct cat gaa gtc acg ggg      528
Ala Lys Glu His Gly Ala Val Ile Leu Thr Ala His Glu Val Thr Gly
                165                 170                 175
```

```
ctg att cgt gaa ggc gcg acg gtg tgc ggt gtt cgt gta cgt aac cat      576
Leu Ile Arg Glu Gly Ala Thr Val Cys Gly Val Arg Val Arg Asn His
            180                 185                 190

ctc acc ggc gaa act cag gcc ctt cat gca cct gtc gtg gtt aat gcc      624
Leu Thr Gly Glu Thr Gln Ala Leu His Ala Pro Val Val Val Asn Ala
        195                 200                 205

gct ggg atc tgg ggg caa cac att gcc gaa tat gcc gat ctg cgc att      672
Ala Gly Ile Trp Gly Gln His Ile Ala Glu Tyr Ala Asp Leu Arg Ile
    210                 215                 220

cgc atg ttc ccg gcg aaa gga tcg ctg ctg atc atg gat cac cgc att      720
Arg Met Phe Pro Ala Lys Gly Ser Leu Leu Ile Met Asp His Arg Ile
225                 230                 235                 240

aac cag cat gtg atc aac cgc tgc cgt aaa cct tcc gac gcc gat att      768
Asn Gln His Val Ile Asn Arg Cys Arg Lys Pro Ser Asp Ala Asp Ile
                245                 250                 255

ctg gtg cct ggc gat acc att tcg ctg att ggt acc acc tct tta cgt      816
Leu Val Pro Gly Asp Thr Ile Ser Leu Ile Gly Thr Thr Ser Leu Arg
            260                 265                 270

att gat tac aac gag att gac gat aat cga gtg acg gca gaa gag gtt      864
Ile Asp Tyr Asn Glu Ile Asp Asp Asn Arg Val Thr Ala Glu Glu Val
        275                 280                 285

gat att ctg ctg cgt gaa ggg gaa aaa ctg gcc ccc gtg atg gcg aaa      912
Asp Ile Leu Leu Arg Glu Gly Glu Lys Leu Ala Pro Val Met Ala Lys
    290                 295                 300

acg cgc att ttg cgg gcc tat tct ggc gtg cgc ccg ctg gtt gcc agc      960
Thr Arg Ile Leu Arg Ala Tyr Ser Gly Val Arg Pro Leu Val Ala Ser
305                 310                 315                 320

gat gac gac ccg agc gga cgt aac gtc agc cgt ggc atc gtg ctg ctc     1008
Asp Asp Asp Pro Ser Gly Arg Asn Val Ser Arg Gly Ile Val Leu Leu
                325                 330                 335

gac cat gct gaa cgc gat ggt ctg gac gga ttt atc acc atc acc ggt     1056
Asp His Ala Glu Arg Asp Gly Leu Asp Gly Phe Ile Thr Ile Thr Gly
            340                 345                 350

ggc aaa ctg atg acc tat cgg ctg atg gct gaa tgg gct acc gac gcg     1104
Gly Lys Leu Met Thr Tyr Arg Leu Met Ala Glu Trp Ala Thr Asp Ala
        355                 360                 365

gta tgc cgc aaa ctg ggc aac acg cgc ccc tgt acg act gcc gat ctg     1152
Val Cys Arg Lys Leu Gly Asn Thr Arg Pro Cys Thr Thr Ala Asp Leu
    370                 375                 380

gca ctg cct ggt tca caa gaa ccc gct gaa gtt acc ttg cgt aaa gtc     1200
Ala Leu Pro Gly Ser Gln Glu Pro Ala Glu Val Thr Leu Arg Lys Val
385                 390                 395                 400

atc tcc ctg cct gcc ccg ctg cgc ggt tct gcg gtt tat cgt cat ggc     1248
Ile Ser Leu Pro Ala Pro Leu Arg Gly Ser Ala Val Tyr Arg His Gly
                405                 410                 415

gat cgc acg cct gcc tgg ctg agc gaa ggc cgt ctg cac cgt agc ctg     1296
Asp Arg Thr Pro Ala Trp Leu Ser Glu Gly Arg Leu His Arg Ser Leu
            420                 425                 430

gta tgt gag tgc gaa gcg gta act gcg ggt gaa gtg cag tac gcg gta     1344
Val Cys Glu Cys Glu Ala Val Thr Ala Gly Glu Val Gln Tyr Ala Val
        435                 440                 445

gaa aat tta aac gtt aat agc ctg ctg gat tta cgc cgt cgt acc cgt     1392
Glu Asn Leu Asn Val Asn Ser Leu Leu Asp Leu Arg Arg Arg Thr Arg
    450                 455                 460

gtg ggg atg ggc acc tgc cag ggc gaa ctc tgc gcc tgc cgc gct gcc     1440
Val Gly Met Gly Thr Cys Gln Gly Glu Leu Cys Ala Cys Arg Ala Ala
465                 470                 475                 480

gga ctg ctg caa cgt ttt aac gtc acg acg tcc gcg caa tct atc gag     1488
Gly Leu Leu Gln Arg Phe Asn Val Thr Thr Ser Ala Gln Ser Ile Glu
                485                 490                 495
```

```
caa ctt tcc acc ttc ctt aac gaa cgc tgg aaa ggc gtg caa ccc atc      1536
Gln Leu Ser Thr Phe Leu Asn Glu Arg Trp Lys Gly Val Gln Pro Ile
            500                 505                 510

gcc tgg gga gat gca ctg cgc gaa agc gaa ttt acc cgc tgg gtt tat      1584
Ala Trp Gly Asp Ala Leu Arg Glu Ser Glu Phe Thr Arg Trp Val Tyr
        515                 520                 525

cag gga ttg tgt ggt ctg gag aag gag cag aaa gat gcg ctt tga          1629
Gln Gly Leu Cys Gly Leu Glu Lys Glu Gln Lys Asp Ala Leu
    530                 535                 540


<210> SEQ ID NO 27
<211> LENGTH: 542
<212> TYPE: PRT
<213> ORGANISM: Escherichia coli

<400> SEQUENCE: 27

Met Lys Thr Arg Asp Ser Gln Ser Ser Asp Val Ile Ile Ile Gly Gly
1               5                   10                  15

Gly Ala Thr Gly Ala Gly Ile Ala Arg Asp Cys Ala Leu Arg Gly Leu
            20                  25                  30

Arg Val Ile Leu Val Glu Arg His Asp Ile Ala Thr Gly Ala Thr Gly
        35                  40                  45

Arg Asn His Gly Leu Leu His Ser Gly Ala Arg Tyr Ala Val Thr Asp
    50                  55                  60

Ala Glu Ser Ala Arg Glu Cys Ile Ser Glu Asn Gln Ile Leu Lys Arg
65                  70                  75                  80

Ile Ala Arg His Cys Val Glu Pro Thr Asn Gly Leu Phe Ile Thr Leu
                85                  90                  95

Pro Glu Asp Asp Leu Ser Phe Gln Ala Thr Phe Ile Arg Ala Cys Glu
            100                 105                 110

Glu Ala Gly Ile Ser Ala Glu Ala Ile Asp Pro Gln Gln Ala Arg Ile
        115                 120                 125

Ile Glu Pro Ala Val Asn Pro Ala Leu Ile Gly Ala Val Lys Val Pro
    130                 135                 140

Asp Gly Thr Val Asp Pro Phe Arg Leu Thr Ala Ala Asn Met Leu Asp
145                 150                 155                 160

Ala Lys Glu His Gly Ala Val Ile Leu Thr Ala His Glu Val Thr Gly
                165                 170                 175

Leu Ile Arg Glu Gly Ala Thr Val Cys Gly Val Arg Val Arg Asn His
            180                 185                 190

Leu Thr Gly Glu Thr Gln Ala Leu His Ala Pro Val Val Val Asn Ala
        195                 200                 205

Ala Gly Ile Trp Gly Gln His Ile Ala Glu Tyr Ala Asp Leu Arg Ile
    210                 215                 220

Arg Met Phe Pro Ala Lys Gly Ser Leu Leu Ile Met Asp His Arg Ile
225                 230                 235                 240

Asn Gln His Val Ile Asn Arg Cys Arg Lys Pro Ser Asp Ala Asp Ile
                245                 250                 255

Leu Val Pro Gly Asp Thr Ile Ser Leu Ile Gly Thr Thr Ser Leu Arg
            260                 265                 270

Ile Asp Tyr Asn Glu Ile Asp Asp Asn Arg Val Thr Ala Glu Glu Val
        275                 280                 285

Asp Ile Leu Leu Arg Glu Gly Glu Lys Leu Ala Pro Val Met Ala Lys
    290                 295                 300

Thr Arg Ile Leu Arg Ala Tyr Ser Gly Val Arg Pro Leu Val Ala Ser
305                 310                 315                 320
```

```
Asp Asp Asp Pro Ser Gly Arg Asn Val Ser Arg Gly Ile Val Leu Leu
                325                 330                 335

Asp His Ala Glu Arg Asp Gly Leu Asp Gly Phe Ile Thr Ile Thr Gly
            340                 345                 350

Gly Lys Leu Met Thr Tyr Arg Leu Met Ala Glu Trp Ala Thr Asp Ala
        355                 360                 365

Val Cys Arg Lys Leu Gly Asn Thr Arg Pro Cys Thr Thr Ala Asp Leu
    370                 375                 380

Ala Leu Pro Gly Ser Gln Glu Pro Ala Glu Val Thr Leu Arg Lys Val
385                 390                 395                 400

Ile Ser Leu Pro Ala Pro Leu Arg Gly Ser Ala Val Tyr Arg His Gly
                405                 410                 415

Asp Arg Thr Pro Ala Trp Leu Ser Glu Gly Arg Leu His Arg Ser Leu
            420                 425                 430

Val Cys Glu Cys Glu Ala Val Thr Ala Gly Glu Val Gln Tyr Ala Val
        435                 440                 445

Glu Asn Leu Asn Val Asn Ser Leu Leu Asp Leu Arg Arg Arg Thr Arg
    450                 455                 460

Val Gly Met Gly Thr Cys Gln Gly Glu Leu Cys Ala Cys Arg Ala Ala
465                 470                 475                 480

Gly Leu Leu Gln Arg Phe Asn Val Thr Thr Ser Ala Gln Ser Ile Glu
                485                 490                 495

Gln Leu Ser Thr Phe Leu Asn Glu Arg Trp Lys Gly Val Gln Pro Ile
            500                 505                 510

Ala Trp Gly Asp Ala Leu Arg Glu Ser Glu Phe Thr Arg Trp Val Tyr
        515                 520                 525

Gln Gly Leu Cys Gly Leu Glu Lys Glu Gln Lys Asp Ala Leu
    530                 535                 540


<210> SEQ ID NO 28
<211> LENGTH: 1260
<212> TYPE: DNA
<213> ORGANISM: Escherichia coli
<220> FEATURE:
<221> NAME/KEY: CDS
<222> LOCATION: (1)..(1260)

<400> SEQUENCE: 28

atg cgc ttt gat act gtc att atg ggc ggc ggc ctc gcc gga tta ctc       48
Met Arg Phe Asp Thr Val Ile Met Gly Gly Gly Leu Ala Gly Leu Leu
1               5                   10                  15

tgt ggc ctg caa ctg caa aaa cac ggc ctg cgc tgt gcc att gtc act       96
Cys Gly Leu Gln Leu Gln Lys His Gly Leu Arg Cys Ala Ile Val Thr
            20                  25                  30

cgt ggt caa agc gca ctg cat ttc tca tcc gga tcg ctg gat ttg ctg      144
Arg Gly Gln Ser Ala Leu His Phe Ser Ser Gly Ser Leu Asp Leu Leu
        35                  40                  45

agc cat ctg cca gat ggt caa ccg gtg aca gac att cac agt gga ctg      192
Ser His Leu Pro Asp Gly Gln Pro Val Thr Asp Ile His Ser Gly Leu
    50                  55                  60

gaa tct ttg cgt cag cag gca cca gcc cat cct tac tcc ctt ctc gag      240
Glu Ser Leu Arg Gln Gln Ala Pro Ala His Pro Tyr Ser Leu Leu Glu
65                  70                  75                  80

cca caa cgc gtg ctc gat ctc gct tgc cag gcg cag gca tta atc gct      288
Pro Gln Arg Val Leu Asp Leu Ala Cys Gln Ala Gln Ala Leu Ile Ala
                85                  90                  95

gaa agc ggt gcg caa ttg cag ggc agc gta gaa ctt gct cac cag cgg      336
Glu Ser Gly Ala Gln Leu Gln Gly Ser Val Glu Leu Ala His Gln Arg
```

```
            100                 105                 110

gtt acg ccg ctc ggc act ctg cgc tct acc tgg cta agt tcg cca gaa      384
Val Thr Pro Leu Gly Thr Leu Arg Ser Thr Trp Leu Ser Ser Pro Glu
        115                 120                 125

gtc ccc gtc tgg ccg ctg ccc gcg aag aaa ata tgt gta gtg gga att      432
Val Pro Val Trp Pro Leu Pro Ala Lys Lys Ile Cys Val Val Gly Ile
    130                 135                 140

agc ggc ctg atg gat ttt cag gcg cac ctt gcg gca gct tcg ttg cgt      480
Ser Gly Leu Met Asp Phe Gln Ala His Leu Ala Ala Ala Ser Leu Arg
145                 150                 155                 160

gaa ctc ggc ctt gcc gtt gaa acc gca gaa ata gag ctg ccg gaa ctg      528
Glu Leu Gly Leu Ala Val Glu Thr Ala Glu Ile Glu Leu Pro Glu Leu
                165                 170                 175

gat gtg ctg cgc aat aac gcc acc gaa ttt cgc gcg gtg aat atc gcc      576
Asp Val Leu Arg Asn Asn Ala Thr Glu Phe Arg Ala Val Asn Ile Ala
            180                 185                 190

cgt ttc ctt gat aat gaa gaa aac tgg ccg ctg tta ctt gat gcg ctt      624
Arg Phe Leu Asp Asn Glu Glu Asn Trp Pro Leu Leu Leu Asp Ala Leu
        195                 200                 205

att cct gtc gcc aat acc tgc gaa atg atc ctg atg ccc gcc tgc ttc      672
Ile Pro Val Ala Asn Thr Cys Glu Met Ile Leu Met Pro Ala Cys Phe
    210                 215                 220

ggt ctg gcc gat gac aaa ctg tgg cgt tgg ttg aat gaa aaa cta cct      720
Gly Leu Ala Asp Asp Lys Leu Trp Arg Trp Leu Asn Glu Lys Leu Pro
225                 230                 235                 240

tgt tca ctg atg ctt ttg cca acg ctg ccg cct tcc gtg ctg ggc att      768
Cys Ser Leu Met Leu Leu Pro Thr Leu Pro Pro Ser Val Leu Gly Ile
                245                 250                 255

cgt ctg caa aac cag tta cag cgc cag ttt gtg cgc cag ggt ggc gtg      816
Arg Leu Gln Asn Gln Leu Gln Arg Gln Phe Val Arg Gln Gly Gly Val
            260                 265                 270

tgg atg ccg ggc gat gaa gtg aaa aaa gtg acc tgt aaa aat ggc gta      864
Trp Met Pro Gly Asp Glu Val Lys Lys Val Thr Cys Lys Asn Gly Val
        275                 280                 285

gtg aac gaa atc tgg acc cgc aat cac gcc gat att ccg cta cgt cca      912
Val Asn Glu Ile Trp Thr Arg Asn His Ala Asp Ile Pro Leu Arg Pro
    290                 295                 300

cgt ttc gcg gtt ctc gcc agc ggc agt ttc ttt agt ggc gga ctg gta      960
Arg Phe Ala Val Leu Ala Ser Gly Ser Phe Phe Ser Gly Gly Leu Val
305                 310                 315                 320

gcg gaa cgt aac ggc att cga gag ccg att ctc ggc ctt gat gtg cta     1008
Ala Glu Arg Asn Gly Ile Arg Glu Pro Ile Leu Gly Leu Asp Val Leu
                325                 330                 335

caa acc gcc acg cgg ggt gaa tgg tat aag gga gat ttt ttt gcg ccg     1056
Gln Thr Ala Thr Arg Gly Glu Trp Tyr Lys Gly Asp Phe Phe Ala Pro
            340                 345                 350

caa ccg tgg cag cag ttc ggt gta acc act gat gag acg cta cgc ccg     1104
Gln Pro Trp Gln Gln Phe Gly Val Thr Thr Asp Glu Thr Leu Arg Pro
        355                 360                 365

tca cag gca ggg caa acc att gaa aac ctg ttt gcc atc ggt tcg gtg     1152
Ser Gln Ala Gly Gln Thr Ile Glu Asn Leu Phe Ala Ile Gly Ser Val
    370                 375                 380

ctg ggc gga ttt gat ccc atc gcc cag gga tgc ggc ggc ggt gtt tgt     1200
Leu Gly Gly Phe Asp Pro Ile Ala Gln Gly Cys Gly Gly Gly Val Cys
385                 390                 395                 400

gcc gtc agt gct tta cat gcc gct caa cag att gcc caa cgc gca gga     1248
Ala Val Ser Ala Leu His Ala Ala Gln Gln Ile Ala Gln Arg Ala Gly
                405                 410                 415

ggc caa caa tga                                                     1260
Gly Gln Gln
```

<210> SEQ ID NO 29
<211> LENGTH: 419
<212> TYPE: PRT
<213> ORGANISM: Escherichia coli

<400> SEQUENCE: 29

```
Met Arg Phe Asp Thr Val Ile Met Gly Gly Gly Leu Ala Gly Leu Leu
1               5                   10                  15

Cys Gly Leu Gln Leu Gln Lys His Gly Leu Arg Cys Ala Ile Val Thr
            20                  25                  30

Arg Gly Gln Ser Ala Leu His Phe Ser Ser Gly Ser Leu Asp Leu Leu
        35                  40                  45

Ser His Leu Pro Asp Gly Gln Pro Val Thr Asp Ile His Ser Gly Leu
    50                  55                  60

Glu Ser Leu Arg Gln Gln Ala Pro Ala His Pro Tyr Ser Leu Leu Glu
65                  70                  75                  80

Pro Gln Arg Val Leu Asp Leu Ala Cys Gln Ala Gln Ala Leu Ile Ala
                85                  90                  95

Glu Ser Gly Ala Gln Leu Gln Gly Ser Val Glu Leu Ala His Gln Arg
            100                 105                 110

Val Thr Pro Leu Gly Thr Leu Arg Ser Thr Trp Leu Ser Ser Pro Glu
        115                 120                 125

Val Pro Val Trp Pro Leu Pro Ala Lys Lys Ile Cys Val Val Gly Ile
    130                 135                 140

Ser Gly Leu Met Asp Phe Gln Ala His Leu Ala Ala Ala Ser Leu Arg
145                 150                 155                 160

Glu Leu Gly Leu Ala Val Glu Thr Ala Glu Ile Glu Leu Pro Glu Leu
                165                 170                 175

Asp Val Leu Arg Asn Asn Ala Thr Glu Phe Arg Ala Val Asn Ile Ala
            180                 185                 190

Arg Phe Leu Asp Asn Glu Glu Asn Trp Pro Leu Leu Leu Asp Ala Leu
        195                 200                 205

Ile Pro Val Ala Asn Thr Cys Glu Met Ile Leu Met Pro Ala Cys Phe
    210                 215                 220

Gly Leu Ala Asp Asp Lys Leu Trp Arg Trp Leu Asn Glu Lys Leu Pro
225                 230                 235                 240

Cys Ser Leu Met Leu Leu Pro Thr Leu Pro Pro Ser Val Leu Gly Ile
                245                 250                 255

Arg Leu Gln Asn Gln Leu Gln Arg Gln Phe Val Arg Gln Gly Gly Val
            260                 265                 270

Trp Met Pro Gly Asp Glu Val Lys Lys Val Thr Cys Lys Asn Gly Val
        275                 280                 285

Val Asn Glu Ile Trp Thr Arg Asn His Ala Asp Ile Pro Leu Arg Pro
    290                 295                 300

Arg Phe Ala Val Leu Ala Ser Gly Ser Phe Phe Ser Gly Gly Leu Val
305                 310                 315                 320

Ala Glu Arg Asn Gly Ile Arg Glu Pro Ile Leu Gly Leu Asp Val Leu
                325                 330                 335

Gln Thr Ala Thr Arg Gly Glu Trp Tyr Lys Gly Asp Phe Phe Ala Pro
            340                 345                 350

Gln Pro Trp Gln Gln Phe Gly Val Thr Thr Asp Glu Thr Leu Arg Pro
        355                 360                 365

Ser Gln Ala Gly Gln Thr Ile Glu Asn Leu Phe Ala Ile Gly Ser Val
    370                 375                 380
```

```
Leu Gly Gly Phe Asp Pro Ile Ala Gln Gly Cys Gly Gly Gly Val Cys
385                 390                 395                 400

Ala Val Ser Ala Leu His Ala Ala Gln Gln Ile Ala Gln Arg Ala Gly
                405                 410                 415

Gly Gln Gln


<210> SEQ ID NO 30
<211> LENGTH: 1191
<212> TYPE: DNA
<213> ORGANISM: Escherichia coli
<220> FEATURE:
<221> NAME/KEY: CDS
<222> LOCATION: (1)..(1191)

<400> SEQUENCE: 30

atg aat gac acc agc ttc gaa aac tgc att aag tgc acc gtc tgc acc       48
Met Asn Asp Thr Ser Phe Glu Asn Cys Ile Lys Cys Thr Val Cys Thr
1               5                   10                  15

acc gcc tgc ccg gtg agc cgg gtg aat ccc ggt tat cca ggg cca aaa       96
Thr Ala Cys Pro Val Ser Arg Val Asn Pro Gly Tyr Pro Gly Pro Lys
            20                  25                  30

caa gcc ggg ccg gat ggc gag cgt ctg cgt ttg aaa gat ggc gca ctg      144
Gln Ala Gly Pro Asp Gly Glu Arg Leu Arg Leu Lys Asp Gly Ala Leu
        35                  40                  45

tat gac gag gcg ctg aaa tat tgc atc aac tgc aaa cgt tgt gaa gtc      192
Tyr Asp Glu Ala Leu Lys Tyr Cys Ile Asn Cys Lys Arg Cys Glu Val
    50                  55                  60

gcc tgc ccg tcc gat gtg aag att ggc gat att atc cag cgc gcg cgg      240
Ala Cys Pro Ser Asp Val Lys Ile Gly Asp Ile Ile Gln Arg Ala Arg
65                  70                  75                  80

gcg aaa tat gac acc acg cgc ccg tcg ctg cgt aat ttt gtg ttg agt      288
Ala Lys Tyr Asp Thr Thr Arg Pro Ser Leu Arg Asn Phe Val Leu Ser
                85                  90                  95

cat acc gac ctg atg ggt agc gtt tcc acg ccg ttc gca cca atc gtc      336
His Thr Asp Leu Met Gly Ser Val Ser Thr Pro Phe Ala Pro Ile Val
            100                 105                 110

aac acc gct acc tcg ctg aaa ccg gtg cgg cag ctg ctt gat gcg gcg      384
Asn Thr Ala Thr Ser Leu Lys Pro Val Arg Gln Leu Leu Asp Ala Ala
        115                 120                 125

tta aaa atc gat cat cgc cgc acg cta ccg aaa tac tcc ttc ggc acg      432
Leu Lys Ile Asp His Arg Arg Thr Leu Pro Lys Tyr Ser Phe Gly Thr
    130                 135                 140

ttc cgt cgc tgg tat cgc agc gtg gcg gct cag caa gca caa tat aaa      480
Phe Arg Arg Trp Tyr Arg Ser Val Ala Ala Gln Gln Ala Gln Tyr Lys
145                 150                 155                 160

gac cag gtc gct ttc ttt cac ggc tgc ttc gtt aac tac aac cat ccg      528
Asp Gln Val Ala Phe Phe His Gly Cys Phe Val Asn Tyr Asn His Pro
                165                 170                 175

cag tta ggt aaa gat tta att aaa gtg ctc aac gca atg ggt acc ggt      576
Gln Leu Gly Lys Asp Leu Ile Lys Val Leu Asn Ala Met Gly Thr Gly
            180                 185                 190

gta caa ctg ctc agc aaa gaa aaa tgc tgc ggc gta ccg cta atc gcc      624
Val Gln Leu Leu Ser Lys Glu Lys Cys Cys Gly Val Pro Leu Ile Ala
        195                 200                 205

aac ggc ttt acc gat aaa gca cgc aaa cag gca att acg aat gta gag      672
Asn Gly Phe Thr Asp Lys Ala Arg Lys Gln Ala Ile Thr Asn Val Glu
    210                 215                 220

tcg atc cgc gaa gct gtg gga gta aaa ggc att ccg gtg att gcc acc      720
Ser Ile Arg Glu Ala Val Gly Val Lys Gly Ile Pro Val Ile Ala Thr
225                 230                 235                 240
```

```
tcc tca acc tgt aca ttt gcc ctg cgc gac gaa tac ccg gaa gtg ctg      768
Ser Ser Thr Cys Thr Phe Ala Leu Arg Asp Glu Tyr Pro Glu Val Leu
                245                 250                 255

aat gtc gac aac aaa ggc ttg cgc gat cat atc gaa ctg gca acc cgc      816
Asn Val Asp Asn Lys Gly Leu Arg Asp His Ile Glu Leu Ala Thr Arg
            260                 265                 270

tgg ctg tgg cgc aag ctg gac gaa ggc aaa acg tta ccg ctg aaa ccg      864
Trp Leu Trp Arg Lys Leu Asp Glu Gly Lys Thr Leu Pro Leu Lys Pro
        275                 280                 285

ctg ccg ctg aaa gtg gtt tat cac act ccg tgc cat atg gaa aaa atg      912
Leu Pro Leu Lys Val Val Tyr His Thr Pro Cys His Met Glu Lys Met
    290                 295                 300

ggc tgg acg ctc tac acc ctg gag ctg ttg cgt aac atc ccg ggg ctt      960
Gly Trp Thr Leu Tyr Thr Leu Glu Leu Leu Arg Asn Ile Pro Gly Leu
305                 310                 315                 320

gag tta acg gtg ctg gat tcc cag tgc tgc ggt att gcg ggt act tac     1008
Glu Leu Thr Val Leu Asp Ser Gln Cys Cys Gly Ile Ala Gly Thr Tyr
                325                 330                 335

ggt ttc aaa aaa gag aac tac ccc acc tca caa gcc atc ggc gca cca     1056
Gly Phe Lys Lys Glu Asn Tyr Pro Thr Ser Gln Ala Ile Gly Ala Pro
            340                 345                 350

ctg ttc cgc cag ata gaa gaa agc ggc gca gat ctg gtg gtc acc gac     1104
Leu Phe Arg Gln Ile Glu Glu Ser Gly Ala Asp Leu Val Val Thr Asp
        355                 360                 365

tgc gaa acc tgt aaa tgg cag att gag atg tcc aca agt ctt cgc tgc     1152
Cys Glu Thr Cys Lys Trp Gln Ile Glu Met Ser Thr Ser Leu Arg Cys
    370                 375                 380

gaa cat ccg att acg cta ctg gcc cag gcg ctg gct taa                 1191
Glu His Pro Ile Thr Leu Leu Ala Gln Ala Leu Ala
385                 390                 395


<210> SEQ ID NO 31
<211> LENGTH: 396
<212> TYPE: PRT
<213> ORGANISM: Escherichia coli

<400> SEQUENCE: 31

Met Asn Asp Thr Ser Phe Glu Asn Cys Ile Lys Cys Thr Val Cys Thr
1               5                   10                  15

Thr Ala Cys Pro Val Ser Arg Val Asn Pro Gly Tyr Pro Gly Pro Lys
            20                  25                  30

Gln Ala Gly Pro Asp Gly Glu Arg Leu Arg Leu Lys Asp Gly Ala Leu
        35                  40                  45

Tyr Asp Glu Ala Leu Lys Tyr Cys Ile Asn Cys Lys Arg Cys Glu Val
    50                  55                  60

Ala Cys Pro Ser Asp Val Lys Ile Gly Asp Ile Ile Gln Arg Ala Arg
65                  70                  75                  80

Ala Lys Tyr Asp Thr Thr Arg Pro Ser Leu Arg Asn Phe Val Leu Ser
                85                  90                  95

His Thr Asp Leu Met Gly Ser Val Ser Thr Pro Phe Ala Pro Ile Val
            100                 105                 110

Asn Thr Ala Thr Ser Leu Lys Pro Val Arg Gln Leu Leu Asp Ala Ala
        115                 120                 125

Leu Lys Ile Asp His Arg Arg Thr Leu Pro Lys Tyr Ser Phe Gly Thr
    130                 135                 140

Phe Arg Arg Trp Tyr Arg Ser Val Ala Ala Gln Gln Ala Gln Tyr Lys
145                 150                 155                 160

Asp Gln Val Ala Phe Phe His Gly Cys Phe Val Asn Tyr Asn His Pro
                165                 170                 175
```

```
Gln Leu Gly Lys Asp Leu Ile Lys Val Leu Asn Ala Met Gly Thr Gly
            180                 185                 190

Val Gln Leu Leu Ser Lys Glu Lys Cys Cys Gly Val Pro Leu Ile Ala
        195                 200                 205

Asn Gly Phe Thr Asp Lys Ala Arg Lys Gln Ala Ile Thr Asn Val Glu
    210                 215                 220

Ser Ile Arg Glu Ala Val Gly Val Lys Gly Ile Pro Val Ile Ala Thr
225                 230                 235                 240

Ser Ser Thr Cys Thr Phe Ala Leu Arg Asp Glu Tyr Pro Glu Val Leu
                245                 250                 255

Asn Val Asp Asn Lys Gly Leu Arg Asp His Ile Glu Leu Ala Thr Arg
            260                 265                 270

Trp Leu Trp Arg Lys Leu Asp Glu Gly Lys Thr Leu Pro Leu Lys Pro
        275                 280                 285

Leu Pro Leu Lys Val Val Tyr His Thr Pro Cys His Met Glu Lys Met
    290                 295                 300

Gly Trp Thr Leu Tyr Thr Leu Glu Leu Leu Arg Asn Ile Pro Gly Leu
305                 310                 315                 320

Glu Leu Thr Val Leu Asp Ser Gln Cys Cys Gly Ile Ala Gly Thr Tyr
                325                 330                 335

Gly Phe Lys Lys Glu Asn Tyr Pro Thr Ser Gln Ala Ile Gly Ala Pro
            340                 345                 350

Leu Phe Arg Gln Ile Glu Glu Ser Gly Ala Asp Leu Val Val Thr Asp
        355                 360                 365

Cys Glu Thr Cys Lys Trp Gln Ile Glu Met Ser Thr Ser Leu Arg Cys
    370                 375                 380

Glu His Pro Ile Thr Leu Leu Ala Gln Ala Leu Ala
385                 390                 395


<210> SEQ ID NO 32
<211> LENGTH: 1506
<212> TYPE: DNA
<213> ORGANISM: Escherichia coli
<220> FEATURE:
<221> NAME/KEY: CDS
<222> LOCATION: (1)..(1506)

<400> SEQUENCE: 32

atg gaa acc aaa gat ctg att gtg ata ggg ggc ggc atc aat ggt gct       48
Met Glu Thr Lys Asp Leu Ile Val Ile Gly Gly Gly Ile Asn Gly Ala
1               5                   10                  15

ggt atc gcg gca gac gcc gct gga cgc ggt tta tcc gtg ctg atg ctg       96
Gly Ile Ala Ala Asp Ala Ala Gly Arg Gly Leu Ser Val Leu Met Leu
            20                  25                  30

gag gcg cag gat ctc gct tgc gcg acc tct tcc gcc agt tca aaa ctc      144
Glu Ala Gln Asp Leu Ala Cys Ala Thr Ser Ser Ala Ser Ser Lys Leu
        35                  40                  45

att cac ggt ggc ctg cgc tac ctt gag cac tat gaa ttc cgc ctg gtc      192
Ile His Gly Gly Leu Arg Tyr Leu Glu His Tyr Glu Phe Arg Leu Val
    50                  55                  60

agc gag gcg ctg gct gaa cgt gaa gtg ctg ctg aaa atg gcc ccg cat      240
Ser Glu Ala Leu Ala Glu Arg Glu Val Leu Leu Lys Met Ala Pro His
65                  70                  75                  80

atc gcc ttc ccg atg cgt ttt cgc ctg cca cat cgt ccg cat ctg cgc      288
Ile Ala Phe Pro Met Arg Phe Arg Leu Pro His Arg Pro His Leu Arg
                85                  90                  95

ccg gcg tgg atg att cgc att ggt ctg ttt atg tac gat cat ctg ggt      336
Pro Ala Trp Met Ile Arg Ile Gly Leu Phe Met Tyr Asp His Leu Gly
```

```
            100                 105                 110

aaa cgc acc agc ttg ccg gga tca act ggt ttg cgt ttt ggc gca aat      384
Lys Arg Thr Ser Leu Pro Gly Ser Thr Gly Leu Arg Phe Gly Ala Asn
        115                 120                 125

tca gtg tta aaa ccg gaa att aag cgc gga ttc gaa tat tct gac tgt      432
Ser Val Leu Lys Pro Glu Ile Lys Arg Gly Phe Glu Tyr Ser Asp Cys
    130                 135                 140

tgg gta gac gac gcc cgt ctg gta ctc gcc aac gcc cag atg gtg gtg      480
Trp Val Asp Asp Ala Arg Leu Val Leu Ala Asn Ala Gln Met Val Val
145                 150                 155                 160

cgt aaa ggc ggc gaa gtg ctt act cgg act cgc gcc acc tct gct cgc      528
Arg Lys Gly Gly Glu Val Leu Thr Arg Thr Arg Ala Thr Ser Ala Arg
            165                 170                 175

cgc gaa aac ggc ctg tgg att gtg gaa gcg gaa gat atc gat acc ggc      576
Arg Glu Asn Gly Leu Trp Ile Val Glu Ala Glu Asp Ile Asp Thr Gly
            180                 185                 190

aaa aaa tat agc tgg caa gcg cgc ggc ttg gtt aac gcc acc ggc ccg      624
Lys Lys Tyr Ser Trp Gln Ala Arg Gly Leu Val Asn Ala Thr Gly Pro
        195                 200                 205

tgg gtg aaa cag ttc ttc gac gac ggg atg cat ctg cct tcg cct tat      672
Trp Val Lys Gln Phe Phe Asp Asp Gly Met His Leu Pro Ser Pro Tyr
    210                 215                 220

ggc att cgc ctg atc aaa ggc agc cat att gtg gtg ccg cgc gtg cat      720
Gly Ile Arg Leu Ile Lys Gly Ser His Ile Val Val Pro Arg Val His
225                 230                 235                 240

acc cag aag caa gcc tac att ctg caa aac gaa gat aaa cgt att gtg      768
Thr Gln Lys Gln Ala Tyr Ile Leu Gln Asn Glu Asp Lys Arg Ile Val
            245                 250                 255

ttc gtg atc ccg tgg atg gac gag ttt tcc atc atc ggc act acc gat      816
Phe Val Ile Pro Trp Met Asp Glu Phe Ser Ile Ile Gly Thr Thr Asp
            260                 265                 270

gtc gag tac aaa ggc gat ccg aaa gcg gtg aag att gaa gag agt gaa      864
Val Glu Tyr Lys Gly Asp Pro Lys Ala Val Lys Ile Glu Glu Ser Glu
        275                 280                 285

atc aat tac ctg ctg aat gtg tat aac acg cac ttt aaa aag cag tta      912
Ile Asn Tyr Leu Leu Asn Val Tyr Asn Thr His Phe Lys Lys Gln Leu
    290                 295                 300

agc cgt gac gat atc gtc tgg acc tac tcc ggt gtg cgt ccg ctg tgt      960
Ser Arg Asp Asp Ile Val Trp Thr Tyr Ser Gly Val Arg Pro Leu Cys
305                 310                 315                 320

gat gat gag tcc gac tcg ccg cag gct att acc cgt gat tac acc ctt     1008
Asp Asp Glu Ser Asp Ser Pro Gln Ala Ile Thr Arg Asp Tyr Thr Leu
            325                 330                 335

gat att cat gat gaa aat ggc aaa gca ccg ctg ctg tcg gta ttc ggc     1056
Asp Ile His Asp Glu Asn Gly Lys Ala Pro Leu Leu Ser Val Phe Gly
            340                 345                 350

ggt aag ctg acc acc tac cga aaa ctg gcg gaa cat gcg ctg gaa aaa     1104
Gly Lys Leu Thr Thr Tyr Arg Lys Leu Ala Glu His Ala Leu Glu Lys
        355                 360                 365

cta acg ccg tat tat cag ggt att ggc ccg gca tgg acg aaa gag agt     1152
Leu Thr Pro Tyr Tyr Gln Gly Ile Gly Pro Ala Trp Thr Lys Glu Ser
    370                 375                 380

gtg cta ccg ggt ggc gcc att gaa ggc gac cgc gac gat tat gcc gct     1200
Val Leu Pro Gly Gly Ala Ile Glu Gly Asp Arg Asp Asp Tyr Ala Ala
385                 390                 395                 400

cgc ctg cgc cgc cgc tat ccg ttc ctg act gaa tcg ctg gcg cgt cat     1248
Arg Leu Arg Arg Arg Tyr Pro Phe Leu Thr Glu Ser Leu Ala Arg His
            405                 410                 415

tac gct cgc act tac ggc agc aac agc gag ctg ctg ctc ggc aat gcg     1296
Tyr Ala Arg Thr Tyr Gly Ser Asn Ser Glu Leu Leu Leu Gly Asn Ala
```

```
            420                 425                 430

gga acg gta agc gat ctc ggg gaa gat ttc ggt cat gag ttc tac gaa      1344
Gly Thr Val Ser Asp Leu Gly Glu Asp Phe Gly His Glu Phe Tyr Glu
        435                 440                 445

gcg gag ctg aaa tac ctg gtg gat cac gaa tgg gtc cgc cgc gcc gac      1392
Ala Glu Leu Lys Tyr Leu Val Asp His Glu Trp Val Arg Arg Ala Asp
    450                 455                 460

gac gcc ctg tgg cgt cgc aca aaa caa ggc atg tgg cta aat gcg gat      1440
Asp Ala Leu Trp Arg Arg Thr Lys Gln Gly Met Trp Leu Asn Ala Asp
465                 470                 475                 480

caa caa tct cgt gtg agt cag tgg ctg gtg gag tat acg cag cag agg      1488
Gln Gln Ser Arg Val Ser Gln Trp Leu Val Glu Tyr Thr Gln Gln Arg
                485                 490                 495

tta tcg ctg gcg tcg taa                                              1506
Leu Ser Leu Ala Ser
            500


<210> SEQ ID NO 33
<211> LENGTH: 501
<212> TYPE: PRT
<213> ORGANISM: Escherichia coli

<400> SEQUENCE: 33

Met Glu Thr Lys Asp Leu Ile Val Ile Gly Gly Gly Ile Asn Gly Ala
1               5                   10                  15

Gly Ile Ala Ala Asp Ala Ala Gly Arg Gly Leu Ser Val Leu Met Leu
            20                  25                  30

Glu Ala Gln Asp Leu Ala Cys Ala Thr Ser Ser Ala Ser Ser Lys Leu
        35                  40                  45

Ile His Gly Gly Leu Arg Tyr Leu Glu His Tyr Glu Phe Arg Leu Val
    50                  55                  60

Ser Glu Ala Leu Ala Glu Arg Glu Val Leu Leu Lys Met Ala Pro His
65                  70                  75                  80

Ile Ala Phe Pro Met Arg Phe Arg Leu Pro His Arg Pro His Leu Arg
                85                  90                  95

Pro Ala Trp Met Ile Arg Ile Gly Leu Phe Met Tyr Asp His Leu Gly
            100                 105                 110

Lys Arg Thr Ser Leu Pro Gly Ser Thr Gly Leu Arg Phe Gly Ala Asn
        115                 120                 125

Ser Val Leu Lys Pro Glu Ile Lys Arg Gly Phe Glu Tyr Ser Asp Cys
    130                 135                 140

Trp Val Asp Asp Ala Arg Leu Val Leu Ala Asn Ala Gln Met Val Val
145                 150                 155                 160

Arg Lys Gly Gly Glu Val Leu Thr Arg Thr Arg Ala Thr Ser Ala Arg
                165                 170                 175

Arg Glu Asn Gly Leu Trp Ile Val Glu Ala Glu Asp Ile Asp Thr Gly
            180                 185                 190

Lys Lys Tyr Ser Trp Gln Ala Arg Gly Leu Val Asn Ala Thr Gly Pro
        195                 200                 205

Trp Val Lys Gln Phe Phe Asp Asp Gly Met His Leu Pro Ser Pro Tyr
    210                 215                 220

Gly Ile Arg Leu Ile Lys Gly Ser His Ile Val Val Pro Arg Val His
225                 230                 235                 240

Thr Gln Lys Gln Ala Tyr Ile Leu Gln Asn Glu Asp Lys Arg Ile Val
                245                 250                 255

Phe Val Ile Pro Trp Met Asp Glu Phe Ser Ile Ile Gly Thr Thr Asp
            260                 265                 270
```

```
Val Glu Tyr Lys Gly Asp Pro Lys Ala Val Lys Ile Glu Glu Ser Glu
        275                 280                 285

Ile Asn Tyr Leu Leu Asn Val Tyr Asn Thr His Phe Lys Lys Gln Leu
    290                 295                 300

Ser Arg Asp Asp Ile Val Trp Thr Tyr Ser Gly Val Arg Pro Leu Cys
305                 310                 315                 320

Asp Asp Glu Ser Asp Ser Pro Gln Ala Ile Thr Arg Asp Tyr Thr Leu
                325                 330                 335

Asp Ile His Asp Glu Asn Gly Lys Ala Pro Leu Leu Ser Val Phe Gly
            340                 345                 350

Gly Lys Leu Thr Thr Tyr Arg Lys Leu Ala Glu His Ala Leu Glu Lys
        355                 360                 365

Leu Thr Pro Tyr Tyr Gln Gly Ile Gly Pro Ala Trp Thr Lys Glu Ser
    370                 375                 380

Val Leu Pro Gly Gly Ala Ile Glu Gly Asp Arg Asp Asp Tyr Ala Ala
385                 390                 395                 400

Arg Leu Arg Arg Arg Tyr Pro Phe Leu Thr Glu Ser Leu Ala Arg His
                405                 410                 415

Tyr Ala Arg Thr Tyr Gly Ser Asn Ser Glu Leu Leu Leu Gly Asn Ala
            420                 425                 430

Gly Thr Val Ser Asp Leu Gly Glu Asp Phe Gly His Glu Phe Tyr Glu
        435                 440                 445

Ala Glu Leu Lys Tyr Leu Val Asp His Glu Trp Val Arg Arg Ala Asp
    450                 455                 460

Asp Ala Leu Trp Arg Arg Thr Lys Gln Gly Met Trp Leu Asn Ala Asp
465                 470                 475                 480

Gln Gln Ser Arg Val Ser Gln Trp Leu Val Glu Tyr Thr Gln Gln Arg
                485                 490                 495

Leu Ser Leu Ala Ser
            500


<210> SEQ ID NO 34
<211> LENGTH: 1071
<212> TYPE: DNA
<213> ORGANISM: Escherichia coli
<220> FEATURE:
<221> NAME/KEY: CDS
<222> LOCATION: (1)..(1071)

<400> SEQUENCE: 34

atg aaa aaa ttg atc aat gat gtg caa gac gta ctg gac gaa caa ctg      48
Met Lys Lys Leu Ile Asn Asp Val Gln Asp Val Leu Asp Glu Gln Leu
1               5                   10                  15

gca gga ctg gcg aaa gcg cat cca tcg ctg aca ctg cat cag gat ccg      96
Ala Gly Leu Ala Lys Ala His Pro Ser Leu Thr Leu His Gln Asp Pro
            20                  25                  30

gtg tat gtc acc cga gct gat gcc cct gtt gca gga aaa gtc gcc ctg     144
Val Tyr Val Thr Arg Ala Asp Ala Pro Val Ala Gly Lys Val Ala Leu
        35                  40                  45

ctg tcg ggt ggc ggc agc gga cac gag ccg atg cac tgt ggt tat atc     192
Leu Ser Gly Gly Gly Ser Gly His Glu Pro Met His Cys Gly Tyr Ile
    50                  55                  60

ggt cag ggg atg ctt tcg ggg gcc tgt ccg ggc gaa att ttc acc tca     240
Gly Gln Gly Met Leu Ser Gly Ala Cys Pro Gly Glu Ile Phe Thr Ser
65                  70                  75                  80

ccg acg ccc gat aaa atc ttt gaa tgc gcc atg caa gtt gat ggc ggc     288
Pro Thr Pro Asp Lys Ile Phe Glu Cys Ala Met Gln Val Asp Gly Gly
                85                  90                  95
```

```
gaa ggt gta ctg ttg att atc aaa aat tac acc ggc gat att ctt aac      336
Glu Gly Val Leu Leu Ile Ile Lys Asn Tyr Thr Gly Asp Ile Leu Asn
            100                 105                 110

ttt gaa aca gcg acc gag tta ctg cac gat agc ggc gta aaa gtg acc      384
Phe Glu Thr Ala Thr Glu Leu Leu His Asp Ser Gly Val Lys Val Thr
        115                 120                 125

act gtg gtc att gat gac gac gtt gcg gta aaa gac agt ctt tat act      432
Thr Val Val Ile Asp Asp Asp Val Ala Val Lys Asp Ser Leu Tyr Thr
    130                 135                 140

gcc ggg cga cgc ggc gtt gcc aac acc gta tta att gaa aaa ctc gta      480
Ala Gly Arg Arg Gly Val Ala Asn Thr Val Leu Ile Glu Lys Leu Val
145                 150                 155                 160

ggc gca gcg gcg gag cgt ggc gac tca ctg gac gcc tgt gcg gaa ctg      528
Gly Ala Ala Ala Glu Arg Gly Asp Ser Leu Asp Ala Cys Ala Glu Leu
                165                 170                 175

ggg cgt aag ctg aat aat caa ggc cac tca ata ggt atc gct ctc ggt      576
Gly Arg Lys Leu Asn Asn Gln Gly His Ser Ile Gly Ile Ala Leu Gly
            180                 185                 190

gcc tgt acc gtt cct gcc gcg ggc aaa cct tct ttt acc ctg gcg gat      624
Ala Cys Thr Val Pro Ala Ala Gly Lys Pro Ser Phe Thr Leu Ala Asp
        195                 200                 205

aat gag atg gag ttt ggc gtc ggc att cat ggt gag ccg ggt att gac      672
Asn Glu Met Glu Phe Gly Val Gly Ile His Gly Glu Pro Gly Ile Asp
    210                 215                 220

cgc cgc ccc ttc tct tcc ctt gat caa acc gtc gat gaa atg ttc gac      720
Arg Arg Pro Phe Ser Ser Leu Asp Gln Thr Val Asp Glu Met Phe Asp
225                 230                 235                 240

acc ctg ctg gta aat ggc tca tac cat cgc act ttg cgt ttc tgg gat      768
Thr Leu Leu Val Asn Gly Ser Tyr His Arg Thr Leu Arg Phe Trp Asp
                245                 250                 255

tat caa caa ggc agt tgg cag gaa gaa caa caa acc aaa caa ccg ctc      816
Tyr Gln Gln Gly Ser Trp Gln Glu Glu Gln Gln Thr Lys Gln Pro Leu
            260                 265                 270

cag tct ggc gat cgg gtg att gcg ctg gtt aac aat ctt ggc gca act      864
Gln Ser Gly Asp Arg Val Ile Ala Leu Val Asn Asn Leu Gly Ala Thr
        275                 280                 285

ccg ctt tct gag ctg tac ggc gtc tat aac cgc ctg acc aca cgt tgc      912
Pro Leu Ser Glu Leu Tyr Gly Val Tyr Asn Arg Leu Thr Thr Arg Cys
    290                 295                 300

cag caa gcg gga ttg act atc gaa cgt aat tta att ggc gcg tac tgc      960
Gln Gln Ala Gly Leu Thr Ile Glu Arg Asn Leu Ile Gly Ala Tyr Cys
305                 310                 315                 320

acc tca ctg gat atg acc ggt ttc tca atc acc tta ctg aaa gtt gat     1008
Thr Ser Leu Asp Met Thr Gly Phe Ser Ile Thr Leu Leu Lys Val Asp
                325                 330                 335

gac gaa acg ctg gca ctc tgg gac gcc ccg gtc cac acc ccg gcc ctt     1056
Asp Glu Thr Leu Ala Leu Trp Asp Ala Pro Val His Thr Pro Ala Leu
            340                 345                 350

aac tgg ggt aaa taa                                                 1071
Asn Trp Gly Lys
        355
```

<210> SEQ ID NO 35
<211> LENGTH: 356
<212> TYPE: PRT
<213> ORGANISM: Escherichia coli

<400> SEQUENCE: 35

```
Met Lys Lys Leu Ile Asn Asp Val Gln Asp Val Leu Asp Glu Gln Leu
1               5                   10                  15
```

```
Ala Gly Leu Ala Lys Ala His Pro Ser Leu Thr Leu His Gln Asp Pro
            20                  25                  30

Val Tyr Val Thr Arg Ala Asp Ala Pro Val Ala Gly Lys Val Ala Leu
        35                  40                  45

Leu Ser Gly Gly Gly Ser Gly His Glu Pro Met His Cys Gly Tyr Ile
    50                  55                  60

Gly Gln Gly Met Leu Ser Gly Ala Cys Pro Gly Glu Ile Phe Thr Ser
65                  70                  75                  80

Pro Thr Pro Asp Lys Ile Phe Glu Cys Ala Met Gln Val Asp Gly Gly
                85                  90                  95

Glu Gly Val Leu Leu Ile Ile Lys Asn Tyr Thr Gly Asp Ile Leu Asn
            100                 105                 110

Phe Glu Thr Ala Thr Glu Leu Leu His Asp Ser Gly Val Lys Val Thr
        115                 120                 125

Thr Val Val Ile Asp Asp Asp Val Ala Val Lys Asp Ser Leu Tyr Thr
    130                 135                 140

Ala Gly Arg Arg Gly Val Ala Asn Thr Val Leu Ile Glu Lys Leu Val
145                 150                 155                 160

Gly Ala Ala Ala Glu Arg Gly Asp Ser Leu Asp Ala Cys Ala Glu Leu
                165                 170                 175

Gly Arg Lys Leu Asn Asn Gln Gly His Ser Ile Gly Ile Ala Leu Gly
            180                 185                 190

Ala Cys Thr Val Pro Ala Ala Gly Lys Pro Ser Phe Thr Leu Ala Asp
        195                 200                 205

Asn Glu Met Glu Phe Gly Val Gly Ile His Gly Glu Pro Gly Ile Asp
    210                 215                 220

Arg Arg Pro Phe Ser Ser Leu Asp Gln Thr Val Asp Glu Met Phe Asp
225                 230                 235                 240

Thr Leu Leu Val Asn Gly Ser Tyr His Arg Thr Leu Arg Phe Trp Asp
                245                 250                 255

Tyr Gln Gln Gly Ser Trp Gln Glu Glu Gln Gln Thr Lys Gln Pro Leu
            260                 265                 270

Gln Ser Gly Asp Arg Val Ile Ala Leu Val Asn Asn Leu Gly Ala Thr
        275                 280                 285

Pro Leu Ser Glu Leu Tyr Gly Val Tyr Asn Arg Leu Thr Thr Arg Cys
    290                 295                 300

Gln Gln Ala Gly Leu Thr Ile Glu Arg Asn Leu Ile Gly Ala Tyr Cys
305                 310                 315                 320

Thr Ser Leu Asp Met Thr Gly Phe Ser Ile Thr Leu Leu Lys Val Asp
                325                 330                 335

Asp Glu Thr Leu Ala Leu Trp Asp Ala Pro Val His Thr Pro Ala Leu
            340                 345                 350

Asn Trp Gly Lys
        355


<210> SEQ ID NO 36
<211> LENGTH: 633
<212> TYPE: DNA
<213> ORGANISM: Escherichia coli
<220> FEATURE:
<221> NAME/KEY: CDS
<222> LOCATION: (1)..(633)

<400> SEQUENCE: 36

atg tca ctg agc aga act caa att gtt aac tgg ctc act cgt tgt ggc       48
Met Ser Leu Ser Arg Thr Gln Ile Val Asn Trp Leu Thr Arg Cys Gly
1               5                   10                  15
```

```
gat att ttc agc acc gag agc gag tat ctt acc gga ctg gat cgc gaa       96
Asp Ile Phe Ser Thr Glu Ser Glu Tyr Leu Thr Gly Leu Asp Arg Glu
            20                  25                  30

att ggc gat gct gac cac ggg cta aat atg aac cga ggc ttt agc aaa      144
Ile Gly Asp Ala Asp His Gly Leu Asn Met Asn Arg Gly Phe Ser Lys
        35                  40                  45

gtg gtg gaa aaa ctc cct gct atc gca gat aaa gat atc ggt ttc att      192
Val Val Glu Lys Leu Pro Ala Ile Ala Asp Lys Asp Ile Gly Phe Ile
    50                  55                  60

ctc aag aat acc ggt atg acg ctg ctt tcc agc gtc ggt ggt gcc agt      240
Leu Lys Asn Thr Gly Met Thr Leu Leu Ser Ser Val Gly Gly Ala Ser
65                  70                  75                  80

ggt ccg ctg ttc ggt acc ttc ttt atc cgc gcc gca cag gcg acc cag      288
Gly Pro Leu Phe Gly Thr Phe Phe Ile Arg Ala Ala Gln Ala Thr Gln
                85                  90                  95

gca cgg caa agc ctg aca ctg gaa gag ctt tat cag atg ttc cgc gat      336
Ala Arg Gln Ser Leu Thr Leu Glu Glu Leu Tyr Gln Met Phe Arg Asp
            100                 105                 110

ggc gcg gac ggc gta atc agt cgc ggg aaa gcc gaa cct ggc gat aaa      384
Gly Ala Asp Gly Val Ile Ser Arg Gly Lys Ala Glu Pro Gly Asp Lys
        115                 120                 125

acc atg tgt gat gtg tgg gtg ccg gtg gtg gaa tcg tta cgt cag tcc      432
Thr Met Cys Asp Val Trp Val Pro Val Val Glu Ser Leu Arg Gln Ser
    130                 135                 140

agc gag caa aat ctc tct gtt ccg gtg gcg ctc gaa gct gcc agt agc      480
Ser Glu Gln Asn Leu Ser Val Pro Val Ala Leu Glu Ala Ala Ser Ser
145                 150                 155                 160

atc gcc gaa tcc gct gca caa agt acg att acg atg caa gcc cgc aaa      528
Ile Ala Glu Ser Ala Ala Gln Ser Thr Ile Thr Met Gln Ala Arg Lys
                165                 170                 175

ggc cgc gcc agt tat ctc ggt gaa cgc agt att ggt cac cag gat ccc      576
Gly Arg Ala Ser Tyr Leu Gly Glu Arg Ser Ile Gly His Gln Asp Pro
            180                 185                 190

ggc gcg acc tcg gtg atg ttt atg atg caa atg ttg gcg tta gcc gca      624
Gly Ala Thr Ser Val Met Phe Met Met Gln Met Leu Ala Leu Ala Ala
        195                 200                 205

aaa gag taa                                                          633
Lys Glu
    210


<210> SEQ ID NO 37
<211> LENGTH: 210
<212> TYPE: PRT
<213> ORGANISM: Escherichia coli

<400> SEQUENCE: 37

Met Ser Leu Ser Arg Thr Gln Ile Val Asn Trp Leu Thr Arg Cys Gly
1               5                   10                  15

Asp Ile Phe Ser Thr Glu Ser Glu Tyr Leu Thr Gly Leu Asp Arg Glu
            20                  25                  30

Ile Gly Asp Ala Asp His Gly Leu Asn Met Asn Arg Gly Phe Ser Lys
        35                  40                  45

Val Val Glu Lys Leu Pro Ala Ile Ala Asp Lys Asp Ile Gly Phe Ile
    50                  55                  60

Leu Lys Asn Thr Gly Met Thr Leu Leu Ser Ser Val Gly Gly Ala Ser
65                  70                  75                  80

Gly Pro Leu Phe Gly Thr Phe Phe Ile Arg Ala Ala Gln Ala Thr Gln
                85                  90                  95

Ala Arg Gln Ser Leu Thr Leu Glu Glu Leu Tyr Gln Met Phe Arg Asp
```

```
            100                 105                 110

Gly Ala Asp Gly Val Ile Ser Arg Gly Lys Ala Glu Pro Gly Asp Lys
        115                 120                 125

Thr Met Cys Asp Val Trp Val Pro Val Val Glu Ser Leu Arg Gln Ser
    130                 135                 140

Ser Glu Gln Asn Leu Ser Val Pro Val Ala Leu Glu Ala Ala Ser Ser
145                 150                 155                 160

Ile Ala Glu Ser Ala Ala Gln Ser Thr Ile Thr Met Gln Ala Arg Lys
                165                 170                 175

Gly Arg Ala Ser Tyr Leu Gly Glu Arg Ser Ile Gly His Gln Asp Pro
            180                 185                 190

Gly Ala Thr Ser Val Met Phe Met Met Gln Met Leu Ala Leu Ala Ala
        195                 200                 205

Lys Glu
    210


<210> SEQ ID NO 38
<211> LENGTH: 1419
<212> TYPE: DNA
<213> ORGANISM: Escherichia coli
<220> FEATURE:
<221> NAME/KEY: CDS
<222> LOCATION: (1)..(1419)

<400> SEQUENCE: 38

atg gta aac ctg gtc ata gtt tca cat agc agc cga ctg gga gaa ggt      48
Met Val Asn Leu Val Ile Val Ser His Ser Ser Arg Leu Gly Glu Gly
1               5                   10                  15

gtc ggt gaa tta gcc cgt cag atg tta atg agt gat agt tgt aaa atc      96
Val Gly Glu Leu Ala Arg Gln Met Leu Met Ser Asp Ser Cys Lys Ile
            20                  25                  30

gcc att gcc gcg gga att gac gat cca caa aat ccc att ggt acc gat     144
Ala Ile Ala Ala Gly Ile Asp Asp Pro Gln Asn Pro Ile Gly Thr Asp
        35                  40                  45

gcc gtc aaa gtg atg gag gcc atc gaa tct gtt gct gat gcc gac cat     192
Ala Val Lys Val Met Glu Ala Ile Glu Ser Val Ala Asp Ala Asp His
    50                  55                  60

gtg ctg gtc atg atg gat atg ggt agc gca tta ttg agt gct gaa act     240
Val Leu Val Met Met Asp Met Gly Ser Ala Leu Leu Ser Ala Glu Thr
65                  70                  75                  80

gcg ctg gaa ttg ctg gct ccc gag atc gcc gca aaa gta cgt ttg tgt     288
Ala Leu Glu Leu Leu Ala Pro Glu Ile Ala Ala Lys Val Arg Leu Cys
                85                  90                  95

gct gcg ccg ttg gtc gaa ggt aca ctg gca gca acg gtc agc gcg gcc     336
Ala Ala Pro Leu Val Glu Gly Thr Leu Ala Ala Thr Val Ser Ala Ala
            100                 105                 110

tcg ggg gcg gat atc gac aaa gtt atc ttt gac gcc atg cat gcg ctg     384
Ser Gly Ala Asp Ile Asp Lys Val Ile Phe Asp Ala Met His Ala Leu
        115                 120                 125

gaa gcc aaa cgt gaa caa ctg ggt tta ccg tcc tcc gac act gaa atc     432
Glu Ala Lys Arg Glu Gln Leu Gly Leu Pro Ser Ser Asp Thr Glu Ile
    130                 135                 140

tct gac aca tgt cct gcg tac gat gaa gaa gcc cgt tct ctg gcg gtg     480
Ser Asp Thr Cys Pro Ala Tyr Asp Glu Glu Ala Arg Ser Leu Ala Val
145                 150                 155                 160

gtc ata aaa aac cgt aac ggc ctg cat gta cgt ccg gcc tcc cgg ctg     528
Val Ile Lys Asn Arg Asn Gly Leu His Val Arg Pro Ala Ser Arg Leu
                165                 170                 175

gtt tat acc tta tcg aca ttt aat gcc gat atg ttg ctg gaa aaa aac     576
Val Tyr Thr Leu Ser Thr Phe Asn Ala Asp Met Leu Leu Glu Lys Asn
```

```
            180                 185                 190

ggc aaa tgc gtc aca cca gag agt att aac cag att gcg tta cta caa      624
Gly Lys Cys Val Thr Pro Glu Ser Ile Asn Gln Ile Ala Leu Leu Gln
        195                 200                 205

gtt cgc tat aac gat acg ctg cgc ctg att gcg aaa ggg cca gaa gct      672
Val Arg Tyr Asn Asp Thr Leu Arg Leu Ile Ala Lys Gly Pro Glu Ala
    210                 215                 220

gaa gag gca ctg atc gct ttc cgt cag ctg gct gaa gat aac ttt ggt      720
Glu Glu Ala Leu Ile Ala Phe Arg Gln Leu Ala Glu Asp Asn Phe Gly
225                 230                 235                 240

gaa acg gag gaa gtc gct cca cct act ctg cgt ccc gtt ccg cct gtt      768
Glu Thr Glu Glu Val Ala Pro Pro Thr Leu Arg Pro Val Pro Pro Val
                245                 250                 255

tcg ggt aaa gcc ttt tat tat caa cca gtt tta tgt acg gta cag gca      816
Ser Gly Lys Ala Phe Tyr Tyr Gln Pro Val Leu Cys Thr Val Gln Ala
            260                 265                 270

aaa tca acc ctg acc gtg gaa gaa gaa caa gat cga tta cgc cag gct      864
Lys Ser Thr Leu Thr Val Glu Glu Glu Gln Asp Arg Leu Arg Gln Ala
        275                 280                 285

att gac ttc acg tta tta gat ctg atg acg tta aca gcg aaa gca gaa      912
Ile Asp Phe Thr Leu Leu Asp Leu Met Thr Leu Thr Ala Lys Ala Glu
    290                 295                 300

gcc agc ggg ctt gac gat att gcc gca atc ttt tct ggt cac cat aca      960
Ala Ser Gly Leu Asp Asp Ile Ala Ala Ile Phe Ser Gly His His Thr
305                 310                 315                 320

ctg tta gat gat ccg gaa ctg ctg gcg gcg gca agc gaa ctc ctt cag     1008
Leu Leu Asp Asp Pro Glu Leu Leu Ala Ala Ala Ser Glu Leu Leu Gln
                325                 330                 335

cat gaa cat tgc acg gca gaa tat gcc tgg cag caa gtt ctt aaa gaa     1056
His Glu His Cys Thr Ala Glu Tyr Ala Trp Gln Gln Val Leu Lys Glu
            340                 345                 350

ctt agc cag caa tac cag caa ctg gat gat gaa tat cta caa gct cgc     1104
Leu Ser Gln Gln Tyr Gln Gln Leu Asp Asp Glu Tyr Leu Gln Ala Arg
        355                 360                 365

tat att gat gtg gac gat ctt ctg cat cgc acc ctg gtc cac ctg acc     1152
Tyr Ile Asp Val Asp Asp Leu Leu His Arg Thr Leu Val His Leu Thr
    370                 375                 380

caa acg aaa gaa gaa ctc ccg cag ttt aac tcg cca act att cta ctg     1200
Gln Thr Lys Glu Glu Leu Pro Gln Phe Asn Ser Pro Thr Ile Leu Leu
385                 390                 395                 400

gcg gag aac att tat cct tcc aca gta ctg caa ctg gat ccg gcg gtt     1248
Ala Glu Asn Ile Tyr Pro Ser Thr Val Leu Gln Leu Asp Pro Ala Val
                405                 410                 415

gta aaa ggt atc tgc ctt agc gcc gga agt ccg gta tcc cac agc gcc     1296
Val Lys Gly Ile Cys Leu Ser Ala Gly Ser Pro Val Ser His Ser Ala
            420                 425                 430

cta atc gcc cgt gaa ctg ggg att ggc tgg att tgc cag cag ggt gag     1344
Leu Ile Ala Arg Glu Leu Gly Ile Gly Trp Ile Cys Gln Gln Gly Glu
        435                 440                 445

aaa ctg tat gcg ata caa cca gaa gaa acg cta acg ctg gac gtt aaa     1392
Lys Leu Tyr Ala Ile Gln Pro Glu Glu Thr Leu Thr Leu Asp Val Lys
    450                 455                 460

acg caa cgt ttc aac cgt cag ggt taa                                 1419
Thr Gln Arg Phe Asn Arg Gln Gly
465                 470

<210> SEQ ID NO 39
<211> LENGTH: 472
<212> TYPE: PRT
<213> ORGANISM: Escherichia coli
```

<400> SEQUENCE: 39

```
Met Val Asn Leu Val Ile Val Ser His Ser Ser Arg Leu Gly Glu Gly
1               5                   10                  15

Val Gly Glu Leu Ala Arg Gln Met Leu Met Ser Asp Ser Cys Lys Ile
            20                  25                  30

Ala Ile Ala Ala Gly Ile Asp Asp Pro Gln Asn Pro Ile Gly Thr Asp
        35                  40                  45

Ala Val Lys Val Met Glu Ala Ile Glu Ser Val Ala Asp Ala Asp His
    50                  55                  60

Val Leu Val Met Met Asp Met Gly Ser Ala Leu Leu Ser Ala Glu Thr
65                  70                  75                  80

Ala Leu Glu Leu Leu Ala Pro Glu Ile Ala Ala Lys Val Arg Leu Cys
                85                  90                  95

Ala Ala Pro Leu Val Glu Gly Thr Leu Ala Ala Thr Val Ser Ala Ala
            100                 105                 110

Ser Gly Ala Asp Ile Asp Lys Val Ile Phe Asp Ala Met His Ala Leu
        115                 120                 125

Glu Ala Lys Arg Glu Gln Leu Gly Leu Pro Ser Ser Asp Thr Glu Ile
    130                 135                 140

Ser Asp Thr Cys Pro Ala Tyr Asp Glu Glu Ala Arg Ser Leu Ala Val
145                 150                 155                 160

Val Ile Lys Asn Arg Asn Gly Leu His Val Arg Pro Ala Ser Arg Leu
                165                 170                 175

Val Tyr Thr Leu Ser Thr Phe Asn Ala Asp Met Leu Leu Glu Lys Asn
            180                 185                 190

Gly Lys Cys Val Thr Pro Glu Ser Ile Asn Gln Ile Ala Leu Leu Gln
        195                 200                 205

Val Arg Tyr Asn Asp Thr Leu Arg Leu Ile Ala Lys Gly Pro Glu Ala
    210                 215                 220

Glu Glu Ala Leu Ile Ala Phe Arg Gln Leu Ala Glu Asp Asn Phe Gly
225                 230                 235                 240

Glu Thr Glu Glu Val Ala Pro Pro Thr Leu Arg Pro Val Pro Pro Val
                245                 250                 255

Ser Gly Lys Ala Phe Tyr Tyr Gln Pro Val Leu Cys Thr Val Gln Ala
            260                 265                 270

Lys Ser Thr Leu Thr Val Glu Glu Glu Gln Asp Arg Leu Arg Gln Ala
        275                 280                 285

Ile Asp Phe Thr Leu Leu Asp Leu Met Thr Leu Thr Ala Lys Ala Glu
    290                 295                 300

Ala Ser Gly Leu Asp Asp Ile Ala Ala Ile Phe Ser Gly His His Thr
305                 310                 315                 320

Leu Leu Asp Asp Pro Glu Leu Leu Ala Ala Ala Ser Glu Leu Leu Gln
                325                 330                 335

His Glu His Cys Thr Ala Glu Tyr Ala Trp Gln Gln Val Leu Lys Glu
            340                 345                 350

Leu Ser Gln Gln Tyr Gln Gln Leu Asp Asp Glu Tyr Leu Gln Ala Arg
        355                 360                 365

Tyr Ile Asp Val Asp Asp Leu Leu His Arg Thr Leu Val His Leu Thr
    370                 375                 380

Gln Thr Lys Glu Glu Leu Pro Gln Phe Asn Ser Pro Thr Ile Leu Leu
385                 390                 395                 400

Ala Glu Asn Ile Tyr Pro Ser Thr Val Leu Gln Leu Asp Pro Ala Val
                405                 410                 415
```

```
Val Lys Gly Ile Cys Leu Ser Ala Gly Ser Pro Val Ser His Ser Ala
            420                 425                 430

Leu Ile Ala Arg Glu Leu Gly Ile Gly Trp Ile Cys Gln Gln Gly Glu
        435                 440                 445

Lys Leu Tyr Ala Ile Gln Pro Glu Glu Thr Leu Thr Leu Asp Val Lys
    450                 455                 460

Thr Gln Arg Phe Asn Arg Gln Gly
465                 470


<210> SEQ ID NO 40
<211> LENGTH: 1776
<212> TYPE: DNA
<213> ORGANISM: Schizosaccharomyces pombe
<220> FEATURE:
<221> NAME/KEY: CDS
<222> LOCATION: (1)..(1776)

<400> SEQUENCE: 40

atg tct gta aaa caa ttt gta tct gaa gga cat ata gta cgc cca tac       48
Met Ser Val Lys Gln Phe Val Ser Glu Gly His Ile Val Arg Pro Tyr
1               5                   10                  15

ttg ctt gga ctt gct aga agt aac cct ggc cta act gtt att gaa cat       96
Leu Leu Gly Leu Ala Arg Ser Asn Pro Gly Leu Thr Val Ile Glu His
            20                  25                  30

gat cgt gta att tac agg aca gcc tct gcc ccg ggt tct ggt gat ccg      144
Asp Arg Val Ile Tyr Arg Thr Ala Ser Ala Pro Gly Ser Gly Asp Pro
        35                  40                  45

cct aaa gta act tta gtg tct ggt ggt ggt agt ggg cac gag cct aca      192
Pro Lys Val Thr Leu Val Ser Gly Gly Gly Ser Gly His Glu Pro Thr
    50                  55                  60

cat gct ggt ttt gtt ggt gat gga gcc ttg gac gcc gta gct tgt gga      240
His Ala Gly Phe Val Gly Asp Gly Ala Leu Asp Ala Val Ala Cys Gly
65                  70                  75                  80

gac att ttt gct tct ccc tct act aaa caa att tac tct gct ctc aaa      288
Asp Ile Phe Ala Ser Pro Ser Thr Lys Gln Ile Tyr Ser Ala Leu Lys
                85                  90                  95

gct gtt gca tct cct aag gga act tta att att gtc aaa aat tac aca      336
Ala Val Ala Ser Pro Lys Gly Thr Leu Ile Ile Val Lys Asn Tyr Thr
            100                 105                 110

ggt gat att att cat ttt ggc ttg gca gct gag aga gcc aag gca gct      384
Gly Asp Ile Ile His Phe Gly Leu Ala Ala Glu Arg Ala Lys Ala Ala
        115                 120                 125

gga atg aac gtt gag ctt gtt gcc gta gga gat gat gtt tct gta ggc      432
Gly Met Asn Val Glu Leu Val Ala Val Gly Asp Asp Val Ser Val Gly
    130                 135                 140

aaa aag aga ggt gca ctc gta gga cga aga ggt tta gga gcc act gtg      480
Lys Lys Arg Gly Ala Leu Val Gly Arg Arg Gly Leu Gly Ala Thr Val
145                 150                 155                 160

cta gta cac aaa att gcg gga tct gca gca gca tta gga ctg gat ctg      528
Leu Val His Lys Ile Ala Gly Ser Ala Ala Ala Leu Gly Leu Asp Leu
                165                 170                 175

cat caa gtt gct caa gtg gcc caa tca gtg att gac aat gct gct acc      576
His Gln Val Ala Gln Val Ala Gln Ser Val Ile Asp Asn Ala Ala Thr
            180                 185                 190

ata gca gct tca ttg gat cac tgc gcc gtt ccc ggt cgc aaa ttt gaa      624
Ile Ala Ala Ser Leu Asp His Cys Ala Val Pro Gly Arg Lys Phe Glu
        195                 200                 205

aca aac ttg ggt cca gac gag tat gag att gga atg ggt att cat aac      672
Thr Asn Leu Gly Pro Asp Glu Tyr Glu Ile Gly Met Gly Ile His Asn
    210                 215                 220

gag cct gga acc ttc aaa tca tca cca ctt cca tct att ccc gag cta      720
```

```
Glu Pro Gly Thr Phe Lys Ser Ser Pro Leu Pro Ser Ile Pro Glu Leu
225                 230                 235                 240

gtt aca gag atg ctt tcg att ttg ttt ggt gag aaa aac ccg gac aat      768
Val Thr Glu Met Leu Ser Ile Leu Phe Gly Glu Lys Asn Pro Asp Asn
                245                 250                 255

agt ttc gta gag ttt tct tca aaa gac gat gtt att ctt cta gta aac      816
Ser Phe Val Glu Phe Ser Ser Lys Asp Asp Val Ile Leu Leu Val Asn
            260                 265                 270

aat atg ggt ggt atg tcc aac tta gag ttg gga tat gct act gaa gta      864
Asn Met Gly Gly Met Ser Asn Leu Glu Leu Gly Tyr Ala Thr Glu Val
        275                 280                 285

gtt tcg gaa caa tta gcc aaa cga ggt atc att cct aaa aga acc atg      912
Val Ser Glu Gln Leu Ala Lys Arg Gly Ile Ile Pro Lys Arg Thr Met
    290                 295                 300

tct ggt act ttt gta acc gca ttg aac gga ccg ggt ttt gga att aca      960
Ser Gly Thr Phe Val Thr Ala Leu Asn Gly Pro Gly Phe Gly Ile Thr
305                 310                 315                 320

ttg gtc aat gct tct aag gct act cca gat att ttc aaa tat ttt gac     1008
Leu Val Asn Ala Ser Lys Ala Thr Pro Asp Ile Phe Lys Tyr Phe Asp
                325                 330                 335

ttg cca aca act gct agt gga tgg aac gtt tct tat cat aac gca aag     1056
Leu Pro Thr Thr Ala Ser Gly Trp Asn Val Ser Tyr His Asn Ala Lys
            340                 345                 350

gac tgg gag gtt ttg gct gac ggc aag gtg cca aca gct ccc gct ttg     1104
Asp Trp Glu Val Leu Ala Asp Gly Lys Val Pro Thr Ala Pro Ala Leu
        355                 360                 365

gag cat acc cgt aat gag aag cac agc ggt gta aag gct gac cca aag     1152
Glu His Thr Arg Asn Glu Lys His Ser Gly Val Lys Ala Asp Pro Lys
    370                 375                 380

atg ttt act aaa att tta aaa gct gcc gtt gac gct atc aat gaa ttt     1200
Met Phe Thr Lys Ile Leu Lys Ala Ala Val Asp Ala Ile Asn Glu Phe
385                 390                 395                 400

gag cca aag aca act tgg tac gat acg att gca gga gat ggt gat tgt     1248
Glu Pro Lys Thr Thr Trp Tyr Asp Thr Ile Ala Gly Asp Gly Asp Cys
                405                 410                 415

gga aca acc ctt gtg aat ggt gga gag gcc atc ata aag gct att aat     1296
Gly Thr Thr Leu Val Asn Gly Gly Glu Ala Ile Ile Lys Ala Ile Asn
            420                 425                 430

gat aaa tca att cga ttg gat gat ggt gta aat ggt att gac gat ttg     1344
Asp Lys Ser Ile Arg Leu Asp Asp Gly Val Asn Gly Ile Asp Asp Leu
        435                 440                 445

gcc tat att gtt gag gat tcg atg gga ggt aca tcg ggt ggt ctt tac     1392
Ala Tyr Ile Val Glu Asp Ser Met Gly Gly Thr Ser Gly Gly Leu Tyr
    450                 455                 460

tcg att tat ttg tct gcg cta gcc aaa gga gtt cgt gag tca ggc gat     1440
Ser Ile Tyr Leu Ser Ala Leu Ala Lys Gly Val Arg Glu Ser Gly Asp
465                 470                 475                 480

tcc gaa tta tcc gtg cat acg ttt gcg ttt gca agc aag tat gca ctt     1488
Ser Glu Leu Ser Val His Thr Phe Ala Phe Ala Ser Lys Tyr Ala Leu
                485                 490                 495

gac gct ctt ttc aaa tac act agg gcc cgt aaa gga ttc cgt act ctg     1536
Asp Ala Leu Phe Lys Tyr Thr Arg Ala Arg Lys Gly Phe Arg Thr Leu
            500                 505                 510

atc gat gct att caa cca ttt gtt gaa act tta aat gaa ggt aag gga     1584
Ile Asp Ala Ile Gln Pro Phe Val Glu Thr Leu Asn Glu Gly Lys Gly
        515                 520                 525

ctt gat gct gct gcg aaa gct gcc acg gaa ggt tct gaa caa act aga     1632
Leu Asp Ala Ala Ala Lys Ala Ala Thr Glu Gly Ser Glu Gln Thr Arg
    530                 535                 540

aaa atg gat gct gtc gtt gga aga gcg tct tat gtt gct aaa gag gaa     1680
```

```
Lys Met Asp Ala Val Val Gly Arg Ala Ser Tyr Val Ala Lys Glu Glu
545                 550                 555                 560

ctt cat aag ctt gat agt gag gga ggc tta ccg gat cct ggt gcc ttt      1728
Leu His Lys Leu Asp Ser Glu Gly Gly Leu Pro Asp Pro Gly Ala Phe
                565                 570                 575

gcg tta gcg gcg atc ttg aaa gca att gtt gag gct agt gaa cat taa      1776
Ala Leu Ala Ala Ile Leu Lys Ala Ile Val Glu Ala Ser Glu His
            580                 585                 590


<210> SEQ ID NO 41
<211> LENGTH: 591
<212> TYPE: PRT
<213> ORGANISM: Schizosaccharomyces pombe

<400> SEQUENCE: 41

Met Ser Val Lys Gln Phe Val Ser Glu Gly His Ile Val Arg Pro Tyr
1               5                   10                  15

Leu Leu Gly Leu Ala Arg Ser Asn Pro Gly Leu Thr Val Ile Glu His
            20                  25                  30

Asp Arg Val Ile Tyr Arg Thr Ala Ser Ala Pro Gly Ser Gly Asp Pro
        35                  40                  45

Pro Lys Val Thr Leu Val Ser Gly Gly Gly Ser Gly His Glu Pro Thr
    50                  55                  60

His Ala Gly Phe Val Gly Asp Gly Ala Leu Asp Ala Val Ala Cys Gly
65                  70                  75                  80

Asp Ile Phe Ala Ser Pro Ser Thr Lys Gln Ile Tyr Ser Ala Leu Lys
                85                  90                  95

Ala Val Ala Ser Pro Lys Gly Thr Leu Ile Ile Val Lys Asn Tyr Thr
            100                 105                 110

Gly Asp Ile Ile His Phe Gly Leu Ala Ala Glu Arg Ala Lys Ala Ala
        115                 120                 125

Gly Met Asn Val Glu Leu Val Ala Val Gly Asp Asp Val Ser Val Gly
    130                 135                 140

Lys Lys Arg Gly Ala Leu Val Gly Arg Arg Gly Leu Gly Ala Thr Val
145                 150                 155                 160

Leu Val His Lys Ile Ala Gly Ser Ala Ala Ala Leu Gly Leu Asp Leu
                165                 170                 175

His Gln Val Ala Gln Val Ala Gln Ser Val Ile Asp Asn Ala Ala Thr
            180                 185                 190

Ile Ala Ala Ser Leu Asp His Cys Ala Val Pro Gly Arg Lys Phe Glu
        195                 200                 205

Thr Asn Leu Gly Pro Asp Glu Tyr Glu Ile Gly Met Gly Ile His Asn
    210                 215                 220

Glu Pro Gly Thr Phe Lys Ser Ser Pro Leu Pro Ser Ile Pro Glu Leu
225                 230                 235                 240

Val Thr Glu Met Leu Ser Ile Leu Phe Gly Glu Lys Asn Pro Asp Asn
                245                 250                 255

Ser Phe Val Glu Phe Ser Ser Lys Asp Asp Val Ile Leu Leu Val Asn
            260                 265                 270

Asn Met Gly Gly Met Ser Asn Leu Glu Leu Gly Tyr Ala Thr Glu Val
        275                 280                 285

Val Ser Glu Gln Leu Ala Lys Arg Gly Ile Ile Pro Lys Arg Thr Met
    290                 295                 300

Ser Gly Thr Phe Val Thr Ala Leu Asn Gly Pro Gly Phe Gly Ile Thr
305                 310                 315                 320

Leu Val Asn Ala Ser Lys Ala Thr Pro Asp Ile Phe Lys Tyr Phe Asp
```

```
                325                 330                 335

Leu Pro Thr Thr Ala Ser Gly Trp Asn Val Ser Tyr His Asn Ala Lys
            340                 345                 350

Asp Trp Glu Val Leu Ala Asp Gly Lys Val Pro Thr Ala Pro Ala Leu
        355                 360                 365

Glu His Thr Arg Asn Glu Lys His Ser Gly Val Lys Ala Asp Pro Lys
    370                 375                 380

Met Phe Thr Lys Ile Leu Lys Ala Ala Val Asp Ala Ile Asn Glu Phe
385                 390                 395                 400

Glu Pro Lys Thr Thr Trp Tyr Asp Thr Ile Ala Gly Asp Gly Asp Cys
                405                 410                 415

Gly Thr Thr Leu Val Asn Gly Gly Glu Ala Ile Ile Lys Ala Ile Asn
            420                 425                 430

Asp Lys Ser Ile Arg Leu Asp Asp Gly Val Asn Gly Ile Asp Asp Leu
        435                 440                 445

Ala Tyr Ile Val Glu Asp Ser Met Gly Gly Thr Ser Gly Gly Leu Tyr
    450                 455                 460

Ser Ile Tyr Leu Ser Ala Leu Ala Lys Gly Val Arg Glu Ser Gly Asp
465                 470                 475                 480

Ser Glu Leu Ser Val His Thr Phe Ala Phe Ala Ser Lys Tyr Ala Leu
                485                 490                 495

Asp Ala Leu Phe Lys Tyr Thr Arg Ala Arg Lys Gly Phe Arg Thr Leu
            500                 505                 510

Ile Asp Ala Ile Gln Pro Phe Val Glu Thr Leu Asn Glu Gly Lys Gly
        515                 520                 525

Leu Asp Ala Ala Ala Lys Ala Ala Thr Glu Gly Ser Glu Gln Thr Arg
    530                 535                 540

Lys Met Asp Ala Val Val Gly Arg Ala Ser Tyr Val Ala Lys Glu Glu
545                 550                 555                 560

Leu His Lys Leu Asp Ser Glu Gly Gly Leu Pro Asp Pro Gly Ala Phe
                565                 570                 575

Ala Leu Ala Ala Ile Leu Lys Ala Ile Val Glu Ala Ser Glu His
            580                 585                 590


<210> SEQ ID NO 42
<211> LENGTH: 1830
<212> TYPE: DNA
<213> ORGANISM: Pichia angusta
<220> FEATURE:
<221> NAME/KEY: CDS
<222> LOCATION: (1)..(1830)

<400> SEQUENCE: 42

atg tcg agc aaa cac tgg aat tac aag caa gac ctg gtc cat gcg cac       48
Met Ser Ser Lys His Trp Asn Tyr Lys Gln Asp Leu Val His Ala His
1               5                   10                  15

ctc aaa ggc ctg tgt cat gcc aat cca gac ctc caa ttc atc gaa tcc       96
Leu Lys Gly Leu Cys His Ala Asn Pro Asp Leu Gln Phe Ile Glu Ser
            20                  25                  30

gag cgt gtg gtg atc aac aag cac tcc aag ccc gac aag gtg atg atc      144
Glu Arg Val Val Ile Asn Lys His Ser Lys Pro Asp Lys Val Met Ile
        35                  40                  45

cta tct ggt gga ggg tct ggc cac gag cca ttg cac gct ggc ttt gtt      192
Leu Ser Gly Gly Gly Ser Gly His Glu Pro Leu His Ala Gly Phe Val
    50                  55                  60

ggt gaa ggc tgt ttg gac gtt gga gtg gct ggt ttt gtt ttc gcc tcg      240
Gly Glu Gly Cys Leu Asp Val Gly Val Ala Gly Phe Val Phe Ala Ser
65                  70                  75                  80
```

```
ccc tct aca aag cag att gtt tca ggt ttg aag gca aag ccc tca gac      288
Pro Ser Thr Lys Gln Ile Val Ser Gly Leu Lys Ala Lys Pro Ser Asp
                85                  90                  95

aaa ggt acg cta att gtg gtg aaa aat tac acc ggc gac att ctt cac      336
Lys Gly Thr Leu Ile Val Val Lys Asn Tyr Thr Gly Asp Ile Leu His
            100                 105                 110

ttt ggg ctt gct gca gag cgg gcc aag gcc gaa ggc gtc ccc gtg gag      384
Phe Gly Leu Ala Ala Glu Arg Ala Lys Ala Glu Gly Val Pro Val Glu
        115                 120                 125

ctg cta att gtc cag gac gac gtt tct gtg ggc aga acc aag aac gga      432
Leu Leu Ile Val Gln Asp Asp Val Ser Val Gly Arg Thr Lys Asn Gly
    130                 135                 140

atg gtg ggc aga cgc ggt ctg gcc ggt acg agt ctg gtg cac aag att      480
Met Val Gly Arg Arg Gly Leu Ala Gly Thr Ser Leu Val His Lys Ile
145                 150                 155                 160

gtc ggt gcc aag gcc gcc aag gac tcg aac aaa gcc tcg ttg agc gag      528
Val Gly Ala Lys Ala Ala Lys Asp Ser Asn Lys Ala Ser Leu Ser Glu
                165                 170                 175

gtg tac cag ctg ggc gag gcc gtg gtg gcc aat ctg gtg acc atc ggc      576
Val Tyr Gln Leu Gly Glu Ala Val Val Ala Asn Leu Val Thr Ile Gly
            180                 185                 190

gcg tcg ctc gac cac tgc aca att ccg ggt aac aga cac cac gag tcc      624
Ala Ser Leu Asp His Cys Thr Ile Pro Gly Asn Arg His His Glu Ser
        195                 200                 205

gag tcc gac gac gag gac gag cag aaa cat ctg ctc aag gag gac gag      672
Glu Ser Asp Asp Glu Asp Glu Gln Lys His Leu Leu Lys Glu Asp Glu
    210                 215                 220

atc gag gtg ggt atg ggg atc cac aac gag tcg ggc atc aag cgc gtt      720
Ile Glu Val Gly Met Gly Ile His Asn Glu Ser Gly Ile Lys Arg Val
225                 230                 235                 240

tcg cca atc ccg acc atc gac acg ctt gtg gca gac ctg ctc aag tac      768
Ser Pro Ile Pro Thr Ile Asp Thr Leu Val Ala Asp Leu Leu Lys Tyr
                245                 250                 255

ttg ctc gac aag agc gac gag gag aga cac tat gtg gac ttc gac tcg      816
Leu Leu Asp Lys Ser Asp Glu Glu Arg His Tyr Val Asp Phe Asp Ser
            260                 265                 270

tcg gac gag gtt gtg ctg atg atc aac aat ttg ggc ggc acg tcg aac      864
Ser Asp Glu Val Val Leu Met Ile Asn Asn Leu Gly Gly Thr Ser Asn
        275                 280                 285

ctc gag ctg tac gct atc cag aac act gtt gtt gag cag ctg gct acc      912
Leu Glu Leu Tyr Ala Ile Gln Asn Thr Val Val Glu Gln Leu Ala Thr
    290                 295                 300

gac tac aag atc aag ccc gca aga gtg tac acg ggc gcg tac acc acg      960
Asp Tyr Lys Ile Lys Pro Ala Arg Val Tyr Thr Gly Ala Tyr Thr Thr
305                 310                 315                 320

tcg cta gac ggt cct ggt ttt tcc atc acg ttg ctg aac gtg act cgg     1008
Ser Leu Asp Gly Pro Gly Phe Ser Ile Thr Leu Leu Asn Val Thr Arg
                325                 330                 335

gcg ggg ggc aag gag gtt ttc gat tgt ctg gac tac cca acc aag gtt     1056
Ala Gly Gly Lys Glu Val Phe Asp Cys Leu Asp Tyr Pro Thr Lys Val
            340                 345                 350

cct ggg tgg aac tcg tcg tac aca acg gca gaa tgg gcg gcg aaa tcc     1104
Pro Gly Trp Asn Ser Ser Tyr Thr Thr Ala Glu Trp Ala Ala Lys Ser
        355                 360                 365

gag tcg ttc gtc atc gac gct ccg cca gtg agc gac gcg tcg gcg acc     1152
Glu Ser Phe Val Ile Asp Ala Pro Pro Val Ser Asp Ala Ser Ala Thr
    370                 375                 380

tcg aaa gtg cgg ttc tca agc agc aca gtc aag gct gtg ttg gag agc     1200
Ser Lys Val Arg Phe Ser Ser Ser Thr Val Lys Ala Val Leu Glu Ser
385                 390                 395                 400
```

```
gga tgc aag aag ttg ctg acc aag gag cca aag atc acg ctg tac gac     1248
Gly Cys Lys Lys Leu Leu Thr Lys Glu Pro Lys Ile Thr Leu Tyr Asp
                405                 410                 415

acg gtt gcg ggc gac ggc gac tgc ggc gag acg ctg gcc aac ggc gcg     1296
Thr Val Ala Gly Asp Gly Asp Cys Gly Glu Thr Leu Ala Asn Gly Ala
            420                 425                 430

cac gcg atc ctg gac ctg ctg gct gcc gac aag ctg gag atc acc gac     1344
His Ala Ile Leu Asp Leu Leu Ala Ala Asp Lys Leu Glu Ile Thr Asp
        435                 440                 445

ggt gtc cgg agt ctg acg cag atc act gac gtc gtc gaa acg gct atg     1392
Gly Val Arg Ser Leu Thr Gln Ile Thr Asp Val Val Glu Thr Ala Met
    450                 455                 460

gga ggc acc tct ggt ggg ctt tac tcg atc ttt atc tct gca ctc gcc     1440
Gly Gly Thr Ser Gly Gly Leu Tyr Ser Ile Phe Ile Ser Ala Leu Ala
465                 470                 475                 480

aag tcg ttg aag gac aga gag ctc cag cag ggc gga tac gag gtg acg     1488
Lys Ser Leu Lys Asp Arg Glu Leu Gln Gln Gly Gly Tyr Glu Val Thr
                485                 490                 495

ccg cag atc ctg gct gca tcg ctc aag gac gcc ctg gag tcg ctg tac     1536
Pro Gln Ile Leu Ala Ala Ser Leu Lys Asp Ala Leu Glu Ser Leu Tyr
            500                 505                 510

aga tac aca cgg gcc cgt gct ggc gac cgg act ctg atc gac gcg ctt     1584
Arg Tyr Thr Arg Ala Arg Ala Gly Asp Arg Thr Leu Ile Asp Ala Leu
        515                 520                 525

gcg ccg ttt gtg gag cag ttt gcg gcc agc aag ggt gac ctc aac cag     1632
Ala Pro Phe Val Glu Gln Phe Ala Ala Ser Lys Gly Asp Leu Asn Gln
    530                 535                 540

gct aac aag gcg tgc cac gag gga gca gag tca acg cga aag ctc aag     1680
Ala Asn Lys Ala Cys His Glu Gly Ala Glu Ser Thr Arg Lys Leu Lys
545                 550                 555                 560

gct aag ttt ggc cgc gcg tcc tac gtc agc gag gag gag ttc aag ccg     1728
Ala Lys Phe Gly Arg Ala Ser Tyr Val Ser Glu Glu Glu Phe Lys Pro
                565                 570                 575

ttt gag gcc gag ggc ggg ctg ccg gat ccc ggc gcc atc ggg ctt gct     1776
Phe Glu Ala Glu Gly Gly Leu Pro Asp Pro Gly Ala Ile Gly Leu Ala
            580                 585                 590

gcg ctg gtc gac ggt ttt gcc gag gcg tac agc aaa ata ggc tcc aac     1824
Ala Leu Val Asp Gly Phe Ala Glu Ala Tyr Ser Lys Ile Gly Ser Asn
        595                 600                 605

ttg tag                                                             1830
Leu


<210> SEQ ID NO 43
<211> LENGTH: 609
<212> TYPE: PRT
<213> ORGANISM: Pichia angusta

<400> SEQUENCE: 43

Met Ser Ser Lys His Trp Asn Tyr Lys Gln Asp Leu Val His Ala His
1               5                   10                  15

Leu Lys Gly Leu Cys His Ala Asn Pro Asp Leu Gln Phe Ile Glu Ser
            20                  25                  30

Glu Arg Val Val Ile Asn Lys His Ser Lys Pro Asp Lys Val Met Ile
        35                  40                  45

Leu Ser Gly Gly Gly Ser Gly His Glu Pro Leu His Ala Gly Phe Val
    50                  55                  60

Gly Glu Gly Cys Leu Asp Val Gly Val Ala Gly Phe Val Phe Ala Ser
65                  70                  75                  80

Pro Ser Thr Lys Gln Ile Val Ser Gly Leu Lys Ala Lys Pro Ser Asp
```

```
                85                  90                  95

Lys Gly Thr Leu Ile Val Val Lys Asn Tyr Thr Gly Asp Ile Leu His
            100                 105                 110

Phe Gly Leu Ala Ala Glu Arg Ala Lys Ala Glu Gly Val Pro Val Glu
        115                 120                 125

Leu Leu Ile Val Gln Asp Asp Val Ser Val Gly Arg Thr Lys Asn Gly
    130                 135                 140

Met Val Gly Arg Arg Gly Leu Ala Gly Thr Ser Leu Val His Lys Ile
145                 150                 155                 160

Val Gly Ala Lys Ala Ala Lys Asp Ser Asn Lys Ala Ser Leu Ser Glu
                165                 170                 175

Val Tyr Gln Leu Gly Glu Ala Val Val Ala Asn Leu Val Thr Ile Gly
            180                 185                 190

Ala Ser Leu Asp His Cys Thr Ile Pro Gly Asn Arg His His Glu Ser
        195                 200                 205

Glu Ser Asp Asp Glu Asp Glu Gln Lys His Leu Leu Lys Glu Asp Glu
    210                 215                 220

Ile Glu Val Gly Met Gly Ile His Asn Glu Ser Gly Ile Lys Arg Val
225                 230                 235                 240

Ser Pro Ile Pro Thr Ile Asp Thr Leu Val Ala Asp Leu Leu Lys Tyr
                245                 250                 255

Leu Leu Asp Lys Ser Asp Glu Glu Arg His Tyr Val Asp Phe Asp Ser
            260                 265                 270

Ser Asp Glu Val Val Leu Met Ile Asn Asn Leu Gly Gly Thr Ser Asn
        275                 280                 285

Leu Glu Leu Tyr Ala Ile Gln Asn Thr Val Val Glu Gln Leu Ala Thr
    290                 295                 300

Asp Tyr Lys Ile Lys Pro Ala Arg Val Tyr Thr Gly Ala Tyr Thr Thr
305                 310                 315                 320

Ser Leu Asp Gly Pro Gly Phe Ser Ile Thr Leu Leu Asn Val Thr Arg
                325                 330                 335

Ala Gly Gly Lys Glu Val Phe Asp Cys Leu Asp Tyr Pro Thr Lys Val
            340                 345                 350

Pro Gly Trp Asn Ser Ser Tyr Thr Thr Ala Glu Trp Ala Ala Lys Ser
        355                 360                 365

Glu Ser Phe Val Ile Asp Ala Pro Pro Val Ser Asp Ala Ser Ala Thr
    370                 375                 380

Ser Lys Val Arg Phe Ser Ser Ser Thr Val Lys Ala Val Leu Glu Ser
385                 390                 395                 400

Gly Cys Lys Lys Leu Leu Thr Lys Glu Pro Lys Ile Thr Leu Tyr Asp
                405                 410                 415

Thr Val Ala Gly Asp Gly Asp Cys Gly Glu Thr Leu Ala Asn Gly Ala
            420                 425                 430

His Ala Ile Leu Asp Leu Leu Ala Ala Asp Lys Leu Glu Ile Thr Asp
        435                 440                 445

Gly Val Arg Ser Leu Thr Gln Ile Thr Asp Val Val Glu Thr Ala Met
    450                 455                 460

Gly Gly Thr Ser Gly Gly Leu Tyr Ser Ile Phe Ile Ser Ala Leu Ala
465                 470                 475                 480

Lys Ser Leu Lys Asp Arg Glu Leu Gln Gln Gly Gly Tyr Glu Val Thr
                485                 490                 495

Pro Gln Ile Leu Ala Ala Ser Leu Lys Asp Ala Leu Glu Ser Leu Tyr
            500                 505                 510
```

```
Arg Tyr Thr Arg Ala Arg Ala Gly Asp Arg Thr Leu Ile Asp Ala Leu
        515                 520                 525

Ala Pro Phe Val Glu Gln Phe Ala Ala Ser Lys Gly Asp Leu Asn Gln
    530                 535                 540

Ala Asn Lys Ala Cys His Glu Gly Ala Glu Ser Thr Arg Lys Leu Lys
545                 550                 555                 560

Ala Lys Phe Gly Arg Ala Ser Tyr Val Ser Glu Glu Glu Phe Lys Pro
                565                 570                 575

Phe Glu Ala Glu Gly Gly Leu Pro Asp Pro Gly Ala Ile Gly Leu Ala
            580                 585                 590

Ala Leu Val Asp Gly Phe Ala Glu Ala Tyr Ser Lys Ile Gly Ser Asn
        595                 600                 605

Leu


<210> SEQ ID NO 44
<211> LENGTH: 1827
<212> TYPE: DNA
<213> ORGANISM: Pichia pastoris
<220> FEATURE:
<221> NAME/KEY: CDS
<222> LOCATION: (1)..(1827)

<400> SEQUENCE: 44

atg tct agt aaa cat tgg gat tac aag aaa gat ctg gta ctc agc cat       48
Met Ser Ser Lys His Trp Asp Tyr Lys Lys Asp Leu Val Leu Ser His
1               5                   10                  15

ctg gct gga tta tgt cag tcc aac ccc cat gta agg cta att gag tcc       96
Leu Ala Gly Leu Cys Gln Ser Asn Pro His Val Arg Leu Ile Glu Ser
            20                  25                  30

gaa aga gtc gtc atc tcc gcc gag aac cag gag gac aag att acc ttg      144
Glu Arg Val Val Ile Ser Ala Glu Asn Gln Glu Asp Lys Ile Thr Leu
        35                  40                  45

atc tct ggt gga ggt tca gga cac gag cct cta cat gct ggc ttt gtc      192
Ile Ser Gly Gly Gly Ser Gly His Glu Pro Leu His Ala Gly Phe Val
    50                  55                  60

acc aag gac ggt ctt ttg gat gcc gct gtg gcc ggg ttc atc ttt gcc      240
Thr Lys Asp Gly Leu Leu Asp Ala Ala Val Ala Gly Phe Ile Phe Ala
65                  70                  75                  80

tcg cca tct act aaa cag ata ttt agc gca atc aaa gcc aaa cct tcg      288
Ser Pro Ser Thr Lys Gln Ile Phe Ser Ala Ile Lys Ala Lys Pro Ser
                85                  90                  95

aag aag gga act ttg atc atc gtc aag aac tat aca gga gac att ctt      336
Lys Lys Gly Thr Leu Ile Ile Val Lys Asn Tyr Thr Gly Asp Ile Leu
            100                 105                 110

cac ttc ggt ctt gcc gcc gaa aag gcc aag gcc gaa ggt ctc aac gca      384
His Phe Gly Leu Ala Ala Glu Lys Ala Lys Ala Glu Gly Leu Asn Ala
        115                 120                 125

gaa ctg ctg att gtt cag gac gat gtc tct gtt ggt aaa gcc aag aat      432
Glu Leu Leu Ile Val Gln Asp Asp Val Ser Val Gly Lys Ala Lys Asn
    130                 135                 140

ggc ctg gta ggg cgt aga ggt ttg gct gga act tct tta gtg cac aag      480
Gly Leu Val Gly Arg Arg Gly Leu Ala Gly Thr Ser Leu Val His Lys
145                 150                 155                 160

att ttg ggt gcc aaa gct tat tta caa aag gac aac ctg gaa ttg cat      528
Ile Leu Gly Ala Lys Ala Tyr Leu Gln Lys Asp Asn Leu Glu Leu His
                165                 170                 175

cag ctg gtc act ttc ggt gag aag gtc gtt gcc aac ctg gtt aca att      576
Gln Leu Val Thr Phe Gly Glu Lys Val Val Ala Asn Leu Val Thr Ile
            180                 185                 190

ggt gct tcc ttg gac cat gtc acc att cca gcc aga gca aac aaa cag      624
```

-continued

```
Gly Ala Ser Leu Asp His Val Thr Ile Pro Ala Arg Ala Asn Lys Gln
        195                 200                 205

gag gaa gat gat tca gat gac gag cac ggc tac gaa gtg cta aag cac      672
Glu Glu Asp Asp Ser Asp Asp Glu His Gly Tyr Glu Val Leu Lys His
    210                 215                 220

gat gaa ttt gaa atc gga atg ggt att cac aac gaa cca ggt atc aag      720
Asp Glu Phe Glu Ile Gly Met Gly Ile His Asn Glu Pro Gly Ile Lys
225                 230                 235                 240

aag tcg tcg cca att cca aca gta gac gaa ttg gtg gct gag cta ctg      768
Lys Ser Ser Pro Ile Pro Thr Val Asp Glu Leu Val Ala Glu Leu Leu
                245                 250                 255

gag tac ctt ctt tcg act acc gat aag gac cga aat tac gtc caa ttt      816
Glu Tyr Leu Leu Ser Thr Thr Asp Lys Asp Arg Asn Tyr Val Gln Phe
            260                 265                 270

gac aag aat gat gaa gtt gtg cta ctg atc aat aac ttg gga gga acc      864
Asp Lys Asn Asp Glu Val Val Leu Leu Ile Asn Asn Leu Gly Gly Thr
        275                 280                 285

tca gtg ttg gaa ttg tac gct att cag aac att gtt gtc gac caa ctg      912
Ser Val Leu Glu Leu Tyr Ala Ile Gln Asn Ile Val Val Asp Gln Leu
    290                 295                 300

gcc tcc aaa tat tcc att aaa cca gtc cgc att ttc act ggc act ttc      960
Ala Ser Lys Tyr Ser Ile Lys Pro Val Arg Ile Phe Thr Gly Thr Phe
305                 310                 315                 320

acc aca tca ctg gat ggg ccc ggt ttt tct atc act tta ttg aat gct     1008
Thr Thr Ser Leu Asp Gly Pro Gly Phe Ser Ile Thr Leu Leu Asn Ala
                325                 330                 335

acc aag aca gga gat aaa gat atc cta aag ttt tta gac cac aag act     1056
Thr Lys Thr Gly Asp Lys Asp Ile Leu Lys Phe Leu Asp His Lys Thr
            340                 345                 350

agt gcc cct ggc tgg aac tcc aac ata tca gac tgg tct ggc agg gtt     1104
Ser Ala Pro Gly Trp Asn Ser Asn Ile Ser Asp Trp Ser Gly Arg Val
        355                 360                 365

gac aat ttt att gtg gct gcc cca gaa ata gac gaa gga gac agt tca     1152
Asp Asn Phe Ile Val Ala Ala Pro Glu Ile Asp Glu Gly Asp Ser Ser
    370                 375                 380

tct aag gta tct gtt gat gct aag ctg tat gct gac ctt ctg gag tct     1200
Ser Lys Val Ser Val Asp Ala Lys Leu Tyr Ala Asp Leu Leu Glu Ser
385                 390                 395                 400

ggt gtg aag aag gtc att tca aaa gag cca aag atc aca ttg tat gac     1248
Gly Val Lys Lys Val Ile Ser Lys Glu Pro Lys Ile Thr Leu Tyr Asp
                405                 410                 415

act gtt gca gga gat ggt gat tgt ggt gaa acg ttg gcg aat ggt tcc     1296
Thr Val Ala Gly Asp Gly Asp Cys Gly Glu Thr Leu Ala Asn Gly Ser
            420                 425                 430

aat gcc att tta aag gct ctg gct gaa gga aag ctt gat ctc aaa gac     1344
Asn Ala Ile Leu Lys Ala Leu Ala Glu Gly Lys Leu Asp Leu Lys Asp
        435                 440                 445

ggt gtt aaa tca ctg gtg caa att aca gac atc gtg gaa act gcc atg     1392
Gly Val Lys Ser Leu Val Gln Ile Thr Asp Ile Val Glu Thr Ala Met
    450                 455                 460

ggt gga aca tct gga ggt ctg tac tcc att ttc atc agc gct tta gca     1440
Gly Gly Thr Ser Gly Gly Leu Tyr Ser Ile Phe Ile Ser Ala Leu Ala
465                 470                 475                 480

aag tct ttg aaa gag aag gaa ctt tcc gag ggt gcc tac aca ctg acc     1488
Lys Ser Leu Lys Glu Lys Glu Leu Ser Glu Gly Ala Tyr Thr Leu Thr
                485                 490                 495

ctt gaa acg atc tct gga tcc tta cag gca gca ctt cag tct cta ttc     1536
Leu Glu Thr Ile Ser Gly Ser Leu Gln Ala Ala Leu Gln Ser Leu Phe
            500                 505                 510

aaa tac aca aga gca cgt act gga gac aga act ctt att gac gct ttg     1584
```

```
Lys Tyr Thr Arg Ala Arg Thr Gly Asp Arg Thr Leu Ile Asp Ala Leu
        515                 520                 525

gag cca ttt gta aag gaa ttc gcc aag tct aag gat ctg aaa ctt gca     1632
Glu Pro Phe Val Lys Glu Phe Ala Lys Ser Lys Asp Leu Lys Leu Ala
    530                 535                 540

aac aaa gct gcc cat gat ggt gct gaa gcc aca aga aag ctc gaa gcc     1680
Asn Lys Ala Ala His Asp Gly Ala Glu Ala Thr Arg Lys Leu Glu Ala
545                 550                 555                 560

aag ttt gga aga gca tct tat gtt gcc gaa gaa gag ttc aaa caa ttc     1728
Lys Phe Gly Arg Ala Ser Tyr Val Ala Glu Glu Glu Phe Lys Gln Phe
                565                 570                 575

gaa agt gaa ggt gga cta cct gat cct ggt gct att ggt ctt gcc gct     1776
Glu Ser Glu Gly Gly Leu Pro Asp Pro Gly Ala Ile Gly Leu Ala Ala
            580                 585                 590

ttg att tca gga att act gat gca tac ttc aaa tct gaa acc aag ttg     1824
Leu Ile Ser Gly Ile Thr Asp Ala Tyr Phe Lys Ser Glu Thr Lys Leu
        595                 600                 605

tag                                                                 1827


<210> SEQ ID NO 45
<211> LENGTH: 608
<212> TYPE: PRT
<213> ORGANISM: Pichia pastoris

<400> SEQUENCE: 45

Met Ser Ser Lys His Trp Asp Tyr Lys Lys Asp Leu Val Leu Ser His
1               5                   10                  15

Leu Ala Gly Leu Cys Gln Ser Asn Pro His Val Arg Leu Ile Glu Ser
            20                  25                  30

Glu Arg Val Val Ile Ser Ala Glu Asn Gln Glu Asp Lys Ile Thr Leu
        35                  40                  45

Ile Ser Gly Gly Gly Ser Gly His Glu Pro Leu His Ala Gly Phe Val
    50                  55                  60

Thr Lys Asp Gly Leu Leu Asp Ala Ala Val Ala Gly Phe Ile Phe Ala
65                  70                  75                  80

Ser Pro Ser Thr Lys Gln Ile Phe Ser Ala Ile Lys Ala Lys Pro Ser
                85                  90                  95

Lys Lys Gly Thr Leu Ile Ile Val Lys Asn Tyr Thr Gly Asp Ile Leu
            100                 105                 110

His Phe Gly Leu Ala Ala Glu Lys Ala Lys Ala Glu Gly Leu Asn Ala
        115                 120                 125

Glu Leu Leu Ile Val Gln Asp Asp Val Ser Val Gly Lys Ala Lys Asn
    130                 135                 140

Gly Leu Val Gly Arg Arg Gly Leu Ala Gly Thr Ser Leu Val His Lys
145                 150                 155                 160

Ile Leu Gly Ala Lys Ala Tyr Leu Gln Lys Asp Asn Leu Glu Leu His
                165                 170                 175

Gln Leu Val Thr Phe Gly Glu Lys Val Val Ala Asn Leu Val Thr Ile
            180                 185                 190

Gly Ala Ser Leu Asp His Val Thr Ile Pro Ala Arg Ala Asn Lys Gln
        195                 200                 205

Glu Glu Asp Asp Ser Asp Asp Glu His Gly Tyr Glu Val Leu Lys His
    210                 215                 220

Asp Glu Phe Glu Ile Gly Met Gly Ile His Asn Glu Pro Gly Ile Lys
225                 230                 235                 240

Lys Ser Ser Pro Ile Pro Thr Val Asp Glu Leu Val Ala Glu Leu Leu
                245                 250                 255
```

```
Glu Tyr Leu Leu Ser Thr Thr Asp Lys Asp Arg Asn Tyr Val Gln Phe
            260                 265                 270

Asp Lys Asn Asp Glu Val Val Leu Leu Ile Asn Asn Leu Gly Gly Thr
        275                 280                 285

Ser Val Leu Glu Leu Tyr Ala Ile Gln Asn Ile Val Val Asp Gln Leu
    290                 295                 300

Ala Ser Lys Tyr Ser Ile Lys Pro Val Arg Ile Phe Thr Gly Thr Phe
305                 310                 315                 320

Thr Thr Ser Leu Asp Gly Pro Gly Phe Ser Ile Thr Leu Leu Asn Ala
                325                 330                 335

Thr Lys Thr Gly Asp Lys Asp Ile Leu Lys Phe Leu Asp His Lys Thr
            340                 345                 350

Ser Ala Pro Gly Trp Asn Ser Asn Ile Ser Asp Trp Ser Gly Arg Val
        355                 360                 365

Asp Asn Phe Ile Val Ala Ala Pro Glu Ile Asp Glu Gly Asp Ser Ser
    370                 375                 380

Ser Lys Val Ser Val Asp Ala Lys Leu Tyr Ala Asp Leu Leu Glu Ser
385                 390                 395                 400

Gly Val Lys Lys Val Ile Ser Lys Glu Pro Lys Ile Thr Leu Tyr Asp
                405                 410                 415

Thr Val Ala Gly Asp Gly Asp Cys Gly Glu Thr Leu Ala Asn Gly Ser
            420                 425                 430

Asn Ala Ile Leu Lys Ala Leu Ala Glu Gly Lys Leu Asp Leu Lys Asp
        435                 440                 445

Gly Val Lys Ser Leu Val Gln Ile Thr Asp Ile Val Glu Thr Ala Met
    450                 455                 460

Gly Gly Thr Ser Gly Gly Leu Tyr Ser Ile Phe Ile Ser Ala Leu Ala
465                 470                 475                 480

Lys Ser Leu Lys Glu Lys Glu Leu Ser Glu Gly Ala Tyr Thr Leu Thr
                485                 490                 495

Leu Glu Thr Ile Ser Gly Ser Leu Gln Ala Ala Leu Gln Ser Leu Phe
            500                 505                 510

Lys Tyr Thr Arg Ala Arg Thr Gly Asp Arg Thr Leu Ile Asp Ala Leu
        515                 520                 525

Glu Pro Phe Val Lys Glu Phe Ala Lys Ser Lys Asp Leu Lys Leu Ala
    530                 535                 540

Asn Lys Ala Ala His Asp Gly Ala Glu Ala Thr Arg Lys Leu Glu Ala
545                 550                 555                 560

Lys Phe Gly Arg Ala Ser Tyr Val Ala Glu Glu Glu Phe Lys Gln Phe
                565                 570                 575

Glu Ser Glu Gly Gly Leu Pro Asp Pro Gly Ala Ile Gly Leu Ala Ala
            580                 585                 590

Leu Ile Ser Gly Ile Thr Asp Ala Tyr Phe Lys Ser Glu Thr Lys Leu
        595                 600                 605
```

<210> SEQ ID NO 46
<211> LENGTH: 1824
<212> TYPE: DNA
<213> ORGANISM: Debaryomyces hansenii
<220> FEATURE:
<221> NAME/KEY: CDS
<222> LOCATION: (1)..(1824)

<400> SEQUENCE: 46

```
atg tcg tta gct aaa cac tgg gga tac tca aag gat ttg gtt ttg gaa      48
Met Ser Leu Ala Lys His Trp Gly Tyr Ser Lys Asp Leu Val Leu Glu
```

```
1               5                   10                  15

aat tta aag ggt ttg gct gct gca aac ccc aaa att tct ctt ata cca       96
Asn Leu Lys Gly Leu Ala Ala Ala Asn Pro Lys Ile Ser Leu Ile Pro
            20                  25                  30

gca gaa aaa aca gtc gtg tat aat gat tcc tta caa tct aaa gga aac      144
Ala Glu Lys Thr Val Val Tyr Asn Asp Ser Leu Gln Ser Lys Gly Asn
        35                  40                  45

aag aat att aat cgt ata atg gtt att tct gga gga ggt tca ggc cat      192
Lys Asn Ile Asn Arg Ile Met Val Ile Ser Gly Gly Gly Ser Gly His
    50                  55                  60

gaa ccg tta cat gcg gga ttt gtt ggt gta aat gca tta gat gct gct      240
Glu Pro Leu His Ala Gly Phe Val Gly Val Asn Ala Leu Asp Ala Ala
65                  70                  75                  80

gta tct ggt tca ata ttt gcc tcc cct tca gcc aag cag att ttt gca      288
Val Ser Gly Ser Ile Phe Ala Ser Pro Ser Ala Lys Gln Ile Phe Ala
                85                  90                  95

gcc att aag tca att agc tcc aaa caa aac aat tct aaa ggt act ttg      336
Ala Ile Lys Ser Ile Ser Ser Lys Gln Asn Asn Ser Lys Gly Thr Leu
            100                 105                 110

gta att gtc aaa aat tat aca gga gat gtt cta cat ttt gga ctt gct      384
Val Ile Val Lys Asn Tyr Thr Gly Asp Val Leu His Phe Gly Leu Ala
        115                 120                 125

gtc gaa aga gca aaa gca cat ggc tac aaa ata gac atg ata att gtt      432
Val Glu Arg Ala Lys Ala His Gly Tyr Lys Ile Asp Met Ile Ile Val
    130                 135                 140

ggt gat gac gca gct gta ggt agg tca aag ggt gga atg gtt gga aga      480
Gly Asp Asp Ala Ala Val Gly Arg Ser Lys Gly Gly Met Val Gly Arg
145                 150                 155                 160

aga gca ttg gca gcc act gca ttg gtt cac aaa att gtt gga tct gct      528
Arg Ala Leu Ala Ala Thr Ala Leu Val His Lys Ile Val Gly Ser Ala
                165                 170                 175

gct tct gaa att gaa gat cta agc aga ctt aaa ata ttg ggt gat tcc      576
Ala Ser Glu Ile Glu Asp Leu Ser Arg Leu Lys Ile Leu Gly Asp Ser
            180                 185                 190

gtt gcg aat aat acg gtg acc att ggt gcc acc tta gat cat tgc tct      624
Val Ala Asn Asn Thr Val Thr Ile Gly Ala Thr Leu Asp His Cys Ser
        195                 200                 205

gtt cct ggg cgt gat att gca aac ttt gag cct att ggc cag aat gat      672
Val Pro Gly Arg Asp Ile Ala Asn Phe Glu Pro Ile Gly Gln Asn Asp
    210                 215                 220

gct gaa ata ggt cta ggg ata cat aac gaa act tcg gtc aag aag gta      720
Ala Glu Ile Gly Leu Gly Ile His Asn Glu Thr Ser Val Lys Lys Val
225                 230                 235                 240

aac cct gta cca atg ata gac tca tta gtt cag gac tta tta gaa ttc      768
Asn Pro Val Pro Met Ile Asp Ser Leu Val Gln Asp Leu Leu Glu Phe
                245                 250                 255

cta tta aac gaa aat gac aaa gat cgt tac ttt gta cca ttt gat ctc      816
Leu Leu Asn Glu Asn Asp Lys Asp Arg Tyr Phe Val Pro Phe Asp Leu
            260                 265                 270

agt aat gat gaa acg gtc ttg ctt gtc aac aat ctc ggg ggt aca tct      864
Ser Asn Asp Glu Thr Val Leu Leu Val Asn Asn Leu Gly Gly Thr Ser
        275                 280                 285

act tta gaa atg tat gct att aca aat tgc gtt atc gaa aca tta tac      912
Thr Leu Glu Met Tyr Ala Ile Thr Asn Cys Val Ile Glu Thr Leu Tyr
    290                 295                 300

caa caa tac agt ttg aga cca aaa aaa gtg ata gtg gga gaa ttt gct      960
Gln Gln Tyr Ser Leu Arg Pro Lys Lys Val Ile Val Gly Glu Phe Ala
305                 310                 315                 320

acg tct tta aat gcc cct ggg ttt tcg att acc tta ctt aac gtc tct     1008
Thr Ser Leu Asn Ala Pro Gly Phe Ser Ile Thr Leu Leu Asn Val Ser
```

```
                325                 330                 335

tgt gca tct aaa caa tcc caa att tcc att tca cat ata atg agt tac      1056
Cys Ala Ser Lys Gln Ser Gln Ile Ser Ile Ser His Ile Met Ser Tyr
            340                 345                 350

ttg gat ttg cca aca gat gcc cct ggt tgg aag gca cat ccg tgt ggg      1104
Leu Asp Leu Pro Thr Asp Ala Pro Gly Trp Lys Ala His Pro Cys Gly
        355                 360                 365

ttt gga ctt gaa aga gac atc aat att gag aca tca atc aat ggt att      1152
Phe Gly Leu Glu Arg Asp Ile Asn Ile Glu Thr Ser Ile Asn Gly Ile
    370                 375                 380

gat tct ttt gtc aag tca caa tta aag ctt tcc aga gaa caa cag acg      1200
Asp Ser Phe Val Lys Ser Gln Leu Lys Leu Ser Arg Glu Gln Gln Thr
385                 390                 395                 400

gac ttt aga agc agt cta gtt aat ggg ttg gaa aaa tta tta gac aaa      1248
Asp Phe Arg Ser Ser Leu Val Asn Gly Leu Glu Lys Leu Leu Asp Lys
                405                 410                 415

gaa cca agc att aca ttt tat gat act gtt gct ggt gat ggt gac tgt      1296
Glu Pro Ser Ile Thr Phe Tyr Asp Thr Val Ala Gly Asp Gly Asp Cys
            420                 425                 430

ggt gaa acc tta gcg tct ggt gca aat gga ata ttg gaa tca tta agg      1344
Gly Glu Thr Leu Ala Ser Gly Ala Asn Gly Ile Leu Glu Ser Leu Arg
        435                 440                 445

aac aac gaa atc tgc ttt gaa gat cca gtt tat tcc ata tct caa ata      1392
Asn Asn Glu Ile Cys Phe Glu Asp Pro Val Tyr Ser Ile Ser Gln Ile
    450                 455                 460

gca aac att gta gag gat aaa atg ggc gga act tca gga ggc tta tat      1440
Ala Asn Ile Val Glu Asp Lys Met Gly Gly Thr Ser Gly Gly Leu Tyr
465                 470                 475                 480

tca att ttc tta acc tcg ttg ata aaa cac ctt caa gat tgt act aca      1488
Ser Ile Phe Leu Thr Ser Leu Ile Lys His Leu Gln Asp Cys Thr Thr
                485                 490                 495

ttg aac tta tgt gaa atg ttt gct agt tct ttg cat aat gcg cta tat      1536
Leu Asn Leu Cys Glu Met Phe Ala Ser Ser Leu His Asn Ala Leu Tyr
            500                 505                 510

cag ggc tta tat aaa tac act agg gca cga gtg ggt gga aga act ttg      1584
Gln Gly Leu Tyr Lys Tyr Thr Arg Ala Arg Val Gly Gly Arg Thr Leu
        515                 520                 525

att gat gct tta gag ccg ttt gtg aat acc ttc aac gac act cta aat      1632
Ile Asp Ala Leu Glu Pro Phe Val Asn Thr Phe Asn Asp Thr Leu Asn
    530                 535                 540

ttc tca aag gct gcc cag gct gct atc gat gga tct gaa tcg act agg      1680
Phe Ser Lys Ala Ala Gln Ala Ala Ile Asp Gly Ser Glu Ser Thr Arg
545                 550                 555                 560

aaa tta gct gca aaa ttt ggg aga gcg tct tat gtc aat gaa caa gaa      1728
Lys Leu Ala Ala Lys Phe Gly Arg Ala Ser Tyr Val Asn Glu Gln Glu
                565                 570                 575

ttt aaa cag ttc gac gaa gaa gga ggc tta ccg gat ccg gga gct att      1776
Phe Lys Gln Phe Asp Glu Glu Gly Gly Leu Pro Asp Pro Gly Ala Ile
            580                 585                 590

gga tta gcc acc tta att gct ggg ttt gcc ggt gtt gac tat aat taa      1824
Gly Leu Ala Thr Leu Ile Ala Gly Phe Ala Gly Val Asp Tyr Asn
        595                 600                 605


<210> SEQ ID NO 47
<211> LENGTH: 607
<212> TYPE: PRT
<213> ORGANISM: Debaryomyces hansenii

<400> SEQUENCE: 47

Met Ser Leu Ala Lys His Trp Gly Tyr Ser Lys Asp Leu Val Leu Glu
1               5                   10                  15
```

```
Asn Leu Lys Gly Leu Ala Ala Ala Asn Pro Lys Ile Ser Leu Ile Pro
            20                  25                  30

Ala Glu Lys Thr Val Val Tyr Asn Asp Ser Leu Gln Ser Lys Gly Asn
        35                  40                  45

Lys Asn Ile Asn Arg Ile Met Val Ile Ser Gly Gly Gly Ser Gly His
    50                  55                  60

Glu Pro Leu His Ala Gly Phe Val Gly Val Asn Ala Leu Asp Ala Ala
65                  70                  75                  80

Val Ser Gly Ser Ile Phe Ala Ser Pro Ser Ala Lys Gln Ile Phe Ala
                85                  90                  95

Ala Ile Lys Ser Ile Ser Ser Lys Gln Asn Asn Ser Lys Gly Thr Leu
            100                 105                 110

Val Ile Val Lys Asn Tyr Thr Gly Asp Val Leu His Phe Gly Leu Ala
        115                 120                 125

Val Glu Arg Ala Lys Ala His Gly Tyr Lys Ile Asp Met Ile Ile Val
    130                 135                 140

Gly Asp Asp Ala Ala Val Gly Arg Ser Lys Gly Gly Met Val Gly Arg
145                 150                 155                 160

Arg Ala Leu Ala Ala Thr Ala Leu Val His Lys Ile Val Gly Ser Ala
                165                 170                 175

Ala Ser Glu Ile Glu Asp Leu Ser Arg Leu Lys Ile Leu Gly Asp Ser
            180                 185                 190

Val Ala Asn Asn Thr Val Thr Ile Gly Ala Thr Leu Asp His Cys Ser
        195                 200                 205

Val Pro Gly Arg Asp Ile Ala Asn Phe Glu Pro Ile Gly Gln Asn Asp
    210                 215                 220

Ala Glu Ile Gly Leu Gly Ile His Asn Glu Thr Ser Val Lys Lys Val
225                 230                 235                 240

Asn Pro Val Pro Met Ile Asp Ser Leu Val Gln Asp Leu Leu Glu Phe
                245                 250                 255

Leu Leu Asn Glu Asn Asp Lys Asp Arg Tyr Phe Val Pro Phe Asp Leu
            260                 265                 270

Ser Asn Asp Glu Thr Val Leu Leu Val Asn Asn Leu Gly Gly Thr Ser
        275                 280                 285

Thr Leu Glu Met Tyr Ala Ile Thr Asn Cys Val Ile Glu Thr Leu Tyr
    290                 295                 300

Gln Gln Tyr Ser Leu Arg Pro Lys Lys Val Ile Val Gly Glu Phe Ala
305                 310                 315                 320

Thr Ser Leu Asn Ala Pro Gly Phe Ser Ile Thr Leu Leu Asn Val Ser
                325                 330                 335

Cys Ala Ser Lys Gln Ser Gln Ile Ser Ile Ser His Ile Met Ser Tyr
            340                 345                 350

Leu Asp Leu Pro Thr Asp Ala Pro Gly Trp Lys Ala His Pro Cys Gly
        355                 360                 365

Phe Gly Leu Glu Arg Asp Ile Asn Ile Glu Thr Ser Ile Asn Gly Ile
    370                 375                 380

Asp Ser Phe Val Lys Ser Gln Leu Lys Leu Ser Arg Glu Gln Gln Thr
385                 390                 395                 400

Asp Phe Arg Ser Ser Leu Val Asn Gly Leu Glu Lys Leu Leu Asp Lys
                405                 410                 415

Glu Pro Ser Ile Thr Phe Tyr Asp Thr Val Ala Gly Asp Gly Asp Cys
            420                 425                 430

Gly Glu Thr Leu Ala Ser Gly Ala Asn Gly Ile Leu Glu Ser Leu Arg
```

```
        435                 440                 445

Asn Asn Glu Ile Cys Phe Glu Asp Pro Val Tyr Ser Ile Ser Gln Ile
    450                 455                 460

Ala Asn Ile Val Glu Asp Lys Met Gly Gly Thr Ser Gly Gly Leu Tyr
465                 470                 475                 480

Ser Ile Phe Leu Thr Ser Leu Ile Lys His Leu Gln Asp Cys Thr Thr
                485                 490                 495

Leu Asn Leu Cys Glu Met Phe Ala Ser Ser Leu His Asn Ala Leu Tyr
            500                 505                 510

Gln Gly Leu Tyr Lys Tyr Thr Arg Ala Arg Val Gly Gly Arg Thr Leu
        515                 520                 525

Ile Asp Ala Leu Glu Pro Phe Val Asn Thr Phe Asn Asp Thr Leu Asn
    530                 535                 540

Phe Ser Lys Ala Ala Gln Ala Ala Ile Asp Gly Ser Glu Ser Thr Arg
545                 550                 555                 560

Lys Leu Ala Ala Lys Phe Gly Arg Ala Ser Tyr Val Asn Glu Gln Glu
                565                 570                 575

Phe Lys Gln Phe Asp Glu Glu Gly Gly Leu Pro Asp Pro Gly Ala Ile
            580                 585                 590

Gly Leu Ala Thr Leu Ile Ala Gly Phe Ala Gly Val Asp Tyr Asn
        595                 600                 605


<210> SEQ ID NO 48
<211> LENGTH: 1752
<212> TYPE: DNA
<213> ORGANISM: Escherichia blattae
<220> FEATURE:
<221> NAME/KEY: CDS
<222> LOCATION: (1)..(1752)

<400> SEQUENCE: 48

atg gtc tgc ccg cca gac ctt aac tca caa cct ttt act tcc cga cac       48
Met Val Cys Pro Pro Asp Leu Asn Ser Gln Pro Phe Thr Ser Arg His
1               5                   10                  15

acg cgc tac agc ccg ctg tac ggg tgt gtt gta cct aac gat cag gaa       96
Thr Arg Tyr Ser Pro Leu Tyr Gly Cys Val Val Pro Asn Asp Gln Glu
            20                  25                  30

acc gtt atg tcg caa ttt ttt tat aac caa cgc gaa aat ctt gtc agt      144
Thr Val Met Ser Gln Phe Phe Tyr Asn Gln Arg Glu Asn Leu Val Ser
        35                  40                  45

gac gcc atc gaa ggg gca atg att gcc agc ccg tgg aac aac ctg gcc      192
Asp Ala Ile Glu Gly Ala Met Ile Ala Ser Pro Trp Asn Asn Leu Ala
    50                  55                  60

cgt ctg gag agc gat ccc gcc atc cgc atc gtg gtg cgc cgg gat ctg      240
Arg Leu Glu Ser Asp Pro Ala Ile Arg Ile Val Val Arg Arg Asp Leu
65                  70                  75                  80

gat aaa tcc cgg gtg gcg gtg atc tcc ggg ggc ggt gcc ggt cac gaa      288
Asp Lys Ser Arg Val Ala Val Ile Ser Gly Gly Gly Ala Gly His Glu
                85                  90                  95

ccg gcc cat gtg ggc ttt gtg ggt aaa ggc atg ctg acc gcc gcc gtg      336
Pro Ala His Val Gly Phe Val Gly Lys Gly Met Leu Thr Ala Ala Val
            100                 105                 110

tgt ggt gat ctg ttt gcc tca ccg agc gtg gat gcg gtg ctt acc gcc      384
Cys Gly Asp Leu Phe Ala Ser Pro Ser Val Asp Ala Val Leu Thr Ala
        115                 120                 125

att cag gcg gtc acc ggc gag gcg ggc tgc ctg ctg att gtc aaa aac      432
Ile Gln Ala Val Thr Gly Glu Ala Gly Cys Leu Leu Ile Val Lys Asn
    130                 135                 140

tac acc ggt gac cgg ctg aac ttc ggg ctg gca gca gag aaa gcc cgg      480
```

```
Tyr Thr Gly Asp Arg Leu Asn Phe Gly Leu Ala Ala Glu Lys Ala Arg
145                 150                 155                 160

cgc atg ggc tac aaa gtg gac atg gtg att gtg ggg gat gat atc tca      528
Arg Met Gly Tyr Lys Val Asp Met Val Ile Val Gly Asp Asp Ile Ser
                165                 170                 175

ctg ccg gag aac aaa cac ccg cgc ggc att gcc ggg acg att atg atc      576
Leu Pro Glu Asn Lys His Pro Arg Gly Ile Ala Gly Thr Ile Met Ile
            180                 185                 190

cac aaa gtg gcg ggg tac ttc gcc gaa acc ggc tgc aac ctg gac acg      624
His Lys Val Ala Gly Tyr Phe Ala Glu Thr Gly Cys Asn Leu Asp Thr
        195                 200                 205

gtc gcc cgg gaa gcc cgg ctg gca atg gag cgg gta ttc agt att ggc      672
Val Ala Arg Glu Ala Arg Leu Ala Met Glu Arg Val Phe Ser Ile Gly
    210                 215                 220

gtg gcc ctt tcc agc tgc cac tta ccg gcc gat ccg cag gat ggc gtg      720
Val Ala Leu Ser Ser Cys His Leu Pro Ala Asp Pro Gln Asp Gly Val
225                 230                 235                 240

cgc cat cac ccg ggc cag gct gag ctg ggc atg ggg atc cac ggg gag      768
Arg His His Pro Gly Gln Ala Glu Leu Gly Met Gly Ile His Gly Glu
                245                 250                 255

ccc ggc gca agc gtc atc gac acc cag aac agc acc gac att gtg cgc      816
Pro Gly Ala Ser Val Ile Asp Thr Gln Asn Ser Thr Asp Ile Val Arg
            260                 265                 270

ctg atg gtg gca aaa atc cgc gct gcc ctg cct gaa acc ggc cgc ctg      864
Leu Met Val Ala Lys Ile Arg Ala Ala Leu Pro Glu Thr Gly Arg Leu
        275                 280                 285

ctg ctg atg ctg aat aac ctt ggc ggc gtc tca gtc acc gaa atg gcg      912
Leu Leu Met Leu Asn Asn Leu Gly Gly Val Ser Val Thr Glu Met Ala
    290                 295                 300

atc ctc acc cgg gag ctg gcc cac tgt gag ctt gcc acc cgc acc gac      960
Ile Leu Thr Arg Glu Leu Ala His Cys Glu Leu Ala Thr Arg Thr Asp
305                 310                 315                 320

tgg ttg atg ggc ccg gca ccg ctg gtc agc gcc ctg gac atg aaa ggc     1008
Trp Leu Met Gly Pro Ala Pro Leu Val Ser Ala Leu Asp Met Lys Gly
                325                 330                 335

ttt tcc atc acc gcc ctg gtc atg gaa gag agc att gaa aaa gcc ctg     1056
Phe Ser Ile Thr Ala Leu Val Met Glu Glu Ser Ile Glu Lys Ala Leu
            340                 345                 350

ctg gca gac gtg gaa acc gca ggc tgg ctg ccg cca gtg cgc ctg cgc     1104
Leu Ala Asp Val Glu Thr Ala Gly Trp Leu Pro Pro Val Arg Leu Arg
        355                 360                 365

gcc agc cag acc cag ccc tgc aat atc cgc agt gcc cgg gtg gca ttc     1152
Ala Ser Gln Thr Gln Pro Cys Asn Ile Arg Ser Ala Arg Val Ala Phe
    370                 375                 380

acc ccg tca gac aac ccg gta gtg ggc cag tat gtg gag acc gtc acc     1200
Thr Pro Ser Asp Asn Pro Val Val Gly Gln Tyr Val Glu Thr Val Thr
385                 390                 395                 400

gcc aca ctc agc gcc cag gaa gcg gaa ctt aac gcc ctg gat gcc aaa     1248
Ala Thr Leu Ser Ala Gln Glu Ala Glu Leu Asn Ala Leu Asp Ala Lys
                405                 410                 415

gtg ggc gac ggc gat acc ggc tcc acc ttt gcc gcc ggg gcc cgc gcc     1296
Val Gly Asp Gly Asp Thr Gly Ser Thr Phe Ala Ala Gly Ala Arg Ala
            420                 425                 430

att gca gaa ctg ctg cac cag cac cag ctg ccg ctc agc cag ctg gat     1344
Ile Ala Glu Leu Leu His Gln His Gln Leu Pro Leu Ser Gln Leu Asp
        435                 440                 445

acc ctg tgc gcc ctg atc ggc gaa cgc tta aca gta gtg atg ggg ggc     1392
Thr Leu Cys Ala Leu Ile Gly Glu Arg Leu Thr Val Val Met Gly Gly
    450                 455                 460

tcc agc ggt gtg ctg atg tcc atc ttc ttt acg gcc gca ggc cag gca     1440
```

```
Ser Ser Gly Val Leu Met Ser Ile Phe Phe Thr Ala Ala Gly Gln Ala
465                 470                 475                 480

atc agc gaa ggg aaa ccg gtg gtg gcc gca ctc cag gcg ggc ctg gcg     1488
Ile Ser Glu Gly Lys Pro Val Val Ala Ala Leu Gln Ala Gly Leu Ala
                485                 490                 495

cag atg aag tat tac ggc ggt gcc gat ctg ggt gac cgc acc ctg att     1536
Gln Met Lys Tyr Tyr Gly Gly Ala Asp Leu Gly Asp Arg Thr Leu Ile
            500                 505                 510

gat gcc ctg caa cct gcg ctg gca gct ctg gca cag cat ccg ggg gat     1584
Asp Ala Leu Gln Pro Ala Leu Ala Ala Leu Ala Gln His Pro Gly Asp
        515                 520                 525

ctg gcg gcg gca tac cag gca gcc cgg gac ggg gca gac gcc acc acc     1632
Leu Ala Ala Ala Tyr Gln Ala Ala Arg Asp Gly Ala Asp Ala Thr Thr
    530                 535                 540

cgc gcc acc aaa gcc aat gcc ggt cgc gcc tct tac ctg aac agc gac     1680
Arg Ala Thr Lys Ala Asn Ala Gly Arg Ala Ser Tyr Leu Asn Ser Asp
545                 550                 555                 560

agc ctg gcg ggc aat atg gac ccg ggc gct cac gca gtc gca atg gtc     1728
Ser Leu Ala Gly Asn Met Asp Pro Gly Ala His Ala Val Ala Met Val
                565                 570                 575

ttt aag gcg ctg gcg ggc gcc tga                                     1752
Phe Lys Ala Leu Ala Gly Ala
            580


<210> SEQ ID NO 49
<211> LENGTH: 583
<212> TYPE: PRT
<213> ORGANISM: Escherichia blattae

<400> SEQUENCE: 49

Met Val Cys Pro Pro Asp Leu Asn Ser Gln Pro Phe Thr Ser Arg His
1               5                   10                  15

Thr Arg Tyr Ser Pro Leu Tyr Gly Cys Val Val Pro Asn Asp Gln Glu
            20                  25                  30

Thr Val Met Ser Gln Phe Phe Tyr Asn Gln Arg Glu Asn Leu Val Ser
        35                  40                  45

Asp Ala Ile Glu Gly Ala Met Ile Ala Ser Pro Trp Asn Asn Leu Ala
    50                  55                  60

Arg Leu Glu Ser Asp Pro Ala Ile Arg Ile Val Val Arg Arg Asp Leu
65                  70                  75                  80

Asp Lys Ser Arg Val Ala Val Ile Ser Gly Gly Gly Ala Gly His Glu
                85                  90                  95

Pro Ala His Val Gly Phe Val Gly Lys Gly Met Leu Thr Ala Ala Val
            100                 105                 110

Cys Gly Asp Leu Phe Ala Ser Pro Ser Val Asp Ala Val Leu Thr Ala
        115                 120                 125

Ile Gln Ala Val Thr Gly Glu Ala Gly Cys Leu Leu Ile Val Lys Asn
    130                 135                 140

Tyr Thr Gly Asp Arg Leu Asn Phe Gly Leu Ala Ala Glu Lys Ala Arg
145                 150                 155                 160

Arg Met Gly Tyr Lys Val Asp Met Val Ile Val Gly Asp Asp Ile Ser
                165                 170                 175

Leu Pro Glu Asn Lys His Pro Arg Gly Ile Ala Gly Thr Ile Met Ile
            180                 185                 190

His Lys Val Ala Gly Tyr Phe Ala Glu Thr Gly Cys Asn Leu Asp Thr
        195                 200                 205

Val Ala Arg Glu Ala Arg Leu Ala Met Glu Arg Val Phe Ser Ile Gly
    210                 215                 220
```

```
Val Ala Leu Ser Ser Cys His Leu Pro Ala Asp Pro Gln Asp Gly Val
225                 230                 235                 240

Arg His His Pro Gly Gln Ala Glu Leu Gly Met Gly Ile His Gly Glu
                245                 250                 255

Pro Gly Ala Ser Val Ile Asp Thr Gln Asn Ser Thr Asp Ile Val Arg
            260                 265                 270

Leu Met Val Ala Lys Ile Arg Ala Ala Leu Pro Glu Thr Gly Arg Leu
        275                 280                 285

Leu Leu Met Leu Asn Asn Leu Gly Gly Val Ser Val Thr Glu Met Ala
    290                 295                 300

Ile Leu Thr Arg Glu Leu Ala His Cys Glu Leu Ala Thr Arg Thr Asp
305                 310                 315                 320

Trp Leu Met Gly Pro Ala Pro Leu Val Ser Ala Leu Asp Met Lys Gly
                325                 330                 335

Phe Ser Ile Thr Ala Leu Val Met Glu Glu Ser Ile Glu Lys Ala Leu
            340                 345                 350

Leu Ala Asp Val Glu Thr Ala Gly Trp Leu Pro Pro Val Arg Leu Arg
        355                 360                 365

Ala Ser Gln Thr Gln Pro Cys Asn Ile Arg Ser Ala Arg Val Ala Phe
    370                 375                 380

Thr Pro Ser Asp Asn Pro Val Val Gly Gln Tyr Val Glu Thr Val Thr
385                 390                 395                 400

Ala Thr Leu Ser Ala Gln Glu Ala Glu Leu Asn Ala Leu Asp Ala Lys
                405                 410                 415

Val Gly Asp Gly Asp Thr Gly Ser Thr Phe Ala Ala Gly Ala Arg Ala
            420                 425                 430

Ile Ala Glu Leu Leu His Gln His Gln Leu Pro Leu Ser Gln Leu Asp
        435                 440                 445

Thr Leu Cys Ala Leu Ile Gly Glu Arg Leu Thr Val Val Met Gly Gly
    450                 455                 460

Ser Ser Gly Val Leu Met Ser Ile Phe Phe Thr Ala Ala Gly Gln Ala
465                 470                 475                 480

Ile Ser Glu Gly Lys Pro Val Val Ala Ala Leu Gln Ala Gly Leu Ala
                485                 490                 495

Gln Met Lys Tyr Tyr Gly Gly Ala Asp Leu Gly Asp Arg Thr Leu Ile
            500                 505                 510

Asp Ala Leu Gln Pro Ala Leu Ala Ala Leu Ala Gln His Pro Gly Asp
        515                 520                 525

Leu Ala Ala Ala Tyr Gln Ala Ala Arg Asp Gly Ala Asp Ala Thr Thr
    530                 535                 540

Arg Ala Thr Lys Ala Asn Ala Gly Arg Ala Ser Tyr Leu Asn Ser Asp
545                 550                 555                 560

Ser Leu Ala Gly Asn Met Asp Pro Gly Ala His Ala Val Ala Met Val
                565                 570                 575

Phe Lys Ala Leu Ala Gly Ala
            580
```

<210> SEQ ID NO 50
<211> LENGTH: 1647
<212> TYPE: DNA
<213> ORGANISM: Enterobacter sp.638
<220> FEATURE:
<221> NAME/KEY: CDS
<222> LOCATION: (1)..(1647)

<400> SEQUENCE: 50

```
atg tcc aga ttc ttt ttt aat gac cgc aaa cag ctg gtc aac gac gcc        48
Met Ser Arg Phe Phe Phe Asn Asp Arg Lys Gln Leu Val Asn Asp Ala
1               5                   10                  15

att gaa ggc ata ctg att tcc gcg ccg cac ggg aat ctt gtc aaa ctt        96
Ile Glu Gly Ile Leu Ile Ser Ala Pro His Gly Asn Leu Val Lys Leu
            20                  25                  30

gat atc gat ccg gcc att cgg gtg gtt gcg cgt agc gac tgg gat aaa       144
Asp Ile Asp Pro Ala Ile Arg Val Val Ala Arg Ser Asp Trp Asp Lys
        35                  40                  45

agc cgc gta gcg gtg att tcc ggt ggt ggg tcg ggg cac gaa ccc gct       192
Ser Arg Val Ala Val Ile Ser Gly Gly Gly Ser Gly His Glu Pro Ala
    50                  55                  60

cat gcc gga ttt gtc ggc aaa ggg atg ttg acc gca gcc gtc tgt ggc       240
His Ala Gly Phe Val Gly Lys Gly Met Leu Thr Ala Ala Val Cys Gly
65                  70                  75                  80

gat ctg ttt gcc tca ccg agc gta gat gcg gtg tta aac gcg att gtg       288
Asp Leu Phe Ala Ser Pro Ser Val Asp Ala Val Leu Asn Ala Ile Val
                85                  90                  95

gcg gta acg ggc gat cgc ggt tgc ctg tta atc gtc aaa aat tat acc       336
Ala Val Thr Gly Asp Arg Gly Cys Leu Leu Ile Val Lys Asn Tyr Thr
            100                 105                 110

ggc gat cgg ctt aac ttt ggc ctc gcg gcg gaa aag gcc aaa cgc tat       384
Gly Asp Arg Leu Asn Phe Gly Leu Ala Ala Glu Lys Ala Lys Arg Tyr
        115                 120                 125

ggg ctg aag gtt gag atg gtg att gtt gct gat gac atc gcc ctg ccg       432
Gly Leu Lys Val Glu Met Val Ile Val Ala Asp Asp Ile Ala Leu Pro
    130                 135                 140

gat aac aaa cag ccg cgt ggc att gcg ggt acg gcg ctg gta cac aaa       480
Asp Asn Lys Gln Pro Arg Gly Ile Ala Gly Thr Ala Leu Val His Lys
145                 150                 155                 160

att gcc gga tat gca gcc gaa cag ggg aaa tca ctg gct gac gtg cgg       528
Ile Ala Gly Tyr Ala Ala Glu Gln Gly Lys Ser Leu Ala Asp Val Arg
                165                 170                 175

gat att gcg cag cag gcc tgt gac aat atc tgg agc ctg ggc gtg gcg       576
Asp Ile Ala Gln Gln Ala Cys Asp Asn Ile Trp Ser Leu Gly Val Ala
            180                 185                 190

atg caa acg tgc aac ctg ccg ggc agc gac gat gaa gaa ggg cgt atc       624
Met Gln Thr Cys Asn Leu Pro Gly Ser Asp Asp Glu Glu Gly Arg Ile
        195                 200                 205

aag gat gga cat gtc gaa ctg ggg ctg ggc att cac ggc gag ccg ggc       672
Lys Asp Gly His Val Glu Leu Gly Leu Gly Ile His Gly Glu Pro Gly
    210                 215                 220

gcg tcg gtg gtt gat acg cac aac agc aaa gag att atc gac acc ctg       720
Ala Ser Val Val Asp Thr His Asn Ser Lys Glu Ile Ile Asp Thr Leu
225                 230                 235                 240

gtg aag ccg tta aaa gag acg gcc ggc gaa ggc aaa ttt gcg gtg ctg       768
Val Lys Pro Leu Lys Glu Thr Ala Gly Glu Gly Lys Phe Ala Val Leu
                245                 250                 255

att aac aat ctc ggc ggt gta tcg gcg ctg gag atg gcg ctg ctc acg       816
Ile Asn Asn Leu Gly Gly Val Ser Ala Leu Glu Met Ala Leu Leu Thr
            260                 265                 270

aaa gaa ctg gcg gat tct gcg ctg aaa gaa aat att gcg tat ctg att       864
Lys Glu Leu Ala Asp Ser Ala Leu Lys Glu Asn Ile Ala Tyr Leu Ile
        275                 280                 285

ggc cct gcg ccg ctg gta agc tcg ctg gat atg aaa ggc ttt tcg ctg       912
Gly Pro Ala Pro Leu Val Ser Ser Leu Asp Met Lys Gly Phe Ser Leu
    290                 295                 300

tca ctg tta cag ctt aac gat acc ttt gag aaa gcc att aac gca ccc       960
Ser Leu Leu Gln Leu Asn Asp Thr Phe Glu Lys Ala Ile Asn Ala Pro
305                 310                 315                 320
```

```
gtc gaa act atc ggc tgg caa aag ccg gta gca ttc gcg cca tta cgc      1008
Val Glu Thr Ile Gly Trp Gln Lys Pro Val Ala Phe Ala Pro Leu Arg
                325                 330                 335

acg ctt tcg cat act gcg att cag gat cgt gtt gaa ttt acg cct tcc      1056
Thr Leu Ser His Thr Ala Ile Gln Asp Arg Val Glu Phe Thr Pro Ser
            340                 345                 350

ggg aac gac gag gtc gca gcg cga gtg gca gcg gcg acg caa acg ttg      1104
Gly Asn Asp Glu Val Ala Ala Arg Val Ala Ala Ala Thr Gln Thr Leu
        355                 360                 365

ctc gct ctg gag aac cgt tta aat gcg ctg gac gcc aaa gtg ggc gac      1152
Leu Ala Leu Glu Asn Arg Leu Asn Ala Leu Asp Ala Lys Val Gly Asp
    370                 375                 380

ggc gat acc ggg tcg act ttt gcg caa ggc gcg cgg gaa att gcg cag      1200
Gly Asp Thr Gly Ser Thr Phe Ala Gln Gly Ala Arg Glu Ile Ala Gln
385                 390                 395                 400

ctt ctg gag caa aaa cag ctt ccg cta aac gat ctt tct aag ctg ctg      1248
Leu Leu Glu Gln Lys Gln Leu Pro Leu Asn Asp Leu Ser Lys Leu Leu
                405                 410                 415

ttg ttg atc ggc gaa cgg ctg gcg acg gtc atg ggc ggg tcg agt ggc      1296
Leu Leu Ile Gly Glu Arg Leu Ala Thr Val Met Gly Gly Ser Ser Gly
            420                 425                 430

gtc ctg atg tcg atc ttc ttc aca gct gcc gga cag aaa atg cat gac      1344
Val Leu Met Ser Ile Phe Phe Thr Ala Ala Gly Gln Lys Met His Asp
        435                 440                 445

gga aaa tca ctg ccg gag gca ttg ctg agt ggg ctt gcg caa atg aag      1392
Gly Lys Ser Leu Pro Glu Ala Leu Leu Ser Gly Leu Ala Gln Met Lys
    450                 455                 460

cat tac ggc gga gcg gat ctt ggc gat cgt acc ttg atc gac gcg cta      1440
His Tyr Gly Gly Ala Asp Leu Gly Asp Arg Thr Leu Ile Asp Ala Leu
465                 470                 475                 480

cag cct gca ctg gag acg ctg cat aac ggc gat att cag gcg gct gcc      1488
Gln Pro Ala Leu Glu Thr Leu His Asn Gly Asp Ile Gln Ala Ala Ala
                485                 490                 495

cag gca gcg aaa aaa ggc gca gac gct acg gct ggc atg caa aaa gcg      1536
Gln Ala Ala Lys Lys Gly Ala Asp Ala Thr Ala Gly Met Gln Lys Ala
            500                 505                 510

gga gca ggg cgt tcg tcg tat gtg aat aaa gag aac ctg gaa ggt gta      1584
Gly Ala Gly Arg Ser Ser Tyr Val Asn Lys Glu Asn Leu Glu Gly Val
        515                 520                 525

ata gat cct ggg gca gtg gcc gtt gca gag gtg ttt gcg gca gtg gcc      1632
Ile Asp Pro Gly Ala Val Ala Val Ala Glu Val Phe Ala Ala Val Ala
    530                 535                 540

aaa gca aaa cag tag                                                  1647
Lys Ala Lys Gln
545


<210> SEQ ID NO 51
<211> LENGTH: 548
<212> TYPE: PRT
<213> ORGANISM: Enterobacter sp.638

<400> SEQUENCE: 51

Met Ser Arg Phe Phe Phe Asn Asp Arg Lys Gln Leu Val Asn Asp Ala
1               5                   10                  15

Ile Glu Gly Ile Leu Ile Ser Ala Pro His Gly Asn Leu Val Lys Leu
            20                  25                  30

Asp Ile Asp Pro Ala Ile Arg Val Val Ala Arg Ser Asp Trp Asp Lys
        35                  40                  45

Ser Arg Val Ala Val Ile Ser Gly Gly Gly Ser Gly His Glu Pro Ala
    50                  55                  60
```

```
His Ala Gly Phe Val Gly Lys Gly Met Leu Thr Ala Ala Val Cys Gly
65                  70                  75                  80

Asp Leu Phe Ala Ser Pro Ser Val Asp Ala Val Leu Asn Ala Ile Val
                85                  90                  95

Ala Val Thr Gly Asp Arg Gly Cys Leu Leu Ile Val Lys Asn Tyr Thr
            100                 105                 110

Gly Asp Arg Leu Asn Phe Gly Leu Ala Ala Glu Lys Ala Lys Arg Tyr
        115                 120                 125

Gly Leu Lys Val Glu Met Val Ile Val Ala Asp Asp Ile Ala Leu Pro
    130                 135                 140

Asp Asn Lys Gln Pro Arg Gly Ile Ala Gly Thr Ala Leu Val His Lys
145                 150                 155                 160

Ile Ala Gly Tyr Ala Ala Glu Gln Gly Lys Ser Leu Ala Asp Val Arg
                165                 170                 175

Asp Ile Ala Gln Gln Ala Cys Asp Asn Ile Trp Ser Leu Gly Val Ala
            180                 185                 190

Met Gln Thr Cys Asn Leu Pro Gly Ser Asp Asp Glu Glu Gly Arg Ile
        195                 200                 205

Lys Asp Gly His Val Glu Leu Gly Leu Gly Ile His Gly Glu Pro Gly
    210                 215                 220

Ala Ser Val Val Asp Thr His Asn Ser Lys Glu Ile Ile Asp Thr Leu
225                 230                 235                 240

Val Lys Pro Leu Lys Glu Thr Ala Gly Glu Gly Lys Phe Ala Val Leu
                245                 250                 255

Ile Asn Asn Leu Gly Gly Val Ser Ala Leu Glu Met Ala Leu Leu Thr
            260                 265                 270

Lys Glu Leu Ala Asp Ser Ala Leu Lys Glu Asn Ile Ala Tyr Leu Ile
        275                 280                 285

Gly Pro Ala Pro Leu Val Ser Ser Leu Asp Met Lys Gly Phe Ser Leu
    290                 295                 300

Ser Leu Leu Gln Leu Asn Asp Thr Phe Glu Lys Ala Ile Asn Ala Pro
305                 310                 315                 320

Val Glu Thr Ile Gly Trp Gln Lys Pro Val Ala Phe Ala Pro Leu Arg
                325                 330                 335

Thr Leu Ser His Thr Ala Ile Gln Asp Arg Val Glu Phe Thr Pro Ser
            340                 345                 350

Gly Asn Asp Glu Val Ala Ala Arg Val Ala Ala Ala Thr Gln Thr Leu
        355                 360                 365

Leu Ala Leu Glu Asn Arg Leu Asn Ala Leu Asp Ala Lys Val Gly Asp
    370                 375                 380

Gly Asp Thr Gly Ser Thr Phe Ala Gln Gly Ala Arg Glu Ile Ala Gln
385                 390                 395                 400

Leu Leu Glu Gln Lys Gln Leu Pro Leu Asn Asp Leu Ser Lys Leu Leu
                405                 410                 415

Leu Leu Ile Gly Glu Arg Leu Ala Thr Val Met Gly Gly Ser Ser Gly
            420                 425                 430

Val Leu Met Ser Ile Phe Phe Thr Ala Ala Gly Gln Lys Met His Asp
        435                 440                 445

Gly Lys Ser Leu Pro Glu Ala Leu Leu Ser Gly Leu Ala Gln Met Lys
    450                 455                 460

His Tyr Gly Gly Ala Asp Leu Gly Asp Arg Thr Leu Ile Asp Ala Leu
465                 470                 475                 480

Gln Pro Ala Leu Glu Thr Leu His Asn Gly Asp Ile Gln Ala Ala Ala
```

```
                485                 490                 495

Gln Ala Ala Lys Lys Gly Ala Asp Ala Thr Ala Gly Met Gln Lys Ala
            500                 505                 510

Gly Ala Gly Arg Ser Ser Tyr Val Asn Lys Glu Asn Leu Glu Gly Val
        515                 520                 525

Ile Asp Pro Gly Ala Val Ala Val Ala Glu Val Phe Ala Ala Val Ala
    530                 535                 540

Lys Ala Lys Gln
545


<210> SEQ ID NO 52
<211> LENGTH: 1695
<212> TYPE: DNA
<213> ORGANISM: Psychromonas sp. CNPT3
<220> FEATURE:
<221> NAME/KEY: CDS
<222> LOCATION: (1)..(1695)

<400> SEQUENCE: 52

atg gtt ata tta ttt ttt aac cta ctt tat ttt aaa cta ctt ttt gga       48
Met Val Ile Leu Phe Phe Asn Leu Leu Tyr Phe Lys Leu Leu Phe Gly
1               5                   10                  15

gta att atg agc cgt tta ttt att aat gat aaa gca acg tta gtc cat       96
Val Ile Met Ser Arg Leu Phe Ile Asn Asp Lys Ala Thr Leu Val His
            20                  25                  30

gat gcg att gat ggc atc tta tat agc aat aag cat aat aac ctt gtt      144
Asp Ala Ile Asp Gly Ile Leu Tyr Ser Asn Lys His Asn Asn Leu Val
        35                  40                  45

cgt ttg gat gtt gat ccg caa att aga att gtg acg cgt aat gat tgg      192
Arg Leu Asp Val Asp Pro Gln Ile Arg Ile Val Thr Arg Asn Asp Trp
    50                  55                  60

cat cac gat aaa gtt gcc att atc tct ggt ggt ggc tct ggg cat gag      240
His His Asp Lys Val Ala Ile Ile Ser Gly Gly Gly Ser Gly His Glu
65                  70                  75                  80

cct gct cat gtt ggt ttt att ggt aaa ggt atg tta acg gct gct gtt      288
Pro Ala His Val Gly Phe Ile Gly Lys Gly Met Leu Thr Ala Ala Val
                85                  90                  95

tgt ggc gat gtt ttt gcc tca cca agt gtg gat gcg gtg tta aat gcc      336
Cys Gly Asp Val Phe Ala Ser Pro Ser Val Asp Ala Val Leu Asn Ala
            100                 105                 110

ata gtc cat gtc aca gga gag aaa ggt tgt ttg gtc att gtt aaa aac      384
Ile Val His Val Thr Gly Glu Lys Gly Cys Leu Val Ile Val Lys Asn
        115                 120                 125

tat acc ggc gac cgt ttg aac ttt ggc ctt gct tgt gaa aaa gcc aaa      432
Tyr Thr Gly Asp Arg Leu Asn Phe Gly Leu Ala Cys Glu Lys Ala Lys
    130                 135                 140

aaa atg ggt tta aac gtt gaa atg gta ata gta gac gat gat atc tct      480
Lys Met Gly Leu Asn Val Glu Met Val Ile Val Asp Asp Asp Ile Ser
145                 150                 155                 160

att cct gac aat ctt aaa cct cgt ggt att gct ggc aca ttg ttt gtc      528
Ile Pro Asp Asn Leu Lys Pro Arg Gly Ile Ala Gly Thr Leu Phe Val
                165                 170                 175

cat aaa gtg gca ggt aat gca gca gag caa ggc gct tct tta aat gtc      576
His Lys Val Ala Gly Asn Ala Ala Glu Gln Gly Ala Ser Leu Asn Val
            180                 185                 190

gtt aaa aag gca gcc caa ggt gcg att gat gca acg gca agt att ggc      624
Val Lys Lys Ala Ala Gln Gly Ala Ile Asp Ala Thr Ala Ser Ile Gly
        195                 200                 205

ctc gca ctg aca agt tgc tct tta ccg gga gaa gaa tca acg cag cgt      672
Leu Ala Leu Thr Ser Cys Ser Leu Pro Gly Glu Glu Ser Thr Gln Arg
    210                 215                 220
```

```
att gca gaa ggc aag gct gaa tta ggg tta ggt att cat gga gag cct      720
Ile Ala Glu Gly Lys Ala Glu Leu Gly Leu Gly Ile His Gly Glu Pro
225                 230                 235                 240

ggc att aaa aca att gat gta aca tgt tgt cgt gat ctt gtg atg atc      768
Gly Ile Lys Thr Ile Asp Val Thr Cys Cys Arg Asp Leu Val Met Ile
                245                 250                 255

atg gtt gat aaa cta aaa caa tcg ttt tct gct cca gat att aaa att      816
Met Val Asp Lys Leu Lys Gln Ser Phe Ser Ala Pro Asp Ile Lys Ile
            260                 265                 270

gca gtg atg atc aac aat tta ggt ggc gtt tct cca tta gag atg agc      864
Ala Val Met Ile Asn Asn Leu Gly Gly Val Ser Pro Leu Glu Met Ser
        275                 280                 285

ctt ata tgt aaa gac atc gtg gaa tct gag tta aaa aat aat att gag      912
Leu Ile Cys Lys Asp Ile Val Glu Ser Glu Leu Lys Asn Asn Ile Glu
    290                 295                 300

tta gtg gtt ggg cct gct cca ttt atg acg gct att gat atg aaa gga      960
Leu Val Val Gly Pro Ala Pro Phe Met Thr Ala Ile Asp Met Lys Gly
305                 310                 315                 320

ttt tca att tca gtg att gaa tta aca ggc gat cat gct caa gct ctg     1008
Phe Ser Ile Ser Val Ile Glu Leu Thr Gly Asp His Ala Gln Ala Leu
                325                 330                 335

tgc gcc cct gtt gaa gtg gat gca tgg gtt gaa gcc att cca ttg cgc     1056
Cys Ala Pro Val Glu Val Asp Ala Trp Val Glu Ala Ile Pro Leu Arg
            340                 345                 350

cca tta aat gtg ata aaa aaa gat aaa gtg tcc att aac ttt gca ttt     1104
Pro Leu Asn Val Ile Lys Lys Asp Lys Val Ser Ile Asn Phe Ala Phe
        355                 360                 365

gaa gcg tct gaa aat gca cag gtt gca agt att gtt aaa aca gta acc     1152
Glu Ala Ser Glu Asn Ala Gln Val Ala Ser Ile Val Lys Thr Val Thr
    370                 375                 380

ttg gct ttg att aat gca gaa aaa gag tta aat cgt ctg gat acg tta     1200
Leu Ala Leu Ile Asn Ala Glu Lys Glu Leu Asn Arg Leu Asp Thr Leu
385                 390                 395                 400

gtg ggc gat ggg gat acc ggt tca acg ttc tct gcg ggt gct cga caa     1248
Val Gly Asp Gly Asp Thr Gly Ser Thr Phe Ser Ala Gly Ala Arg Gln
                405                 410                 415

gtt tta gct gag ctc aat gcg ggt aat tta cca ctt aat gat act ggc     1296
Val Leu Ala Glu Leu Asn Ala Gly Asn Leu Pro Leu Asn Asp Thr Gly
            420                 425                 430

gcg ttg ctt aat gtc att ggg gaa caa ctt gct acc gtt atg ggg gga     1344
Ala Leu Leu Asn Val Ile Gly Glu Gln Leu Ala Thr Val Met Gly Gly
        435                 440                 445

tcg tca ggc gta tta ttc tct atc ttc ttc aca gca gcg ggt cat cat     1392
Ser Ser Gly Val Leu Phe Ser Ile Phe Phe Thr Ala Ala Gly His His
    450                 455                 460

tac cag caa cat ggt gat aca gta caa gca tta caa gcc ggt tta caa     1440
Tyr Gln Gln His Gly Asp Thr Val Gln Ala Leu Gln Ala Gly Leu Gln
465                 470                 475                 480

caa atg atg caa tac ggt gga gca aaa ccg ggt gat cgt acg atg att     1488
Gln Met Met Gln Tyr Gly Gly Ala Lys Pro Gly Asp Arg Thr Met Ile
                485                 490                 495

gat gca atg tac cca gcc ttt atc gct tgg aaa aat gaa ggt ttt gaa     1536
Asp Ala Met Tyr Pro Ala Phe Ile Ala Trp Lys Asn Glu Gly Phe Glu
            500                 505                 510

gct gcc att gtt gcg gct aaa ata ggg gca gaa agc aca gcc act atg     1584
Ala Ala Ile Val Ala Ala Lys Ile Gly Ala Glu Ser Thr Ala Thr Met
        515                 520                 525

gtc gaa gcc aaa gca gga cgc tct tct tat tta aac agt gag agt tta     1632
Val Glu Ala Lys Ala Gly Arg Ser Ser Tyr Leu Asn Ser Glu Ser Leu
    530                 535                 540
```

```
aaa ggt gtt aaa gat ccg ggc tca gtc gct gtt gag ttg gtt ttt gac      1680
Lys Gly Val Lys Asp Pro Gly Ser Val Ala Val Glu Leu Val Phe Asp
545                 550                 555                 560

gcg ttt aat gtg taa                                                  1695
Ala Phe Asn Val


<210> SEQ ID NO 53
<211> LENGTH: 564
<212> TYPE: PRT
<213> ORGANISM: Psychromonas sp. CNPT3

<400> SEQUENCE: 53

Met Val Ile Leu Phe Phe Asn Leu Leu Tyr Phe Lys Leu Leu Phe Gly
1               5                   10                  15

Val Ile Met Ser Arg Leu Phe Ile Asn Asp Lys Ala Thr Leu Val His
            20                  25                  30

Asp Ala Ile Asp Gly Ile Leu Tyr Ser Asn Lys His Asn Asn Leu Val
        35                  40                  45

Arg Leu Asp Val Asp Pro Gln Ile Arg Ile Val Thr Arg Asn Asp Trp
    50                  55                  60

His His Asp Lys Val Ala Ile Ile Ser Gly Gly Gly Ser Gly His Glu
65                  70                  75                  80

Pro Ala His Val Gly Phe Ile Gly Lys Gly Met Leu Thr Ala Ala Val
                85                  90                  95

Cys Gly Asp Val Phe Ala Ser Pro Ser Val Asp Ala Val Leu Asn Ala
            100                 105                 110

Ile Val His Val Thr Gly Glu Lys Gly Cys Leu Val Ile Val Lys Asn
        115                 120                 125

Tyr Thr Gly Asp Arg Leu Asn Phe Gly Leu Ala Cys Glu Lys Ala Lys
    130                 135                 140

Lys Met Gly Leu Asn Val Glu Met Val Ile Val Asp Asp Asp Ile Ser
145                 150                 155                 160

Ile Pro Asp Asn Leu Lys Pro Arg Gly Ile Ala Gly Thr Leu Phe Val
                165                 170                 175

His Lys Val Ala Gly Asn Ala Ala Glu Gln Gly Ala Ser Leu Asn Val
            180                 185                 190

Val Lys Lys Ala Ala Gln Gly Ala Ile Asp Ala Thr Ala Ser Ile Gly
        195                 200                 205

Leu Ala Leu Thr Ser Cys Ser Leu Pro Gly Glu Glu Ser Thr Gln Arg
    210                 215                 220

Ile Ala Glu Gly Lys Ala Glu Leu Gly Leu Gly Ile His Gly Glu Pro
225                 230                 235                 240

Gly Ile Lys Thr Ile Asp Val Thr Cys Cys Arg Asp Leu Val Met Ile
                245                 250                 255

Met Val Asp Lys Leu Lys Gln Ser Phe Ser Ala Pro Asp Ile Lys Ile
            260                 265                 270

Ala Val Met Ile Asn Asn Leu Gly Gly Val Ser Pro Leu Glu Met Ser
        275                 280                 285

Leu Ile Cys Lys Asp Ile Val Glu Ser Glu Leu Lys Asn Asn Ile Glu
    290                 295                 300

Leu Val Val Gly Pro Ala Pro Phe Met Thr Ala Ile Asp Met Lys Gly
305                 310                 315                 320

Phe Ser Ile Ser Val Ile Glu Leu Thr Gly Asp His Ala Gln Ala Leu
                325                 330                 335

Cys Ala Pro Val Glu Val Asp Ala Trp Val Glu Ala Ile Pro Leu Arg
```

```
            340                 345                 350

Pro Leu Asn Val Ile Lys Lys Asp Lys Val Ser Ile Asn Phe Ala Phe
        355                 360                 365

Glu Ala Ser Glu Asn Ala Gln Val Ala Ser Ile Val Lys Thr Val Thr
    370                 375                 380

Leu Ala Leu Ile Asn Ala Glu Lys Glu Leu Asn Arg Leu Asp Thr Leu
385                 390                 395                 400

Val Gly Asp Gly Asp Thr Gly Ser Thr Phe Ser Ala Gly Ala Arg Gln
                405                 410                 415

Val Leu Ala Glu Leu Asn Ala Gly Asn Leu Pro Leu Asn Asp Thr Gly
            420                 425                 430

Ala Leu Leu Asn Val Ile Gly Glu Gln Leu Ala Thr Val Met Gly Gly
        435                 440                 445

Ser Ser Gly Val Leu Phe Ser Ile Phe Phe Thr Ala Ala Gly His His
    450                 455                 460

Tyr Gln Gln His Gly Asp Thr Val Gln Ala Leu Gln Ala Gly Leu Gln
465                 470                 475                 480

Gln Met Met Gln Tyr Gly Gly Ala Lys Pro Gly Asp Arg Thr Met Ile
                485                 490                 495

Asp Ala Met Tyr Pro Ala Phe Ile Ala Trp Lys Asn Glu Gly Phe Glu
            500                 505                 510

Ala Ala Ile Val Ala Ala Lys Ile Gly Ala Glu Ser Thr Ala Thr Met
        515                 520                 525

Val Glu Ala Lys Ala Gly Arg Ser Ser Tyr Leu Asn Ser Glu Ser Leu
    530                 535                 540

Lys Gly Val Lys Asp Pro Gly Ser Val Ala Val Glu Leu Val Phe Asp
545                 550                 555                 560

Ala Phe Asn Val


<210> SEQ ID NO 54
<211> LENGTH: 1647
<212> TYPE: DNA
<213> ORGANISM: Stapia aggregata IAM12614
<220> FEATURE:
<221> NAME/KEY: CDS1
<222> LOCATION: (1)..(1647)
<220> FEATURE:
<221> NAME/KEY: CDS
<222> LOCATION: (1)..(1647)

<400> SEQUENCE: 54

atg aag caa ttc atc aat acc aag gaa acg ctc gtc acc gaa gcg att       48
Met Lys Gln Phe Ile Asn Thr Lys Glu Thr Leu Val Thr Glu Ala Ile
1               5                   10                  15

gac ggc atg ttg cgc acg gcc ggc ggg cgg ctt gcc cgg ctt gac ggc       96
Asp Gly Met Leu Arg Thr Ala Gly Gly Arg Leu Ala Arg Leu Asp Gly
            20                  25                  30

tat ccg cat atc aag gtg gtc gtg cgc acc gac tgg gac aaa tcg aag      144
Tyr Pro His Ile Lys Val Val Val Arg Thr Asp Trp Asp Lys Ser Lys
        35                  40                  45

gtg gct ctg gtg tcc ggc ggc ggt tcc ggc cac gag ccg agc cat gcc      192
Val Ala Leu Val Ser Gly Gly Gly Ser Gly His Glu Pro Ser His Ala
    50                  55                  60

ggt ttc gtc ggc cag ggc atg ctg acg gcg gcc gtc tgc ggc gaa gtg      240
Gly Phe Val Gly Gln Gly Met Leu Thr Ala Ala Val Cys Gly Glu Val
65                  70                  75                  80

ttt gcc tcg cct tcc gtg gat gcg gtg ctg gcg ggc att ctg gcc gtc      288
Phe Ala Ser Pro Ser Val Asp Ala Val Leu Ala Gly Ile Leu Ala Val
                85                  90                  95
```

```
acc ggc aag gct ggc tgc ctg ctg atc gtc aag aac tac acc ggc gac      336
Thr Gly Lys Ala Gly Cys Leu Leu Ile Val Lys Asn Tyr Thr Gly Asp
            100                 105                 110

cgg ctg aac ttc ggt ctg gcc gcc gag cgg gcc cgc tcc ttc gga ctg      384
Arg Leu Asn Phe Gly Leu Ala Ala Glu Arg Ala Arg Ser Phe Gly Leu
        115                 120                 125

aag gtc aac atg gtg atc gtc gac gac gac gtt gcc ctg ccg gac ctg      432
Lys Val Asn Met Val Ile Val Asp Asp Asp Val Ala Leu Pro Asp Leu
    130                 135                 140

ccg cag gcg cgc ggt gtc gcc ggc acg ctg ttc gtg cac aag atc gcc      480
Pro Gln Ala Arg Gly Val Ala Gly Thr Leu Phe Val His Lys Ile Ala
145                 150                 155                 160

gga gcg ctt gcc gat cag ggt gcg gat ctg gaa acc atc acg gag gcc      528
Gly Ala Leu Ala Asp Gln Gly Ala Asp Leu Glu Thr Ile Thr Glu Ala
                165                 170                 175

gcc agg aaa acc atc ggc ggt gcg att tcc atc ggc atg tcg ctg gac      576
Ala Arg Lys Thr Ile Gly Gly Ala Ile Ser Ile Gly Met Ser Leu Asp
            180                 185                 190

acc tgc acg gtg ccg gga tcg ccc aag gaa gac cgc att gca cac ggc      624
Thr Cys Thr Val Pro Gly Ser Pro Lys Glu Asp Arg Ile Ala His Gly
        195                 200                 205

aag gcg gaa ctc gga ctt ggc att cac ggc gag gcg ggg atc gag cag      672
Lys Ala Glu Leu Gly Leu Gly Ile His Gly Glu Ala Gly Ile Glu Gln
    210                 215                 220

gtc gac tat tcc aac gcc cgc gcg gcc atg gcc atg gtg gtg gac cgg      720
Val Asp Tyr Ser Asn Ala Arg Ala Ala Met Ala Met Val Val Asp Arg
225                 230                 235                 240

ctg gcg ccg aac ctc tcg ccc gga ccg cat gtg gcg atc ctc aac aat      768
Leu Ala Pro Asn Leu Ser Pro Gly Pro His Val Ala Ile Leu Asn Asn
                245                 250                 255

ctg ggc agc acg acg ccg ctg gaa atg tcg gtg ctt ctg gaa gaa ctc      816
Leu Gly Ser Thr Thr Pro Leu Glu Met Ser Val Leu Leu Glu Glu Leu
            260                 265                 270

acg gct tcg cgc atc ggc agc cag atc cgc tgg gtc atc ggc ccg gcg      864
Thr Ala Ser Arg Ile Gly Ser Gln Ile Arg Trp Val Ile Gly Pro Ala
        275                 280                 285

gcg atg atg acc tcg ctc gac atg cat ggg ttc tcc gtg tcg ctg ctg      912
Ala Met Met Thr Ser Leu Asp Met His Gly Phe Ser Val Ser Leu Leu
    290                 295                 300

ccg gtc ggc aag acc gaa gaa gcc ttg ctg cag gcc ccg gtc gcg ccc      960
Pro Val Gly Lys Thr Glu Glu Ala Leu Leu Gln Ala Pro Val Ala Pro
305                 310                 315                 320

tgg gca tgg ccc ggc tgc ctt gcg ctt ggc gca gtg tcc gtg ctg ccg     1008
Trp Ala Trp Pro Gly Cys Leu Ala Leu Gly Ala Val Ser Val Leu Pro
                325                 330                 335

cta ccg gac ggc ctg acg ccg atc cag ccg ctg ccg tcc aag aac ccg     1056
Leu Pro Asp Gly Leu Thr Pro Ile Gln Pro Leu Pro Ser Lys Asn Pro
            340                 345                 350

gag acg cgg aag ttc atc gag cgc tgc tgc gat atc ctg atc gcc gcc     1104
Glu Thr Arg Lys Phe Ile Glu Arg Cys Cys Asp Ile Leu Ile Ala Ala
        355                 360                 365

gag gac gac ctc aat gcg ctc gac gcc aag tcg ggc gac ggc gac acc     1152
Glu Asp Asp Leu Asn Ala Leu Asp Ala Lys Ser Gly Asp Gly Asp Thr
    370                 375                 380

ggc agc acg ctt gcc acc gcc gcc cgg gcg ctg gtg aag gcg ctc gac     1200
Gly Ser Thr Leu Ala Thr Ala Ala Arg Ala Leu Val Lys Ala Leu Asp
385                 390                 395                 400

cgg ctg ccg ctg gcg gat ctc acc cag ctc tac cgg gcc atc ggg ctg     1248
Arg Leu Pro Leu Ala Asp Leu Thr Gln Leu Tyr Arg Ala Ile Gly Leu
                405                 410                 415
```

```
gaa ctc agc cag acc atg ggc ggg tct tcc ggg gtg ctg ctg gcg atc      1296
Glu Leu Ser Gln Thr Met Gly Gly Ser Ser Gly Val Leu Leu Ala Ile
            420                 425                 430

ttc ttt gcc gct gcg ggc gat gcg tcg tcc agc ggg cgc ggg gcc atc      1344
Phe Phe Ala Ala Ala Gly Asp Ala Ser Ser Ser Gly Arg Gly Ala Ile
        435                 440                 445

gga gcc ctg aag gcc ggt ctt gac cgg atc atg cag gtg ggc ggc gcc      1392
Gly Ala Leu Lys Ala Gly Leu Asp Arg Ile Met Gln Val Gly Gly Ala
    450                 455                 460

cag ccg ggc gac cgc acc atg atc gac gcg ctg ctg ccg gca ctg aat      1440
Gln Pro Gly Asp Arg Thr Met Ile Asp Ala Leu Leu Pro Ala Leu Asn
465                 470                 475                 480

gcg ctg gaa aac ggt atc gag gct gcg gcg agc gag gcc cgt cag ggg      1488
Ala Leu Glu Asn Gly Ile Glu Ala Ala Ala Ser Glu Ala Arg Gln Gly
                485                 490                 495

gcg gat gcg acg tcg cgg atc acg cgg gca cgc gcg ggc agg gcg tct      1536
Ala Asp Ala Thr Ser Arg Ile Thr Arg Ala Arg Ala Gly Arg Ala Ser
            500                 505                 510

tat gtc tcc gag gcc agc ctc tcc gga cac aac gat ccg ggc gcg gaa      1584
Tyr Val Ser Glu Ala Ser Leu Ser Gly His Asn Asp Pro Gly Ala Glu
        515                 520                 525

gcc gtt gcg cgg ctg ttc gag caa ttg acc ctt tct ccg gcc ctt acc      1632
Ala Val Ala Arg Leu Phe Glu Gln Leu Thr Leu Ser Pro Ala Leu Thr
    530                 535                 540

tcc aag tcc gca tag                                                  1647
Ser Lys Ser Ala
545


<210> SEQ ID NO 55
<211> LENGTH: 548
<212> TYPE: PRT
<213> ORGANISM: Stapia aggregata IAM12614

<400> SEQUENCE: 55

Met Lys Gln Phe Ile Asn Thr Lys Glu Thr Leu Val Thr Glu Ala Ile
1               5                   10                  15

Asp Gly Met Leu Arg Thr Ala Gly Gly Arg Leu Ala Arg Leu Asp Gly
            20                  25                  30

Tyr Pro His Ile Lys Val Val Val Arg Thr Asp Trp Asp Lys Ser Lys
        35                  40                  45

Val Ala Leu Val Ser Gly Gly Gly Ser Gly His Glu Pro Ser His Ala
    50                  55                  60

Gly Phe Val Gly Gln Gly Met Leu Thr Ala Ala Val Cys Gly Glu Val
65                  70                  75                  80

Phe Ala Ser Pro Ser Val Asp Ala Val Leu Ala Gly Ile Leu Ala Val
                85                  90                  95

Thr Gly Lys Ala Gly Cys Leu Leu Ile Val Lys Asn Tyr Thr Gly Asp
            100                 105                 110

Arg Leu Asn Phe Gly Leu Ala Ala Glu Arg Ala Arg Ser Phe Gly Leu
        115                 120                 125

Lys Val Asn Met Val Ile Val Asp Asp Asp Val Ala Leu Pro Asp Leu
    130                 135                 140

Pro Gln Ala Arg Gly Val Ala Gly Thr Leu Phe Val His Lys Ile Ala
145                 150                 155                 160

Gly Ala Leu Ala Asp Gln Gly Ala Asp Leu Glu Thr Ile Thr Glu Ala
                165                 170                 175

Ala Arg Lys Thr Ile Gly Gly Ala Ile Ser Ile Gly Met Ser Leu Asp
            180                 185                 190
```

```
Thr Cys Thr Val Pro Gly Ser Pro Lys Glu Asp Arg Ile Ala His Gly
        195                 200                 205

Lys Ala Glu Leu Gly Leu Gly Ile His Gly Glu Ala Gly Ile Glu Gln
    210                 215                 220

Val Asp Tyr Ser Asn Ala Arg Ala Ala Met Ala Met Val Val Asp Arg
225                 230                 235                 240

Leu Ala Pro Asn Leu Ser Pro Gly Pro His Val Ala Ile Leu Asn Asn
                245                 250                 255

Leu Gly Ser Thr Thr Pro Leu Glu Met Ser Val Leu Leu Glu Glu Leu
            260                 265                 270

Thr Ala Ser Arg Ile Gly Ser Gln Ile Arg Trp Val Ile Gly Pro Ala
        275                 280                 285

Ala Met Met Thr Ser Leu Asp Met His Gly Phe Ser Val Ser Leu Leu
    290                 295                 300

Pro Val Gly Lys Thr Glu Glu Ala Leu Leu Gln Ala Pro Val Ala Pro
305                 310                 315                 320

Trp Ala Trp Pro Gly Cys Leu Ala Leu Gly Ala Val Ser Val Leu Pro
                325                 330                 335

Leu Pro Asp Gly Leu Thr Pro Ile Gln Pro Leu Pro Ser Lys Asn Pro
            340                 345                 350

Glu Thr Arg Lys Phe Ile Glu Arg Cys Cys Asp Ile Leu Ile Ala Ala
        355                 360                 365

Glu Asp Asp Leu Asn Ala Leu Asp Ala Lys Ser Gly Asp Gly Asp Thr
    370                 375                 380

Gly Ser Thr Leu Ala Thr Ala Ala Arg Ala Leu Val Lys Ala Leu Asp
385                 390                 395                 400

Arg Leu Pro Leu Ala Asp Leu Thr Gln Leu Tyr Arg Ala Ile Gly Leu
                405                 410                 415

Glu Leu Ser Gln Thr Met Gly Gly Ser Ser Gly Val Leu Leu Ala Ile
            420                 425                 430

Phe Phe Ala Ala Ala Gly Asp Ala Ser Ser Ser Gly Arg Gly Ala Ile
        435                 440                 445

Gly Ala Leu Lys Ala Gly Leu Asp Arg Ile Met Gln Val Gly Gly Ala
    450                 455                 460

Gln Pro Gly Asp Arg Thr Met Ile Asp Ala Leu Leu Pro Ala Leu Asn
465                 470                 475                 480

Ala Leu Glu Asn Gly Ile Glu Ala Ala Ala Ser Glu Ala Arg Gln Gly
                485                 490                 495

Ala Asp Ala Thr Ser Arg Ile Thr Arg Ala Arg Ala Gly Arg Ala Ser
            500                 505                 510

Tyr Val Ser Glu Ala Ser Leu Ser Gly His Asn Asp Pro Gly Ala Glu
        515                 520                 525

Ala Val Ala Arg Leu Phe Glu Gln Leu Thr Leu Ser Pro Ala Leu Thr
    530                 535                 540

Ser Lys Ser Ala
545
```

```
<210> SEQ ID NO 56
<211> LENGTH: 1641
<212> TYPE: DNA
<213> ORGANISM: Rhizobium leguminosarum
<220> FEATURE:
<221> NAME/KEY: CDS
<222> LOCATION: (1)..(1641)

<400> SEQUENCE: 56
```

```
atg aaa cac ttc ttc aac cgc agg gaa aac atc gtc acc gaa gcc ttg       48
Met Lys His Phe Phe Asn Arg Arg Glu Asn Ile Val Thr Glu Ala Leu
1               5                   10                  15

gac ggt ctg ctt ctg acg agc agc aag ggt cgt ctt gcc cgc ctc gac       96
Asp Gly Leu Leu Leu Thr Ser Ser Lys Gly Arg Leu Ala Arg Leu Asp
            20                  25                  30

agc ttt ccc gac atc aag gtg atc ctg cgc gct gac tgg gac aag tcg      144
Ser Phe Pro Asp Ile Lys Val Ile Leu Arg Ala Asp Trp Asp Lys Ser
        35                  40                  45

aag gtg gcg atc atc tca ggc ggc ggc gcc ggt cat gag ccc tcc cat      192
Lys Val Ala Ile Ile Ser Gly Gly Gly Ala Gly His Glu Pro Ser His
    50                  55                  60

gcc ggc ttc gtc ggt aag ggc atg ctg acg gct gcc gta tcc ggc gag      240
Ala Gly Phe Val Gly Lys Gly Met Leu Thr Ala Ala Val Ser Gly Glu
65                  70                  75                  80

att ttc gcc tcg ccg agc gtc gat gcc gtg ctg aca gcg atc cgc gcc      288
Ile Phe Ala Ser Pro Ser Val Asp Ala Val Leu Thr Ala Ile Arg Ala
                85                  90                  95

gtc gcc ggc gaa aag ggc gcc ttg ctg atc gtc aag aac tat acc ggc      336
Val Ala Gly Glu Lys Gly Ala Leu Leu Ile Val Lys Asn Tyr Thr Gly
            100                 105                 110

gac cgg ctg aat ttc ggc ctc gcc gcc gag aag gcg cgc gcc gaa ggt      384
Asp Arg Leu Asn Phe Gly Leu Ala Ala Glu Lys Ala Arg Ala Glu Gly
        115                 120                 125

ttc gac gtc gaa atg gtc atc gtc gcc gac gat atc gcc atc ccc gag      432
Phe Asp Val Glu Met Val Ile Val Ala Asp Asp Ile Ala Ile Pro Glu
    130                 135                 140

atc aac cag ccg cgc ggc gtc gcc ggg act ctg ttc gtc cac aag atc      480
Ile Asn Gln Pro Arg Gly Val Ala Gly Thr Leu Phe Val His Lys Ile
145                 150                 155                 160

gct ggc tat cac gcc gaa agg ggc gag gac ctg aag acg gtc gca gcc      528
Ala Gly Tyr His Ala Glu Arg Gly Glu Asp Leu Lys Thr Val Ala Ala
                165                 170                 175

cat gcc gcg gca gcg gcc ggc gac atc gtc tcg ctc ggc atg tct ctg      576
His Ala Ala Ala Ala Ala Gly Asp Ile Val Ser Leu Gly Met Ser Leu
            180                 185                 190

tcc acc tgc agc gtg ccc ggc cag gcg cat gag agc cgc ctc ggc gag      624
Ser Thr Cys Ser Val Pro Gly Gln Ala His Glu Ser Arg Leu Gly Glu
        195                 200                 205

aac gag ggc gaa ctc ggt ctc ggc atc cat ggc gag ccc ggc gtc gag      672
Asn Glu Gly Glu Leu Gly Leu Gly Ile His Gly Glu Pro Gly Val Glu
    210                 215                 220

cgc att gcg ctg cag ccg gtc gtc gat atc gtc gcc acc atg gtg gcg      720
Arg Ile Ala Leu Gln Pro Val Val Asp Ile Val Ala Thr Met Val Ala
225                 230                 235                 240

cgc cta tcg cct gcg ctg cgc gaa ggg gga aac cac gcc ctt ctc atc      768
Arg Leu Ser Pro Ala Leu Arg Glu Gly Gly Asn His Ala Leu Leu Ile
                245                 250                 255

aac aat ctc ggc gcc gta ccg ccg ctc gaa atg acc gtt att gcc aat      816
Asn Asn Leu Gly Ala Val Pro Pro Leu Glu Met Thr Val Ile Ala Asn
            260                 265                 270

gtg gtg ctg tcc tcg tcg ctt gcc gat cgc gtc agg ctg atc atc ggc      864
Val Val Leu Ser Ser Ser Leu Ala Asp Arg Val Arg Leu Ile Ile Gly
        275                 280                 285

ccg gcg ccg atg atg acc gcg ctc aac atg aac ggc ttc tcg ctg tcg      912
Pro Ala Pro Met Met Thr Ala Leu Asn Met Asn Gly Phe Ser Leu Ser
    290                 295                 300

ctg atc cga ctg gat gcc gct cgc gag gcg gcg ctg acg gca gcg gtc      960
Leu Ile Arg Leu Asp Ala Ala Arg Glu Ala Ala Leu Thr Ala Ala Val
305                 310                 315                 320
```

```
gaa ccg cat gcc tgg atg cca gcc gtc gaa cgc cac gag atc agg gtc      1008
Glu Pro His Ala Trp Met Pro Ala Val Glu Arg His Glu Ile Arg Val
                325                 330                 335

atc gcc gca ccg cga aca tca gcc gga ctg aac ggc gcg cca gtg gcc      1056
Ile Ala Ala Pro Arg Thr Ser Ala Gly Leu Asn Gly Ala Pro Val Ala
            340                 345                 350

ggg gat aat ctc cgc aac cgg cgt ctg atc aca gcg ctc tgc gag cat      1104
Gly Asp Asn Leu Arg Asn Arg Arg Leu Ile Thr Ala Leu Cys Glu His
        355                 360                 365

ctg atc tcg cag gaa agc gaa ctc aac cgg ctg gat ggc cgc gtc ggc      1152
Leu Ile Ser Gln Glu Ser Glu Leu Asn Arg Leu Asp Gly Arg Val Gly
    370                 375                 380

gac ggt gat acc ggc tcg acg gtg gcg aca ggc gcc cgc agc gtg ctt      1200
Asp Gly Asp Thr Gly Ser Thr Val Ala Thr Gly Ala Arg Ser Val Leu
385                 390                 395                 400

gcc cgc ctg gac acg ctg ccg ctt gat cgg ccg gct gca acg ctt gcc      1248
Ala Arg Leu Asp Thr Leu Pro Leu Asp Arg Pro Ala Ala Thr Leu Ala
                405                 410                 415

tcg ctc ggc gac atc ctc ggc acc agc atg ggc gga tcg agc ggc gtg      1296
Ser Leu Gly Asp Ile Leu Gly Thr Ser Met Gly Gly Ser Ser Gly Val
            420                 425                 430

ctg ctg tcg atc ttc ttc acc gca gcg gca aag gcg atg gcc gac aag      1344
Leu Leu Ser Ile Phe Phe Thr Ala Ala Ala Lys Ala Met Ala Asp Lys
        435                 440                 445

gcc gat ata tca gca gcc ctt att gcc ggg ctc gac agg atg acg ttc      1392
Ala Asp Ile Ser Ala Ala Leu Ile Ala Gly Leu Asp Arg Met Thr Phe
    450                 455                 460

tat ggc gga gcc gaa gtc ggc gac cgg acg atg gtc gat gcg ctg tcg      1440
Tyr Gly Gly Ala Glu Val Gly Asp Arg Thr Met Val Asp Ala Leu Ser
465                 470                 475                 480

cct gcc ctg cag gcg ctc gca tcc ggc gat gtc gcg gca gcg gcc agg      1488
Pro Ala Leu Gln Ala Leu Ala Ser Gly Asp Val Ala Ala Ala Ala Arg
                485                 490                 495

gct gct gcc gca ggt gcg gag tcg acg aag acg atg atg aaa gcg aga      1536
Ala Ala Ala Ala Gly Ala Glu Ser Thr Lys Thr Met Met Lys Ala Arg
            500                 505                 510

gcc ggc cgc gcc tcc tat gtc ggc gaa agg gat ctg gca ggt gtc gct      1584
Ala Gly Arg Ala Ser Tyr Val Gly Glu Arg Asp Leu Ala Gly Val Ala
        515                 520                 525

gat ccc ggc gcc gtc gcg gtt gcc ggc gcg ttc ggt gtg gcg gca agc      1632
Asp Pro Gly Ala Val Ala Val Ala Gly Ala Phe Gly Val Ala Ala Ser
    530                 535                 540

ctc gcc tga                                                          1641
Leu Ala
545
```

<210> SEQ ID NO 57
<211> LENGTH: 546
<212> TYPE: PRT
<213> ORGANISM: Rhizobium leguminosarum

<400> SEQUENCE: 57

```
Met Lys His Phe Phe Asn Arg Arg Glu Asn Ile Val Thr Glu Ala Leu
1               5                   10                  15

Asp Gly Leu Leu Leu Thr Ser Ser Lys Gly Arg Leu Ala Arg Leu Asp
            20                  25                  30

Ser Phe Pro Asp Ile Lys Val Ile Leu Arg Ala Asp Trp Asp Lys Ser
        35                  40                  45

Lys Val Ala Ile Ile Ser Gly Gly Gly Ala Gly His Glu Pro Ser His
    50                  55                  60
```

```
Ala Gly Phe Val Gly Lys Gly Met Leu Thr Ala Ala Val Ser Gly Glu
65                  70                  75                  80

Ile Phe Ala Ser Pro Ser Val Asp Ala Val Leu Thr Ala Ile Arg Ala
                85                  90                  95

Val Ala Gly Glu Lys Gly Ala Leu Leu Ile Val Lys Asn Tyr Thr Gly
            100                 105                 110

Asp Arg Leu Asn Phe Gly Leu Ala Ala Glu Lys Ala Arg Ala Glu Gly
        115                 120                 125

Phe Asp Val Glu Met Val Ile Val Ala Asp Asp Ile Ala Ile Pro Glu
    130                 135                 140

Ile Asn Gln Pro Arg Gly Val Ala Gly Thr Leu Phe Val His Lys Ile
145                 150                 155                 160

Ala Gly Tyr His Ala Glu Arg Gly Glu Asp Leu Lys Thr Val Ala Ala
                165                 170                 175

His Ala Ala Ala Ala Ala Gly Asp Ile Val Ser Leu Gly Met Ser Leu
            180                 185                 190

Ser Thr Cys Ser Val Pro Gly Gln Ala His Glu Ser Arg Leu Gly Glu
        195                 200                 205

Asn Glu Gly Glu Leu Gly Leu Gly Ile His Gly Glu Pro Gly Val Glu
    210                 215                 220

Arg Ile Ala Leu Gln Pro Val Val Asp Ile Val Ala Thr Met Val Ala
225                 230                 235                 240

Arg Leu Ser Pro Ala Leu Arg Glu Gly Gly Asn His Ala Leu Leu Ile
                245                 250                 255

Asn Asn Leu Gly Ala Val Pro Pro Leu Glu Met Thr Val Ile Ala Asn
            260                 265                 270

Val Val Leu Ser Ser Ser Leu Ala Asp Arg Val Arg Leu Ile Ile Gly
        275                 280                 285

Pro Ala Pro Met Met Thr Ala Leu Asn Met Asn Gly Phe Ser Leu Ser
    290                 295                 300

Leu Ile Arg Leu Asp Ala Ala Arg Glu Ala Ala Leu Thr Ala Ala Val
305                 310                 315                 320

Glu Pro His Ala Trp Met Pro Ala Val Glu Arg His Glu Ile Arg Val
                325                 330                 335

Ile Ala Ala Pro Arg Thr Ser Ala Gly Leu Asn Gly Ala Pro Val Ala
            340                 345                 350

Gly Asp Asn Leu Arg Asn Arg Arg Leu Ile Thr Ala Leu Cys Glu His
        355                 360                 365

Leu Ile Ser Gln Glu Ser Glu Leu Asn Arg Leu Asp Gly Arg Val Gly
    370                 375                 380

Asp Gly Asp Thr Gly Ser Thr Val Ala Thr Gly Ala Arg Ser Val Leu
385                 390                 395                 400

Ala Arg Leu Asp Thr Leu Pro Leu Asp Arg Pro Ala Ala Thr Leu Ala
                405                 410                 415

Ser Leu Gly Asp Ile Leu Gly Thr Ser Met Gly Gly Ser Ser Gly Val
            420                 425                 430

Leu Leu Ser Ile Phe Phe Thr Ala Ala Ala Lys Ala Met Ala Asp Lys
        435                 440                 445

Ala Asp Ile Ser Ala Ala Leu Ile Ala Gly Leu Asp Arg Met Thr Phe
    450                 455                 460

Tyr Gly Gly Ala Glu Val Gly Asp Arg Thr Met Val Asp Ala Leu Ser
465                 470                 475                 480

Pro Ala Leu Gln Ala Leu Ala Ser Gly Asp Val Ala Ala Ala Ala Arg
```

```
                485                 490                 495

Ala Ala Ala Ala Gly Ala Glu Ser Thr Lys Thr Met Met Lys Ala Arg
            500                 505                 510

Ala Gly Arg Ala Ser Tyr Val Gly Glu Arg Asp Leu Ala Gly Val Ala
        515                 520                 525

Asp Pro Gly Ala Val Ala Val Ala Gly Ala Phe Gly Val Ala Ala Ser
    530                 535                 540

Leu Ala
545


<210> SEQ ID NO 58
<211> LENGTH: 1701
<212> TYPE: DNA
<213> ORGANISM: Myxococcus xanthus
<220> FEATURE:
<221> NAME/KEY: CDS
<222> LOCATION: (1)..(1701)

<400> SEQUENCE: 58

atg aag aag ctg gtc aac gcc cct cgc gcg gtg gtg cgg gag atg ctg       48
Met Lys Lys Leu Val Asn Ala Pro Arg Ala Val Val Arg Glu Met Leu
1               5                   10                  15

gag ggg ttg gtc tcg ctc gcc ccc ggg cag gtg ctg ctg gac ggg gag       96
Glu Gly Leu Val Ser Leu Ala Pro Gly Gln Val Leu Leu Asp Gly Glu
            20                  25                  30

tcg gtg gtg ctc cgc gcc gac acg cct tcc gac gtc cgc gcg cgc aag      144
Ser Val Val Leu Arg Ala Asp Thr Pro Ser Asp Val Arg Ala Arg Lys
        35                  40                  45

gtg gct gtc atc tcc ggt ggc ggc agc ggc cat gag ccg gcg cac gcg      192
Val Ala Val Ile Ser Gly Gly Gly Ser Gly His Glu Pro Ala His Ala
    50                  55                  60

ggc tac gtg ggc gcg ggc atg ctg gac gcg gcg gtg gcc ggt gac gtc      240
Gly Tyr Val Gly Ala Gly Met Leu Asp Ala Ala Val Ala Gly Asp Val
65                  70                  75                  80

ttc acc tcg ccc agc acc gat gcc gtg ctg gcc gcc atc cgc gcc gtc      288
Phe Thr Ser Pro Ser Thr Asp Ala Val Leu Ala Ala Ile Arg Ala Val
                85                  90                  95

gcg ggg ccc gcg ggc gcg ctg ctc gtc gtg aag aac tac acc ggg gac      336
Ala Gly Pro Ala Gly Ala Leu Leu Val Val Lys Asn Tyr Thr Gly Asp
            100                 105                 110

cgg ctc aac ttc ggg ctc gcc gcc gag ctg gcg cgc gcc gag ggc atc      384
Arg Leu Asn Phe Gly Leu Ala Ala Glu Leu Ala Arg Ala Glu Gly Ile
        115                 120                 125

ccc gtg gag acg gtg gtg gtg gcg gac gac gtg tcc ctg cac gac acg      432
Pro Val Glu Thr Val Val Val Ala Asp Asp Val Ser Leu His Asp Thr
    130                 135                 140

gtg gag ccc gcg cgg cgc cgg ggc atc gct ggc acg gtg ctg gtc cac      480
Val Glu Pro Ala Arg Arg Arg Gly Ile Ala Gly Thr Val Leu Val His
145                 150                 155                 160

aag gtc gcg ggc gcg gcg gcc gag gcg ggc gcg gcg ctc cag gac gtc      528
Lys Val Ala Gly Ala Ala Ala Glu Ala Gly Ala Ala Leu Gln Asp Val
                165                 170                 175

ctc cgc gag gcc acc gcg gcg gcg gag gtg ctg ggc acc atg ggc gtg      576
Leu Arg Glu Ala Thr Ala Ala Ala Glu Val Leu Gly Thr Met Gly Val
            180                 185                 190

gcc ctg ggg ccc tgc acc gtg ccc gcg gcg ggc aag ccg ggc ttc acg      624
Ala Leu Gly Pro Cys Thr Val Pro Ala Ala Gly Lys Pro Gly Phe Thr
        195                 200                 205

ctg gag gag gac gaa atc gag ctg ggc ctg ggc atc cac ggc gag cag      672
Leu Glu Glu Asp Glu Ile Glu Leu Gly Leu Gly Ile His Gly Glu Gln
    210                 215                 220
```

```
ggc gtg cgg cgc gtg ccg atg cag acg gcg gac agc ctg gtg gac acg      720
Gly Val Arg Arg Val Pro Met Gln Thr Ala Asp Ser Leu Val Asp Thr
225                 230                 235                 240

ctg ctc acc acc atc gtc gag gac cgg cgc atc acc tcg gga gac agg      768
Leu Leu Thr Thr Ile Val Glu Asp Arg Arg Ile Thr Ser Gly Asp Arg
                245                 250                 255

gtg gtg ctg gtg gtc aac gga ttg ggc ggc acg ccg ccc atg gag ctg      816
Val Val Leu Val Val Asn Gly Leu Gly Gly Thr Pro Pro Met Glu Leu
            260                 265                 270

gcc atc gtc gcc cgg cgc gca ctg gcc gct ctg cgt cag ggc ggc atc      864
Ala Ile Val Ala Arg Arg Ala Leu Ala Ala Leu Arg Gln Gly Gly Ile
        275                 280                 285

cgc gtg gag cgc gcg tgg agc ggg acg ttc ctc tcc gcg ctg gag atg      912
Arg Val Glu Arg Ala Trp Ser Gly Thr Phe Leu Ser Ala Leu Glu Met
    290                 295                 300

ccc ggc tgc tcg ttg acg ctg ctg aag gtg gac gac gcg cgg ctg gcc      960
Pro Gly Cys Ser Leu Thr Leu Leu Lys Val Asp Asp Ala Arg Leu Ala
305                 310                 315                 320

cgc ctg gat gcg gcg gtg gat gcg ccc gcg tgg ccc ggc gcg gga cgg     1008
Arg Leu Asp Ala Ala Val Asp Ala Pro Ala Trp Pro Gly Ala Gly Arg
                325                 330                 335

ctg ccg aag gag ccg ggg gtg tac cgg cct tcg tcc acg gcg tct cca     1056
Leu Pro Lys Glu Pro Gly Val Tyr Arg Pro Ser Ser Thr Ala Ser Pro
            340                 345                 350

gca tcg ctt ccg gcg gag gcg ccg caa ccg ggg atg gac cgc ttc cgg     1104
Ala Ser Leu Pro Ala Glu Ala Pro Gln Pro Gly Met Asp Arg Phe Arg
        355                 360                 365

aag gcc gcc ttg cgg gtg gcg gac gca ttc gag cag tcg gag ccc cgg     1152
Lys Ala Ala Leu Arg Val Ala Asp Ala Phe Glu Gln Ser Glu Pro Arg
    370                 375                 380

ctg acc gcg ctc gat agc gcc gcg ggc gac ggt gac ctg ggc ctc agt     1200
Leu Thr Ala Leu Asp Ser Ala Ala Gly Asp Gly Asp Leu Gly Leu Ser
385                 390                 395                 400

ctg gtg cgt ggc gcc gag gcg att cgc gct ctt ccg gag gac gcg tgg     1248
Leu Val Arg Gly Ala Glu Ala Ile Arg Ala Leu Pro Glu Asp Ala Trp
                405                 410                 415

acg agc ccc gcg cgt gcg ctg acg gcc att ggc aat gcc ttg cgg cgc     1296
Thr Ser Pro Ala Arg Ala Leu Thr Ala Ile Gly Asn Ala Leu Arg Arg
            420                 425                 430

agc att ggc ggc agc tcg ggg ccc ttc tac gcg acg gcg ctg ctg cgc     1344
Ser Ile Gly Gly Ser Ser Gly Pro Phe Tyr Ala Thr Ala Leu Leu Arg
        435                 440                 445

gcc gcg cgc agg ctg gcg gaa ggg ccc gtg gat gcc gcc gca tgg gcc     1392
Ala Ala Arg Arg Leu Ala Glu Gly Pro Val Asp Ala Ala Ala Trp Ala
    450                 455                 460

gag gcc ttc gac ctc gcc gtc acc gcc gta tcg gag ctg ggc ggc gcg     1440
Glu Ala Phe Asp Leu Ala Val Thr Ala Val Ser Glu Leu Gly Gly Ala
465                 470                 475                 480

cgg cct ggg gac cgc acc atg ctc gat gca ctc cgg ccc gcc gcc gac     1488
Arg Pro Gly Asp Arg Thr Met Leu Asp Ala Leu Arg Pro Ala Ala Asp
                485                 490                 495

gcc ttc gcg aag gcg gtg cgt tgc ggg cag ggg gct cgc gag gcc tgg     1536
Ala Phe Ala Lys Ala Val Arg Cys Gly Gln Gly Ala Arg Glu Ala Trp
            500                 505                 510

gcc tcg gcg gtg cac gcg gcc gag gcg gga gag gag gcg acg tcc cgg     1584
Ala Ser Ala Val His Ala Ala Glu Ala Gly Glu Glu Ala Thr Ser Arg
        515                 520                 525

atg cag ccg cgc ctg gga cgc gcc agc tac ctg ggt gcg cgc gcc gtc     1632
Met Gln Pro Arg Leu Gly Arg Ala Ser Tyr Leu Gly Ala Arg Ala Val
    530                 535                 540
```

```
ggt gtg ccg gac gcg ggc gcc gcg gcc gtg gtg gtg tgg atg aag gcg     1680
Gly Val Pro Asp Ala Gly Ala Ala Ala Val Val Val Trp Met Lys Ala
545                 550                 555                 560

ctc acg cct ggc atc ggc tga                                         1701
Leu Thr Pro Gly Ile Gly
                565


<210> SEQ ID NO 59
<211> LENGTH: 566
<212> TYPE: PRT
<213> ORGANISM: Myxococcus xanthus

<400> SEQUENCE: 59

Met Lys Lys Leu Val Asn Ala Pro Arg Ala Val Val Arg Glu Met Leu
1               5                   10                  15

Glu Gly Leu Val Ser Leu Ala Pro Gly Gln Val Leu Leu Asp Gly Glu
            20                  25                  30

Ser Val Val Leu Arg Ala Asp Thr Pro Ser Asp Val Arg Ala Arg Lys
        35                  40                  45

Val Ala Val Ile Ser Gly Gly Gly Ser Gly His Glu Pro Ala His Ala
    50                  55                  60

Gly Tyr Val Gly Ala Gly Met Leu Asp Ala Ala Val Ala Gly Asp Val
65                  70                  75                  80

Phe Thr Ser Pro Ser Thr Asp Ala Val Leu Ala Ala Ile Arg Ala Val
                85                  90                  95

Ala Gly Pro Ala Gly Ala Leu Leu Val Val Lys Asn Tyr Thr Gly Asp
            100                 105                 110

Arg Leu Asn Phe Gly Leu Ala Ala Glu Leu Ala Arg Ala Glu Gly Ile
        115                 120                 125

Pro Val Glu Thr Val Val Val Ala Asp Asp Val Ser Leu His Asp Thr
    130                 135                 140

Val Glu Pro Ala Arg Arg Arg Gly Ile Ala Gly Thr Val Leu Val His
145                 150                 155                 160

Lys Val Ala Gly Ala Ala Ala Glu Ala Gly Ala Ala Leu Gln Asp Val
                165                 170                 175

Leu Arg Glu Ala Thr Ala Ala Ala Glu Val Leu Gly Thr Met Gly Val
            180                 185                 190

Ala Leu Gly Pro Cys Thr Val Pro Ala Ala Gly Lys Pro Gly Phe Thr
        195                 200                 205

Leu Glu Glu Asp Glu Ile Glu Leu Gly Leu Gly Ile His Gly Glu Gln
    210                 215                 220

Gly Val Arg Arg Val Pro Met Gln Thr Ala Asp Ser Leu Val Asp Thr
225                 230                 235                 240

Leu Leu Thr Thr Ile Val Glu Asp Arg Arg Ile Thr Ser Gly Asp Arg
                245                 250                 255

Val Val Leu Val Val Asn Gly Leu Gly Gly Thr Pro Pro Met Glu Leu
            260                 265                 270

Ala Ile Val Ala Arg Arg Ala Leu Ala Ala Leu Arg Gln Gly Gly Ile
        275                 280                 285

Arg Val Glu Arg Ala Trp Ser Gly Thr Phe Leu Ser Ala Leu Glu Met
    290                 295                 300

Pro Gly Cys Ser Leu Thr Leu Leu Lys Val Asp Asp Ala Arg Leu Ala
305                 310                 315                 320

Arg Leu Asp Ala Ala Val Asp Ala Pro Ala Trp Pro Gly Ala Gly Arg
                325                 330                 335
```

```
Leu Pro Lys Glu Pro Gly Val Tyr Arg Pro Ser Ser Thr Ala Ser Pro
            340                 345                 350

Ala Ser Leu Pro Ala Glu Ala Pro Gln Pro Gly Met Asp Arg Phe Arg
        355                 360                 365

Lys Ala Ala Leu Arg Val Ala Asp Ala Phe Glu Gln Ser Glu Pro Arg
    370                 375                 380

Leu Thr Ala Leu Asp Ser Ala Ala Gly Asp Gly Asp Leu Gly Leu Ser
385                 390                 395                 400

Leu Val Arg Gly Ala Glu Ala Ile Arg Ala Leu Pro Glu Asp Ala Trp
                405                 410                 415

Thr Ser Pro Ala Arg Ala Leu Thr Ala Ile Gly Asn Ala Leu Arg Arg
            420                 425                 430

Ser Ile Gly Gly Ser Ser Gly Pro Phe Tyr Ala Thr Ala Leu Leu Arg
        435                 440                 445

Ala Ala Arg Arg Leu Ala Glu Gly Pro Val Asp Ala Ala Ala Trp Ala
    450                 455                 460

Glu Ala Phe Asp Leu Ala Val Thr Ala Val Ser Glu Leu Gly Gly Ala
465                 470                 475                 480

Arg Pro Gly Asp Arg Thr Met Leu Asp Ala Leu Arg Pro Ala Ala Asp
                485                 490                 495

Ala Phe Ala Lys Ala Val Arg Cys Gly Gln Gly Ala Arg Glu Ala Trp
            500                 505                 510

Ala Ser Ala Val His Ala Ala Glu Ala Gly Glu Glu Ala Thr Ser Arg
        515                 520                 525

Met Gln Pro Arg Leu Gly Arg Ala Ser Tyr Leu Gly Ala Arg Ala Val
    530                 535                 540

Gly Val Pro Asp Ala Gly Ala Ala Ala Val Val Val Trp Met Lys Ala
545                 550                 555                 560

Leu Thr Pro Gly Ile Gly
                565


<210> SEQ ID NO 60
<211> LENGTH: 1701
<212> TYPE: DNA
<213> ORGANISM: Burkholderia sp. 383
<220> FEATURE:
<221> NAME/KEY: CDS
<222> LOCATION: (1)..(1701)

<400> SEQUENCE: 60

atg aaa aag ctt gtc aac cgc ccg tcc gat gtc gtg cga gaa atg ctg       48
Met Lys Lys Leu Val Asn Arg Pro Ser Asp Val Val Arg Glu Met Leu
1               5                   10                  15

gaa ggc atc gcg cgg cag tcg ccg cat gtc gcg atc ctc ggc gac gag       96
Glu Gly Ile Ala Arg Gln Ser Pro His Val Ala Ile Leu Gly Asp Glu
            20                  25                  30

cac gtg ctc gtc cgc cag ccg ctg ccc gag ccc gcg caa cgc ccc gtc      144
His Val Leu Val Arg Gln Pro Leu Pro Glu Pro Ala Gln Arg Pro Val
        35                  40                  45

gcc atc ctg tcc ggt ggc ggc agc ggc cac gag ccc gcg cac ggc ggc      192
Ala Ile Leu Ser Gly Gly Gly Ser Gly His Glu Pro Ala His Gly Gly
    50                  55                  60

tat gtc ggc gaa gga atg ctg agc gcg gcc gtc tgc ggc gaa gtg ttc      240
Tyr Val Gly Glu Gly Met Leu Ser Ala Ala Val Cys Gly Glu Val Phe
65                  70                  75                  80

acg tcg ccg tcc aca gac gcc gtg ctc gcc gcg atc cgc gcg agc gcc      288
Thr Ser Pro Ser Thr Asp Ala Val Leu Ala Ala Ile Arg Ala Ser Ala
                85                  90                  95
```

-continued

```
ggc ccg aac ggc gcc ttg ctg atc gtg aag aac tac acg ggc gac cgg      336
Gly Pro Asn Gly Ala Leu Leu Ile Val Lys Asn Tyr Thr Gly Asp Arg
            100                 105                 110

ctc aat ttc ggg ctc gcc gcc gaa ctc gca cgc gcc gaa ggc att ccg      384
Leu Asn Phe Gly Leu Ala Ala Glu Leu Ala Arg Ala Glu Gly Ile Pro
        115                 120                 125

gtc gag acg gtc atc gtc gcc gac gac gta tcg ctg cgc ggc cgc gtc      432
Val Glu Thr Val Ile Val Ala Asp Asp Val Ser Leu Arg Gly Arg Val
    130                 135                 140

gag cgc ggc cag cgg cgc ggg atc gcc ggt acc gtg ctg atc cac aag      480
Glu Arg Gly Gln Arg Arg Gly Ile Ala Gly Thr Val Leu Ile His Lys
145                 150                 155                 160

ctc gcc ggc gcg gca gcc gcg cgc ggg ctg ccg ctc gcc cgc gtc gcg      528
Leu Ala Gly Ala Ala Ala Ala Arg Gly Leu Pro Leu Ala Arg Val Ala
                165                 170                 175

gcc atc gcg cgc gac gcg gcg gcc gaa ctc ggc acg atg ggt gtc gca      576
Ala Ile Ala Arg Asp Ala Ala Ala Glu Leu Gly Thr Met Gly Val Ala
            180                 185                 190

ctc gac ggc tgc acg atc ccg ggc gcc gac aag tcg ggc ttc agc ctc      624
Leu Asp Gly Cys Thr Ile Pro Gly Ala Asp Lys Ser Gly Phe Ser Leu
        195                 200                 205

ggc gat cac gag atc gaa ctc ggc ctc ggc atc cat ggc gag aaa ggc      672
Gly Asp His Glu Ile Glu Leu Gly Leu Gly Ile His Gly Glu Lys Gly
    210                 215                 220

gtc gag cgc cgc gcg ccg ctg ccg gcc gat gcg ctt gtc gac acg ctg      720
Val Glu Arg Arg Ala Pro Leu Pro Ala Asp Ala Leu Val Asp Thr Leu
225                 230                 235                 240

ctg tcg agc atc gcc gcc gat ctc gtg ctc gac cgc ggc gaa cgc gtt      768
Leu Ser Ser Ile Ala Ala Asp Leu Val Leu Asp Arg Gly Glu Arg Val
                245                 250                 255

gcg ctg ttc gtc aac ggc ctc ggc gcg acg ccg gac atg gaa ctc gcg      816
Ala Leu Phe Val Asn Gly Leu Gly Ala Thr Pro Asp Met Glu Leu Ala
            260                 265                 270

atc gtg ctg cgc gcc gcg cac gac aac ctg cac cgg cgc ggc atc gtc      864
Ile Val Leu Arg Ala Ala His Asp Asn Leu His Arg Arg Gly Ile Val
        275                 280                 285

gtc gcg cgt gcg tgg gcc ggc acg ttc ctg tcg gcg ctg aac atg ccc      912
Val Ala Arg Ala Trp Ala Gly Thr Phe Leu Ser Ala Leu Asn Met Pro
    290                 295                 300

ggc tgc tcg atc tcg gtg ctg cgg ctg aac gac gaa cgc gcg gtg ctg      960
Gly Cys Ser Ile Ser Val Leu Arg Leu Asn Asp Glu Arg Ala Val Leu
305                 310                 315                 320

ctc gac gca ccg acg cag gcg cgt gca tgg cca ggc ggc ggc gcg gtg     1008
Leu Asp Ala Pro Thr Gln Ala Arg Ala Trp Pro Gly Gly Gly Ala Val
                325                 330                 335

aat acg cag atc cgt gtg gcc tcg gcc gcc gtg cag gaa gcg ccg ttg     1056
Asn Thr Gln Ile Arg Val Ala Ser Ala Ala Val Gln Glu Ala Pro Leu
            340                 345                 350

ccg ccg ctc gat gcg gcc ggc cgc gcg tgg gcc gcg cgc ctg caa ccg     1104
Pro Pro Leu Asp Ala Ala Gly Arg Ala Trp Ala Ala Arg Leu Gln Pro
        355                 360                 365

gca ttg cac gcg gtc gcg caa acg ctg atc gat cac gag cag acg ctg     1152
Ala Leu His Ala Val Ala Gln Thr Leu Ile Asp His Glu Gln Thr Leu
    370                 375                 380

acc gac ctc gat gcg gcg gcc ggc gac ggc gat ctc ggc gcg agc atg     1200
Thr Asp Leu Asp Ala Ala Ala Gly Asp Gly Asp Leu Gly Ala Ser Met
385                 390                 395                 400

ctg cgc gcc gcg cag gcg atc ctc gca ctg ccg gaa agc gca tac ggc     1248
Leu Arg Ala Ala Gln Ala Ile Leu Ala Leu Pro Glu Ser Ala Tyr Gly
                405                 410                 415
```

```
acg ccg gcc ggc gcg ctc tcg gcg ctc ggc gcc gcg ttg cgc cgc gcg     1296
Thr Pro Ala Gly Ala Leu Ser Ala Leu Gly Ala Ala Leu Arg Arg Ala
            420                 425                 430

atc gcc ggc agc tcg ggg ccg ttc tat gcg acc gcg ctg ctg cgc gcg     1344
Ile Ala Gly Ser Ser Gly Pro Phe Tyr Ala Thr Ala Leu Leu Arg Ala
        435                 440                 445

tcg cgc cgg ctg gcc gat atc gcc gag ccg tcc gca cgc gac tgg gcc     1392
Ser Arg Arg Leu Ala Asp Ile Ala Glu Pro Ser Ala Arg Asp Trp Ala
    450                 455                 460

gcg gcg ttc cgc ggc gcg gtg gat tcg atc agc gaa ctg ggc ggc gcg     1440
Ala Ala Phe Arg Gly Ala Val Asp Ser Ile Ser Glu Leu Gly Gly Ala
465                 470                 475                 480

cac gcc ggc gac cgg acc atg ctc gat gcg ctg gtc ccg gcc gtc gcg     1488
His Ala Gly Asp Arg Thr Met Leu Asp Ala Leu Val Pro Ala Val Ala
                485                 490                 495

gca ttc gag cgg gcg ctc gac aac gat cgc gat ccc gcc ggc gca tgg     1536
Ala Phe Glu Arg Ala Leu Asp Asn Asp Arg Asp Pro Ala Gly Ala Trp
            500                 505                 510

acg gcc gcg gtc gaa gcc gcc gag cac ggt gcg cag gaa acc gca cgc     1584
Thr Ala Ala Val Glu Ala Ala Glu His Gly Ala Gln Glu Thr Ala Arg
        515                 520                 525

atg acg cca cgc gcc ggg cgc gcg agc tat ctc ggc gaa cgt gcg atc     1632
Met Thr Pro Arg Ala Gly Arg Ala Ser Tyr Leu Gly Glu Arg Ala Ile
    530                 535                 540

ggc acg ccg gac ggc ggc gcg gtc gcg gtg tcg tat tgg ctg cgt gcg     1680
Gly Thr Pro Asp Gly Gly Ala Val Ala Val Ser Tyr Trp Leu Arg Ala
545                 550                 555                 560

ttg cag gca cac atc ggg tga                                         1701
Leu Gln Ala His Ile Gly
                565


<210> SEQ ID NO 61
<211> LENGTH: 566
<212> TYPE: PRT
<213> ORGANISM: Burkholderia sp. 383

<400> SEQUENCE: 61

Met Lys Lys Leu Val Asn Arg Pro Ser Asp Val Val Arg Glu Met Leu
1               5                   10                  15

Glu Gly Ile Ala Arg Gln Ser Pro His Val Ala Ile Leu Gly Asp Glu
            20                  25                  30

His Val Leu Val Arg Gln Pro Leu Pro Glu Pro Ala Gln Arg Pro Val
        35                  40                  45

Ala Ile Leu Ser Gly Gly Gly Ser Gly His Glu Pro Ala His Gly Gly
    50                  55                  60

Tyr Val Gly Glu Gly Met Leu Ser Ala Ala Val Cys Gly Glu Val Phe
65                  70                  75                  80

Thr Ser Pro Ser Thr Asp Ala Val Leu Ala Ala Ile Arg Ala Ser Ala
                85                  90                  95

Gly Pro Asn Gly Ala Leu Leu Ile Val Lys Asn Tyr Thr Gly Asp Arg
            100                 105                 110

Leu Asn Phe Gly Leu Ala Ala Glu Leu Ala Arg Ala Glu Gly Ile Pro
        115                 120                 125

Val Glu Thr Val Ile Val Ala Asp Asp Val Ser Leu Arg Gly Arg Val
    130                 135                 140

Glu Arg Gly Gln Arg Arg Gly Ile Ala Gly Thr Val Leu Ile His Lys
145                 150                 155                 160

Leu Ala Gly Ala Ala Ala Ala Arg Gly Leu Pro Leu Ala Arg Val Ala
                165                 170                 175
```

```
Ala Ile Ala Arg Asp Ala Ala Ala Glu Leu Gly Thr Met Gly Val Ala
            180                 185                 190

Leu Asp Gly Cys Thr Ile Pro Gly Ala Asp Lys Ser Gly Phe Ser Leu
        195                 200                 205

Gly Asp His Glu Ile Glu Leu Gly Leu Gly Ile His Gly Glu Lys Gly
    210                 215                 220

Val Glu Arg Arg Ala Pro Leu Pro Ala Asp Ala Leu Val Asp Thr Leu
225                 230                 235                 240

Leu Ser Ser Ile Ala Ala Asp Leu Val Leu Asp Arg Gly Glu Arg Val
                245                 250                 255

Ala Leu Phe Val Asn Gly Leu Gly Ala Thr Pro Asp Met Glu Leu Ala
            260                 265                 270

Ile Val Leu Arg Ala Ala His Asp Asn Leu His Arg Arg Gly Ile Val
        275                 280                 285

Val Ala Arg Ala Trp Ala Gly Thr Phe Leu Ser Ala Leu Asn Met Pro
    290                 295                 300

Gly Cys Ser Ile Ser Val Leu Arg Leu Asn Asp Glu Arg Ala Val Leu
305                 310                 315                 320

Leu Asp Ala Pro Thr Gln Ala Arg Ala Trp Pro Gly Gly Gly Ala Val
                325                 330                 335

Asn Thr Gln Ile Arg Val Ala Ser Ala Ala Val Gln Glu Ala Pro Leu
            340                 345                 350

Pro Pro Leu Asp Ala Ala Gly Arg Ala Trp Ala Ala Arg Leu Gln Pro
        355                 360                 365

Ala Leu His Ala Val Ala Gln Thr Leu Ile Asp His Glu Gln Thr Leu
    370                 375                 380

Thr Asp Leu Asp Ala Ala Ala Gly Asp Gly Asp Leu Gly Ala Ser Met
385                 390                 395                 400

Leu Arg Ala Ala Gln Ala Ile Leu Ala Leu Pro Glu Ser Ala Tyr Gly
                405                 410                 415

Thr Pro Ala Gly Ala Leu Ser Ala Leu Gly Ala Ala Leu Arg Arg Ala
            420                 425                 430

Ile Ala Gly Ser Ser Gly Pro Phe Tyr Ala Thr Ala Leu Leu Arg Ala
        435                 440                 445

Ser Arg Arg Leu Ala Asp Ile Ala Glu Pro Ser Ala Arg Asp Trp Ala
    450                 455                 460

Ala Ala Phe Arg Gly Ala Val Asp Ser Ile Ser Glu Leu Gly Gly Ala
465                 470                 475                 480

His Ala Gly Asp Arg Thr Met Leu Asp Ala Leu Val Pro Ala Val Ala
                485                 490                 495

Ala Phe Glu Arg Ala Leu Asp Asn Asp Arg Asp Pro Ala Gly Ala Trp
            500                 505                 510

Thr Ala Ala Val Glu Ala Ala Glu His Gly Ala Gln Glu Thr Ala Arg
        515                 520                 525

Met Thr Pro Arg Ala Gly Arg Ala Ser Tyr Leu Gly Glu Arg Ala Ile
    530                 535                 540

Gly Thr Pro Asp Gly Gly Ala Val Ala Val Ser Tyr Trp Leu Arg Ala
545                 550                 555                 560

Leu Gln Ala His Ile Gly
                565
```

<210> SEQ ID NO 62
<211> LENGTH: 1704
<212> TYPE: DNA

```
<213> ORGANISM: Burkholderia thailandensis E264
<220> FEATURE:
<221> NAME/KEY: CDS
<222> LOCATION: (1)..(1704)

<400> SEQUENCE: 62

atg aag aag ctc gtc aac cac ccg tcc gac gtc gtg cgc gaa atg ctg      48
Met Lys Lys Leu Val Asn His Pro Ser Asp Val Val Arg Glu Met Leu
1               5                   10                  15

gag ggc atc gcg cgg cag tcg ccg cat gtc gcg atg ctc ggc gac gaa      96
Glu Gly Ile Ala Arg Gln Ser Pro His Val Ala Met Leu Gly Asp Glu
            20                  25                  30

cac gtg ctg atc cgg cgc ccc ttg ccg gag ccg gcg cgg cgt gcg gtc     144
His Val Leu Ile Arg Arg Pro Leu Pro Glu Pro Ala Arg Arg Ala Val
        35                  40                  45

gcg atc atc tcc ggc ggc ggc agc ggc cac gag ccg gcg cac ggc ggc     192
Ala Ile Ile Ser Gly Gly Gly Ser Gly His Glu Pro Ala His Gly Gly
    50                  55                  60

tac gtc ggc gcg ggg atg ctg agc gcg gcc gtg tgc ggc gag gtc ttc     240
Tyr Val Gly Ala Gly Met Leu Ser Ala Ala Val Cys Gly Glu Val Phe
65                  70                  75                  80

acg tcg ccg ccc gcc gat gcg gtg ctc gcc gcg att cgc gcg acc gcg     288
Thr Ser Pro Pro Ala Asp Ala Val Leu Ala Ala Ile Arg Ala Thr Ala
                85                  90                  95

ggc cag aac ggc gcg ctc ctc atc gtg aag aac tac acg ggc gat cgc     336
Gly Gln Asn Gly Ala Leu Leu Ile Val Lys Asn Tyr Thr Gly Asp Arg
            100                 105                 110

ctc aat ttc ggg ctc gcg gcc gag ctc gcg cgc gcg cag ggc att ccg     384
Leu Asn Phe Gly Leu Ala Ala Glu Leu Ala Arg Ala Gln Gly Ile Pro
        115                 120                 125

gtc gag atc gtc gtc gtc gcg gac gac gtg tcg ctg cgc gaa ctc acc     432
Val Glu Ile Val Val Val Ala Asp Asp Val Ser Leu Arg Glu Leu Thr
    130                 135                 140

gag cgc ggg cgc cgc cgc ggc atc gcc ggc acc gtg ctc gtg cac aag     480
Glu Arg Gly Arg Arg Arg Gly Ile Ala Gly Thr Val Leu Val His Lys
145                 150                 155                 160

ctc gcc ggc gcg gcc gcc gag cgc ggc ctc gcg ctg cgg gag gtg gcc     528
Leu Ala Gly Ala Ala Ala Glu Arg Gly Leu Ala Leu Arg Glu Val Ala
                165                 170                 175

gcc gtc gcg agc gag gcg gcg gcg aat ctc ggc acg atg ggc gtc gca     576
Ala Val Ala Ser Glu Ala Ala Ala Asn Leu Gly Thr Met Gly Val Ala
            180                 185                 190

ctc gac ggc tgc acg att ccg ggc gcc ggg caa tcg ggc ttc cgc ctc     624
Leu Asp Gly Cys Thr Ile Pro Gly Ala Gly Gln Ser Gly Phe Arg Leu
        195                 200                 205

gcc gat cac gag atc gag ctc gga ttg ggc att cac ggc gaa aag ggc     672
Ala Asp His Glu Ile Glu Leu Gly Leu Gly Ile His Gly Glu Lys Gly
    210                 215                 220

gtg cag cgc acg gcg ccg atg ccg gcc gac gcg ctg tcg gaa acg ctc     720
Val Gln Arg Thr Ala Pro Met Pro Ala Asp Ala Leu Ser Glu Thr Leu
225                 230                 235                 240

gtg gcg acg atc gtc gac gat cag gcg atc gcg cgc ggc gat cgg gtc     768
Val Ala Thr Ile Val Asp Asp Gln Ala Ile Ala Arg Gly Asp Arg Val
                245                 250                 255

gcg ctt ctg gtg aac ggg ctc ggc gcg acg ccg gac atg gag ctc ggc     816
Ala Leu Leu Val Asn Gly Leu Gly Ala Thr Pro Asp Met Glu Leu Gly
            260                 265                 270

atc gtg ctg cgc gcg gcg tac gac agc ctg agc cgg cgt ggc gtc gag     864
Ile Val Leu Arg Ala Ala Tyr Asp Ser Leu Ser Arg Arg Gly Val Glu
        275                 280                 285

gtg gcg cgc gcg tgg gcg ggc acg ttc ctg tcc gcg ctc gac atg ccc     912
```

```
Val Ala Arg Ala Trp Ala Gly Thr Phe Leu Ser Ala Leu Asp Met Pro
    290                 295                 300

ggc tgc tcg att tcg ctg ctc aag ctg aac gat cgc atg ctc gaa ctg      960
Gly Cys Ser Ile Ser Leu Leu Lys Leu Asn Asp Arg Met Leu Glu Leu
305                 310                 315                 320

ctc gac gcg ccg acg caa gcg cga gcg tgg ccg ggc ggc ggc gcg gtg     1008
Leu Asp Ala Pro Thr Gln Ala Arg Ala Trp Pro Gly Gly Gly Ala Val
                325                 330                 335

aac cgg gac att cgc gtg gcc gcc gcc ggg acc ggc gca gga gac gga     1056
Asn Arg Asp Ile Arg Val Ala Ala Ala Gly Thr Gly Ala Gly Asp Gly
            340                 345                 350

cag ccg gaa tgg gcg acg gcc ggc gcg gcg ggt tcc gac gga ctg cgg     1104
Gln Pro Glu Trp Ala Thr Ala Gly Ala Ala Gly Ser Asp Gly Leu Arg
        355                 360                 365

ccc gcg ctg cat gcg gtt gcc gcc gcg ctg atc gac agc gag ccc gtg     1152
Pro Ala Leu His Ala Val Ala Ala Ala Leu Ile Asp Ser Glu Pro Val
    370                 375                 380

ttg acc gag ctc gat tcc gtc gcc ggc gac ggc gat ctg ggc gcg agc     1200
Leu Thr Glu Leu Asp Ser Val Ala Gly Asp Gly Asp Leu Gly Ala Ser
385                 390                 395                 400

atg cgc cgc gcg gcg aac gcg atg ctc gcg ctg ccc gcc gat gcg tat     1248
Met Arg Arg Ala Ala Asn Ala Met Leu Ala Leu Pro Ala Asp Ala Tyr
                405                 410                 415

cga ggg ccg gcg aac ctg ctc gcc gcg ctg ggc atg gcg ctg cgc cgg     1296
Arg Gly Pro Ala Asn Leu Leu Ala Ala Leu Gly Met Ala Leu Arg Arg
            420                 425                 430

gcg atc gcg ggc agc tcc ggg ccg ttt tac gca acg gcg ctg gtg cgc     1344
Ala Ile Ala Gly Ser Ser Gly Pro Phe Tyr Ala Thr Ala Leu Val Arg
        435                 440                 445

gcg ggc cgc cgg ctc gcc gat gca tcg gcg ccg acc gcg cgc gac tgg     1392
Ala Gly Arg Arg Leu Ala Asp Ala Ser Ala Pro Thr Ala Arg Asp Trp
    450                 455                 460

gcg agc gcg ttc cgg agc ggt gtc gac gcg atc ggc gat ctg ggc ggc     1440
Ala Ser Ala Phe Arg Ser Gly Val Asp Ala Ile Gly Asp Leu Gly Gly
465                 470                 475                 480

gcg aag ccc gga gac cgc acg atg ctc gac gcc ttg gtg ccc gcc gtc     1488
Ala Lys Pro Gly Asp Arg Thr Met Leu Asp Ala Leu Val Pro Ala Val
                485                 490                 495

gat gcg ttc gag cac gcg ctg tcg gcg ggc ggg agc gcg agc gat gcg     1536
Asp Ala Phe Glu His Ala Leu Ser Ala Gly Gly Ser Ala Ser Asp Ala
            500                 505                 510

tgg gcg gcg gcg gtg cgc gcc gcg gag gca ggc gcg gcg aaa acc gcg     1584
Trp Ala Ala Ala Val Arg Ala Ala Glu Ala Gly Ala Ala Lys Thr Ala
        515                 520                 525

ggc atg acg ccg cgc gcg ggg cgc gcg agc tat ctg ggc gag cgc gcc     1632
Gly Met Thr Pro Arg Ala Gly Arg Ala Ser Tyr Leu Gly Glu Arg Ala
    530                 535                 540

gtg ggc tcg ccc gac ggc ggc gcg gtg gcc gtg gcg tgc tgg atg cgc     1680
Val Gly Ser Pro Asp Gly Gly Ala Val Ala Val Ala Cys Trp Met Arg
545                 550                 555                 560

gcg ttg cag ccg cac gtc gcg tag                                     1704
Ala Leu Gln Pro His Val Ala
                565


<210> SEQ ID NO 63
<211> LENGTH: 567
<212> TYPE: PRT
<213> ORGANISM: Burkholderia thailandensis E264

<400> SEQUENCE: 63

Met Lys Lys Leu Val Asn His Pro Ser Asp Val Val Arg Glu Met Leu
```

-continued

```
1               5                   10                  15

Glu Gly Ile Ala Arg Gln Ser Pro His Val Ala Met Leu Gly Asp Glu
            20                  25                  30

His Val Leu Ile Arg Arg Pro Leu Pro Glu Pro Ala Arg Arg Ala Val
        35                  40                  45

Ala Ile Ile Ser Gly Gly Gly Ser Gly His Glu Pro Ala His Gly Gly
    50                  55                  60

Tyr Val Gly Ala Gly Met Leu Ser Ala Ala Val Cys Gly Glu Val Phe
65                  70                  75                  80

Thr Ser Pro Pro Ala Asp Ala Val Leu Ala Ala Ile Arg Ala Thr Ala
                85                  90                  95

Gly Gln Asn Gly Ala Leu Leu Ile Val Lys Asn Tyr Thr Gly Asp Arg
            100                 105                 110

Leu Asn Phe Gly Leu Ala Ala Glu Leu Ala Arg Ala Gln Gly Ile Pro
        115                 120                 125

Val Glu Ile Val Val Val Ala Asp Asp Val Ser Leu Arg Glu Leu Thr
    130                 135                 140

Glu Arg Gly Arg Arg Arg Gly Ile Ala Gly Thr Val Leu Val His Lys
145                 150                 155                 160

Leu Ala Gly Ala Ala Ala Glu Arg Gly Leu Ala Leu Arg Glu Val Ala
                165                 170                 175

Ala Val Ala Ser Glu Ala Ala Ala Asn Leu Gly Thr Met Gly Val Ala
            180                 185                 190

Leu Asp Gly Cys Thr Ile Pro Gly Ala Gly Gln Ser Gly Phe Arg Leu
        195                 200                 205

Ala Asp His Glu Ile Glu Leu Gly Leu Gly Ile His Gly Glu Lys Gly
    210                 215                 220

Val Gln Arg Thr Ala Pro Met Pro Ala Asp Ala Leu Ser Glu Thr Leu
225                 230                 235                 240

Val Ala Thr Ile Val Asp Asp Gln Ala Ile Ala Arg Gly Asp Arg Val
                245                 250                 255

Ala Leu Leu Val Asn Gly Leu Gly Ala Thr Pro Asp Met Glu Leu Gly
            260                 265                 270

Ile Val Leu Arg Ala Ala Tyr Asp Ser Leu Ser Arg Arg Gly Val Glu
        275                 280                 285

Val Ala Arg Ala Trp Ala Gly Thr Phe Leu Ser Ala Leu Asp Met Pro
    290                 295                 300

Gly Cys Ser Ile Ser Leu Leu Lys Leu Asn Asp Arg Met Leu Glu Leu
305                 310                 315                 320

Leu Asp Ala Pro Thr Gln Ala Arg Ala Trp Pro Gly Gly Gly Ala Val
                325                 330                 335

Asn Arg Asp Ile Arg Val Ala Ala Ala Gly Thr Gly Ala Gly Asp Gly
            340                 345                 350

Gln Pro Glu Trp Ala Thr Ala Gly Ala Ala Gly Ser Asp Gly Leu Arg
        355                 360                 365

Pro Ala Leu His Ala Val Ala Ala Ala Leu Ile Asp Ser Glu Pro Val
    370                 375                 380

Leu Thr Glu Leu Asp Ser Val Ala Gly Asp Gly Asp Leu Gly Ala Ser
385                 390                 395                 400

Met Arg Arg Ala Ala Asn Ala Met Leu Ala Leu Pro Ala Asp Ala Tyr
                405                 410                 415

Arg Gly Pro Ala Asn Leu Leu Ala Ala Leu Gly Met Ala Leu Arg Arg
            420                 425                 430
```

```
Ala Ile Ala Gly Ser Ser Gly Pro Phe Tyr Ala Thr Ala Leu Val Arg
        435                 440                 445

Ala Gly Arg Arg Leu Ala Asp Ala Ser Ala Pro Thr Ala Arg Asp Trp
    450                 455                 460

Ala Ser Ala Phe Arg Ser Gly Val Asp Ala Ile Gly Asp Leu Gly Gly
465                 470                 475                 480

Ala Lys Pro Gly Asp Arg Thr Met Leu Asp Ala Leu Val Pro Ala Val
                485                 490                 495

Asp Ala Phe Glu His Ala Leu Ser Ala Gly Gly Ser Ala Ser Asp Ala
            500                 505                 510

Trp Ala Ala Ala Val Arg Ala Ala Glu Ala Gly Ala Ala Lys Thr Ala
        515                 520                 525

Gly Met Thr Pro Arg Ala Gly Arg Ala Ser Tyr Leu Gly Glu Arg Ala
    530                 535                 540

Val Gly Ser Pro Asp Gly Gly Ala Val Ala Val Ala Cys Trp Met Arg
545                 550                 555                 560

Ala Leu Gln Pro His Val Ala
                565


<210> SEQ ID NO 64
<211> LENGTH: 1851
<212> TYPE: DNA
<213> ORGANISM: Burkholderia multivorans
<220> FEATURE:
<221> NAME/KEY: CDS
<222> LOCATION: (1)..(1851)

<400> SEQUENCE: 64

atg tat cgt ggc acc gaa gcg cgc acc ggc gag atc cat ggc act gct       48
Met Tyr Arg Gly Thr Glu Ala Arg Thr Gly Glu Ile His Gly Thr Ala
1               5                   10                  15

cca cgc cac cgc cgc cac ggc gcg cgc att ccc gca acc cga cag ccc       96
Pro Arg His Arg Arg His Gly Ala Arg Ile Pro Ala Thr Arg Gln Pro
            20                  25                  30

gag gcg ccg gat cgg ttc ggc ccg cgg gct ttc atc tgc ccg gaa acc      144
Glu Ala Pro Asp Arg Phe Gly Pro Arg Ala Phe Ile Cys Pro Glu Thr
        35                  40                  45

gtc gcc atg aaa aaa ctc gtg aac cgt ccg tcc gac gtc gtg cgt gaa      192
Val Ala Met Lys Lys Leu Val Asn Arg Pro Ser Asp Val Val Arg Glu
    50                  55                  60

atg ctc gaa ggc att gcg cga cag tcg ccg cat ctc gcg atg ctc ggc      240
Met Leu Glu Gly Ile Ala Arg Gln Ser Pro His Leu Ala Met Leu Gly
65                  70                  75                  80

gac gag cac gtg ctc gtc cgc cgc ccg ctg ccc gaa ccg tcg cag cgc      288
Asp Glu His Val Leu Val Arg Arg Pro Leu Pro Glu Pro Ser Gln Arg
                85                  90                  95

acg gtt gcg gtg ctg tcg ggc ggc ggc agc ggg cac gag cct gcg cac      336
Thr Val Ala Val Leu Ser Gly Gly Gly Ser Gly His Glu Pro Ala His
            100                 105                 110

ggc ggc tat gtc ggc gac gga atg ctc agt gcg gcc gtg tgc ggc gaa      384
Gly Gly Tyr Val Gly Asp Gly Met Leu Ser Ala Ala Val Cys Gly Glu
        115                 120                 125

gtg ttc acg tcg ccg tcc acc gac gcg gtg ctc gcc gcg atc cgc gcg      432
Val Phe Thr Ser Pro Ser Thr Asp Ala Val Leu Ala Ala Ile Arg Ala
    130                 135                 140

acg gcc ggc ccg aac ggc gcg ctg ctc gtc gtg aag aac tac acc ggc      480
Thr Ala Gly Pro Asn Gly Ala Leu Leu Val Val Lys Asn Tyr Thr Gly
145                 150                 155                 160

gac cgg ctc aac ttc ggt ctg gca gcc gaa ctc gcg cgc gca gaa ggc      528
Asp Arg Leu Asn Phe Gly Leu Ala Ala Glu Leu Ala Arg Ala Glu Gly
```

```
                165                 170                 175

att ccg gtc gag acc gtg atc gtc gcg gac gac gta tcg ctg cgc ggc       576
Ile Pro Val Glu Thr Val Ile Val Ala Asp Asp Val Ser Leu Arg Gly
            180                 185                 190

cgc gtc gag cgc gga cag cgg cgc ggc atc gcg ggc acc gtg ctg atc       624
Arg Val Glu Arg Gly Gln Arg Arg Gly Ile Ala Gly Thr Val Leu Ile
        195                 200                 205

cac aag ctc gcg ggc gcg gcg gcc gcg cgc ggg ctg tcg ctg ccg cgc       672
His Lys Leu Ala Gly Ala Ala Ala Ala Arg Gly Leu Ser Leu Pro Arg
    210                 215                 220

gtc gcg gcg atc gcg cgc gat gcg gcc gcc gat ctc ggc acg atg ggc       720
Val Ala Ala Ile Ala Arg Asp Ala Ala Ala Asp Leu Gly Thr Met Gly
225                 230                 235                 240

gtc gcg ctc gac ggc tgt acg ctg ccg ggc gcc gac cag tcc gga ttc       768
Val Ala Leu Asp Gly Cys Thr Leu Pro Gly Ala Asp Gln Ser Gly Phe
                245                 250                 255

agc ctc gcc gac gac gaa atc gag ctc ggt ctc ggc att cat ggc gaa       816
Ser Leu Ala Asp Asp Glu Ile Glu Leu Gly Leu Gly Ile His Gly Glu
            260                 265                 270

aaa ggc gtc gaa cgc acg gcg ccg ctg ccg gcc gac gcg ctc gcc gat       864
Lys Gly Val Glu Arg Thr Ala Pro Leu Pro Ala Asp Ala Leu Ala Asp
        275                 280                 285

acg ctg ctg tcc ggg atc gtc gcc gac ctc gtg ctc gat cgc ggc gaa       912
Thr Leu Leu Ser Gly Ile Val Ala Asp Leu Val Leu Asp Arg Gly Glu
    290                 295                 300

cgc gtc gcg ctg ctc gtc aac ggt ctc ggc gcg acg ccc gac atg gag       960
Arg Val Ala Leu Leu Val Asn Gly Leu Gly Ala Thr Pro Asp Met Glu
305                 310                 315                 320

ctt gcg atc gtg ctg cgc gcc gcc tac gag aac ctg agc cgt cgc ggc      1008
Leu Ala Ile Val Leu Arg Ala Ala Tyr Glu Asn Leu Ser Arg Arg Gly
                325                 330                 335

atc gcg gtc gag cgc gcg tgg gcc ggt acg ttc ctg tcg gcg ctg aac      1056
Ile Ala Val Glu Arg Ala Trp Ala Gly Thr Phe Leu Ser Ala Leu Asn
            340                 345                 350

atg ccc ggc tgt tcg atc tcg gtg ctg cgg ctc gac gac gag cgg gcg      1104
Met Pro Gly Cys Ser Ile Ser Val Leu Arg Leu Asp Asp Glu Arg Ala
        355                 360                 365

gcg ctg ctc gac gca ccg acg caa gcg cgc gcg tgg ccc ggc ggc ggc      1152
Ala Leu Leu Asp Ala Pro Thr Gln Ala Arg Ala Trp Pro Gly Gly Gly
    370                 375                 380

gcc gtc aac gca cag atc cgc atc gcc gcc gcg gcg ccg cag gaa ccg      1200
Ala Val Asn Ala Gln Ile Arg Ile Ala Ala Ala Ala Pro Gln Glu Pro
385                 390                 395                 400

tcg ccg ccg ccg ctc gac gcg gcg ggc cgc gtg tgg gcc gag cgg ctg      1248
Ser Pro Pro Pro Leu Asp Ala Ala Gly Arg Val Trp Ala Glu Arg Leu
                405                 410                 415

cgc ccg gcg ctg cac gcg gtc gcg cac acg ctg atc gac cac gaa gca      1296
Arg Pro Ala Leu His Ala Val Ala His Thr Leu Ile Asp His Glu Ala
            420                 425                 430

acg ctg acc gag ctc gat gcc gcc gcc ggc gac ggc gac ctc ggc gcg      1344
Thr Leu Thr Glu Leu Asp Ala Ala Ala Gly Asp Gly Asp Leu Gly Ala
        435                 440                 445

agc atg cgt cgt gcc gcg gac gcg atg ctc gcg ttg ccg gaa acc gcg      1392
Ser Met Arg Arg Ala Ala Asp Ala Met Leu Ala Leu Pro Glu Thr Ala
    450                 455                 460

tat gcg acg ccg gcc ggt gcg ctc gcc gcg ctc ggc gcc gcg ctg cgc      1440
Tyr Ala Thr Pro Ala Gly Ala Leu Ala Ala Leu Gly Ala Ala Leu Arg
465                 470                 475                 480

cgt gcg atc gcg ggc agc tcg ggc ccc ttc tac gcg acc gcg ctg ctg      1488
Arg Ala Ile Ala Gly Ser Ser Gly Pro Phe Tyr Ala Thr Ala Leu Leu
```

```
                485                 490                 495

cgc gca tcg cgg cgc ctg gcc ggc ctc gcg cag ccg tcg gca cgc gac     1536
Arg Ala Ser Arg Arg Leu Ala Gly Leu Ala Gln Pro Ser Ala Arg Asp
            500                 505                 510

tgg gcc gcg gca ttg cgc agc gca gcc gat gcg atc gcc gaa ctc ggc     1584
Trp Ala Ala Ala Leu Arg Ser Ala Ala Asp Ala Ile Ala Glu Leu Gly
        515                 520                 525

ggc gcc cgt gcc ggt gac aga acg atg ctc gac gcg ctg gtg ccg gcc     1632
Gly Ala Arg Ala Gly Asp Arg Thr Met Leu Asp Ala Leu Val Pro Ala
    530                 535                 540

gcc gcc gcg ttc gac cgt gca ctc gac gac ggt cgc gac agc gcc ggc     1680
Ala Ala Ala Phe Asp Arg Ala Leu Asp Asp Gly Arg Asp Ser Ala Gly
545                 550                 555                 560

gcg tgg gcg gcc gcc gtc gac gcc gcc gag cgc ggt gcg cag gac acc     1728
Ala Trp Ala Ala Ala Val Asp Ala Ala Glu Arg Gly Ala Gln Asp Thr
            565                 570                 575

gcg cgc atg acg ccg cgc gcg ggc cgt gcg agc tat ctc ggc gaa cgc     1776
Ala Arg Met Thr Pro Arg Ala Gly Arg Ala Ser Tyr Leu Gly Glu Arg
            580                 585                 590

gcg atc ggc acg ccc gac ggc ggc gcc atc gcc gtc gcg tac tgg ctg     1824
Ala Ile Gly Thr Pro Asp Gly Gly Ala Ile Ala Val Ala Tyr Trp Leu
        595                 600                 605

cgc gca ctg ctg ccg cac gtc cga taa                                 1851
Arg Ala Leu Leu Pro His Val Arg
    610                 615


<210> SEQ ID NO 65
<211> LENGTH: 616
<212> TYPE: PRT
<213> ORGANISM: Burkholderia multivorans

<400> SEQUENCE: 65

Met Tyr Arg Gly Thr Glu Ala Arg Thr Gly Glu Ile His Gly Thr Ala
1               5                   10                  15

Pro Arg His Arg Arg His Gly Ala Arg Ile Pro Ala Thr Arg Gln Pro
            20                  25                  30

Glu Ala Pro Asp Arg Phe Gly Pro Arg Ala Phe Ile Cys Pro Glu Thr
        35                  40                  45

Val Ala Met Lys Lys Leu Val Asn Arg Pro Ser Asp Val Val Arg Glu
    50                  55                  60

Met Leu Glu Gly Ile Ala Arg Gln Ser Pro His Leu Ala Met Leu Gly
65                  70                  75                  80

Asp Glu His Val Leu Val Arg Arg Pro Leu Pro Glu Pro Ser Gln Arg
                85                  90                  95

Thr Val Ala Val Leu Ser Gly Gly Gly Ser Gly His Glu Pro Ala His
            100                 105                 110

Gly Gly Tyr Val Gly Asp Gly Met Leu Ser Ala Ala Val Cys Gly Glu
        115                 120                 125

Val Phe Thr Ser Pro Ser Thr Asp Ala Val Leu Ala Ala Ile Arg Ala
    130                 135                 140

Thr Ala Gly Pro Asn Gly Ala Leu Leu Val Val Lys Asn Tyr Thr Gly
145                 150                 155                 160

Asp Arg Leu Asn Phe Gly Leu Ala Ala Glu Leu Ala Arg Ala Glu Gly
                165                 170                 175

Ile Pro Val Glu Thr Val Ile Val Ala Asp Asp Val Ser Leu Arg Gly
            180                 185                 190

Arg Val Glu Arg Gly Gln Arg Arg Gly Ile Ala Gly Thr Val Leu Ile
        195                 200                 205
```

```
His Lys Leu Ala Gly Ala Ala Ala Ala Arg Gly Leu Ser Leu Pro Arg
    210                 215                 220

Val Ala Ala Ile Ala Arg Asp Ala Ala Ala Asp Leu Gly Thr Met Gly
225                 230                 235                 240

Val Ala Leu Asp Gly Cys Thr Leu Pro Gly Ala Asp Gln Ser Gly Phe
                245                 250                 255

Ser Leu Ala Asp Asp Glu Ile Glu Leu Gly Leu Gly Ile His Gly Glu
            260                 265                 270

Lys Gly Val Glu Arg Thr Ala Pro Leu Pro Ala Asp Ala Leu Ala Asp
        275                 280                 285

Thr Leu Leu Ser Gly Ile Val Ala Asp Leu Val Leu Asp Arg Gly Glu
    290                 295                 300

Arg Val Ala Leu Leu Val Asn Gly Leu Gly Ala Thr Pro Asp Met Glu
305                 310                 315                 320

Leu Ala Ile Val Leu Arg Ala Ala Tyr Glu Asn Leu Ser Arg Arg Gly
                325                 330                 335

Ile Ala Val Glu Arg Ala Trp Ala Gly Thr Phe Leu Ser Ala Leu Asn
            340                 345                 350

Met Pro Gly Cys Ser Ile Ser Val Leu Arg Leu Asp Asp Glu Arg Ala
        355                 360                 365

Ala Leu Leu Asp Ala Pro Thr Gln Ala Arg Ala Trp Pro Gly Gly Gly
    370                 375                 380

Ala Val Asn Ala Gln Ile Arg Ile Ala Ala Ala Ala Pro Gln Glu Pro
385                 390                 395                 400

Ser Pro Pro Pro Leu Asp Ala Ala Gly Arg Val Trp Ala Glu Arg Leu
                405                 410                 415

Arg Pro Ala Leu His Ala Val Ala His Thr Leu Ile Asp His Glu Ala
            420                 425                 430

Thr Leu Thr Glu Leu Asp Ala Ala Ala Gly Asp Gly Asp Leu Gly Ala
        435                 440                 445

Ser Met Arg Arg Ala Ala Asp Ala Met Leu Ala Leu Pro Glu Thr Ala
    450                 455                 460

Tyr Ala Thr Pro Ala Gly Ala Leu Ala Ala Leu Gly Ala Ala Leu Arg
465                 470                 475                 480

Arg Ala Ile Ala Gly Ser Ser Gly Pro Phe Tyr Ala Thr Ala Leu Leu
                485                 490                 495

Arg Ala Ser Arg Arg Leu Ala Gly Leu Ala Gln Pro Ser Ala Arg Asp
            500                 505                 510

Trp Ala Ala Ala Leu Arg Ser Ala Ala Asp Ala Ile Ala Glu Leu Gly
        515                 520                 525

Gly Ala Arg Ala Gly Asp Arg Thr Met Leu Asp Ala Leu Val Pro Ala
    530                 535                 540

Ala Ala Ala Phe Asp Arg Ala Leu Asp Asp Gly Arg Asp Ser Ala Gly
545                 550                 555                 560

Ala Trp Ala Ala Ala Val Asp Ala Ala Glu Arg Gly Ala Gln Asp Thr
                565                 570                 575

Ala Arg Met Thr Pro Arg Ala Gly Arg Ala Ser Tyr Leu Gly Glu Arg
            580                 585                 590

Ala Ile Gly Thr Pro Asp Gly Gly Ala Ile Ala Val Ala Tyr Trp Leu
        595                 600                 605

Arg Ala Leu Leu Pro His Val Arg
    610                 615
```

```
<210> SEQ ID NO 66
<211> LENGTH: 1920
<212> TYPE: DNA
<213> ORGANISM: Escherichia coli
<220> FEATURE:
<221> NAME/KEY: CDS
<222> LOCATION: (1)..(1920)

<400> SEQUENCE: 66

atg agt ggc gct ttt aac aac gat ggt cgg ggc ata tct ccc tta att       48
Met Ser Gly Ala Phe Asn Asn Asp Gly Arg Gly Ile Ser Pro Leu Ile
1               5                   10                  15

gca acc tcc tgg gag cga tgc aat aag ctg atg aaa cgg gag aca tgg       96
Ala Thr Ser Trp Glu Arg Cys Asn Lys Leu Met Lys Arg Glu Thr Trp
            20                  25                  30

aac gta cca cat cag gcc cag ggc gtg aca ttt gct tct att tat cgg      144
Asn Val Pro His Gln Ala Gln Gly Val Thr Phe Ala Ser Ile Tyr Arg
        35                  40                  45

cgt aag aaa gcg atg ctg acg ctc ggg cag gct gcg ctg gaa gat gcc      192
Arg Lys Lys Ala Met Leu Thr Leu Gly Gln Ala Ala Leu Glu Asp Ala
    50                  55                  60

tgg gaa tat atg gca ccg cga gag tgt gcg ctg ttt atc ctc gat gaa      240
Trp Glu Tyr Met Ala Pro Arg Glu Cys Ala Leu Phe Ile Leu Asp Glu
65                  70                  75                  80

acc gcc tgc att ctc agc cgt aat ggc gat ccg caa acc ttg cag cag      288
Thr Ala Cys Ile Leu Ser Arg Asn Gly Asp Pro Gln Thr Leu Gln Gln
                85                  90                  95

cta agt gca ctg gga ttc aat gac ggc acg tat tgc gcc gag gga att      336
Leu Ser Ala Leu Gly Phe Asn Asp Gly Thr Tyr Cys Ala Glu Gly Ile
            100                 105                 110

att ggt act tgt gcg cta tcg tta gcg gct atc tct ggt cag gcc gtg      384
Ile Gly Thr Cys Ala Leu Ser Leu Ala Ala Ile Ser Gly Gln Ala Val
        115                 120                 125

aaa acg atg gcc gat caa cat ttc aaa cag gta ctc tgg aac tgg gcc      432
Lys Thr Met Ala Asp Gln His Phe Lys Gln Val Leu Trp Asn Trp Ala
    130                 135                 140

ttt tgt gca acg ccg ttg ttt gac agc aag ggc cga ttg acg gga aca      480
Phe Cys Ala Thr Pro Leu Phe Asp Ser Lys Gly Arg Leu Thr Gly Thr
145                 150                 155                 160

ata gcg ctg gcg tgt ccg gtt gag caa act acc gca gct gat ttg ccg      528
Ile Ala Leu Ala Cys Pro Val Glu Gln Thr Thr Ala Ala Asp Leu Pro
                165                 170                 175

ttg acg ttg gca atc gcc cgc gag gtc gga aat tta ctg ctg acg gac      576
Leu Thr Leu Ala Ile Ala Arg Glu Val Gly Asn Leu Leu Leu Thr Asp
            180                 185                 190

agt ttg ctc gct gaa act aac cgt cat tta aat caa ctt aat gcc ctg      624
Ser Leu Leu Ala Glu Thr Asn Arg His Leu Asn Gln Leu Asn Ala Leu
        195                 200                 205

tta gaa agt atg gat gat ggc gtg att agc tgg gac gag cag ggt aat      672
Leu Glu Ser Met Asp Asp Gly Val Ile Ser Trp Asp Glu Gln Gly Asn
    210                 215                 220

ttg caa ttt att aat gcc cag gcg gcg cgg gtc ttg cgc ctt gac gcg      720
Leu Gln Phe Ile Asn Ala Gln Ala Ala Arg Val Leu Arg Leu Asp Ala
225                 230                 235                 240

acg gca agt cag gga cgg gca atc act gaa ctc tta acg tta ccc gcc      768
Thr Ala Ser Gln Gly Arg Ala Ile Thr Glu Leu Leu Thr Leu Pro Ala
                245                 250                 255

gta ttg caa caa gca ata aaa cag gca cat ccg ctc aaa cac gta gaa      816
Val Leu Gln Gln Ala Ile Lys Gln Ala His Pro Leu Lys His Val Glu
            260                 265                 270

gca acc ttt gaa agc cag cac cag ttt att gat gcg gtg ata acc ctt      864
Ala Thr Phe Glu Ser Gln His Gln Phe Ile Asp Ala Val Ile Thr Leu
```

```
        275                 280                 285

aaa ccg ata ata gaa acg cag gga acc agc ttt att ttg ttg ctc cat      912
Lys Pro Ile Ile Glu Thr Gln Gly Thr Ser Phe Ile Leu Leu Leu His
    290                 295                 300

cct gtg gaa cag atg cgg cag ttg atg acc agt caa tta gga aaa gtc      960
Pro Val Glu Gln Met Arg Gln Leu Met Thr Ser Gln Leu Gly Lys Val
305                 310                 315                 320

agc cat acc ttc gct cat atg cca cag gac gat ccg caa acc cgc cgc     1008
Ser His Thr Phe Ala His Met Pro Gln Asp Asp Pro Gln Thr Arg Arg
                325                 330                 335

ttg att cat ttt ggt cgc cag gcg gcg cgc agt agc ttt cct gtc ctg     1056
Leu Ile His Phe Gly Arg Gln Ala Ala Arg Ser Ser Phe Pro Val Leu
            340                 345                 350

ctt tgt gga gaa gag ggc gtg ggc aag gca ctg cta agt cag gca att     1104
Leu Cys Gly Glu Glu Gly Val Gly Lys Ala Leu Leu Ser Gln Ala Ile
        355                 360                 365

cat aat gaa agc gag cgt gct gca ggt cct tat atc gcc gtc aat tgt     1152
His Asn Glu Ser Glu Arg Ala Ala Gly Pro Tyr Ile Ala Val Asn Cys
    370                 375                 380

gag tta tat ggt gat gct gcg ctg gcg gaa gaa ttt att ggt ggc gat     1200
Glu Leu Tyr Gly Asp Ala Ala Leu Ala Glu Glu Phe Ile Gly Gly Asp
385                 390                 395                 400

cgc acg gac aat gaa aat ggc cgt ctg agt cgg ctg gaa ctg gca cac     1248
Arg Thr Asp Asn Glu Asn Gly Arg Leu Ser Arg Leu Glu Leu Ala His
                405                 410                 415

ggc ggc acg ctg ttt ctt gaa aag att gaa tat ctg gcg gtg gag tta     1296
Gly Gly Thr Leu Phe Leu Glu Lys Ile Glu Tyr Leu Ala Val Glu Leu
            420                 425                 430

cag tct gct ttg ctt cag gtt atc aag cag ggg gtt atc acg cga ctg     1344
Gln Ser Ala Leu Leu Gln Val Ile Lys Gln Gly Val Ile Thr Arg Leu
        435                 440                 445

gat gcg cgg cgt tta ata cca att gat gtc aaa gtg att gca aca acg     1392
Asp Ala Arg Arg Leu Ile Pro Ile Asp Val Lys Val Ile Ala Thr Thr
    450                 455                 460

acc gcg gac ctc gca atg ctg gtg gaa caa aat cgt ttt agt cgc cag     1440
Thr Ala Asp Leu Ala Met Leu Val Glu Gln Asn Arg Phe Ser Arg Gln
465                 470                 475                 480

ctg tat tac gcg ctg cat gca ttt gaa att acc atc ccg cct ctg cgt     1488
Leu Tyr Tyr Ala Leu His Ala Phe Glu Ile Thr Ile Pro Pro Leu Arg
                485                 490                 495

atg cgg cgt ggc agc att ccg gcg ctg gtg aat aac aaa tta cgc agt     1536
Met Arg Arg Gly Ser Ile Pro Ala Leu Val Asn Asn Lys Leu Arg Ser
            500                 505                 510

ctt gaa aaa cgc ttc tct acg cgg ctg aaa att gat gac gat gcc ctc     1584
Leu Glu Lys Arg Phe Ser Thr Arg Leu Lys Ile Asp Asp Asp Ala Leu
        515                 520                 525

gct cgc ctg gtt tct tgt gca tgg cca ggc aac gat ttt gaa ctt tac     1632
Ala Arg Leu Val Ser Cys Ala Trp Pro Gly Asn Asp Phe Glu Leu Tyr
    530                 535                 540

agc gtc atc gag aat ctt gct ctg agt agt gat aac ggg cgc att cgc     1680
Ser Val Ile Glu Asn Leu Ala Leu Ser Ser Asp Asn Gly Arg Ile Arg
545                 550                 555                 560

gtc agt gat ttg ccg gaa cat ctg ttt acc gag cag gcg aca gat gat     1728
Val Ser Asp Leu Pro Glu His Leu Phe Thr Glu Gln Ala Thr Asp Asp
                565                 570                 575

gtc agc gcc acc cgc ctt tcc acc agt ctg tca ttt gcg gaa gtt gaa     1776
Val Ser Ala Thr Arg Leu Ser Thr Ser Leu Ser Phe Ala Glu Val Glu
            580                 585                 590

aaa gag gca att att aac gca gcc cag gtc aca ggc ggt cgc att cag     1824
Lys Glu Ala Ile Ile Asn Ala Ala Gln Val Thr Gly Gly Arg Ile Gln
```

```
        595                 600                 605

gaa atg tcg gct tta ctt ggg atc ggc cgc act acg ctg tgg cgg aaa      1872
Glu Met Ser Ala Leu Leu Gly Ile Gly Arg Thr Thr Leu Trp Arg Lys
    610                 615                 620

atg aag caa cat ggc att gat gca ggg cag ttt aag cgc cgg gta tga      1920
Met Lys Gln His Gly Ile Asp Ala Gly Gln Phe Lys Arg Arg Val
625                 630                 635


<210> SEQ ID NO 67
<211> LENGTH: 639
<212> TYPE: PRT
<213> ORGANISM: Escherichia coli

<400> SEQUENCE: 67

Met Ser Gly Ala Phe Asn Asn Asp Gly Arg Gly Ile Ser Pro Leu Ile
1               5                   10                  15

Ala Thr Ser Trp Glu Arg Cys Asn Lys Leu Met Lys Arg Glu Thr Trp
            20                  25                  30

Asn Val Pro His Gln Ala Gln Gly Val Thr Phe Ala Ser Ile Tyr Arg
        35                  40                  45

Arg Lys Lys Ala Met Leu Thr Leu Gly Gln Ala Ala Leu Glu Asp Ala
    50                  55                  60

Trp Glu Tyr Met Ala Pro Arg Glu Cys Ala Leu Phe Ile Leu Asp Glu
65                  70                  75                  80

Thr Ala Cys Ile Leu Ser Arg Asn Gly Asp Pro Gln Thr Leu Gln Gln
                85                  90                  95

Leu Ser Ala Leu Gly Phe Asn Asp Gly Thr Tyr Cys Ala Glu Gly Ile
            100                 105                 110

Ile Gly Thr Cys Ala Leu Ser Leu Ala Ala Ile Ser Gly Gln Ala Val
        115                 120                 125

Lys Thr Met Ala Asp Gln His Phe Lys Gln Val Leu Trp Asn Trp Ala
    130                 135                 140

Phe Cys Ala Thr Pro Leu Phe Asp Ser Lys Gly Arg Leu Thr Gly Thr
145                 150                 155                 160

Ile Ala Leu Ala Cys Pro Val Glu Gln Thr Thr Ala Ala Asp Leu Pro
                165                 170                 175

Leu Thr Leu Ala Ile Ala Arg Glu Val Gly Asn Leu Leu Leu Thr Asp
            180                 185                 190

Ser Leu Leu Ala Glu Thr Asn Arg His Leu Asn Gln Leu Asn Ala Leu
        195                 200                 205

Leu Glu Ser Met Asp Asp Gly Val Ile Ser Trp Asp Glu Gln Gly Asn
    210                 215                 220

Leu Gln Phe Ile Asn Ala Gln Ala Ala Arg Val Leu Arg Leu Asp Ala
225                 230                 235                 240

Thr Ala Ser Gln Gly Arg Ala Ile Thr Glu Leu Leu Thr Leu Pro Ala
                245                 250                 255

Val Leu Gln Gln Ala Ile Lys Gln Ala His Pro Leu Lys His Val Glu
            260                 265                 270

Ala Thr Phe Glu Ser Gln His Gln Phe Ile Asp Ala Val Ile Thr Leu
        275                 280                 285

Lys Pro Ile Ile Glu Thr Gln Gly Thr Ser Phe Ile Leu Leu Leu His
    290                 295                 300

Pro Val Glu Gln Met Arg Gln Leu Met Thr Ser Gln Leu Gly Lys Val
305                 310                 315                 320

Ser His Thr Phe Ala His Met Pro Gln Asp Asp Pro Gln Thr Arg Arg
                325                 330                 335
```

```
Leu Ile His Phe Gly Arg Gln Ala Ala Arg Ser Ser Phe Pro Val Leu
            340                 345                 350

Leu Cys Gly Glu Glu Gly Val Gly Lys Ala Leu Leu Ser Gln Ala Ile
        355                 360                 365

His Asn Glu Ser Glu Arg Ala Ala Gly Pro Tyr Ile Ala Val Asn Cys
    370                 375                 380

Glu Leu Tyr Gly Asp Ala Ala Leu Ala Glu Glu Phe Ile Gly Gly Asp
385                 390                 395                 400

Arg Thr Asp Asn Glu Asn Gly Arg Leu Ser Arg Leu Glu Leu Ala His
                405                 410                 415

Gly Gly Thr Leu Phe Leu Glu Lys Ile Glu Tyr Leu Ala Val Glu Leu
            420                 425                 430

Gln Ser Ala Leu Leu Gln Val Ile Lys Gln Gly Val Ile Thr Arg Leu
        435                 440                 445

Asp Ala Arg Arg Leu Ile Pro Ile Asp Val Lys Val Ile Ala Thr Thr
    450                 455                 460

Thr Ala Asp Leu Ala Met Leu Val Glu Gln Asn Arg Phe Ser Arg Gln
465                 470                 475                 480

Leu Tyr Tyr Ala Leu His Ala Phe Glu Ile Thr Ile Pro Pro Leu Arg
                485                 490                 495

Met Arg Arg Gly Ser Ile Pro Ala Leu Val Asn Asn Lys Leu Arg Ser
            500                 505                 510

Leu Glu Lys Arg Phe Ser Thr Arg Leu Lys Ile Asp Asp Ala Leu
        515                 520                 525

Ala Arg Leu Val Ser Cys Ala Trp Pro Gly Asn Asp Phe Glu Leu Tyr
    530                 535                 540

Ser Val Ile Glu Asn Leu Ala Leu Ser Ser Asp Asn Gly Arg Ile Arg
545                 550                 555                 560

Val Ser Asp Leu Pro Glu His Leu Phe Thr Glu Gln Ala Thr Asp Asp
                565                 570                 575

Val Ser Ala Thr Arg Leu Ser Thr Ser Leu Ser Phe Ala Glu Val Glu
            580                 585                 590

Lys Glu Ala Ile Ile Asn Ala Ala Gln Val Thr Gly Gly Arg Ile Gln
        595                 600                 605

Glu Met Ser Ala Leu Leu Gly Ile Gly Arg Thr Thr Leu Trp Arg Lys
    610                 615                 620

Met Lys Gln His Gly Ile Asp Ala Gly Gln Phe Lys Arg Arg Val
625                 630                 635
```

```
<210> SEQ ID NO 68
<211> LENGTH: 663
<212> TYPE: DNA
<213> ORGANISM: Escherichia coli
<220> FEATURE:
<221> NAME/KEY: CDS
<222> LOCATION: (1)..(663)

<400> SEQUENCE: 68

atg gaa ctg tat ctg gat act tca gac gtt gtt gcg gtg aag gcg ctg       48
Met Glu Leu Tyr Leu Asp Thr Ser Asp Val Val Ala Val Lys Ala Leu
1               5                   10                  15

tca cgt att ttt ccg ctg gcg ggt gtg acc act aac cca agc att atc       96
Ser Arg Ile Phe Pro Leu Ala Gly Val Thr Thr Asn Pro Ser Ile Ile
            20                  25                  30

gcc gcg ggt aaa aaa ccg ctg gat gtt gtg ctt ccg caa ctt cat gaa      144
Ala Ala Gly Lys Lys Pro Leu Asp Val Val Leu Pro Gln Leu His Glu
        35                  40                  45
```

```
gcg atg ggc ggt cag ggg cgt ctg ttt gcc cag gta atg gct acc act      192
Ala Met Gly Gly Gln Gly Arg Leu Phe Ala Gln Val Met Ala Thr Thr
    50                  55                  60

gcc gaa ggg atg gtt aat gac gcg ctt aag ctg cgt tct att att gcg      240
Ala Glu Gly Met Val Asn Asp Ala Leu Lys Leu Arg Ser Ile Ile Ala
65                  70                  75                  80

gat atc gtg gtg aaa gtt ccg gtg acc gcc gag ggg ctg gca gct att      288
Asp Ile Val Val Lys Val Pro Val Thr Ala Glu Gly Leu Ala Ala Ile
                85                  90                  95

aag atg tta aaa gcg gaa ggg att ccg acg ctg gga acc gcg gta tat      336
Lys Met Leu Lys Ala Glu Gly Ile Pro Thr Leu Gly Thr Ala Val Tyr
            100                 105                 110

ggc gca gca caa ggg ctg ctg tcg gcg ctg gca ggt gcg gaa tat gtt      384
Gly Ala Ala Gln Gly Leu Leu Ser Ala Leu Ala Gly Ala Glu Tyr Val
        115                 120                 125

gcg cct tac gtt aat cgt att gat gct cag ggc ggt agc ggc att cag      432
Ala Pro Tyr Val Asn Arg Ile Asp Ala Gln Gly Gly Ser Gly Ile Gln
    130                 135                 140

act gtg acc gac tta cac cag tta ttg aaa atg cat gcg ccg cag gcg      480
Thr Val Thr Asp Leu His Gln Leu Leu Lys Met His Ala Pro Gln Ala
145                 150                 155                 160

aaa gtg ctg gca gcg agt ttc aaa acc ccg cgt cag gcg ctg gac tgc      528
Lys Val Leu Ala Ala Ser Phe Lys Thr Pro Arg Gln Ala Leu Asp Cys
                165                 170                 175

tta ctg gca gga tgt gaa tca att act ctg cca ctg gat gtg gca caa      576
Leu Leu Ala Gly Cys Glu Ser Ile Thr Leu Pro Leu Asp Val Ala Gln
            180                 185                 190

cag atg att agc tat ccg gcg gtt gat gcc gct gtg gcg aag ttt gag      624
Gln Met Ile Ser Tyr Pro Ala Val Asp Ala Ala Val Ala Lys Phe Glu
        195                 200                 205

cag gac tgg cag gga gcg ttt ggc aga acg tcg att taa                  663
Gln Asp Trp Gln Gly Ala Phe Gly Arg Thr Ser Ile
    210                 215                 220


<210> SEQ ID NO 69
<211> LENGTH: 220
<212> TYPE: PRT
<213> ORGANISM: Escherichia coli

<400> SEQUENCE: 69

Met Glu Leu Tyr Leu Asp Thr Ser Asp Val Val Ala Val Lys Ala Leu
1               5                   10                  15

Ser Arg Ile Phe Pro Leu Ala Gly Val Thr Thr Asn Pro Ser Ile Ile
            20                  25                  30

Ala Ala Gly Lys Lys Pro Leu Asp Val Val Leu Pro Gln Leu His Glu
        35                  40                  45

Ala Met Gly Gly Gln Gly Arg Leu Phe Ala Gln Val Met Ala Thr Thr
    50                  55                  60

Ala Glu Gly Met Val Asn Asp Ala Leu Lys Leu Arg Ser Ile Ile Ala
65                  70                  75                  80

Asp Ile Val Val Lys Val Pro Val Thr Ala Glu Gly Leu Ala Ala Ile
                85                  90                  95

Lys Met Leu Lys Ala Glu Gly Ile Pro Thr Leu Gly Thr Ala Val Tyr
            100                 105                 110

Gly Ala Ala Gln Gly Leu Leu Ser Ala Leu Ala Gly Ala Glu Tyr Val
        115                 120                 125

Ala Pro Tyr Val Asn Arg Ile Asp Ala Gln Gly Gly Ser Gly Ile Gln
    130                 135                 140
```

```
Thr Val Thr Asp Leu His Gln Leu Leu Lys Met His Ala Pro Gln Ala
145                 150                 155                 160

Lys Val Leu Ala Ala Ser Phe Lys Thr Pro Arg Gln Ala Leu Asp Cys
                165                 170                 175

Leu Leu Ala Gly Cys Glu Ser Ile Thr Leu Pro Leu Asp Val Ala Gln
            180                 185                 190

Gln Met Ile Ser Tyr Pro Ala Val Asp Ala Ala Val Ala Lys Phe Glu
        195                 200                 205

Gln Asp Trp Gln Gly Ala Phe Gly Arg Thr Ser Ile
    210                 215                 220


<210> SEQ ID NO 70
<211> LENGTH: 663
<212> TYPE: DNA
<213> ORGANISM: Escherichia coli
<220> FEATURE:
<221> NAME/KEY: CDS
<222> LOCATION: (1)..(663)

<400> SEQUENCE: 70

atg gaa ctg tat ctg gac acc gct aac gtc gca gaa gtc gaa cgt ctg       48
Met Glu Leu Tyr Leu Asp Thr Ala Asn Val Ala Glu Val Glu Arg Leu
1               5                   10                  15

gca cgc ata ttc ccc att gcc ggg gtg aca act aac ccg agc att atc       96
Ala Arg Ile Phe Pro Ile Ala Gly Val Thr Thr Asn Pro Ser Ile Ile
            20                  25                  30

gct gcc agc aag gag tcc ata tgg gaa gtg ctg ccg cgt ctg caa aaa      144
Ala Ala Ser Lys Glu Ser Ile Trp Glu Val Leu Pro Arg Leu Gln Lys
        35                  40                  45

gcg att ggt gat gag ggc att ctg ttt gct cag acc atg agc cgc gac      192
Ala Ile Gly Asp Glu Gly Ile Leu Phe Ala Gln Thr Met Ser Arg Asp
    50                  55                  60

gcg cag ggg atg gtg gaa gaa gcg aag cgc ctg cgc gac gct att ccg      240
Ala Gln Gly Met Val Glu Glu Ala Lys Arg Leu Arg Asp Ala Ile Pro
65                  70                  75                  80

ggt att gtg gtg aaa atc ccg gtg act tcc gaa ggt ctg gca gca att      288
Gly Ile Val Val Lys Ile Pro Val Thr Ser Glu Gly Leu Ala Ala Ile
                85                  90                  95

aaa ata ctg aaa aaa gag ggt att act aca ctt ggc act gct gta tat      336
Lys Ile Leu Lys Lys Glu Gly Ile Thr Thr Leu Gly Thr Ala Val Tyr
            100                 105                 110

agc gcc gca caa ggg tta tta gcc gca ctg gca ggg gca aaa tac gtt      384
Ser Ala Ala Gln Gly Leu Leu Ala Ala Leu Ala Gly Ala Lys Tyr Val
        115                 120                 125

gct ccg tat gtt aac cgc gta gat gcc cag ggc gga gac ggc att cgt      432
Ala Pro Tyr Val Asn Arg Val Asp Ala Gln Gly Gly Asp Gly Ile Arg
    130                 135                 140

acg gtt cag gag ctg caa acg ctg tta gaa atg cac gcg cca gaa agc      480
Thr Val Gln Glu Leu Gln Thr Leu Leu Glu Met His Ala Pro Glu Ser
145                 150                 155                 160

atg gtg ctg gca gcc agc ttt aaa acg ccg cgt cag gcg ctg gac tgt      528
Met Val Leu Ala Ala Ser Phe Lys Thr Pro Arg Gln Ala Leu Asp Cys
                165                 170                 175

tta ctg gca gga tgt gaa tcc atc acc ctg ccc tta gat gta gcg caa      576
Leu Leu Ala Gly Cys Glu Ser Ile Thr Leu Pro Leu Asp Val Ala Gln
            180                 185                 190

caa atg ctc aac acc cct gcg gta gag tca gct ata gag aag ttc gaa      624
Gln Met Leu Asn Thr Pro Ala Val Glu Ser Ala Ile Glu Lys Phe Glu
        195                 200                 205

cac gac tgg aat gcc gca ttt ggc act act cat ctc taa                  663
His Asp Trp Asn Ala Ala Phe Gly Thr Thr His Leu
```

```
    210                 215                 220


<210> SEQ ID NO 71
<211> LENGTH: 220
<212> TYPE: PRT
<213> ORGANISM: Escherichia coli

<400> SEQUENCE: 71

Met Glu Leu Tyr Leu Asp Thr Ala Asn Val Ala Glu Val Glu Arg Leu
1               5                   10                  15

Ala Arg Ile Phe Pro Ile Ala Gly Val Thr Thr Asn Pro Ser Ile Ile
            20                  25                  30

Ala Ala Ser Lys Glu Ser Ile Trp Glu Val Leu Pro Arg Leu Gln Lys
        35                  40                  45

Ala Ile Gly Asp Glu Gly Ile Leu Phe Ala Gln Thr Met Ser Arg Asp
    50                  55                  60

Ala Gln Gly Met Val Glu Glu Ala Lys Arg Leu Arg Asp Ala Ile Pro
65                  70                  75                  80

Gly Ile Val Val Lys Ile Pro Val Thr Ser Glu Gly Leu Ala Ala Ile
                85                  90                  95

Lys Ile Leu Lys Lys Glu Gly Ile Thr Thr Leu Gly Thr Ala Val Tyr
            100                 105                 110

Ser Ala Ala Gln Gly Leu Leu Ala Ala Leu Ala Gly Ala Lys Tyr Val
        115                 120                 125

Ala Pro Tyr Val Asn Arg Val Asp Ala Gln Gly Gly Asp Gly Ile Arg
    130                 135                 140

Thr Val Gln Glu Leu Gln Thr Leu Leu Glu Met His Ala Pro Glu Ser
145                 150                 155                 160

Met Val Leu Ala Ala Ser Phe Lys Thr Pro Arg Gln Ala Leu Asp Cys
                165                 170                 175

Leu Leu Ala Gly Cys Glu Ser Ile Thr Leu Pro Leu Asp Val Ala Gln
            180                 185                 190

Gln Met Leu Asn Thr Pro Ala Val Glu Ser Ala Ile Glu Lys Phe Glu
        195                 200                 205

His Asp Trp Asn Ala Ala Phe Gly Thr Thr His Leu
    210                 215                 220


<210> SEQ ID NO 72
<211> LENGTH: 1053
<212> TYPE: DNA
<213> ORGANISM: Escherichia coli
<220> FEATURE:
<221> NAME/KEY: CDS
<222> LOCATION: (1)..(1053)

<400> SEQUENCE: 72

atg aca gat att gcg cag ttg ctt ggc aaa gac gcc gac aac ctt tta       48
Met Thr Asp Ile Ala Gln Leu Leu Gly Lys Asp Ala Asp Asn Leu Leu
1               5                   10                  15

cag cac cgt tgt atg aca att cct tct gac cag ctt tat ctc ccc gga       96
Gln His Arg Cys Met Thr Ile Pro Ser Asp Gln Leu Tyr Leu Pro Gly
            20                  25                  30

cat gac tac gta gac cgc gta atg att gac aat aat cgc ccg cca gcg      144
His Asp Tyr Val Asp Arg Val Met Ile Asp Asn Asn Arg Pro Pro Ala
        35                  40                  45

gtg tta cgt aat atg cag acg ttg tac aac acc ggg cgt ctg gct ggc      192
Val Leu Arg Asn Met Gln Thr Leu Tyr Asn Thr Gly Arg Leu Ala Gly
    50                  55                  60

aca gga tat ctt tct att ctg ccg gtt gac cag ggc gtt gag cac tct      240
```

```
Thr Gly Tyr Leu Ser Ile Leu Pro Val Asp Gln Gly Val Glu His Ser
65                  70                  75                  80

gcc gga gct tca ttt gct gct aac ccg ctc tac ttt gac ccg aaa aac      288
Ala Gly Ala Ser Phe Ala Ala Asn Pro Leu Tyr Phe Asp Pro Lys Asn
                85                  90                  95

att gtt gaa ctg gcg atc gaa gcg ggc tgt aac tgt gtg gcg tca act      336
Ile Val Glu Leu Ala Ile Glu Ala Gly Cys Asn Cys Val Ala Ser Thr
            100                 105                 110

tac ggc gtg ctg gcg tcg gta tcg cgg cgt tat gcg cat cgc att cca      384
Tyr Gly Val Leu Ala Ser Val Ser Arg Arg Tyr Ala His Arg Ile Pro
        115                 120                 125

ttc ctc gtc aaa ctt aat cac aac gag acg cta agt tac ccg aat acc      432
Phe Leu Val Lys Leu Asn His Asn Glu Thr Leu Ser Tyr Pro Asn Thr
    130                 135                 140

tac gat caa acg ctg tat gcc agc gtg gag cag gcg ttc aac atg ggc      480
Tyr Asp Gln Thr Leu Tyr Ala Ser Val Glu Gln Ala Phe Asn Met Gly
145                 150                 155                 160

gcg gtt gcg gtt ggt gcg act atc tat ttt ggc tcg gaa gag tca cgt      528
Ala Val Ala Val Gly Ala Thr Ile Tyr Phe Gly Ser Glu Glu Ser Arg
                165                 170                 175

cgc cag att gaa gaa att tct gcg gct ttt gaa cgt gcg cac gag ctg      576
Arg Gln Ile Glu Glu Ile Ser Ala Ala Phe Glu Arg Ala His Glu Leu
            180                 185                 190

ggt atg gtg aca gtg ctg tgg gcc tat ttg cgt aac tcc gcc ttt aag      624
Gly Met Val Thr Val Leu Trp Ala Tyr Leu Arg Asn Ser Ala Phe Lys
        195                 200                 205

aaa gat ggc gtt gat tac cat gtt tcc gcc gac ctg acc ggt cag gca      672
Lys Asp Gly Val Asp Tyr His Val Ser Ala Asp Leu Thr Gly Gln Ala
    210                 215                 220

aac cat ctg gcg gca acc atc ggt gca gat atc gtc aaa caa aaa atg      720
Asn His Leu Ala Ala Thr Ile Gly Ala Asp Ile Val Lys Gln Lys Met
225                 230                 235                 240

gcg gaa aat aac ggc ggc tat aaa gca att aat tac ggt tac acc gac      768
Ala Glu Asn Asn Gly Gly Tyr Lys Ala Ile Asn Tyr Gly Tyr Thr Asp
                245                 250                 255

gat cgt gtt tac agc aaa ttg acc agc gaa aac ccg att gat ctg gtg      816
Asp Arg Val Tyr Ser Lys Leu Thr Ser Glu Asn Pro Ile Asp Leu Val
            260                 265                 270

cgt tat cag tta gct aac tgc tat atg ggt cgg gct ggg ttg ata aac      864
Arg Tyr Gln Leu Ala Asn Cys Tyr Met Gly Arg Ala Gly Leu Ile Asn
        275                 280                 285

tcc ggc ggt gct gcg ggc ggt gaa act gac ctc agc gat gca gtg cgt      912
Ser Gly Gly Ala Ala Gly Gly Glu Thr Asp Leu Ser Asp Ala Val Arg
    290                 295                 300

act gcg gtt atc aac aaa cgc gca ggc gga atg ggg ctg att ctt gga      960
Thr Ala Val Ile Asn Lys Arg Ala Gly Gly Met Gly Leu Ile Leu Gly
305                 310                 315                 320

cgt aaa gcg ttc aag aaa tcg atg gct gac ggc gtg aaa ctg att aac     1008
Arg Lys Ala Phe Lys Lys Ser Met Ala Asp Gly Val Lys Leu Ile Asn
                325                 330                 335

gcc gtg cag gac gtt tat ctc gat agc aaa att act atc gcc tga         1053
Ala Val Gln Asp Val Tyr Leu Asp Ser Lys Ile Thr Ile Ala
            340                 345                 350

<210> SEQ ID NO 73
<211> LENGTH: 350
<212> TYPE: PRT
<213> ORGANISM: Escherichia coli

<400> SEQUENCE: 73

Met Thr Asp Ile Ala Gln Leu Leu Gly Lys Asp Ala Asp Asn Leu Leu
```

```
1               5                   10                  15

Gln His Arg Cys Met Thr Ile Pro Ser Asp Gln Leu Tyr Leu Pro Gly
            20                  25                  30

His Asp Tyr Val Asp Arg Val Met Ile Asp Asn Asn Arg Pro Pro Ala
        35                  40                  45

Val Leu Arg Asn Met Gln Thr Leu Tyr Asn Thr Gly Arg Leu Ala Gly
    50                  55                  60

Thr Gly Tyr Leu Ser Ile Leu Pro Val Asp Gln Gly Val Glu His Ser
65                  70                  75                  80

Ala Gly Ala Ser Phe Ala Ala Asn Pro Leu Tyr Phe Asp Pro Lys Asn
                85                  90                  95

Ile Val Glu Leu Ala Ile Glu Ala Gly Cys Asn Cys Val Ala Ser Thr
            100                 105                 110

Tyr Gly Val Leu Ala Ser Val Ser Arg Arg Tyr Ala His Arg Ile Pro
        115                 120                 125

Phe Leu Val Lys Leu Asn His Asn Glu Thr Leu Ser Tyr Pro Asn Thr
    130                 135                 140

Tyr Asp Gln Thr Leu Tyr Ala Ser Val Glu Gln Ala Phe Asn Met Gly
145                 150                 155                 160

Ala Val Ala Val Gly Ala Thr Ile Tyr Phe Gly Ser Glu Glu Ser Arg
                165                 170                 175

Arg Gln Ile Glu Glu Ile Ser Ala Ala Phe Glu Arg Ala His Glu Leu
            180                 185                 190

Gly Met Val Thr Val Leu Trp Ala Tyr Leu Arg Asn Ser Ala Phe Lys
        195                 200                 205

Lys Asp Gly Val Asp Tyr His Val Ser Ala Asp Leu Thr Gly Gln Ala
    210                 215                 220

Asn His Leu Ala Ala Thr Ile Gly Ala Asp Ile Val Lys Gln Lys Met
225                 230                 235                 240

Ala Glu Asn Asn Gly Gly Tyr Lys Ala Ile Asn Tyr Gly Tyr Thr Asp
                245                 250                 255

Asp Arg Val Tyr Ser Lys Leu Thr Ser Glu Asn Pro Ile Asp Leu Val
            260                 265                 270

Arg Tyr Gln Leu Ala Asn Cys Tyr Met Gly Arg Ala Gly Leu Ile Asn
        275                 280                 285

Ser Gly Gly Ala Ala Gly Gly Glu Thr Asp Leu Ser Asp Ala Val Arg
    290                 295                 300

Thr Ala Val Ile Asn Lys Arg Ala Gly Gly Met Gly Leu Ile Leu Gly
305                 310                 315                 320

Arg Lys Ala Phe Lys Lys Ser Met Ala Asp Gly Val Lys Leu Ile Asn
                325                 330                 335

Ala Val Gln Asp Val Tyr Leu Asp Ser Lys Ile Thr Ile Ala
            340                 345                 350


<210> SEQ ID NO 74
<211> LENGTH: 1143
<212> TYPE: DNA
<213> ORGANISM: Shigella dysenteriae
<220> FEATURE:
<221> NAME/KEY: CDS
<222> LOCATION: (1)..(1143)

<400> SEQUENCE: 74

atg ccg cat ttg gca cta ctc atc tct aaa gga gca att atg gac cgc       48
Met Pro His Leu Ala Leu Leu Ile Ser Lys Gly Ala Ile Met Asp Arg
1               5                   10                  15
```

```
att att caa tca ccg ggt aaa tac atc cag ggc gct gat gtg att aat       96
Ile Ile Gln Ser Pro Gly Lys Tyr Ile Gln Gly Ala Asp Val Ile Asn
            20                  25                  30

cgt ctg ggc gaa tac ctg aag ccg ctg gca gaa ctc tgg tta gtg gtg      144
Arg Leu Gly Glu Tyr Leu Lys Pro Leu Ala Glu Leu Trp Leu Val Val
        35                  40                  45

ggt gac aaa ttt gtt tta ggt ttt gct caa tcc act gtc gag aaa agc      192
Gly Asp Lys Phe Val Leu Gly Phe Ala Gln Ser Thr Val Glu Lys Ser
    50                  55                  60

ttt aaa gat gct gga ctg gta gta gaa att gcg ccg ttt ggc ggt gaa      240
Phe Lys Asp Ala Gly Leu Val Val Glu Ile Ala Pro Phe Gly Gly Glu
65                  70                  75                  80

tgt tcg caa aat gag atc gac cgt ctg cgt ggc atc gcg gag act gcg      288
Cys Ser Gln Asn Glu Ile Asp Arg Leu Arg Gly Ile Ala Glu Thr Ala
                85                  90                  95

cag tgt ggc gca att ctc ggt atc ggt ggc gga aaa act ttc gat act      336
Gln Cys Gly Ala Ile Leu Gly Ile Gly Gly Gly Lys Thr Phe Asp Thr
            100                 105                 110

gcc aaa gca ctg gca cat ttc atg ggt gtt ccg gta gcg atc gca ccg      384
Ala Lys Ala Leu Ala His Phe Met Gly Val Pro Val Ala Ile Ala Pro
        115                 120                 125

acg atc gcc tct acc gac gca ccg tgc agc gca ttg tct gtt atc tac      432
Thr Ile Ala Ser Thr Asp Ala Pro Cys Ser Ala Leu Ser Val Ile Tyr
    130                 135                 140

acc gat gag ggt gag ttt gac cgc tat ctg ctg ttg cca aat aac cct      480
Thr Asp Glu Gly Glu Phe Asp Arg Tyr Leu Leu Leu Pro Asn Asn Pro
145                 150                 155                 160

aat atg gtc att gtc gac acc aaa atc gtc gct ggc gca cct gca cgt      528
Asn Met Val Ile Val Asp Thr Lys Ile Val Ala Gly Ala Pro Ala Arg
                165                 170                 175

ctg tta gcg gcg ggt atc ggc gat gcg ctg gca acc tgg ttt gaa gcg      576
Leu Leu Ala Ala Gly Ile Gly Asp Ala Leu Ala Thr Trp Phe Glu Ala
            180                 185                 190

cgt gcc tgc tct cgt agc ggc gcg acc acc atg gcg ggc ggc aag tgc      624
Arg Ala Cys Ser Arg Ser Gly Ala Thr Thr Met Ala Gly Gly Lys Cys
        195                 200                 205

acc cag gct gcg ctg gca ctg gct gaa ctg tgc tac aac acc ctg ctg      672
Thr Gln Ala Ala Leu Ala Leu Ala Glu Leu Cys Tyr Asn Thr Leu Leu
    210                 215                 220

gaa gaa ggc gaa aaa gcg atg ctt gct gcc gaa cag cat gta gtg act      720
Glu Glu Gly Glu Lys Ala Met Leu Ala Ala Glu Gln His Val Val Thr
225                 230                 235                 240

ccg gcg ctg gag cgc gtg att gaa gcg aac acc tat ttg agc ggt gtt      768
Pro Ala Leu Glu Arg Val Ile Glu Ala Asn Thr Tyr Leu Ser Gly Val
                245                 250                 255

ggt ttt gaa agt ggt ggt ctg gct gcg gcg cac gca gtg cat aac ggc      816
Gly Phe Glu Ser Gly Gly Leu Ala Ala Ala His Ala Val His Asn Gly
            260                 265                 270

ctg acc gct atc ccg gac gcg cat cac tat tat cac ggt gaa aaa gtg      864
Leu Thr Ala Ile Pro Asp Ala His His Tyr Tyr His Gly Glu Lys Val
        275                 280                 285

gca ttc ggt acg ctg acg cag ctg gtt ctg gaa aat gcg ccg gtg gag      912
Ala Phe Gly Thr Leu Thr Gln Leu Val Leu Glu Asn Ala Pro Val Glu
    290                 295                 300

gaa atc gaa acc gta gct gcc ctt agc cat gcg gta ggt ttg cca ata      960
Glu Ile Glu Thr Val Ala Ala Leu Ser His Ala Val Gly Leu Pro Ile
305                 310                 315                 320

act ctc gct caa ctg gat att aaa gaa gat gtc ccg gcg aaa atg cga     1008
Thr Leu Ala Gln Leu Asp Ile Lys Glu Asp Val Pro Ala Lys Met Arg
                325                 330                 335
```

```
att gtg gca gaa gcg gca tgt gca gaa ggt gaa acc att cac aac atg      1056
Ile Val Ala Glu Ala Ala Cys Ala Glu Gly Glu Thr Ile His Asn Met
            340                 345                 350

cct ggc ggc gcg acg cca gat cag gtt tac gcc gca ctg ctg gta gct      1104
Pro Gly Gly Ala Thr Pro Asp Gln Val Tyr Ala Ala Leu Leu Val Ala
        355                 360                 365

gac cag tat gga caa cgt ttc ctg caa gag tgg gaa taa                  1143
Asp Gln Tyr Gly Gln Arg Phe Leu Gln Glu Trp Glu
    370                 375                 380


<210> SEQ ID NO 75
<211> LENGTH: 380
<212> TYPE: PRT
<213> ORGANISM: Shigella dysenteriae

<400> SEQUENCE: 75

Met Pro His Leu Ala Leu Leu Ile Ser Lys Gly Ala Ile Met Asp Arg
1               5                   10                  15

Ile Ile Gln Ser Pro Gly Lys Tyr Ile Gln Gly Ala Asp Val Ile Asn
            20                  25                  30

Arg Leu Gly Glu Tyr Leu Lys Pro Leu Ala Glu Leu Trp Leu Val Val
        35                  40                  45

Gly Asp Lys Phe Val Leu Gly Phe Ala Gln Ser Thr Val Glu Lys Ser
    50                  55                  60

Phe Lys Asp Ala Gly Leu Val Val Glu Ile Ala Pro Phe Gly Gly Glu
65                  70                  75                  80

Cys Ser Gln Asn Glu Ile Asp Arg Leu Arg Gly Ile Ala Glu Thr Ala
                85                  90                  95

Gln Cys Gly Ala Ile Leu Gly Ile Gly Gly Gly Lys Thr Phe Asp Thr
            100                 105                 110

Ala Lys Ala Leu Ala His Phe Met Gly Val Pro Val Ala Ile Ala Pro
        115                 120                 125

Thr Ile Ala Ser Thr Asp Ala Pro Cys Ser Ala Leu Ser Val Ile Tyr
    130                 135                 140

Thr Asp Glu Gly Glu Phe Asp Arg Tyr Leu Leu Leu Pro Asn Asn Pro
145                 150                 155                 160

Asn Met Val Ile Val Asp Thr Lys Ile Val Ala Gly Ala Pro Ala Arg
                165                 170                 175

Leu Leu Ala Ala Gly Ile Gly Asp Ala Leu Ala Thr Trp Phe Glu Ala
            180                 185                 190

Arg Ala Cys Ser Arg Ser Gly Ala Thr Thr Met Ala Gly Gly Lys Cys
        195                 200                 205

Thr Gln Ala Ala Leu Ala Leu Ala Glu Leu Cys Tyr Asn Thr Leu Leu
    210                 215                 220

Glu Glu Gly Glu Lys Ala Met Leu Ala Ala Glu Gln His Val Val Thr
225                 230                 235                 240

Pro Ala Leu Glu Arg Val Ile Glu Ala Asn Thr Tyr Leu Ser Gly Val
                245                 250                 255

Gly Phe Glu Ser Gly Gly Leu Ala Ala Ala His Ala Val His Asn Gly
            260                 265                 270

Leu Thr Ala Ile Pro Asp Ala His His Tyr Tyr His Gly Glu Lys Val
        275                 280                 285

Ala Phe Gly Thr Leu Thr Gln Leu Val Leu Glu Asn Ala Pro Val Glu
    290                 295                 300

Glu Ile Glu Thr Val Ala Ala Leu Ser His Ala Val Gly Leu Pro Ile
305                 310                 315                 320
```

```
Thr Leu Ala Gln Leu Asp Ile Lys Glu Asp Val Pro Ala Lys Met Arg
                325                 330                 335

Ile Val Ala Glu Ala Ala Cys Ala Glu Gly Glu Thr Ile His Asn Met
            340                 345                 350

Pro Gly Gly Ala Thr Pro Asp Gln Val Tyr Ala Ala Leu Leu Val Ala
        355                 360                 365

Asp Gln Tyr Gly Gln Arg Phe Leu Gln Glu Trp Glu
    370                 375                 380


<210> SEQ ID NO 76
<211> LENGTH: 1104
<212> TYPE: DNA
<213> ORGANISM: Salmonella typhimurium
<220> FEATURE:
<221> NAME/KEY: CDS
<222> LOCATION: (1)..(1104)

<400> SEQUENCE: 76

atg gat cgc att att cag tca cca ggt aag tat att cag ggt gca aac       48
Met Asp Arg Ile Ile Gln Ser Pro Gly Lys Tyr Ile Gln Gly Ala Asn
1               5                   10                  15

gtc atc gcg cgt ctt ggc gat tat tta aaa cca atg gcg aac aac tgg       96
Val Ile Ala Arg Leu Gly Asp Tyr Leu Lys Pro Met Ala Asn Asn Trp
            20                  25                  30

ctg gtt gtg ggc gat aaa ttc gtg ctg gga ttt gcc gaa gag acg ctg      144
Leu Val Val Gly Asp Lys Phe Val Leu Gly Phe Ala Glu Glu Thr Leu
        35                  40                  45

cgc aaa agc ctg acg gat gcc ggt ttg tca gta gaa atc gcc ccg ttt      192
Arg Lys Ser Leu Thr Asp Ala Gly Leu Ser Val Glu Ile Ala Pro Phe
    50                  55                  60

ggc ggc gaa tgt tcg caa aat gag atc gac agg ctg cgc gcc gtc gcc      240
Gly Gly Glu Cys Ser Gln Asn Glu Ile Asp Arg Leu Arg Ala Val Ala
65                  70                  75                  80

gaa aaa agt cag tgt ggc gcc gta ctg ggt atc ggc ggc ggt aaa acg      288
Glu Lys Ser Gln Cys Gly Ala Val Leu Gly Ile Gly Gly Gly Lys Thr
                85                  90                  95

ctg gat acc gcc aaa gcg ctg gcg cac ttt atg aac gtc ccg gtc gct      336
Leu Asp Thr Ala Lys Ala Leu Ala His Phe Met Asn Val Pro Val Ala
            100                 105                 110

atc gcg ccg acc atc gcc tct acc gac gca ccg tgc agc gca ctc tcg      384
Ile Ala Pro Thr Ile Ala Ser Thr Asp Ala Pro Cys Ser Ala Leu Ser
        115                 120                 125

gtt att tat acc gat gcc ggt gag ttt gac cgt tat ctg ctg ctg ccg      432
Val Ile Tyr Thr Asp Ala Gly Glu Phe Asp Arg Tyr Leu Leu Leu Pro
    130                 135                 140

cat aac ccg aat atg gtt att gtc gat acg cag ata gtg gcg ggc gcg      480
His Asn Pro Asn Met Val Ile Val Asp Thr Gln Ile Val Ala Gly Ala
145                 150                 155                 160

ccg gcg cgt ctg ctg gca gcc ggt atc ggc gat gca ctg gcg acc tgg      528
Pro Ala Arg Leu Leu Ala Ala Gly Ile Gly Asp Ala Leu Ala Thr Trp
                165                 170                 175

ttt gaa gcg cgc gcc tgc tca cgc agc ggc gcc acc aca atg gcg ggc      576
Phe Glu Ala Arg Ala Cys Ser Arg Ser Gly Ala Thr Thr Met Ala Gly
            180                 185                 190

ggc aag tgt aca cag gcc gcg ctg gcg ctg gcg gag cta tgc tat aac      624
Gly Lys Cys Thr Gln Ala Ala Leu Ala Leu Ala Glu Leu Cys Tyr Asn
        195                 200                 205

acg ctg atc gaa gaa ggc gaa aaa gcc atg ttg gcc gcc gaa cag cac      672
Thr Leu Ile Glu Glu Gly Glu Lys Ala Met Leu Ala Ala Glu Gln His
    210                 215                 220

gtc gtc acg cca gcg ctg gaa cgc gtc atc gaa gcc aac acc tac ctg      720
```

```
Val Val Thr Pro Ala Leu Glu Arg Val Ile Glu Ala Asn Thr Tyr Leu
225                 230                 235                 240

agc ggg gtc ggt ttt gaa agc ggc ggt ctg gcc gca gcg cac gcg att      768
Ser Gly Val Gly Phe Glu Ser Gly Gly Leu Ala Ala Ala His Ala Ile
                245                 250                 255

cat aac ggt tta acg gcg att ccg gat gcg cac cac tat tat cac ggt      816
His Asn Gly Leu Thr Ala Ile Pro Asp Ala His His Tyr Tyr His Gly
            260                 265                 270

gag aag gtc gct ttc ggt acg ctg acg caa ctg gtg ctg gaa aac gcg      864
Glu Lys Val Ala Phe Gly Thr Leu Thr Gln Leu Val Leu Glu Asn Ala
        275                 280                 285

ccg gtc gaa gaa atc gaa acc gtt gcg gcg ctg tgc cat tcc gtt ggc      912
Pro Val Glu Glu Ile Glu Thr Val Ala Ala Leu Cys His Ser Val Gly
    290                 295                 300

ctg ccg att acg ctg gcg caa ctg gat att aaa cag gat att ccg gcc      960
Leu Pro Ile Thr Leu Ala Gln Leu Asp Ile Lys Gln Asp Ile Pro Ala
305                 310                 315                 320

aag atg cgc acc gtc gcg gaa gcc tcc tgc gca gaa ggt gaa act att     1008
Lys Met Arg Thr Val Ala Glu Ala Ser Cys Ala Glu Gly Glu Thr Ile
                325                 330                 335

cat aac atg cct ggc ggc gca acg ccg gat gaa gtg tac gcc gcg ctg     1056
His Asn Met Pro Gly Gly Ala Thr Pro Asp Glu Val Tyr Ala Ala Leu
            340                 345                 350

ctg gtc gcc gac cag tac ggt caa cgc ttc ttg cag gaa tgg gaa taa     1104
Leu Val Ala Asp Gln Tyr Gly Gln Arg Phe Leu Gln Glu Trp Glu
        355                 360                 365


<210> SEQ ID NO 77
<211> LENGTH: 367
<212> TYPE: PRT
<213> ORGANISM: Salmonella typhimurium

<400> SEQUENCE: 77

Met Asp Arg Ile Ile Gln Ser Pro Gly Lys Tyr Ile Gln Gly Ala Asn
1               5                   10                  15

Val Ile Ala Arg Leu Gly Asp Tyr Leu Lys Pro Met Ala Asn Asn Trp
            20                  25                  30

Leu Val Val Gly Asp Lys Phe Val Leu Gly Phe Ala Glu Glu Thr Leu
        35                  40                  45

Arg Lys Ser Leu Thr Asp Ala Gly Leu Ser Val Glu Ile Ala Pro Phe
    50                  55                  60

Gly Gly Glu Cys Ser Gln Asn Glu Ile Asp Arg Leu Arg Ala Val Ala
65                  70                  75                  80

Glu Lys Ser Gln Cys Gly Ala Val Leu Gly Ile Gly Gly Gly Lys Thr
                85                  90                  95

Leu Asp Thr Ala Lys Ala Leu Ala His Phe Met Asn Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Ala Gly Glu Phe Asp Arg Tyr Leu Leu Leu Pro
    130                 135                 140

His Asn Pro Asn Met Val Ile Val Asp Thr Gln Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
```

```
        195                 200                 205

Thr Leu Ile Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala Ala His Ala Ile
                245                 250                 255

His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
        275                 280                 285

Pro Val Glu Glu Ile Glu Thr Val Ala Ala Leu Cys His Ser Val Gly
    290                 295                 300

Leu Pro Ile Thr Leu Ala Gln Leu Asp Ile Lys Gln Asp Ile Pro Ala
305                 310                 315                 320

Lys Met Arg Thr Val Ala Glu Ala Ser Cys Ala Glu Gly Glu Thr Ile
                325                 330                 335

His Asn Met Pro Gly Gly Ala Thr Pro Asp Glu Val Tyr Ala Ala Leu
            340                 345                 350

Leu Val Ala Asp Gln Tyr Gly Gln Arg Phe Leu Gln Glu Trp Glu
        355                 360                 365


<210> SEQ ID NO 78
<211> LENGTH: 1098
<212> TYPE: DNA
<213> ORGANISM: Pseudomonas putida
<220> FEATURE:
<221> NAME/KEY: CDS
<222> LOCATION: (1)..(1098)

<400> SEQUENCE: 78

atg gac cgc gcc att caa tca ccc ggc aaa tat gta caa ggg gcc gat       48
Met Asp Arg Ala Ile Gln Ser Pro Gly Lys Tyr Val Gln Gly Ala Asp
1               5                   10                  15

gcg ctg caa cgg ctg ggg gac tac ctc aag ccg ctg gcg gac agc tgg       96
Ala Leu Gln Arg Leu Gly Asp Tyr Leu Lys Pro Leu Ala Asp Ser Trp
            20                  25                  30

ctg gtg att gcc gac aag ttc gtg ctg ggc ttt gcc gaa gac acc atc      144
Leu Val Ile Ala Asp Lys Phe Val Leu Gly Phe Ala Glu Asp Thr Ile
        35                  40                  45

cgc caa agc ctc agc aag gcc ggg ctg gcc atg gac atc gtc gcc ttc      192
Arg Gln Ser Leu Ser Lys Ala Gly Leu Ala Met Asp Ile Val Ala Phe
    50                  55                  60

aac ggc gaa tgc tcg cag ggc gag gtc gat cgc ctg tgc caa ctg gcc      240
Asn Gly Glu Cys Ser Gln Gly Glu Val Asp Arg Leu Cys Gln Leu Ala
65                  70                  75                  80

acg caa aac ggg cgc agc gcc atc gtc ggc att ggt ggc ggc aag acg      288
Thr Gln Asn Gly Arg Ser Ala Ile Val Gly Ile Gly Gly Gly Lys Thr
                85                  90                  95

ctg gac acc gcc aag gcc gtg gcc ttt ttc cag aaa gtg ccc gtg gcc      336
Leu Asp Thr Ala Lys Ala Val Ala Phe Phe Gln Lys Val Pro Val Ala
            100                 105                 110

gtg gcc ccc acc atc gcc tcc acc gac gcg ccc tgc agc gcg ctg tcg      384
Val Ala Pro Thr Ile Ala Ser Thr Asp Ala Pro Cys Ser Ala Leu Ser
        115                 120                 125

gtg ctc tat acc gat gaa ggt gag ttc gac cgc tat ctg atg ctg ccc      432
Val Leu Tyr Thr Asp Glu Gly Glu Phe Asp Arg Tyr Leu Met Leu Pro
    130                 135                 140

acc aac ccc gcc ctg gtg gtg gtg gac acc gcc atc gtc gcc cgt gca      480
```

```
Thr Asn Pro Ala Leu Val Val Val Asp Thr Ala Ile Val Ala Arg Ala
145                 150                 155                 160

ccg gcg cgg ctg ttg gcg gcc ggc att ggt gat gcc ctg gcc acc tgg      528
Pro Ala Arg Leu Leu Ala Ala Gly Ile Gly Asp Ala Leu Ala Thr Trp
                165                 170                 175

ttc gag gcg cgt gcc gca tcg cgc agc agc gct gcc acc atg gcc ggc      576
Phe Glu Ala Arg Ala Ala Ser Arg Ser Ser Ala Ala Thr Met Ala Gly
            180                 185                 190

ggc ccg gcc acg cag acc gca ctg aac ctg gcc agg ttc tgc tac gac      624
Gly Pro Ala Thr Gln Thr Ala Leu Asn Leu Ala Arg Phe Cys Tyr Asp
        195                 200                 205

acc ctg ctg gaa gag ggt gaa aaa gcc atg ttg gcc gtg cag gcc cag      672
Thr Leu Leu Glu Glu Gly Glu Lys Ala Met Leu Ala Val Gln Ala Gln
    210                 215                 220

gtg gtg acg ccg gcg ctg gag cgc atc gtc gag gcc aac acc tat ctg      720
Val Val Thr Pro Ala Leu Glu Arg Ile Val Glu Ala Asn Thr Tyr Leu
225                 230                 235                 240

agc ggg gtc ggg ttt gaa agc ggt ggc gtg gcc gcc gcc cac gcg gtg      768
Ser Gly Val Gly Phe Glu Ser Gly Gly Val Ala Ala Ala His Ala Val
                245                 250                 255

cac aac ggc ctg acc gcc gtg gcc gaa acc cac cac ttc tac cac ggc      816
His Asn Gly Leu Thr Ala Val Ala Glu Thr His His Phe Tyr His Gly
            260                 265                 270

gaa aaa gtg gcg ttt ggc gtg ctg gtg caa ctg gcg ctg gaa aac gcc      864
Glu Lys Val Ala Phe Gly Val Leu Val Gln Leu Ala Leu Glu Asn Ala
        275                 280                 285

tcc aac gcg gaa atg cag gaa gtg atg tcg ctg tgc cac gcc gtg ggc      912
Ser Asn Ala Glu Met Gln Glu Val Met Ser Leu Cys His Ala Val Gly
    290                 295                 300

ctg ccc atc acg ctg gcg cag ctg gac att acc gaa gac atc ccc acc      960
Leu Pro Ile Thr Leu Ala Gln Leu Asp Ile Thr Glu Asp Ile Pro Thr
305                 310                 315                 320

aag atg cgc gcc gtg gcc gag ctg gcc tgc gcc cca ggc gag acc atc     1008
Lys Met Arg Ala Val Ala Glu Leu Ala Cys Ala Pro Gly Glu Thr Ile
                325                 330                 335

cac aac atg ccc ggc ggc gtg acg gtg gag cag gtc tat ggc gcg ctg     1056
His Asn Met Pro Gly Gly Val Thr Val Glu Gln Val Tyr Gly Ala Leu
            340                 345                 350

ctg gtg gcg gac cag ctg ggg cag cat ttt ctg gag ttt tga             1098
Leu Val Ala Asp Gln Leu Gly Gln His Phe Leu Glu Phe
        355                 360                 365


<210> SEQ ID NO 79
<211> LENGTH: 365
<212> TYPE: PRT
<213> ORGANISM: Pseudomonas putida

<400> SEQUENCE: 79

Met Asp Arg Ala Ile Gln Ser Pro Gly Lys Tyr Val Gln Gly Ala Asp
1               5                   10                  15

Ala Leu Gln Arg Leu Gly Asp Tyr Leu Lys Pro Leu Ala Asp Ser Trp
            20                  25                  30

Leu Val Ile Ala Asp Lys Phe Val Leu Gly Phe Ala Glu Asp Thr Ile
        35                  40                  45

Arg Gln Ser Leu Ser Lys Ala Gly Leu Ala Met Asp Ile Val Ala Phe
    50                  55                  60

Asn Gly Glu Cys Ser Gln Gly Glu Val Asp Arg Leu Cys Gln Leu Ala
65                  70                  75                  80

Thr Gln Asn Gly Arg Ser Ala Ile Val Gly Ile Gly Gly Gly Lys Thr
                85                  90                  95
```

```
Leu Asp Thr Ala Lys Ala Val Ala Phe Phe Gln Lys Val Pro Val Ala
            100                 105                 110

Val Ala Pro Thr Ile Ala Ser Thr Asp Ala Pro Cys Ser Ala Leu Ser
        115                 120                 125

Val Leu Tyr Thr Asp Glu Gly Glu Phe Asp Arg Tyr Leu Met Leu Pro
    130                 135                 140

Thr Asn Pro Ala Leu Val Val Val Asp Thr Ala Ile Val Ala Arg Ala
145                 150                 155                 160

Pro Ala Arg Leu Leu Ala Ala Gly Ile Gly Asp Ala Leu Ala Thr Trp
                165                 170                 175

Phe Glu Ala Arg Ala Ala Ser Arg Ser Ser Ala Ala Thr Met Ala Gly
            180                 185                 190

Gly Pro Ala Thr Gln Thr Ala Leu Asn Leu Ala Arg Phe Cys Tyr Asp
        195                 200                 205

Thr Leu Leu Glu Glu Gly Glu Lys Ala Met Leu Ala Val Gln Ala Gln
    210                 215                 220

Val Val Thr Pro Ala Leu Glu Arg Ile Val Glu Ala Asn Thr Tyr Leu
225                 230                 235                 240

Ser Gly Val Gly Phe Glu Ser Gly Gly Val Ala Ala Ala His Ala Val
                245                 250                 255

His Asn Gly Leu Thr Ala Val Ala Glu Thr His His Phe Tyr His Gly
            260                 265                 270

Glu Lys Val Ala Phe Gly Val Leu Val Gln Leu Ala Leu Glu Asn Ala
        275                 280                 285

Ser Asn Ala Glu Met Gln Glu Val Met Ser Leu Cys His Ala Val Gly
    290                 295                 300

Leu Pro Ile Thr Leu Ala Gln Leu Asp Ile Thr Glu Asp Ile Pro Thr
305                 310                 315                 320

Lys Met Arg Ala Val Ala Glu Leu Ala Cys Ala Pro Gly Glu Thr Ile
                325                 330                 335

His Asn Met Pro Gly Gly Val Thr Val Glu Gln Val Tyr Gly Ala Leu
            340                 345                 350

Leu Val Ala Asp Gln Leu Gly Gln His Phe Leu Glu Phe
        355                 360                 365


<210> SEQ ID NO 80
<211> LENGTH: 1104
<212> TYPE: DNA
<213> ORGANISM: Bacillus coagulans
<220> FEATURE:
<221> NAME/KEY: CDS
<222> LOCATION: (1)..(1104)

<400> SEQUENCE: 80

atg acg aaa atc att acc tct cca agc aag ttt ata caa ggc ccc gat       48
Met Thr Lys Ile Ile Thr Ser Pro Ser Lys Phe Ile Gln Gly Pro Asp
1               5                   10                  15

gaa ttg tcc agg ctt tcg gcg tat acg gaa agg ctt ggc aaa aaa gca       96
Glu Leu Ser Arg Leu Ser Ala Tyr Thr Glu Arg Leu Gly Lys Lys Ala
            20                  25                  30

ttt att att gcg gat gat ttt gtc acc ggc ctt gtc ggc aaa acg gtt      144
Phe Ile Ile Ala Asp Asp Phe Val Thr Gly Leu Val Gly Lys Thr Val
        35                  40                  45

gaa gaa agc tat gcc ggc aaa gaa acg ggg tat caa atg gca tta ttc      192
Glu Glu Ser Tyr Ala Gly Lys Glu Thr Gly Tyr Gln Met Ala Leu Phe
    50                  55                  60

ggt ggt gag tgt tct aaa ccg gaa atc gaa cgg ctt tgt gaa atg agc      240
```

```
Gly Gly Glu Cys Ser Lys Pro Glu Ile Glu Arg Leu Cys Glu Met Ser
65                  70                  75                  80

aaa tcc gag gaa gcc gat gtc gtt gtc gga atc ggc ggc gga aaa aca      288
Lys Ser Glu Glu Ala Asp Val Val Val Gly Ile Gly Gly Gly Lys Thr
                85                  90                  95

ttg gat acc gca aaa gca gtc ggg tat tac aat aac att ccg gtg att      336
Leu Asp Thr Ala Lys Ala Val Gly Tyr Tyr Asn Asn Ile Pro Val Ile
            100                 105                 110

gtc gcg ccg acc atc gct tcc acc gat gcc ccg aca agc gcc ctg tct      384
Val Ala Pro Thr Ile Ala Ser Thr Asp Ala Pro Thr Ser Ala Leu Ser
        115                 120                 125

gtt att tac aaa gag aac ggc gag ttt gaa gaa tac ttg atg ctg ccg      432
Val Ile Tyr Lys Glu Asn Gly Glu Phe Glu Glu Tyr Leu Met Leu Pro
    130                 135                 140

ctg aac ccg act ttt gtc att atg gat acg aaa gtg att gcc tct gcc      480
Leu Asn Pro Thr Phe Val Ile Met Asp Thr Lys Val Ile Ala Ser Ala
145                 150                 155                 160

cct gcc cgc ctg ctc gtt tcc ggc atg gga gat gcg ctt gca acg tat      528
Pro Ala Arg Leu Leu Val Ser Gly Met Gly Asp Ala Leu Ala Thr Tyr
                165                 170                 175

ttt gaa gcg cgc gcc act aag cgg gca aat aaa acg acg atg gca ggc      576
Phe Glu Ala Arg Ala Thr Lys Arg Ala Asn Lys Thr Thr Met Ala Gly
            180                 185                 190

ggg cgt gtt acg gaa gcg gcg atc gcg ctt gca aaa ctt tgt tat gac      624
Gly Arg Val Thr Glu Ala Ala Ile Ala Leu Ala Lys Leu Cys Tyr Asp
        195                 200                 205

acg caa att tcg gaa ggt tta aaa gca aaa ctg gca gcg gaa aaa cat      672
Thr Gln Ile Ser Glu Gly Leu Lys Ala Lys Leu Ala Ala Glu Lys His
    210                 215                 220

ctt gtt acg gaa gca gtg gaa aaa atc att gaa gcg aat acg tat ctg      720
Leu Val Thr Glu Ala Val Glu Lys Ile Ile Glu Ala Asn Thr Tyr Leu
225                 230                 235                 240

agc gga atc ggt ttt gaa agc ggc ggc ctt gct gcg gca cat gcg atc      768
Ser Gly Ile Gly Phe Glu Ser Gly Gly Leu Ala Ala Ala His Ala Ile
                245                 250                 255

cat aat ggg ctt acc gtg ctc gaa gaa acc cat cat atg tac cac ggc      816
His Asn Gly Leu Thr Val Leu Glu Glu Thr His His Met Tyr His Gly
            260                 265                 270

gaa aaa gtg gca ttc ggt acc ctc gcc cag ctg att ttg gaa gat gcg      864
Glu Lys Val Ala Phe Gly Thr Leu Ala Gln Leu Ile Leu Glu Asp Ala
        275                 280                 285

ccg aaa gcg gaa att gaa gag gtg gtc tcc ttc tgc ctg agt gtc gga      912
Pro Lys Ala Glu Ile Glu Glu Val Val Ser Phe Cys Leu Ser Val Gly
    290                 295                 300

ctt ccc gtc acg ctc ggg gat ttg ggc gtg aaa gaa ctg aat gag gaa      960
Leu Pro Val Thr Leu Gly Asp Leu Gly Val Lys Glu Leu Asn Glu Glu
305                 310                 315                 320

aag ctc cga aaa gtg gct gaa ctt tcc tgt gcg gaa ggc gaa acg att     1008
Lys Leu Arg Lys Val Ala Glu Leu Ser Cys Ala Glu Gly Glu Thr Ile
                325                 330                 335

tat aac atg ccg ttt gaa gtc acg cct gac ctt gtg tac gca gca atc     1056
Tyr Asn Met Pro Phe Glu Val Thr Pro Asp Leu Val Tyr Ala Ala Ile
            340                 345                 350

gtt acc gct gat tcc gtc ggg cgg tat tat aag gaa aaa tgg gca tga     1104
Val Thr Ala Asp Ser Val Gly Arg Tyr Tyr Lys Glu Lys Trp Ala
        355                 360                 365
```

<210> SEQ ID NO 81
<211> LENGTH: 367
<212> TYPE: PRT
<213> ORGANISM: Bacillus coagulans

<400> SEQUENCE: 81

```
Met Thr Lys Ile Ile Thr Ser Pro Ser Lys Phe Ile Gln Gly Pro Asp
1               5                   10                  15

Glu Leu Ser Arg Leu Ser Ala Tyr Thr Glu Arg Leu Gly Lys Lys Ala
            20                  25                  30

Phe Ile Ile Ala Asp Asp Phe Val Thr Gly Leu Val Gly Lys Thr Val
        35                  40                  45

Glu Glu Ser Tyr Ala Gly Lys Glu Thr Gly Tyr Gln Met Ala Leu Phe
    50                  55                  60

Gly Gly Glu Cys Ser Lys Pro Glu Ile Glu Arg Leu Cys Glu Met Ser
65                  70                  75                  80

Lys Ser Glu Glu Ala Asp Val Val Val Gly Ile Gly Gly Gly Lys Thr
                85                  90                  95

Leu Asp Thr Ala Lys Ala Val Gly Tyr Tyr Asn Asn Ile Pro Val Ile
            100                 105                 110

Val Ala Pro Thr Ile Ala Ser Thr Asp Ala Pro Thr Ser Ala Leu Ser
        115                 120                 125

Val Ile Tyr Lys Glu Asn Gly Glu Phe Glu Glu Tyr Leu Met Leu Pro
    130                 135                 140

Leu Asn Pro Thr Phe Val Ile Met Asp Thr Lys Val Ile Ala Ser Ala
145                 150                 155                 160

Pro Ala Arg Leu Leu Val Ser Gly Met Gly Asp Ala Leu Ala Thr Tyr
                165                 170                 175

Phe Glu Ala Arg Ala Thr Lys Arg Ala Asn Lys Thr Thr Met Ala Gly
            180                 185                 190

Gly Arg Val Thr Glu Ala Ala Ile Ala Leu Ala Lys Leu Cys Tyr Asp
        195                 200                 205

Thr Gln Ile Ser Glu Gly Leu Lys Ala Lys Leu Ala Ala Glu Lys His
    210                 215                 220

Leu Val Thr Glu Ala Val Glu Lys Ile Ile Glu Ala Asn Thr Tyr Leu
225                 230                 235                 240

Ser Gly Ile Gly Phe Glu Ser Gly Gly Leu Ala Ala Ala His Ala Ile
                245                 250                 255

His Asn Gly Leu Thr Val Leu Glu Glu Thr His His Met Tyr His Gly
            260                 265                 270

Glu Lys Val Ala Phe Gly Thr Leu Ala Gln Leu Ile Leu Glu Asp Ala
        275                 280                 285

Pro Lys Ala Glu Ile Glu Glu Val Val Ser Phe Cys Leu Ser Val Gly
    290                 295                 300

Leu Pro Val Thr Leu Gly Asp Leu Gly Val Lys Glu Leu Asn Glu Glu
305                 310                 315                 320

Lys Leu Arg Lys Val Ala Glu Leu Ser Cys Ala Glu Gly Glu Thr Ile
                325                 330                 335

Tyr Asn Met Pro Phe Glu Val Thr Pro Asp Leu Val Tyr Ala Ala Ile
            340                 345                 350

Val Thr Ala Asp Ser Val Gly Arg Tyr Tyr Lys Glu Lys Trp Ala
        355                 360                 365
```

<210> SEQ ID NO 82
<211> LENGTH: 999
<212> TYPE: DNA
<213> ORGANISM: Escherichia coli
<220> FEATURE:
<221> NAME/KEY: CDS
<222> LOCATION: (1)..(999)

```
<400> SEQUENCE: 82

atg aaa acg tta ggt gaa ttt att gtc gaa aag cag cac gag ttt tct       48
Met Lys Thr Leu Gly Glu Phe Ile Val Glu Lys Gln His Glu Phe Ser
1               5                   10                  15

cat gct acc ggt gag ctc act gct ttg ctg tcg gca ata aaa ctg ggc       96
His Ala Thr Gly Glu Leu Thr Ala Leu Leu Ser Ala Ile Lys Leu Gly
            20                  25                  30

gcc aag att atc cat cgc gat atc aac aaa gca gga ctg gtt gat atc      144
Ala Lys Ile Ile His Arg Asp Ile Asn Lys Ala Gly Leu Val Asp Ile
        35                  40                  45

ctg ggt gcc agc ggt gct gag aac gtg cag ggc gag gtt cag cag aaa      192
Leu Gly Ala Ser Gly Ala Glu Asn Val Gln Gly Glu Val Gln Gln Lys
    50                  55                  60

ctc gac ttg ttc gct aat gaa aaa ctg aaa gcc gca ctg aaa gca cgc      240
Leu Asp Leu Phe Ala Asn Glu Lys Leu Lys Ala Ala Leu Lys Ala Arg
65                  70                  75                  80

gat atc gtt gcg ggc att gcc tct gaa gaa gaa gat gag att gtc gtc      288
Asp Ile Val Ala Gly Ile Ala Ser Glu Glu Glu Asp Glu Ile Val Val
                85                  90                  95

ttt gaa ggc tgt gaa cac gca aaa tac gtg gtg ctg atg gac ccc ctg      336
Phe Glu Gly Cys Glu His Ala Lys Tyr Val Val Leu Met Asp Pro Leu
            100                 105                 110

gat ggc tcg tcc aac atc gat gtt aac gtc tct gtc ggt acc att ttc      384
Asp Gly Ser Ser Asn Ile Asp Val Asn Val Ser Val Gly Thr Ile Phe
        115                 120                 125

tcc atc tac cgc cgc gtt acg cct gtt ggc acg ccg gta acg gaa gaa      432
Ser Ile Tyr Arg Arg Val Thr Pro Val Gly Thr Pro Val Thr Glu Glu
    130                 135                 140

gat ttc ctc cag cct ggt aac aaa cag gtt gcg gca ggt tac gtg gta      480
Asp Phe Leu Gln Pro Gly Asn Lys Gln Val Ala Ala Gly Tyr Val Val
145                 150                 155                 160

tac ggc tcc tct acc atg ctg gtt tac acc acc gga tgc ggt gtt cac      528
Tyr Gly Ser Ser Thr Met Leu Val Tyr Thr Thr Gly Cys Gly Val His
                165                 170                 175

gcc ttt act tac gat cct tcg ctc ggc gtt ttc tgc ctg tgc cag gaa      576
Ala Phe Thr Tyr Asp Pro Ser Leu Gly Val Phe Cys Leu Cys Gln Glu
            180                 185                 190

cgg atg cgc ttc ccg gag aaa ggc aaa acc tac tcc atc aac gaa gga      624
Arg Met Arg Phe Pro Glu Lys Gly Lys Thr Tyr Ser Ile Asn Glu Gly
        195                 200                 205

aac tac att aag ttt ccg aac ggg gtg aag aag tac att aaa ttc tgc      672
Asn Tyr Ile Lys Phe Pro Asn Gly Val Lys Lys Tyr Ile Lys Phe Cys
    210                 215                 220

cag gaa gaa gat aaa tcc acc aac cgc cct tat acc tca cgt tat atc      720
Gln Glu Glu Asp Lys Ser Thr Asn Arg Pro Tyr Thr Ser Arg Tyr Ile
225                 230                 235                 240

ggt tca ctg gtc gcg gat ttc cac cgt aac ctg ctg aaa ggc ggt att      768
Gly Ser Leu Val Ala Asp Phe His Arg Asn Leu Leu Lys Gly Gly Ile
                245                 250                 255

tat ctc tac cca agc acc gcc agc cac ccg gac ggc aaa ctg cgt ttg      816
Tyr Leu Tyr Pro Ser Thr Ala Ser His Pro Asp Gly Lys Leu Arg Leu
            260                 265                 270

ctg tat gag tgc aac ccg atg gca ttc ctg gcg gaa caa gcg ggc ggt      864
Leu Tyr Glu Cys Asn Pro Met Ala Phe Leu Ala Glu Gln Ala Gly Gly
        275                 280                 285

aaa gcg agc gat ggc aaa gag cgt att ctg gat atc atc ccg gaa acc      912
Lys Ala Ser Asp Gly Lys Glu Arg Ile Leu Asp Ile Ile Pro Glu Thr
    290                 295                 300

ctg cac cag cgc cgt tca ttc ttt gtc ggc aac gac cat atg gtt gaa      960
```

```
Leu His Gln Arg Arg Ser Phe Phe Val Gly Asn Asp His Met Val Glu
305                 310                 315                 320

gat gtc gaa cgc ttt atc cgt gag ttc ccg gac gcg taa                 999
Asp Val Glu Arg Phe Ile Arg Glu Phe Pro Asp Ala
                325                 330


<210> SEQ ID NO 83
<211> LENGTH: 332
<212> TYPE: PRT
<213> ORGANISM: Escherichia coli

<400> SEQUENCE: 83

Met Lys Thr Leu Gly Glu Phe Ile Val Glu Lys Gln His Glu Phe Ser
1               5                   10                  15

His Ala Thr Gly Glu Leu Thr Ala Leu Leu Ser Ala Ile Lys Leu Gly
            20                  25                  30

Ala Lys Ile Ile His Arg Asp Ile Asn Lys Ala Gly Leu Val Asp Ile
        35                  40                  45

Leu Gly Ala Ser Gly Ala Glu Asn Val Gln Gly Glu Val Gln Gln Lys
    50                  55                  60

Leu Asp Leu Phe Ala Asn Glu Lys Leu Lys Ala Ala Leu Lys Ala Arg
65                  70                  75                  80

Asp Ile Val Ala Gly Ile Ala Ser Glu Glu Glu Asp Glu Ile Val Val
                85                  90                  95

Phe Glu Gly Cys Glu His Ala Lys Tyr Val Val Leu Met Asp Pro Leu
            100                 105                 110

Asp Gly Ser Ser Asn Ile Asp Val Asn Val Ser Val Gly Thr Ile Phe
        115                 120                 125

Ser Ile Tyr Arg Arg Val Thr Pro Val Gly Thr Pro Val Thr Glu Glu
    130                 135                 140

Asp Phe Leu Gln Pro Gly Asn Lys Gln Val Ala Ala Gly Tyr Val Val
145                 150                 155                 160

Tyr Gly Ser Ser Thr Met Leu Val Tyr Thr Thr Gly Cys Gly Val His
                165                 170                 175

Ala Phe Thr Tyr Asp Pro Ser Leu Gly Val Phe Cys Leu Cys Gln Glu
            180                 185                 190

Arg Met Arg Phe Pro Glu Lys Gly Lys Thr Tyr Ser Ile Asn Glu Gly
        195                 200                 205

Asn Tyr Ile Lys Phe Pro Asn Gly Val Lys Lys Tyr Ile Lys Phe Cys
    210                 215                 220

Gln Glu Glu Asp Lys Ser Thr Asn Arg Pro Tyr Thr Ser Arg Tyr Ile
225                 230                 235                 240

Gly Ser Leu Val Ala Asp Phe His Arg Asn Leu Leu Lys Gly Gly Ile
                245                 250                 255

Tyr Leu Tyr Pro Ser Thr Ala Ser His Pro Asp Gly Lys Leu Arg Leu
            260                 265                 270

Leu Tyr Glu Cys Asn Pro Met Ala Phe Leu Ala Glu Gln Ala Gly Gly
        275                 280                 285

Lys Ala Ser Asp Gly Lys Glu Arg Ile Leu Asp Ile Ile Pro Glu Thr
    290                 295                 300

Leu His Gln Arg Arg Ser Phe Phe Val Gly Asn Asp His Met Val Glu
305                 310                 315                 320

Asp Val Glu Arg Phe Ile Arg Glu Phe Pro Asp Ala
                325                 330


<210> SEQ ID NO 84
```

```
<211> LENGTH: 819
<212> TYPE: DNA
<213> ORGANISM: Escherichia coli
<220> FEATURE:
<221> NAME/KEY: CDS
<222> LOCATION: (1)..(819)

<400> SEQUENCE: 84

atg acc aca cgc gtg att gct ctc gac tta gac ggc acc tta ttg acc       48
Met Thr Thr Arg Val Ile Ala Leu Asp Leu Asp Gly Thr Leu Leu Thr
1               5                   10                  15

ccg aaa aag acc ctg ctt cct tca tcg ata gaa gcc ctg gcc cgc gct       96
Pro Lys Lys Thr Leu Leu Pro Ser Ser Ile Glu Ala Leu Ala Arg Ala
            20                  25                  30

cgc gaa gca ggc tat caa tta atc atc gtc aca ggt cgc cat cac gtc      144
Arg Glu Ala Gly Tyr Gln Leu Ile Ile Val Thr Gly Arg His His Val
        35                  40                  45

gct att cat cct ttt tat cag gcg ctg gcg ctg gat aca cct gct att      192
Ala Ile His Pro Phe Tyr Gln Ala Leu Ala Leu Asp Thr Pro Ala Ile
    50                  55                  60

tgc tgt aat ggc acc tat ttg tat gat tat cat gca aaa acc gtg ctg      240
Cys Cys Asn Gly Thr Tyr Leu Tyr Asp Tyr His Ala Lys Thr Val Leu
65                  70                  75                  80

gaa gcg gac cca atg ccc gtt att aaa gcc ctg caa ctc att gag atg      288
Glu Ala Asp Pro Met Pro Val Ile Lys Ala Leu Gln Leu Ile Glu Met
                85                  90                  95

ctg aat gaa cac cac att cac ggt ctg atg tat gtc gat gat gca atg      336
Leu Asn Glu His His Ile His Gly Leu Met Tyr Val Asp Asp Ala Met
            100                 105                 110

gtc tat gag cac ccg acc ggg cat gtc att cgc aca tct aac tgg gcg      384
Val Tyr Glu His Pro Thr Gly His Val Ile Arg Thr Ser Asn Trp Ala
        115                 120                 125

caa acc ctg ccg ccg gaa cag cgt ccg act ttc aca caa gtc gct tct      432
Gln Thr Leu Pro Pro Glu Gln Arg Pro Thr Phe Thr Gln Val Ala Ser
    130                 135                 140

ctg gct gaa acg gcg caa caa gtt aac gcc gta tgg aag ttc gcc ctg      480
Leu Ala Glu Thr Ala Gln Gln Val Asn Ala Val Trp Lys Phe Ala Leu
145                 150                 155                 160

acg cac gat gac ctg ccg caa ttg cag cat ttt ggt aag cat gtc gaa      528
Thr His Asp Asp Leu Pro Gln Leu Gln His Phe Gly Lys His Val Glu
                165                 170                 175

cat gaa ctg gga ctg gag tgt gaa tgg tcc tgg cac gat cag gtt gat      576
His Glu Leu Gly Leu Glu Cys Glu Trp Ser Trp His Asp Gln Val Asp
            180                 185                 190

att gca cgc ggc ggc aac agc aaa ggt aaa cgt ttg acg aaa tgg gtt      624
Ile Ala Arg Gly Gly Asn Ser Lys Gly Lys Arg Leu Thr Lys Trp Val
        195                 200                 205

gag gcg caa ggt tgg tcg atg gaa aac gtc gtg gca ttc ggc gat aac      672
Glu Ala Gln Gly Trp Ser Met Glu Asn Val Val Ala Phe Gly Asp Asn
    210                 215                 220

ttt aat gat atc agt atg ctg gaa gcc gct ggt aca ggc gtg gcg atg      720
Phe Asn Asp Ile Ser Met Leu Glu Ala Ala Gly Thr Gly Val Ala Met
225                 230                 235                 240

ggc aac gcc gat gac gcg gta aaa gcg cgc gcc aac att gtg att ggt      768
Gly Asn Ala Asp Asp Ala Val Lys Ala Arg Ala Asn Ile Val Ile Gly
                245                 250                 255

gat aac acc acc gac agc att gcc cag ttc att tat agc cac ctg att      816
Asp Asn Thr Thr Asp Ser Ile Ala Gln Phe Ile Tyr Ser His Leu Ile
            260                 265                 270

taa                                                                  819
```

<210> SEQ ID NO 85
<211> LENGTH: 272
<212> TYPE: PRT
<213> ORGANISM: Escherichia coli

<400> SEQUENCE: 85

```
Met Thr Thr Arg Val Ile Ala Leu Asp Leu Asp Gly Thr Leu Leu Thr
1               5                   10                  15

Pro Lys Lys Thr Leu Leu Pro Ser Ser Ile Glu Ala Leu Ala Arg Ala
            20                  25                  30

Arg Glu Ala Gly Tyr Gln Leu Ile Ile Val Thr Gly Arg His His Val
        35                  40                  45

Ala Ile His Pro Phe Tyr Gln Ala Leu Ala Leu Asp Thr Pro Ala Ile
    50                  55                  60

Cys Cys Asn Gly Thr Tyr Leu Tyr Asp Tyr His Ala Lys Thr Val Leu
65                  70                  75                  80

Glu Ala Asp Pro Met Pro Val Ile Lys Ala Leu Gln Leu Ile Glu Met
                85                  90                  95

Leu Asn Glu His His Ile His Gly Leu Met Tyr Val Asp Asp Ala Met
            100                 105                 110

Val Tyr Glu His Pro Thr Gly His Val Ile Arg Thr Ser Asn Trp Ala
        115                 120                 125

Gln Thr Leu Pro Pro Glu Gln Arg Pro Thr Phe Thr Gln Val Ala Ser
    130                 135                 140

Leu Ala Glu Thr Ala Gln Gln Val Asn Ala Val Trp Lys Phe Ala Leu
145                 150                 155                 160

Thr His Asp Asp Leu Pro Gln Leu Gln His Phe Gly Lys His Val Glu
                165                 170                 175

His Glu Leu Gly Leu Glu Cys Glu Trp Ser Trp His Asp Gln Val Asp
            180                 185                 190

Ile Ala Arg Gly Gly Asn Ser Lys Gly Lys Arg Leu Thr Lys Trp Val
        195                 200                 205

Glu Ala Gln Gly Trp Ser Met Glu Asn Val Val Ala Phe Gly Asp Asn
    210                 215                 220

Phe Asn Asp Ile Ser Met Leu Glu Ala Ala Gly Thr Gly Val Ala Met
225                 230                 235                 240

Gly Asn Ala Asp Asp Ala Val Lys Ala Arg Ala Asn Ile Val Ile Gly
                245                 250                 255

Asp Asn Thr Thr Asp Ser Ile Ala Gln Phe Ile Tyr Ser His Leu Ile
            260                 265                 270
```

<210> SEQ ID NO 86
<211> LENGTH: 1728
<212> TYPE: DNA
<213> ORGANISM: Escherichia coli
<220> FEATURE:
<221> NAME/KEY: CDS
<222> LOCATION: (1)..(1728)

<400> SEQUENCE: 86

```
atg att tca ggc att tta gca tcc ccg ggt atc gct ttc ggt aaa gct       48
Met Ile Ser Gly Ile Leu Ala Ser Pro Gly Ile Ala Phe Gly Lys Ala
1               5                   10                  15

ctg ctt ctg aaa gaa gac gaa att gtc att gac cgg aaa aaa att tct       96
Leu Leu Leu Lys Glu Asp Glu Ile Val Ile Asp Arg Lys Lys Ile Ser
            20                  25                  30

gcc gac cag gtt gat cag gaa gtt gaa cgt ttt ctg agc ggt cgt gcc      144
Ala Asp Gln Val Asp Gln Glu Val Glu Arg Phe Leu Ser Gly Arg Ala
        35                  40                  45
```

```
aag gca tca gcc cag ctg gaa acg atc aaa acg aaa gct ggt gaa acg      192
Lys Ala Ser Ala Gln Leu Glu Thr Ile Lys Thr Lys Ala Gly Glu Thr
    50                  55                  60

ttc ggt gaa gaa aaa gaa gcc atc ttt gaa ggg cat att atg ctg ctc      240
Phe Gly Glu Glu Lys Glu Ala Ile Phe Glu Gly His Ile Met Leu Leu
65                  70                  75                  80

gaa gat gag gag ctg gag cag gaa atc ata gcc ctg att aaa gat aag      288
Glu Asp Glu Glu Leu Glu Gln Glu Ile Ile Ala Leu Ile Lys Asp Lys
                85                  90                  95

cac atg aca gct gac gca gct gct cat gaa gtt atc gaa ggt cag gct      336
His Met Thr Ala Asp Ala Ala Ala His Glu Val Ile Glu Gly Gln Ala
            100                 105                 110

tct gcc ctg gaa gag ctg gat gat gaa tac ctg aaa gaa cgt gcg gct      384
Ser Ala Leu Glu Glu Leu Asp Asp Glu Tyr Leu Lys Glu Arg Ala Ala
        115                 120                 125

gac gta cgt gat atc ggt aag cgc ctg ctg cgc aac atc ctg ggc ctg      432
Asp Val Arg Asp Ile Gly Lys Arg Leu Leu Arg Asn Ile Leu Gly Leu
    130                 135                 140

aag att atc gac ctg agc gcc att cag gat gaa gtc att ctg gtt gcc      480
Lys Ile Ile Asp Leu Ser Ala Ile Gln Asp Glu Val Ile Leu Val Ala
145                 150                 155                 160

gct gac ctg acg ccg tcc gaa acc gca cag ctg aac ctg aag aag gtg      528
Ala Asp Leu Thr Pro Ser Glu Thr Ala Gln Leu Asn Leu Lys Lys Val
                165                 170                 175

ctg ggt ttc atc acc gac gcg ggt ggc cgt act tcc cac acc tct atc      576
Leu Gly Phe Ile Thr Asp Ala Gly Gly Arg Thr Ser His Thr Ser Ile
            180                 185                 190

atg gcg cgt tct ctg gaa cta cct gct atc gtg ggt acc ggt agc gtc      624
Met Ala Arg Ser Leu Glu Leu Pro Ala Ile Val Gly Thr Gly Ser Val
        195                 200                 205

acc tct cag gtg aaa aat gac gac tat ctg att ctg gat gcc gta aat      672
Thr Ser Gln Val Lys Asn Asp Asp Tyr Leu Ile Leu Asp Ala Val Asn
    210                 215                 220

aat cag gtt tac gtc aat cca acc aac gaa gtt att gat aaa atg cgc      720
Asn Gln Val Tyr Val Asn Pro Thr Asn Glu Val Ile Asp Lys Met Arg
225                 230                 235                 240

gct gtt cag gag caa gtg gct tct gaa aaa gca gag ctt gct aaa ctg      768
Ala Val Gln Glu Gln Val Ala Ser Glu Lys Ala Glu Leu Ala Lys Leu
                245                 250                 255

aaa gat ctg cca gct att acg ctg gac ggt cac cag gta gaa gta tgc      816
Lys Asp Leu Pro Ala Ile Thr Leu Asp Gly His Gln Val Glu Val Cys
            260                 265                 270

gct aac att ggt acg gtt cgt gac gtt gaa ggt gca gag cgt aac ggc      864
Ala Asn Ile Gly Thr Val Arg Asp Val Glu Gly Ala Glu Arg Asn Gly
        275                 280                 285

gct gaa ggc gtt ggt ctg tat cgt act gag ttc ctg ttc atg gac cgc      912
Ala Glu Gly Val Gly Leu Tyr Arg Thr Glu Phe Leu Phe Met Asp Arg
    290                 295                 300

gac gca ctg ccc act gaa gaa gaa cag ttt gct gct tac aaa gca gtg      960
Asp Ala Leu Pro Thr Glu Glu Glu Gln Phe Ala Ala Tyr Lys Ala Val
305                 310                 315                 320

gct gaa gcg tgt ggc tcg caa gcg gtt atc gtt cgt acc atg gac atc     1008
Ala Glu Ala Cys Gly Ser Gln Ala Val Ile Val Arg Thr Met Asp Ile
                325                 330                 335

ggc ggc gac aaa gag ctg cca tac atg aac ttc ccg aaa gaa gag aac     1056
Gly Gly Asp Lys Glu Leu Pro Tyr Met Asn Phe Pro Lys Glu Glu Asn
            340                 345                 350

ccg ttc ctc ggc tgg cgc gct atc cgt atc gcg atg gat cgt aga gag     1104
Pro Phe Leu Gly Trp Arg Ala Ile Arg Ile Ala Met Asp Arg Arg Glu
        355                 360                 365
```

```
atc ctg cgc gat cag ctc cgc gct atc ctg cgt gcc tcg gct ttc ggt     1152
Ile Leu Arg Asp Gln Leu Arg Ala Ile Leu Arg Ala Ser Ala Phe Gly
    370                 375                 380

aaa ttg cgc att atg ttc ccg atg atc atc tct gtt gaa gaa gtg cgt     1200
Lys Leu Arg Ile Met Phe Pro Met Ile Ile Ser Val Glu Glu Val Arg
385                 390                 395                 400

gca ctg cgc aaa gag atc gaa atc tac aaa cag gaa ctg cgc gac gaa     1248
Ala Leu Arg Lys Glu Ile Glu Ile Tyr Lys Gln Glu Leu Arg Asp Glu
                405                 410                 415

ggt aaa gcg ttt gac gag tca att gaa atc ggc gta atg gtg gaa aca     1296
Gly Lys Ala Phe Asp Glu Ser Ile Glu Ile Gly Val Met Val Glu Thr
            420                 425                 430

ccg gct gcc gca aca att gca cgt cat tta gcc aaa gaa gtt gat ttc     1344
Pro Ala Ala Ala Thr Ile Ala Arg His Leu Ala Lys Glu Val Asp Phe
        435                 440                 445

ttt agt atc ggc acc aat gat tta acg cag tac act ctg gca gtt gac     1392
Phe Ser Ile Gly Thr Asn Asp Leu Thr Gln Tyr Thr Leu Ala Val Asp
    450                 455                 460

cgt ggt aat gat atg att tca cac ctt tac cag cca atg tca ccg tcc     1440
Arg Gly Asn Asp Met Ile Ser His Leu Tyr Gln Pro Met Ser Pro Ser
465                 470                 475                 480

gtg ctg aac ttg atc aag caa gtt att gat gct tct cat gct gaa ggc     1488
Val Leu Asn Leu Ile Lys Gln Val Ile Asp Ala Ser His Ala Glu Gly
                485                 490                 495

aaa tgg act ggc atg tgt ggt gag ctt gct ggc gat gaa cgt gct aca     1536
Lys Trp Thr Gly Met Cys Gly Glu Leu Ala Gly Asp Glu Arg Ala Thr
            500                 505                 510

ctt ctg ttg ctg ggg atg ggt ctg gac gaa ttc tct atg agc gcc att     1584
Leu Leu Leu Leu Gly Met Gly Leu Asp Glu Phe Ser Met Ser Ala Ile
        515                 520                 525

tct atc ccg cgc att aag aag att atc cgt aac acg aac ttc gaa gat     1632
Ser Ile Pro Arg Ile Lys Lys Ile Ile Arg Asn Thr Asn Phe Glu Asp
    530                 535                 540

gcg aag gtg tta gca gag cag gct ctt gct caa ccg aca acg gac gag     1680
Ala Lys Val Leu Ala Glu Gln Ala Leu Ala Gln Pro Thr Thr Asp Glu
545                 550                 555                 560

tta atg acg ctg gtt aac aag ttc att gaa gaa aaa aca atc tgc taa     1728
Leu Met Thr Leu Val Asn Lys Phe Ile Glu Glu Lys Thr Ile Cys
                565                 570                 575


<210> SEQ ID NO 87
<211> LENGTH: 575
<212> TYPE: PRT
<213> ORGANISM: Escherichia coli

<400> SEQUENCE: 87

Met Ile Ser Gly Ile Leu Ala Ser Pro Gly Ile Ala Phe Gly Lys Ala
1               5                   10                  15

Leu Leu Leu Lys Glu Asp Glu Ile Val Ile Asp Arg Lys Lys Ile Ser
            20                  25                  30

Ala Asp Gln Val Asp Gln Glu Val Glu Arg Phe Leu Ser Gly Arg Ala
        35                  40                  45

Lys Ala Ser Ala Gln Leu Glu Thr Ile Lys Thr Lys Ala Gly Glu Thr
    50                  55                  60

Phe Gly Glu Glu Lys Glu Ala Ile Phe Glu Gly His Ile Met Leu Leu
65                  70                  75                  80

Glu Asp Glu Glu Leu Glu Gln Glu Ile Ile Ala Leu Ile Lys Asp Lys
                85                  90                  95

His Met Thr Ala Asp Ala Ala Ala His Glu Val Ile Glu Gly Gln Ala
```

```
            100                 105                 110

Ser Ala Leu Glu Glu Leu Asp Asp Glu Tyr Leu Lys Glu Arg Ala Ala
        115                 120                 125

Asp Val Arg Asp Ile Gly Lys Arg Leu Leu Arg Asn Ile Leu Gly Leu
    130                 135                 140

Lys Ile Ile Asp Leu Ser Ala Ile Gln Asp Glu Val Ile Leu Val Ala
145                 150                 155                 160

Ala Asp Leu Thr Pro Ser Glu Thr Ala Gln Leu Asn Leu Lys Lys Val
                165                 170                 175

Leu Gly Phe Ile Thr Asp Ala Gly Gly Arg Thr Ser His Thr Ser Ile
            180                 185                 190

Met Ala Arg Ser Leu Glu Leu Pro Ala Ile Val Gly Thr Gly Ser Val
        195                 200                 205

Thr Ser Gln Val Lys Asn Asp Asp Tyr Leu Ile Leu Asp Ala Val Asn
    210                 215                 220

Asn Gln Val Tyr Val Asn Pro Thr Asn Glu Val Ile Asp Lys Met Arg
225                 230                 235                 240

Ala Val Gln Glu Gln Val Ala Ser Glu Lys Ala Glu Leu Ala Lys Leu
                245                 250                 255

Lys Asp Leu Pro Ala Ile Thr Leu Asp Gly His Gln Val Glu Val Cys
            260                 265                 270

Ala Asn Ile Gly Thr Val Arg Asp Val Glu Gly Ala Glu Arg Asn Gly
        275                 280                 285

Ala Glu Gly Val Gly Leu Tyr Arg Thr Glu Phe Leu Phe Met Asp Arg
    290                 295                 300

Asp Ala Leu Pro Thr Glu Glu Glu Gln Phe Ala Ala Tyr Lys Ala Val
305                 310                 315                 320

Ala Glu Ala Cys Gly Ser Gln Ala Val Ile Val Arg Thr Met Asp Ile
                325                 330                 335

Gly Gly Asp Lys Glu Leu Pro Tyr Met Asn Phe Pro Lys Glu Glu Asn
            340                 345                 350

Pro Phe Leu Gly Trp Arg Ala Ile Arg Ile Ala Met Asp Arg Arg Glu
        355                 360                 365

Ile Leu Arg Asp Gln Leu Arg Ala Ile Leu Arg Ala Ser Ala Phe Gly
    370                 375                 380

Lys Leu Arg Ile Met Phe Pro Met Ile Ile Ser Val Glu Glu Val Arg
385                 390                 395                 400

Ala Leu Arg Lys Glu Ile Glu Ile Tyr Lys Gln Glu Leu Arg Asp Glu
                405                 410                 415

Gly Lys Ala Phe Asp Glu Ser Ile Glu Ile Gly Val Met Val Glu Thr
            420                 425                 430

Pro Ala Ala Ala Thr Ile Ala Arg His Leu Ala Lys Glu Val Asp Phe
        435                 440                 445

Phe Ser Ile Gly Thr Asn Asp Leu Thr Gln Tyr Thr Leu Ala Val Asp
    450                 455                 460

Arg Gly Asn Asp Met Ile Ser His Leu Tyr Gln Pro Met Ser Pro Ser
465                 470                 475                 480

Val Leu Asn Leu Ile Lys Gln Val Ile Asp Ala Ser His Ala Glu Gly
                485                 490                 495

Lys Trp Thr Gly Met Cys Gly Glu Leu Ala Gly Asp Glu Arg Ala Thr
            500                 505                 510

Leu Leu Leu Leu Gly Met Gly Leu Asp Glu Phe Ser Met Ser Ala Ile
        515                 520                 525
```

```
Ser Ile Pro Arg Ile Lys Lys Ile Ile Arg Asn Thr Asn Phe Glu Asp
    530                 535                 540

Ala Lys Val Leu Ala Glu Gln Ala Leu Ala Gln Pro Thr Thr Asp Glu
545                 550                 555                 560

Leu Met Thr Leu Val Asn Lys Phe Ile Glu Glu Lys Thr Ile Cys
                565                 570                 575


<210> SEQ ID NO 88
<211> LENGTH: 1740
<212> TYPE: DNA
<213> ORGANISM: Artificial sequence
<220> FEATURE:
<223> OTHER INFORMATION: attR-cat-attL-PtacM2-SD-spacer

<400> SEQUENCE: 88

tctagacgct caagttagta taaaaaagct gaacgagaaa cgtaaaatga tataaatatc     60

aatatattaa attagatttt gcataaaaaa cagactacat aatactgtaa aacacaacat    120

atgcagtcac tatgaatcaa ctacttagat ggtattagtg acctgtaaca gactgcagtg    180

gtcgaaaaaa aaagcccgca ctgtcaggtg cgggcttttt tctgtgttaa gcttcgacga    240

atttctgcca ttcatccgct tattatcact tattcaggcg tagcaccagg cgtttaaggg    300

caccaataac tgccttaaaa aaattacgcc ccgccctgcc actcatcgca gtactgttgt    360

aattcattaa gcattctgcc gacatggaag ccatcacaga cggcatgatg aacctgaatc    420

gccagcggca tcagcacctt gtcgccttgc gtataatatt tgcccatggt gaaaacgggg    480

gcgaagaagt tgtccatatt ggccacgttt aaatcaaaac tggtgaaact cacccaggga    540

ttggctgaga cgaaaaacat attctcaata aaccctttag ggaaataggc caggttttca    600

ccgtaacacg ccacatcttg cgaatatatg tgtagaaact gccggaaatc gtcgtggtat    660

tcactccaga gcgatgaaaa cgtttcagtt tgctcatgga aaacggtgta acaagggtga    720

acactatccc atatcaccag ctcaccgtct ttcattgcca tacggaattc cggatgagca    780

ttcatcaggc gggcaagaat gtgaataaag gccggataaa acttgtgctt atttttcttt    840

acggtcttta aaaaggccgt aatatccagc tgaacggtct ggttataggt acattgagca    900

actgactgaa atgcctcaaa atgttcttta cgatgccatt gggatatatc aacggtggta    960

tatccagtga tttttttctc cattttagct tccttagctc ctgaaaatct cggatccggc   1020

caagctagct tggctctagc tagagcgccc ggttgacgct gctagtgtta cctagcgatt   1080

tgtatcttac tgcatgttac ttcatgttgt caatacctgt ttttcgtgcg acttatcagg   1140

ctgtctactt atccggagat ccacaggacg ggtgtggtcg ccatgatcgc gtagtcgata   1200

gtggctccaa gtagcgaagc gagcaggact gggcggcggc caaagcggtc ggacagtgct   1260

ccgagaacgg gtgcgcatag aaattgcatc aacgcatata gcgctagcag cacgccatag   1320

tgactggcga tgctgtcgga atggacgata tcccgcaaga ggcccggcag taccggcata   1380

accaagccta tgcctacagc atccagggtg acggtgccga ggatgacgat gagcgcattg   1440

ttagatttca tacacggtgc ctgactgcgt tagcaattta actgtgataa actaccgcat   1500

taaagcttat cgatgataag ctgtcaaaca tgagaattcg aaatcaaata atgattttat   1560

tttgactgat agtgacctgt tcgttgcaac aaattgataa gcaatgcttt tttataatgc   1620

caacttagta taaaaaagca ggcttcaaga tctctcccca tccccctgtg tacaattaat   1680

catcggctcg tataatgtgt ggaattgtga gcggataaca atttcacaca ggagactgcc   1740


<210> SEQ ID NO 89
<211> LENGTH: 1740
```

<212> TYPE: DNA
<213> ORGANISM: Artificial sequence
<220> FEATURE:
<223> OTHER INFORMATION: attR-cat-attL-PtacM3-SD-spacer

<400> SEQUENCE: 89

```
tctagacgct caagttagta taaaaaagct gaacgagaaa cgtaaaatga tataaatatc     60

aatatattaa attagatttt gcataaaaaa cagactacat aatactgtaa aacacaacat    120

atgcagtcac tatgaatcaa ctacttagat ggtattagtg acctgtaaca gactgcagtg    180

gtcgaaaaaa aaagcccgca ctgtcaggtg cgggcttttt tctgtgttaa gcttcgacga    240

atttctgcca ttcatccgct tattatcact tattcaggcg tagcaccagg cgtttaaggg    300

caccaataac tgccttaaaa aaattacgcc ccgccctgcc actcatcgca gtactgttgt    360

aattcattaa gcattctgcc gacatggaag ccatcacaga cggcatgatg aacctgaatc    420

gccagcggca tcagcacctt gtcgccttgc gtataatatt tgcccatggt gaaaacgggg    480

gcgaagaagt tgtccatatt ggccacgttt aaatcaaaac tggtgaaact cacccaggga    540

ttggctgaga cgaaaaacat attctcaata aaccctttag ggaaataggc caggttttca    600

ccgtaacacg ccacatcttg cgaatatatg tgtagaaact gccggaaatc gtcgtggtat    660

tcactccaga gcgatgaaaa cgtttcagtt tgctcatgga aaacggtgta acaagggtga    720

acactatccc atatcaccag ctcaccgtct ttcattgcca tacggaattc cggatgagca    780

ttcatcaggc gggcaagaat gtgaataaag gccggataaa acttgtgctt atttttcttt    840

acggtcttta aaaaggccgt aatatccagc tgaacggtct ggttataggt acattgagca    900

actgactgaa atgcctcaaa atgttcttta cgatgccatt gggatatatc aacggtggta    960

tatccagtga tttttttctc cattttagct tccttagctc ctgaaaatct cggatccggc   1020

caagctagct tggctctagc tagagcgccc ggttgacgct gctagtgtta cctagcgatt   1080

tgtatcttac tgcatgttac ttcatgttgt caatacctgt ttttcgtgcg acttatcagg   1140

ctgtctactt atccggagat ccacaggacg ggtgtggtcg ccatgatcgc gtagtcgata   1200

gtggctccaa gtagcgaagc gagcaggact gggcggcggc caaagcggtc ggacagtgct   1260

ccgagaacgg gtgcgcatag aaattgcatc aacgcatata gcgctagcag cacgccatag   1320

tgactggcga tgctgtcgga atggacgata tcccgcaaga ggcccggcag taccggcata   1380

accaagccta tgcctacagc atccagggtg acggtgccga ggatgacgat gagcgcattg   1440

ttagatttca tacacggtgc ctgactgcgt tagcaattta actgtgataa actaccgcat   1500

taaagcttat cgatgataag ctgtcaaaca tgagaattcg aaatcaaata atgattttat   1560

tttgactgat agtgacctgt tcgttgcaac aaattgataa gcaatgcttt tttataatgc   1620

caacttagta taaaaaagca ggcttcaaga tctctcccca tccccctgtt ggcaattaat   1680

catcggctcg tataatgtgt ggaattgtga gcggataaca atttcacaca ggagactgcc   1740
```

<210> SEQ ID NO 90
<211> LENGTH: 2847
<212> TYPE: DNA
<213> ORGANISM: Artificial sequence
<220> FEATURE:
<223> OTHER INFORMATION: PtacM2gldA::Cm

<400> SEQUENCE: 90

```
tctagacgct caagttagta taaaaaagct gaacgagaaa cgtaaaatga tataaatatc     60

aatatattaa attagatttt gcataaaaaa cagactacat aatactgtaa aacacaacat    120

atgcagtcac tatgaatcaa ctacttagat ggtattagtg acctgtaaca gactgcagtg    180
```

```
gtcgaaaaaa aaagcccgca ctgtcaggtg cgggcttttt tctgtgttaa gcttcgacga    240
atttctgcca ttcatccgct tattatcact tattcaggcg tagcaccagg cgtttaaggg    300
caccaataac tgccttaaaa aaattacgcc ccgccctgcc actcatcgca gtactgttgt    360
aattcattaa gcattctgcc gacatggaag ccatcacaga cggcatgatg aacctgaatc    420
gccagcggca tcagcacctt gtcgccttgc gtataatatt tgcccatggt gaaaacgggg    480
gcgaagaagt tgtccatatt ggccacgttt aaatcaaaac tggtgaaact cacccaggga    540
ttggctgaga cgaaaaacat attctcaata aaccctttag ggaaataggc caggttttca    600
ccgtaacacg ccacatcttg cgaatatatg tgtagaaact gccggaaatc gtcgtggtat    660
tcactccaga gcgatgaaaa cgtttcagtt tgctcatgga aaacggtgta acaagggtga    720
acactatccc atatcaccag ctcaccgtct ttcattgcca tacggaattc cggatgagca    780
ttcatcaggc gggcaagaat gtgaataaag gccggataaa acttgtgctt atttttcttt    840
acggtcttta aaaaggccgt aatatccagc tgaacggtct ggttataggt acattgagca    900
actgactgaa atgcctcaaa atgttcttta cgatgccatt gggatatatc aacggtggta    960
tatccagtga tttttttctc cattttagct tccttagctc ctgaaaatct cggatccggc   1020
caagctagct tggctctagc tagagcgccc ggttgacgct gctagtgtta cctagcgatt   1080
tgtatcttac tgcatgttac ttcatgttgt caatacctgt ttttcgtgcg acttatcagg   1140
ctgtctactt atccggagat ccacaggacg ggtgtggtcg ccatgatcgc gtagtcgata   1200
gtggctccaa gtagcgaagc gagcaggact gggcggcggc caaagcggtc ggacagtgct   1260
ccgagaacgg gtgcgcatag aaattgcatc aacgcatata gcgctagcag cacgccatag   1320
tgactggcga tgctgtcgga atggacgata tcccgcaaga ggcccggcag taccggcata   1380
accaagccta tgcctacagc atccagggtg acggtgccga ggatgacgat gagcgcattg   1440
ttagatttca tacacggtgc ctgactgcgt tagcaattta actgtgataa actaccgcat   1500
taaagcttat cgatgataag ctgtcaaaca tgagaattcg aaatcaaata atgattttat   1560
tttgactgat agtgacctgt tcgttgcaac aaattgataa gcaatgcttt tttataatgc   1620
caacttagta taaaaaagca ggcttcaaga tcttctctcc ccatccccct gtgtacaatt   1680
aatcatcggc tcgtataatg tgtggaattg tgagcggata acaatttcac acaggagact   1740
gccatggacc gcattattca atcaccgggt aaatacatcc agggcgctga tgtgattaat   1800
cgtctgggcg aatacctgaa gccgctggca gaacgctggt tagtggtggg tgacaaattt   1860
gttttaggtt ttgctcaatc cactgtcgag aaaagcttta aagatgctgg actggtagta   1920
gaaattgcgc cgtttggcgg tgaatgttcg caaaatgaga tcgaccgtct gcgtggcatc   1980
gcggagactg cgcagtgtgg cgcaattctc ggtatcggtg gcggaaaaac cctcgatact   2040
gccaaagcac tggcacattt catgggtgtt ccggtagcga tcgcaccgac tatcgcctct   2100
accgatgcac cgtgcagcgc attgtctgtt atctacaccg atgagggtga gtttgaccgc   2160
tatctgctgt tgccaaataa cccgaatatg gtcattgtcg acaccaaaat cgtcgctggc   2220
gcacctgcac gtctgttagc ggcgggtatc ggcgatgcgc tggcaacctg gtttgaagcg   2280
cgtgcctgct ctcgtagcgg cgcgaccacc atggcgggcg gcaagtgcac ccaggctgcg   2340
ctggcactgg ctgaactgtg ctacaacacc ctgctggaag aaggcgaaaa agcgatgctt   2400
gctgccgaac agcatgtagt gactccggcg ctggagcgcg tgattgaagc gaacacctat   2460
ttgagcggtg ttggttttga aagtggtggt ctggctgcgg cgcacgcagt gcataacggc   2520
ctgaccgcta tcccggacgc gcatcactat tatcacggtg aaaaagtggc attcggtacg   2580
```

```
ctgacgcagc tggttctgga aaatgcgccg gtggaggaaa tcgaaaccgt agctgccctt   2640

agccatgcgg taggtttgcc aataactctc gctcaactgg atattaaaga agatgtcccg   2700

gcgaaaatgc gaattgtggc agaagcggca tgtgcagaag gtgaaaccat tcacaacatg   2760

cctggcggcg cgacgccaga tcaggtttac gccgctctgc tggtagccga ccagtacggt   2820

cagcgtttcc tgcaagagtg ggaataa                                      2847
```

<210> SEQ ID NO 91
<211> LENGTH: 2847
<212> TYPE: DNA
<213> ORGANISM: Artificial sequence
<220> FEATURE:
<223> OTHER INFORMATION: PtacM3gldA::Cm

<400> SEQUENCE: 91

```
tctagacgct caagttagta taaaaaagct gaacgagaaa cgtaaaatga tataaatatc     60

aatatattaa attagatttt gcataaaaaa cagactacat aatactgtaa aacacaacat    120

atgcagtcac tatgaatcaa ctacttagat ggtattagtg acctgtaaca gactgcagtg    180

gtcgaaaaaa aaagcccgca ctgtcaggtg cgggcttttt tctgtgttaa gcttcgacga    240

atttctgcca ttcatccgct tattatcact tattcaggcg tagcaccagg cgtttaaggg    300

caccaataac tgccttaaaa aaattacgcc ccgccctgcc actcatcgca gtactgttgt    360

aattcattaa gcattctgcc gacatggaag ccatcacaga cggcatgatg aacctgaatc    420

gccagcggca tcagcacctt gtcgccttgc gtataatatt tgcccatggt gaaaacgggg    480

gcgaagaagt tgtccatatt ggccacgttt aaatcaaaac tggtgaaact cacccaggga    540

ttggctgaga cgaaaaacat attctcaata aaccctttag ggaaataggc caggttttca    600

ccgtaacacg ccacatcttg cgaatatatg tgtagaaact gccggaaatc gtcgtggtat    660

tcactccaga gcgatgaaaa cgtttcagtt tgctcatgga aaacggtgta acaagggtga    720

acactatccc atatcaccag ctcaccgtct ttcattgcca tacggaattc cggatgagca    780

ttcatcaggc gggcaagaat gtgaataaag gccggataaa acttgtgctt atttttcttt    840

acggtcttta aaaaggccgt aatatccagc tgaacggtct ggttataggt acattgagca    900

actgactgaa atgcctcaaa atgttcttta cgatgccatt gggatatatc aacggtggta    960

tatccagtga tttttttctc cattttagct tccttagctc ctgaaaatct cggatccggc   1020

caagctagct tggctctagc tagagcgccc ggttgacgct gctagtgtta cctagcgatt   1080

tgtatcttac tgcatgttac ttcatgttgt caatacctgt ttttcgtgcg acttatcagg   1140

ctgtctactt atccggagat ccacaggacg ggtgtggtcg ccatgatcgc gtagtcgata   1200

gtggctccaa gtagcgaagc gagcaggact gggcggcggc caaagcggtc ggacagtgct   1260

ccgagaacgg gtgcgcatag aaattgcatc aacgcatata gcgctagcag cacgccatag   1320

tgactggcga tgctgtcgga atggacgata tcccgcaaga ggcccggcag taccggcata   1380

accaagccta tgcctacagc atccagggtg acggtgccga ggatgacgat gagcgcattg   1440

ttagatttca tacacggtgc ctgactgcgt tagcaattta actgtgataa actaccgcat   1500

taaagcttat cgatgataag ctgtcaaaca tgagaattcg aaatcaaata atgattttat   1560

tttgactgat agtgacctgt tcgttgcaac aaattgataa gcaatgcttt tttataatgc   1620

caacttagta taaaaaagca ggcttcaaga tcttctctcc ccatccccct gttggcaatt   1680

aatcatcggc tcgtataatg tgtggaattg tgagcggata acaatttcac acaggagact   1740

gccatggacc gcattattca atcaccgggt aaatacatcc agggcgctga tgtgattaat   1800
```

```
cgtctgggcg aatacctgaa gccgctggca gaacgctggt tagtggtggg tgacaaattt   1860
gttttaggtt ttgctcaatc cactgtcgag aaaagcttta aagatgctgg actggtagta   1920
gaaattgcgc cgtttggcgg tgaatgttcg caaaatgaga tcgaccgtct gcgtggcatc   1980
gcggagactg cgcagtgtgg cgcaattctc ggtatcggtg gcggaaaaac cctcgatact   2040
gccaaagcac tggcacattt catgggtgtt ccggtagcga tcgcaccgac tatcgcctct   2100
accgatgcac cgtgcagcgc attgtctgtt atctacaccg atgagggtga gtttgaccgc   2160
tatctgctgt tgccaaataa cccgaatatg gtcattgtcg acaccaaaat cgtcgctggc   2220
gcacctgcac gtctgttagc ggcgggtatc ggcgatgcgc tggcaacctg gtttgaagcg   2280
cgtgcctgct ctcgtagcgg cgcgaccacc atggcgggcg gcaagtgcac ccaggctgcg   2340
ctggcactgg ctgaactgtg ctacaacacc ctgctggaag aaggcgaaaa agcgatgctt   2400
gctgccgaac agcatgtagt gactccggcg ctggagcgcg tgattgaagc gaacacctat   2460
ttgagcggtg ttggttttga aagtggtggt ctggctgcgg cgcacgcagt gcataacggc   2520
ctgaccgcta tcccggacgc gcatcactat tatcacggtg aaaaagtggc attcggtacg   2580
ctgacgcagc tggttctgga aaatgcgccg gtggaggaaa tcgaaaccgt agctgccctt   2640
agccatgcgg taggtttgcc aataactctc gctcaactgg atattaaaga agatgtcccg   2700
gcgaaaatgc gaattgtggc agaagcggca tgtgcagaag gtgaaaccat tcacaacatg   2760
cctggcggcg cgacgccaga tcaggtttac gccgctctgc tggtagccga ccagtacggt   2820
cagcgtttcc tgcaagagtg ggaataa                                     2847
```

<210> SEQ ID NO 92
<211> LENGTH: 2903
<212> TYPE: DNA
<213> ORGANISM: Artificial sequence
<220> FEATURE:
<223> OTHER INFORMATION: PtacM fsaB-gldA::Cm

<400> SEQUENCE: 92

```
tctagacgct caagttagta taaaaaagct gaacgagaaa cgtaaaatga tataaatatc     60
aatatattaa attagatttt gcataaaaaa cagactacat aatactgtaa aacacaacat    120
atgcagtcac tatgaatcaa ctacttagat ggtattagtg acctgtaaca gactgcagtg    180
gtcgaaaaaa aaagcccgca ctgtcaggtg cgggcttttt tctgtgttaa gcttcgacga    240
atttctgcca ttcatccgct tattatcact tattcaggcg tagcaccagg cgtttaaggg    300
caccaataac tgccttaaaa aaattacgcc ccgccctgcc actcatcgca gtactgttgt    360
aattcattaa gcattctgcc gacatggaag ccatcacaga cggcatgatg aacctgaatc    420
gccagcggca tcagcacctt gtcgccttgc gtataatatt tgcccatggt gaaaacgggg    480
gcgaagaagt tgtccatatt ggccacgttt aaatcaaaac tggtgaaact cacccaggga    540
ttggctgaga cgaaaaacat attctcaata aaccctttag ggaaataggc caggttttca    600
ccgtaacacg ccacatcttg cgaatatatg tgtagaaact gccggaaatc gtcgtggtat    660
tcactccaga gcgatgaaaa cgtttcagtt tgctcatgga aaacggtgta acaagggtga    720
acactatccc atatcaccag ctcaccgtct ttcattgcca tacggaattc cggatgagca    780
ttcatcaggc gggcaagaat gtgaataaag gccggataaa acttgtgctt atttttcttt    840
acggtcttta aaaaggccgt aatatccagc tgaacggtct ggttataggt acattgagca    900
actgactgaa atgcctcaaa atgttcttta cgatgccatt gggatatatc aacggtggta    960
tatccagtga tttttttctc cattttagct tccttagctc ctgaaaatct cggatccggc   1020
```

caagctagct tggctctagc tagagcgccc ggttgacgct gctagtgtta cctagcgatt 1080
tgtatcttac tgcatgttac ttcatgttgt caatacctgt ttttcgtgcg acttatcagg 1140
ctgtctactt atccggagat ccacaggacg ggtgtggtcg ccatgatcgc gtagtcgata 1200
gtggctccaa gtagcgaagc gagcaggact gggcggcggc caaagcggtc ggacagtgct 1260
ccgagaacgg gtgcgcatag aaattgcatc aacgcatata gcgctagcag cacgccatag 1320
tgactggcga tgctgtcgga atggacgata tcccgcaaga ggcccggcag taccggcata 1380
accaagccta tgcctacagc atccagggtg acggtgccga ggatgacgat gagcgcattg 1440
ttagatttca tacacggtgc ctgactgcgt tagcaattta actgtgataa actaccgcat 1500
taaagcttat cgatgataag ctgtcaaaca tgagaattcg aaatcaaata atgattttat 1560
tttgactgat agtgacctgt tcgttgcaac aaattgataa gcaatgcttt tttataatgc 1620
caacttagta taaaaaagca ggcttcaaga tcttctctcc ccatccccct gttcacaatt 1680
aatcatcggc tcgtataatg tgtggaattg tgagcggata acaatttcac acaggacatc 1740
atggaactgt atctggacac cgctaacgtc gcagaagtcg aacgtctggc acgcatattc 1800
cccattgccg gggtgacaac taacccgagc attatcgctg ccagcaagga gtccatatgg 1860
gaagtgctgc cgcgtctgca aaaagcgatt ggtgatgagg gcattctgtt tgctcagacc 1920
atgagccgcg acgcgcaggg gatggtggaa gaagcgaagc gcctgcgcga cgctattccg 1980
ggtattgtgg tgaaaatccc ggtgacttcc gaaggtctgg cagcaattaa aatactgaaa 2040
aaagagggta ttactacact tggcactgct gtatatagcg ccgcacaagg gttattagcc 2100
gcactggcag ggcaaaata cgttgctccg tatgttaacc gcgtagatgc ccagggcgga 2160
gacggcattc gtacggttca ggagctgcaa acgctgttag aaatgcacgc gccagaaagc 2220
atggtgctgg cagccagctt taaaacgccg cgtcaggcgc tggactgttt actggcagga 2280
tgtgaatcca tcaccctgcc cttagatgta gcgcaacaaa tgctcaacac ccctgcggta 2340
gagtcagcta tagagaagtt cgaacacgac tggaatgccg catttggcac tactcatctc 2400
taaaggagca attatggacc gcattattca atcaccgggt aaatacatcc agggcgctga 2460
tgtgattaat cgtctgggcg aatacctgaa gccgctggca gaacgctggt tagtggtggg 2520
tgacaaattt gttttaggtt ttgctcaatc cactgtcgag aaaagcttta aagatgctgg 2580
actggtagta gaaattgcgc cgtttggcgg tgaatgttcg caaaatgaga tcgaccgtct 2640
gcgtggcatc gcggagactg cgcagtgtgg cgcaattctc ggtatcggtg gcggaaaaac 2700
cctcgatact gccaaagcac tggcacattt catgggtgtt ccggtagcga tcgcaccgac 2760
tatcgcctct accgatgcac cgtgcagcgc attgtctgtt atctacaccg atgagggtga 2820
gtttgaccgc tatctgctgt tgccaaataa cccgaatatg gtcattgtcg acaccaaaat 2880
cgtcgctggc gcacctgcac gtc 2903

<210> SEQ ID NO 93
<211> LENGTH: 79
<212> TYPE: DNA
<213> ORGANISM: Artificial sequence
<220> FEATURE:
<223> OTHER INFORMATION: atL-Ptac-fsaB

<400> SEQUENCE: 93
tgcgtgccag acgttcgact tctgcgacgt tagcggtgtc cagatacagt tccatgatgt 60
cctgtgtgaa attgttatc 79

```
<210> SEQ ID NO 94
<211> LENGTH: 77
<212> TYPE: DNA
<213> ORGANISM: Artificial sequence
<220> FEATURE:
<223> OTHER INFORMATION: atR-Ptac-fsaB

<400> SEQUENCE: 94

aacgccgcct ctgccgacgc tatcgccagc ctgctgcaac atgaactgga actgtaaatc     60

tagacgctca agttagt                                                    77
```

METHOD OF PRODUCING L-AMINO ACID

This application is a continuation under 35 U.S.C. §120 of PCT Patent Application No. PCT/JP2008/053020, filed Feb. 22, 2008, which claims priority under 35 U.S.C. §119 to Japanese Patent Application No. 2007-041724, filed on Feb. 22, 2007, which are incorporated in their entireties by reference. The Sequence Listing in electronic format filed herewith is also hereby incorporated by reference in its entirety (File Name: US-405_Seq_List; File Size: 438 KB; Date Created: Aug. 24, 2009).

BACKGROUND OF THE INVENTION

1. Field of the Invention

The present invention is related to the field of fermentation, and more specifically to the production of L-amino acids via the fermentation of microorganisms.

2. Brief Description of the Related Art

L-Amino acids are industrially produced by fermentation using microorganisms belonging to the genus *Brevibacterium, Corynebacterium, Escherichia*, or the like. In such production methods, strains are used which are isolated from nature, or artificial variants of such strains. Furthermore, microorganism strains can be used which are modified by a recombinant DNA technique to increase activity of a basic L-amino acid biosynthesis enzyme, and so forth (EP 0643135 B, EP 0733712 B, EP 1477565 A, EP 0796912 A, EP 0837134 A, WO01/53459, EP 1170376 A, WO2005/010175, and WO96/17930).

When amino acids are produced using microorganisms, sugars are generally used as a main component of substrate, but glycerol can also be used as a substrate (EP 1715055 A and EP 1715056 A).

It is known that *Escherichia coli* has a plurality of genes which participate in glycerol metabolism. However, it has been revealed that, since a mutant strain deficient in glpK, which is a gene coding for glycerol kinase, or glpD, which is a gene coding for glycerol-3-phosphate dehydrogenase, cannot grow in a medium when glycerol is the sole carbon source, the major glycerol assimilation pathway of *E. coli* consists of glycerol kinase and glycerol-3-phosphate dehydrogenase (J. Bacteriol., 23 (2006) 8259-8271).

It is known that glycerol dehydrogenase of *E. coli* is also one of the enzymes which participate in glycerol metabolism, and it recovers a mutant strain deficient in the three genes of glpK, glpD and glpR, which is a gene of repressor of the glp regulon, from lethality thereof in a medium containing glycerol as a sole carbon source in screening using that strain (J. Bacteriol., 131 (1977) 1026-1028).

The pathway via glycerol-3-phosphate including glycerol kinase and glycerol-3-phosphate dehydrogenase is thought to be the main glycerol assimilation pathway of microorganisms belonging to the family Enterobacteriaceae as described above, and the glycerol assimilation pathway via dihydroxyacetone is an unnecessary pathway for glycerol assimilation of microorganisms belonging to the family Enterobacteriaceae.

SUMMARY OF THE INVENTION

An aspect of the present invention is to provide a method for producing an L-amino acid by fermentation using a substrate containing glycerol, which is improved compared with conventional techniques.

It has been found that enhancing either glycerol dehydrogenase or dihydroxyacetone kinase, which are enzymes of the glycerol assimilation pathway via dihydroxyacetone, was not effective for production of L-amino acids from glycerol. However, enhancing both glycerol dehydrogenase and dihydroxyacetone kinase markedly improved the production of L-amino acids from glycerol.

It is an aspect of the present invention to provide a method for producing an L-amino acid by (A) modifying a microorganism belonging to the family Enterobacteriaceae having an L-amino acid-producing ability to increase glycerol dehydrogenase and dihydroxyacetone kinase activities, (B) culturing said microorganism in a medium containing glycerol as a carbon source to produce and accumulate an L-amino acid in the medium or cells, and (C) collecting the L-amino acid from the medium or the cells.

It is a further aspect of the present invention to provide the method as described above, wherein the glycerol dehydrogenase and dihydroxyacetone kinase activities are increased by increasing copy numbers of genes coding for glycerol dehydrogenase and dihydroxyacetone kinase, or modifying expression control sequences of the genes.

It is a further aspect of the present invention to provide the method as described above, wherein the dihydroxyacetone kinase uses ATP as a phosphate donor.

It is a further aspect of the present invention to provide the method as described above, wherein the microorganism is further modified to increase glycerol uptake activity.

It is a further aspect of the present invention to provide the method as described above, wherein the microorganism is further modified to increase the activity or activities of an enzyme selected from the group consisting of triosephosphate isomerase, fructose bisphosphate aldolase, fructose-1,6-bisphosphatase, fructose-6-phosphate aldolase, and combinations thereof.

It is a further aspect of the present invention to provide the method as described above, wherein the microorganism is further modified to reduce the activity or activities of glycerol kinase and/or membrane-binding type glycerol-3-phosphate dehydrogenase.

It is a further aspect of the present invention to provide the method as described above, wherein the microorganism belonging to the family Enterobacteriaceae is an *Escherichia* bacterium, or a *Pantoea* bacterium.

It is a further aspect of the present invention to provide the method as described above, wherein the L-amino acid is selected from the group consisting of L-glutamic acid, L-lysine, L-leucine, L-isoleucine, L-valine, L-tryptophan, L-phenylalanine, L-tyrosine, L-threonine, L-methionine, L-cysteine, L-arginine, L-serine, L-proline, L-asparatic acid, L-asparagine, L-glutamine, and L-histidine.

DETAILED DESCRIPTION OF EXEMPLARY EMBODIMENTS

Hereafter, the present invention will be explained in detail.

<1> Microorganism

Exemplary microorganisms of the present invention include a microorganism belonging to the family Enterobacteriaceae, which has an ability to produce an L-amino acid and is modified to increase glycerol dehydrogenase and dihydroxyacetone kinase activities. The ability to produce an L-amino acid (L-amino acid-producing ability) can mean an ability of exemplary microorganisms of the present invention to produce and accumulate an L-amino acid in a medium or cells when cultured in the medium. An exemplary microorganism of the present invention may have an ability to produce two or more kinds of L-amino acids. Although the microorganism having L-amino acid-producing ability may inherently have L-amino acid-producing ability, the microorganism can also be obtained by modifying such microorganisms as mentioned below using a recombinant DNA technique so that they have L-amino acid-producing ability.

Although the type of L-amino acid is not particularly limited, examples include basic amino acids such as L-lysine, L-ornithine, L-arginine, L-histidine and L-citrulline, aliphatic amino acids such as L-isoleucine, L-alanine, L-valine, L-leucine and L-glycine, amino acids which are hydroxy-monoaminocarboxylic acids such as L-threonine and L-serine, cyclic amino acids such as L-proline, aromatic amino acids such as L-phenylalanine, L-tyrosine and L-tryptophan, sulfur-containing amino acids such as L-cysteine, L-cystine and L-methionine, acidic amino acids such as L-glutamic acid and L-aspartic acid, and amino acids with amide group at the side chain such as L-glutamine and L-asparagine. An exemplary microorganism of the present invention may have an ability to produce two or more kinds of L-amino acids.

Microorganisms belonging to the family Enterobacteriaceae include *Escherichia bacteria* and *Pantoea* bacteria. Other examples of microorganisms belonging to the family Enterobacteriaceae include microorganisms belonging to γ-proteobacteria such as those of the genus *Enterobacter, Klebsiella, Serratia, Erwinia, Salmonella, Morganella* or the like.

"Glycerol dehydrogenase" can mean an enzyme which reversibly catalyzes the following oxidation reaction that converts glycerol into dihydroxyacetone by using NAD as a coenzyme (EC: 1.1.1.6).

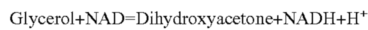
Glycerol+NAD=Dihydroxyacetone+NADH+$H^+$

The phrase "to increase the glycerol dehydrogenase activity" can mean that the number of the glycerol dehydrogenase molecules per cell can be increased compared with that of a wild-type strain or non-modified strain, or that the activity of the glycerol dehydrogenase per molecule can be improved compared with that of a wild-type strain or non-modified strain. Moreover, when the enzyme activity is undetectable in a wild-type strain, and it is improved to a detectable level, this can also be included in the state of "the activity increases". The glycerol dehydrogenase activity can be at any level so long as it can be detected, but the modification is preferably performed so that the glycerol dehydrogenase activity is 0.05 U/mg or higher, in another example 0.25 U/mg or higher, and in another example 0.5 U/mg or higher. Examples of wild-type strains of the microorganism belonging to the family Enterobacteriaceae which can serve as a reference for comparison include the *Escherichia coli* MG1655 strain (ATCC No. 47076) and W3110 strain (ATCC No. 27325), *Pantoea ananatis* AJ13335 strain (FERM BP-6615), and so forth. The glycerol dehydrogenase activity can be measured by referring to the method of Ansis, R. E. et al. (J. Biol. Chem., 2-3, 153-159 (1953))

"Dihydroxyacetone kinase" is an enzyme which reversibly catalyzes the following reaction that converts dihydroxyacetone into dihydroxyacetone phosphate, and one uses ATP as a phosphate donor (EC 2.7.1.29), and one uses PEP as a phosphate donor (EC 2.7.1.29) (Cell. Mol. Life. Sci., 63 (2006) 890-900; Biochemistry, 43 (2004) 13037-13045)

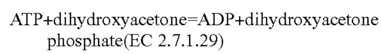
ATP+dihydroxyacetone=ADP+dihydroxyacetone phosphate(EC 2.7.1.29)

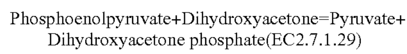
Phosphoenolpyruvate+Dihydroxyacetone=Pyruvate+Dihydroxyacetone phosphate(EC2.7.1.29)

In one example, dihydroxyacetone kinase can use ATP as a phosphate donor.

The phrase "to increase the dihydroxyacetone kinase activity" can mean that number of dihydroxyacetone kinase molecules per cell can be increased compared with that of a wild-type strain or non-modified strain, or that the activity of the dihydroxyacetone kinase per molecule can be improved compared with that of a wild-type strain or non-modified strain. The modification is preferably performed so that the dihydroxyacetone kinase activity per cell can be improved to 150% or more, in another example 200% or more, in another example 300% or more, of the activity of a wild-type strain or non-modified strain. Examples of wild-type strains of the microorganism belonging to the family Enterobacteriaceae which can serve as a reference for the comparison include the *Escherichia coli* MG1655 strain (ATCC No. 47076) and W3110 strain (ATCC No. 27325), *Pantoea ananatis* AJ13335 strain (FERM BP-6615), and so forth. The dihydroxyacetone kinase activity can be measured by referring to the method of Johnson E. A. (J. Bacteriol., 1984 October; 160 (1):55-60).

Examples of the gene coding for glycerol dehydrogenase include the gldA gene, and one example is the gldA gene derived from a microorganism belonging the family Enterobacteriaceae. Examples of the microorganism belonging the family Enterobacteriaceae include *Escherichia coli*. Examples of the gene of *Escherichia coli* include, for example, the gldA gene of SEQ ID NO: 1 (complementary strand of the nucleotide numbers 4135955..4137058 of GenBank Accession No. NC_000913).

Furthermore, homologues of the gene coding for glycerol dehydrogenase can be those cloned on the basis of homology to the gene exemplified above from a bacterium of the genus *Escherichia, Enterobacter, Klebsiella, Serratia, Erwinia, Yersinia, Shigella, Salmonella, Vibrio, Aeromonas, Bacillus, Staphylococcus, Lactobacillus, Enterococcus, Clostridium, Pseudomonas, Agrobacterium, Citrobacter, Corynebacterium*, or the like. Examples of the gene which show high homology to the gldA gene of *Escherichia coli* and can be used as the gene coding for glycerol dehydrogenase are mentioned in Table 1.

TABLE 1

Genes showing high homology to gldA gene of *Escherichia coli* and coding for glycerol dehydrogenase

| Gene | Microorganism | Description | Genbank Accession No. | SEQ ID NO |
|---|---|---|---|---|
| gldA | *Shigella dysenteriae* Sd197 | Glycerol dehydrogenase (NAD) | YP_405216.1 GI: 82778867 | 74, 75 |
| gldA | *Salmonella typhimurium* LT2 | Similar to *E. coli* glycerol dehydrogenase (NAD) | AE008892.1 GI: 16422675 | 76, 77 |
| gldA | *Pseudomonas putida* | Glycerol dehydrogenase | AF148496.1 GI: 6552505 | 78, 79 |
| gldA | *Bacillus coagulans* | Glycerol dehydrogenase and related enzymes | ZP_01697292.1 GI: 124522908 | 80, 81 |

Homology (identity etc.) of amino acid sequences and nucleotide sequences can be determined by using, for example, the algorithm BLAST of Karlin and Altschul (Pro. Natl. Acad. Sci. USA, 90, 5873 (1993)) or FASTA of Pearson (Methods Enzymol., 183, 63 (1990)). Programs called BLASTN and BLASTX have been developed on the basis of this algorithm BLAST (refer to www.ncbi.nlm.nih.gov).

As the gene coding for dihydroxyacetone kinase, the genes designated dhaKLM gene, dak1 gene, dhaK gene and dhbK gene can be used. Examples of the gene coding for the enzyme using PEP as a phosphate donor include those genes derived from *Escherichia coli*, such as the dhaK gene of SEQ ID NO: 34 (complementary strand of the nucleotide numbers 1248991..1250061 of GenBank Accession No. NC_000913), the dhaL gene of SEQ ID NO: 36 (complementary strand of the nucleotide numbers 1248348..1248980 of GenBank Accession No. NC_000913), and the dhaM gene of SEQ ID NO: 38 (complementary strand of the nucleotide numbers 1246919..1248337 of GenBank Accession No. NC_000913).

The gene coding for dihydroxyacetone kinase which uses ATP as a phosphate donor can be used, and includes the dak1 gene derived from yeast, the dhbK gene derived from *Agrobacterium* bacteria, and the dhaK gene derived from *Citrobacter* bacteria. Examples of the dak1 gene derived from yeast include the dak1 gene of SEQ ID NO: 3 derived from *Saccharomyces cerevisiae* (GenBank Accession No NP_013641.1 GI: 6323570), examples of the dhbK gene derived from *Agrobacterium* bacteria include the dhbK gene of SEQ ID NO: 5 derived from *Agrobacterium tumefaciens* (GenBank Accession No. NP_357070.1 GI: 15891398), and examples of the dhaK gene derived from *Citrobacter* bacteria include the dhaK gene of SEQ ID NO: 7 derived from *Citrobacter freundii* (GenBank Accession No. U09771).

Furthermore, homologues of the gene coding for dihydroxyacetone kinase can be those cloned on the basis of homology to the gene exemplified above from a bacterium such as those of the genus *Escherichia, Enterobacter, Klebsiella, Serratia, Erwinia, Yersinia, Shigella, Salmonella, Vibrio, Aeromonas, Bacillus, Staphylococcus, Lactobacillus, Enterococcus, Clostridium, Agrobacterium, Citrobacter*, and *Mycobacterium*, yeast such as those of the genus *Saccharomyces, Schizosaccharomyces* or *Pichia*, or the like.

In particular, as the gene coding for dihydroxyacetone kinase which uses ATP as a phosphate donor, the following sequences can be used. Genes coding for dihydroxyacetone kinase and showing high homology to the dak1 gene derived from *Saccharomyces cerevisiae* are shown in Table 2, dihydroxyacetone kinase genes showing high homology to the dhbK gene derived from *Agrobacterium tumefaciens* are shown in Table 3, and dihydroxyacetone kinase genes showing high homology to the dhaK gene derived from *Citrobacter freundii* are shown in Table 4.

TABLE 2

Genes coding for dihydroxyacetone kinase and showing high homology to the dak1 gene derived from *Saccharomyces cerevisiae*

| Gene | Microorganism | Description | Genbank Accession No. | SEQ ID NO |
|---|---|---|---|---|
| T43702 | *Schizosaccharomyces pombe* | Dihydroxyacetone kinase | gi\|3493578\|gb\|AAC78808.1\| | 40, 41 |
| AAC27705 | *Pichia angusta* | Dihydroxyacetone kinase | gi\|3171001\|gb\|AAC27705.1\| | 42, 43 |
| AAC39490.1 | *Pichia pastoris* | Dihydroxyacetone kinase | gi\|3287486\|gb\|AAC39490.1\| | 44, 45 |
| CAG88710.1 | *Debaryomyces hansenii* CBS767 | Dihydroxyacetone kinase | gi\|49656075\|emb\|CAG88710.1\| | 46, 47 |

TABLE 3

Genes coding for dihydroxyacetone kinase and showing high homology to the dhbK gene derived from *Agrobacterium tumefaciens*

| Gene | Microorganism | Description | Genbank Accession No. | SEQ ID NO |
|---|---|---|---|---|
| ABF89849.1 | *Myxococcus xanthus* DK 1622 | Dihydroxyacetone kinase family protein | gi\|108464664\|gb\|ABF89849.1\| | 58, 59 |
| ABB06761.1 | *Burkholderia* sp. 383 | Glycerone kinase | gi\|77965380\|gb\|ABB06761.1\| Glycerone kinase [*Burkholderia* sp. 383] | 60 61 |
| ABC38950.1 | *Burkholderia thailandensis* E264 | Dihydroxyacetone kinase | gi\|83654887\|gb\|ABC38950.1\| | 62, 63 |
| EAV65448.1 | *Burkholderia multivorans* ATCC 17616 | Glycerone kinase | gi\|118658702\|gb\|EAV65448.1\| | 64, 65 |

TABLE 4

Genes coding for dihydroxyacetone kinase and showing high homology to the dhaK gene derived from *Citrobacter freundii*

| Gene | Microorganism | Description | Genbank Accession No. | SEQ ID NO |
|---|---|---|---|---|
| AAX12907.1 | *Escherichia blattae* | Dihydroxyacetone kinase | gi\|60099603\|gb\|AAX12907.1\| | 48, 49 |
| EAV82971.1 | *Enterobacter* sp. 638 | Dihydroxyacetone kinase | gi\|118676428\|gb\|EAV82971.1\| | 50, 51 |
| EAS39398.1 | *Psychromonas* sp. CNPT3 | Dihydroxyacetone kinase | gi\|90311294\|gb\|EAS39398.1\| | 52, 53 |

TABLE 4-continued

Genes coding for dihydroxyacetone kinase and showing high homology to the dhaK gene derived from *Citrobacter freundii*

| Gene | Microorganism | Description | Genbank Accession No. | SEQ ID NO |
|---|---|---|---|---|
| EAV42339.1 | *Stappia aggregata* IAM 12614 | Dihydroxyacetone kinase protein | gi\|118434594\|gb\|EVA42339.1\| | 54, 55 |
| CAK08390.1 | *Rhizobium leguminosarum* bv. *viciae* 3841 | Putative dihydroxyacetone kinase | gi\|115257295\|emb\|CAK08390.1\| | 56, 57 |

"Homologues" of the aforementioned genes mean mutant genes derived from other microorganisms, or natural or artificial mutant genes, which show high structural similarity to the aforementioned genes and are able to improve the glycerol dehydrogenase activity and dihydroxyacetone kinase activity when they are introduced into a host or amplified. Homologues of glycerol dehydrogenase and dihydroxyacetone kinase genes mean genes coding for a protein showing a homology of 80% or more, in another example 90% or more, in another example 95% or more, in another example 98% or more, to the total amino acid sequence of SEQ ID NO: 2, 4, 6 or 8 or any of the amino acid sequences encoded by the sequences mentioned in Tables 1 to 4, and having a function of glycerol dehydrogenase or dihydroxyacetone kinase. Whether a gene codes for a protein having glycerol dehydrogenase activity or dihydroxyacetone kinase activity can be confirmed by expressing the gene in a host cell and examining whether the enzymatic activity is increased compared with a non-modified strain according to the aforementioned enzymatic activity measurement method. Moreover, whether a gene is a homologue or not can be confirmed by preparing a gene-disrupted strain in which the corresponding wild-type gene is disrupted, introducing the gene into the disrupted strain, and examining whether the gene complements the function of the wild-type gene, for example, whether the enzymatic activity reduced by the gene disruption is restored.

Furthermore, the genes coding for glycerol dehydrogenase and dihydroxyacetone kinase are not limited to wild-type genes, and they may be mutant or artificially modified genes coding for a protein having an amino acid sequence of SEQ ID NO: 2, 4, 6 or 8 or any of the amino acid sequences mentioned in Table 1 to 4, and which can include substitution, deletion, insertion, addition or the like of one or more amino acid residues at one or more positions so long as the function of encoded glycerol dehydrogenase or dihydroxyacetone kinase is not reduced. Although the number of the "one or several" amino acid residues may differ depending on positions in the three-dimensional structure or types of amino acid residues of the protein, it may be specifically 1 to 20, in another example 1 to 10, in another example 1 to 5, and in another example 1 to 3. These substitutions can be conservative substitutions. The conservative substitution is a mutation wherein substitution takes place mutually among Phe, Trp and Tyr, if the substitution site is an aromatic amino acid; among Leu, Ile and Val, if it is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group. Examples of the conservative substitution include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. The aforementioned amino acid substitution, deletion, insertion, addition, inversion or the like may be the result of a naturally-occurring mutation due to an individual difference or difference of species (mutant or variant) of a microorganism having the genes coding for glycerol dehydrogenase and dihydroxyacetone kinase.

The genes coding for glycerol dehydrogenase and dihydroxyacetone kinase may also be a DNA which is able to hybridize with a sequence complementary to the nucleotide sequence of SEQ ID NO: 2, 4, 6 or 8 or any of the nucleotide sequences mentioned in Table 1 to 4, or a probe that can be prepared from the nucleotide sequences, under stringent conditions, and codes for a protein having the glycerol dehydrogenase activity or the dihydroxyacetone kinase activity. The "stringent conditions" are conditions under which a so-called specific hybrid is formed, and a non-specific hybrid is not formed. Examples of the stringent condition include those under which highly homologous DNAs hybridize to each other, for example, DNAs not less than 80% homologous, in another example not less than 90% homologous, in another example not less than 95% homologous, and in another example not less than 98% homologous, hybridize to each other, and DNAs less homologous than the above do not hybridize to each other, or conditions of washing of typical Southern hybridization, i.e., washing once, preferably 2 or 3 times, at a salt concentration and temperature corresponding to 1×SSC, 0.1% SDS at 60° C., in another example 0.1×SSC, 0.1% SDS at 60° C., in another example 0.1×SSC, 0.1% SDS at 68° C.

The phrase "intracellular activity of an enzyme increases" can mean when the intracellular activity of the enzyme is increased compared with a wild-type strain (for example, *Escherichia coli* W3110 and MG1655 strains), or a parent strain (strain in which intracellular activities of all the enzymes specified in the present invention are not enhanced), and also includes when the cells have the activity that a wild-type strain or the parent strain does not have.

Examples of the means for increasing the intracellular activity include the following means and combinations thereof. However, the means are not limited to these. As the means for increasing the activities of glycerol dehydrogenase and dihydroxyacetone kinase, any of (1) to (5) can be used, and the same or different means may be used.

(1) Increase in copy number of a gene coding for each protein by transformation using a vector containing the gene.

(2) Increase in copy number of a gene coding for each protein by integration of the gene into chromosome.

(3) Increase in expression amount of a gene coding for each protein by modification of an expression control region of the gene.

(4) Increase in expression amount by modification of a factor which affects on expression control.

(5) Increase in enzymatic activity by introduction of a mutation into a coding region of a gene coding for each protein.

(6) Increase in amount of protein by improvement of translation efficiency.

Henceforth the genes coding for glycerol dehydrogenase and dihydroxyacetone kinase can be each referred to as an objective gene.

(1) Increase in Copy Number of Gene Coding for Each Protein by Transformation Using Vector Containing the Gene For example, a DNA fragment containing an objective gene can be ligated to a vector which functions in a host microorganism, for example, a vector of multi-copy type, to prepare a recombinant DNA, and the recombinant DNA can be introduced into a microorganism to transform it. The objective gene can be obtained by PCR (polymerase chain reaction, refer to White, T. J. et al., Trends Genet., 5, 185 (1989)) using chromosomal DNA of *Escherichia coli*, yeast, *Citrobacter* bacterium, *Agrobacterium* bacterium or the like as a template. The objective genes derived from other microorganisms can also be obtained from the chromosomal DNA or a chromosomal DNA library of each microorganism by PCR using, as primers, oligonucleotides prepared based on a known objective gene of the microorganism or sequence information of the objective gene or the protein of a microorganism of other species, or hybridization using an oligonucleotide prepared based on such sequence information as mentioned above as a probe. A chromosomal DNA can be prepared from a microorganism that serves as a DNA donor by the method of Saito and Miura (refer to Saito H. and Miura K., Biochem. Biophys. Acta, 72, 619 (1963); Experimental Manual for Biotechnology, edited by The Society for Biotechnology, Japan, pp. 97-98, Baifukan Co., Ltd., 1992) or the like.

Then, the objective gene amplified by PCR can be ligated to a vector DNA which can function in the cell of a host microorganism to prepare a recombinant DNA. Examples of the vector which can function in a cell of host microorganism include vectors which are autonomously replicable in cells of the host microorganism.

Examples of vectors which are autonomously replicable in microorganisms belonging to the family Enterobacteriaceae include pUC19, pUC18, pHSG299, pHSG399, pHSG398, pACYC184, (pHSG and pACYC series vectors are available from Takara Bio), RSF1010 (Gene, vol. 75 (2), p 271-288, 1989), pBR322, pMW219, pMW119 (pMW series vectors are available form Nippon Gene), pSTV28, pSTV29 (Takara Bio) and so forth. A phage DNA vector can also be used.

To prepare recombinant DNA by ligating any of the genes to the above-mentioned vector, the vector is digested with a restriction enzyme corresponding to termini of a DNA fragment containing the objective gene. Ligation is generally performed by using a ligase such as T4 DNA ligase. As methods for digesting and ligating DNA, preparation of chromosomal DNA, PCR, preparation of plasmid DNA, transformation, design of oligonucleotides to be used as primers and so forth, methods well known to a person skilled in the art can be employed. These methods are described in Sambrook, J., Fritsch, E. F., and Maniatis, T., "Molecular Cloning A Laboratory Manual, Second Edition", Cold Sprig Harbor Laboratory Press, (1989), and so forth.

The recombinant DNA prepared as described above may be introduced into a bacterium in accordance with a conventional known transformation method. Examples include electroporation (Canadian Journal of Microbiology, 43, 197 (1997)). It is also possible to use a method of increasing the DNA permeability by treating recipient cells with calcium chloride, which is reported for *Escherichia coli* K-12 (Mandel, M. and Higa, A., J. Mol. Biol., 53, 159 (1970), or a method of introducing a DNA into a competent cell prepared from a cell at proliferation stage, which is reported for *Bacillus subtilis* (Duncan, C. H., Wilson, G. A and Young, F. E, Gene, 1, 153 (1977)).

(2) Increase in Copy Number of Gene Coding for Each Protein by Integration of the Gene into Chromosome Increase of intracellular activity of each enzyme can be achieved by increasing the copy number of the objective gene by introducing the objective gene into chromosomal DNA of the microorganism. Introduction of the objective gene into the chromosomal DNA of the microorganism can be attained by homologous recombination using a target sequence present on the chromosomal DNA in multiple copies. As such a sequence present on a chromosomal DNA in multiple copies, a repetitive DNA or an inverted repeat present on the termini of a transposing element can be used. Alternatively, as disclosed in Japanese Patent Laid-open (Kokai) No. 2-109985, the objective gene can be introduced into the chromosomal DNA by inserting the gene into a transposon, and transferring it so that the gene is integrated into the chromosomal DNA. Moreover, it is also possible to introduce an objective gene into a chromosome by using the Red driven integration method (WO2005/010175). An objective gene can also be introduced into a chromosome by transduction using a phage such as P1 phage, or by using a vector for conjugative transfer. Transfer of a gene to a chromosome can be confirmed by performing Southern hybridization using a part of the gene as a probe. Amplification of copy number can be confirmed by Southern hybridization using a probe complementary to the objective gene. Although the copy number may be amplified to any extent so long as it is amplified by one or more copies, the gene coding for glycerol dehydrogenase can be amplified by two or more copies, in another example three or more copies, in another example five or more copies, and the gene coding for dihydroxyacetone kinase can be amplified by two or more copies, in another example three or more copies, in another example five or more copies. When the gene is not native to the chosen host microorganism, any number of copies can be introduced, so long as one or more copies are introduced.

(3) Increase in Expression Amount of Gene Coding for Each Protein by Modification of Expression Control Region of the Gene Furthermore, besides increasing the copy number of objective gene mentioned above, increasing the intracellular activity of each enzyme can be achieved by replacing an expression regulatory sequence such as a promoter of the gene on a chromosomal DNA or on a plasmid with a stronger promoter by the method described in WO0/18935. As strong promoters, for example, there are known the lac promoter, trp promoter, trc promoter, lambda phage PR promoter, PL promoter, lpp promoter, T7 promoter, tet promoter, and so forth. To amplify glycerol dehydrogenase, the tacM promoter (SEQ ID NO: 10) is one example. dhaK, dhaL and dhaM coding for dihydroxyacetone kinase of *Escherichia coli* take an operon structure, and expression amounts of all the three genes are improved by enhancing the promoter locating upstream of dhaK.

Moreover, it is also possible to introduce nucleotide substitution or the like into a promoter region of an objective gene to modify it into a stronger promoter. Methods for evaluating potency of promoters and examples of potent promoters are described in the paper of Goldstein et al. (Prokaryotic promoters in biotechnology, Biotechnol. Annu. Rev., 1995, 1, 105-128), and so forth. Furthermore, it is known that substitution of several nucleotides in the spacer region between the ribosome binding site (RBS) and the start codon, in particular, in the region immediately upstream of the start codon, significantly affects the translation efficiency of mRNA, and such a region can also be modified. Expression of the objective gene is enhanced by such substitution or modification of promoter.

As for substitution of a stronger promoter for a promoter on a chromosome, a promoter located upstream of the objective gene on a genome can be replaced with a stronger promoter by transforming a microorganism belonging to the family Enterobacteriaceae with a DNA containing the stronger promoter amplified by PCR or the like to cause recombination of the stronger promoter and the wild-type promoter on the genome. For such gene substitution utilizing homologous recombination, there can be utilized a method called Red-driven integration (Datsenko, K. A, and Wanner, B. L., Proc. Natl. Acad. Sci. USA, 97:6640-6645 (2000)), a method of using a linear DNA such as a method utilizing the Red driven integration in combination with an excisive system derived from λ phage (Cho, E. H., Gumport, R. I., Gardner, J. F., J. Bacteriol., 184:5200-5203 (2002)) (refer to WO2005/010175), a method of using a plasmid containing a temperature sensitive replication origin (Datsenko, K. A, and Wanner, B. L., Proc. Natl. Acad. Sci. USA, 97:6640-6645 (2000), U.S. Pat. No. 6,303,383, Japanese Patent Laid-open No. 05-007491), and so forth.

(4) Increase in Expression Amount by Modification of Factor which Affects on Expression Control Increase in expression amount by modification of a factor which affects on expression control can be attained by amplifying a gene coding for an activator which increases expression of the genes coding for glycerol dehydrogenase and dihydroxyacetone kinase, or by deleting or attenuating a gene coding for a regulator which reduces expression of the genes. Examples of the activator of dhaKLM coding for dihydroxyacetone kinase include, for example, dhaR (SEQ ID NO: 66, the nucleotide numbers 1250289..1252208 of GenBank Accession No. NC_000913), and expression amount of dhaKLM coding for dihydroxyacetone kinase is increased by a mutation of the dhaR gene (1: EMBO J., 2005 Jan. 26, 24 (2):283-93). The expression amount of dhaKLM coding for dihydroxyacetone kinase is also increased by disruption of the ptsI gene (SEQ ID NO: 86, the nucleotide numbers 2532088..2533815 of GenBank Accession No. NC_000913) (Microbiology, 147 (2001) 247-253)

(5) Increase in Enzymatic Activity by Introduction of Mutation into Coding Region of Gene Coding for Each Protein Furthermore, increase of the activities of glycerol dehydrogenase and dihydroxyacetone kinase can also be achieved by introducing a mutation which increases specific activities of the proteins or improves substrate specificities of the enzymes into the coding regions of the objective genes.

Such a gene coding for each enzyme having a mutation can be obtained by, for example, modifying the nucleotide sequence of the SEQ ID NO: 1, 3, 5 or 7, or a coding region in any of the nucleotide sequences mentioned in Tables 1 to 4, so that amino acid residues of a specific part of the encoded protein include substitution, deletion, insertion, addition or the like of amino acid residues. Furthermore, it can also be obtained by the conventionally known mutagenizing treatments described below. As for the mutagenizing treatments, by a method of treating the nucleotide sequence of the SEQ ID NO: 1, 3, 5 or 7, any of the nucleotide sequences mentioned in Tables 1 to 4, or a coding region sequence in any of these with hydroxylamine or the like in vitro, a method of treating a microorganism such as microorganisms belonging to the family Enterobacteriaceae containing the gene with ultraviolet radiation or a mutagenizing agent used for usual mutagenizing treatment such as N-methyl-N'-nitro-N-nitrosoguanidine (NTG) or ethyl methanesulfonate (EMS), error-prone PCR (Cadwell, R. C., PCR Meth. Appl., 2, 28 (1992)), DNA shuffling (Stemmer, W. P., Nature, 370, 389 (1994)), or StEP-PCR (Zhao, H., Nature Biotechnol., 16, 258 (1998)), a mutation can be artificially introduced into the genes coding for glycerol dehydrogenase and dihydroxyacetone kinase by gene recombination to obtain genes coding for highly active glycerol dehydrogenase and dihydroxyacetone kinase. Whether such mutant enzymes code for glycerol dehydrogenase and dihydroxyacetone kinase can be confirmed by, for example, introducing the genes into a microorganism belonging to the family Enterobacteriaceae and having an L-amino acid-producing ability, culturing it in a medium containing glycerol as a carbon source, and confirming whether the L-amino acid-producing ability is improved, or measuring the enzyme activities by the aforementioned methods.

(6) Increase in Amount of Protein by Improvement of Translation Efficiency

An increase in the amount of protein by improvement of translation efficiency can be attained by increasing the tRNA corresponding to codons less frequently used in the host, or by modifying the objective gene so that it has optimal codons according to frequency of use of codons in the host (Gene 85, 109-114 (1989), Biochemistry, 31, 2598-2608 (1992), J. Bacteriol., 175, 716-722 (1993), Protein Expression and Purification, 50, 49-57 (2006)). An increase in the amount of the objective protein compared with a non-modifying strain or wild-type strain can be confirmed by, for example, detection by Western blotting using antibodies (Molecular Cloning (Cold Spring Harbor Laboratory Press, Cold spring Harbor (USA), 2001)).

The microorganism can be modified to increase glycerol uptake activity, in addition to enhancing glycerol dehydrogenase and dihydroxyacetone kinase. The glycerol uptake activity can mean an activity for incorporating glycerol into cytoplasm, and a glycerol facilitator which is a membrane protein is also involved. Examples of the gene coding for the glycerol facilitator include, for example, the glpF gene of *Escherichia coli* (SEQ ID NO: 16, complementary strand of the nucleotide numbers 4115268..4116113 of GenBank Accession No. NC_000913).

The gene coding for the glycerol facilitator may be a DNA which hybridizes with a complementary sequence of the nucleotide sequence of SEQ ID NO: 16 or a probe which can be prepared from the complementary sequence under a stringent condition, and codes for a protein having the glycerol uptake activity. Examples also include a DNA coding for the protein of SEQ ID NO: 17. The protein can be a protein showing a homology of 80% or more, in another example 90% or more, in another example 95% or more, and in another example 98% or more, to the total amino acid sequence of SEQ ID NO: 17, so long as it increases the glycerol uptake ability in a microorganism belonging to the family Enterobacteriaceae, when it is introduced into the microorganism.

Moreover, the gene may be a DNA coding for a protein having an amino acid sequence of SEQ ID NO: 17 including substitution, deletion, insertion, addition or the like of one or several amino acid residues, so long as the glycerol uptake activity is not reduced. The activity can be increased by a method similar to the aforementioned methods for enhancing glycerol dehydrogenase and dihydroxyacetone kinase.

The glycerol uptake activity can be measured by using the transport assay method using a membrane protein (Voegele, R. T., Sweet, G. D., and Boos, W. J., Bacteriol., 175:1087-1094 (1993)).

The microorganism can be modified to increase activities of one or more enzymes including triosephosphate isomerase, fructose bisphosphate aldolase, fructose-1,6-bisphosphatase and fructose-6-phosphate aldolase, in addition to enhancing glycerol dehydrogenase and dihydroxyacetone kinase and the enhancement of glycerol uptake activity.

Triosephosphate isomerase is an enzyme which catalyzes a reaction which reversibly converts dihydroxyacetone phosphate into glyceraldehyde-3-phosphate (EC:5.3.1.1).

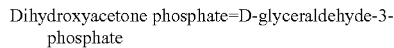
Dihydroxyacetone phosphate=D-glyceraldehyde-3-phosphate

The phrase "being modified to increase the triosephosphate isomerase activity" can mean that the number of the triosephosphate isomerase molecules per cell can be increased compared with that of a wild-type strain or non-modified strain, or when the activity of the triosephosphate isomerase per molecule can be improved compared with that of a wild-type strain or non-modified strain. The modification can be performed so that the triosephosphate isomerase activity per cell can be improved to 150% or more, in another example 200% or more, in another example 300% or more, of the activity of a wild-type strain or non-modified strain. Examples of wild-type strains of the microorganism belonging to the family Enterobacteriaceae which can serve as a reference for comparison include the *Escherichia coli* MG1655 strain (ATCC No. 47076) and W3110 strain (ATCC No. 27325), *Pantoea ananatis* AJ13335 strain (FERM BP-6615), and so forth.

Examples of the gene coding for triosephosphate isomerase include the tpiA gene derived from *Escherichia coli* (SEQ ID NO: 18, complementary strand of the nucleotide numbers 4108763..4109530 of GenBank Accession No. NC_000913).

The gene coding for triosephosphate isomerase may be a DNA which hybridizes with a complementary sequence of the nucleotide sequence of SEQ ID NO: 18 or a probe which can be prepared from the complementary sequence under stringent conditions, and codes for a protein having the triosephosphate isomerase activity. Examples also include a DNA coding for the protein of SEQ ID NO: 19. The protein can be a protein showing a homology of 80% or more, in another example 90% or more, in another example 95% or more, in another example 98% or more, to the total amino acid sequence of SEQ ID NO: 19, so long as it shows increased triosephosphate isomerase activity in a microorganism belonging to the family Enterobacteriaceae, when it is introduced into the microorganism.

Moreover, the gene may be a DNA coding for a protein having an amino acid sequence of SEQ ID NO: 19 including substitution, deletion, insertion, addition or the like of one or several amino acid residues, so long as the triosephosphate isomerase activity is not reduced.

The triosephosphate isomerase activity can be measured by using the method of Andersen and Cooper (FEBS Lett., 4, 19-20 (1969)). The activity can be increased by methods similar to the aforementioned methods for enhancing glycerol dehydrogenase and dihydroxyacetone kinase.

Fructose bisphosphate aldolase" is an enzyme which reversibly catalyzes the following reaction which converts dihydroxyacetone phosphate and glyceroaldehyde-3-phosphate into D-fructose-1,6-bisphosphate (EC:4.1.2.13).

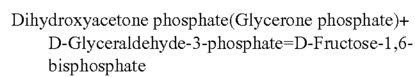
Dihydroxyacetone phosphate(Glycerone phosphate)+D-Glyceraldehyde-3-phosphate=D-Fructose-1,6-bisphosphate The phrase "being modified to increase the fructose bisphosphate aldolase activity" can mean that number of the fructose bisphosphate aldolase molecules per cell can be increased compared with that of a wild-type strain or non-modified strain, or when the activity of the fructose bisphosphate aldolase per molecule can be improved compared with that of a wild-type strain or non-modified strain. The modification can be performed so that the fructose bisphosphate aldolase activity per cell can be improved to 150% or more, in another example 200% or more, in another example 300% or more, of the activity of a wild-type strain or non-modified strain. Examples of wild-type strains of the microorganism belonging to the family Enterobacteriaceae which can serve as a reference for the comparison include the *Escherichia coli* MG1655 strain (ATCC No. 47076) and W3110 strain (ATCC No. 27325), *Pantoea ananatis* AJ13335 strain (FERM BP-6615), and so forth.

Examples of the gene coding for fructose bisphosphate aldolase include the fbaA gene derived from *Escherichia coli* (SEQ ID NO: 20, complementary strand of the nucleotide numbers 3068187..3069266 of GenBank Accession No. NC_000913) and the fbaB gene derived from *Escherichia coli* (SEQ ID NO: 72, complementary strand of the nucleotide numbers 2175534..2176586 of GenBank Accession No. NC_000913).

The gene coding for fructose bisphosphate aldolase can be a DNA which hybridizes with a complementary sequence of the nucleotide sequence of SEQ ID NO: 20 or 72 or a probe which can be prepared from the complementary sequence under a stringent condition, and codes for a protein having the fructose bisphosphate aldolase activity. Examples also include a DNA coding for the protein of SEQ ID NO: 21 or 73. The protein may be show a homology of 80% or more, in another example 90% or more, in another example 95% or more, in another example 98% or more, to the total amino acid sequence of SEQ ID NO: 21, so long as it shows increased fructose bisphosphate aldolase activity in a microorganism belonging to the family Enterobacteriaceae, when it is introduced into the microorganism.

Moreover, the gene can be a DNA coding for a protein having an amino acid sequence of SEQ ID NO: 21 or 73, but which can include substitution, deletion, insertion, addition or the like of one or several amino acid residues, so long as the fructose bisphosphate aldolase activity is not reduced.

The fructose bisphosphate aldolase activity can be measured by using the method of Richard & Rutter (J. Biol. Chem., 236, 3177-3184). The activity can be increased by methods similar to the aforementioned methods for enhancing glycerol dehydrogenase and dihydroxyacetone kinase.

The fructose-1,6-bisphosphatase is an enzyme which reversibly catalyzes the following reaction that converts D-fructose-1,6-bisphosphate into D-fructose-6-phosphate (EC:3.1.3.11).

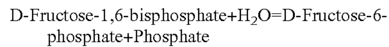

D-Fructose-1,6-bisphosphate+$H_2O$=D-Fructose-6-phosphate+Phosphate

The phrase "being modified to increase the fructose-1,6-bisphosphatase activity" can mean that the number of the fructose-1,6-bisphosphatase molecules per cell can be increased compared with that of a wild-type strain or non-modified strain, or when the activity of the fructose-1,6-bisphosphatase per molecule can be improved compared with that of a wild-type strain or non-modified strain. The modification can be performed so that the fructose-1,6-bisphosphatase activity per cell can be improved to 150% or more, in another example 200% or more, in another example 300% or more, of the activity of a wild-type strain or non-modified strain. Examples of wild-type strains of the microorganism belonging to the family Enterobacteriaceae which serve as a reference for the comparison include the *Escherichia coli* MG1655 strain (ATCC No. 47076) and W3110 strain (ATCC No. 27325), *Pantoea ananatis* AJ13335 strain (FERM BP-6615), and so forth.

Examples of the gene coding for fructose-1,6-bisphosphatase include the glpX gene (SEQ ID NO: 22, complementary strand of the nucleotide numbers 4112592..4113602 of GenBank Accession No. NC_000913), the fbp gene (SEQ ID NO: 82, the nucleotide numbers 4452634..4453632 of GenBank Accession No. NC_000913), and the ybhA gene (SEQ ID NO: 84, the nucleotide numbers 796836..7976554 of GenBank Accession No. NC_000913), which are derived from *Escherichia coli*. The gene coding for the fructose-1,6-bisphosphatase may be a DNA which hybridizes with a complementary sequence of the nucleotide sequence of SEQ ID NO: 22, 82 or 84 or a probe which can be prepared from the complementary sequence under a stringent condition, and codes for a protein having the fructose-1,6-bisphosphatase activity. Examples also include a DNA coding for the protein of SEQ ID NO: 23, 83 or 85. The protein may show a homology of 80% or more, in another example 90% or more, in another example 95% or more, in another example 98% or more, to the total amino acid sequence of SEQ ID NO: 23, 83 or 85, so long as it shows increased fructose-1,6-bisphosphatase activity in a microorganism belonging to the family Enterobacteriaceae, when it is introduced into the microorganism.

Moreover, the gene can be a DNA coding for a protein having an amino acid sequence of SEQ ID NO: 23, 83 or 85, but can include substitution, deletion, insertion, addition or the like of one or several amino acid residues, so long as the fructose-1,6-bisphosphatase activity is not reduced.

The fructose-1,6-bisphosphatase activity can be measured by using the method of Nakajima et al. (Protein Nucleic Enzyme, 22, 1585-1589). The activity can be increased by methods similar to the aforementioned methods for enhancing glycerol dehydrogenase and dihydroxyacetone kinase.

In the present invention, "fructose-6-phosphate aldolase" is an enzyme which reversibly catalyzes the following reaction that converts dihydroxyacetone into fructose-6-phosphate.

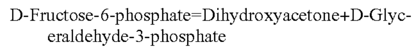

D-Fructose-6-phosphate=Dihydroxyacetone+D-Glyceraldehyde-3-phosphate

The phrase "being modified to increase the fructose-6-phosphate aldolase activity" can mean that the number of the fructose-6-phosphate aldolase molecules per cell can be increased compared with that of a wild-type strain or non-modified strain, or when the activity of the fructose-6-phosphate aldolase per molecule can be improved compared with that of a wild-type strain or non-modified strain. The modification can be performed so that the fructose-6-phosphate aldolase activity per cell can be improved to 150% or more, in another example 200% or more, and in another example 300% or more, of the activity observed in a wild-type strain or non-modified strain. Examples of wild-type strains of the microorganism belonging to the family Enterobacteriaceae which can serve as a reference for comparison include the *Escherichia coli* MG1655 strain (ATCC No. 47076) and W3110 strain (ATCC No. 27325), *Pantoea ananatis* AJ13335 strain (FERM BP-6615), and so forth.

Examples of the gene coding for fructose-6-phosphate aldolase include the fsaA gene coding for type I aldolase (SEQ ID NO: 68, the nucleotide numbers 862865..863527 of GenBank Accession No. NC_000913), and the fsaB gene (talC gene) (SEQ ID NO: 70, complementary strand of the nucleotide numbers 4137069..4137731 of GenBank Accession No. NC_000913) coding for type II aldolase, which are derived from *Escherichia coli*.

The gene coding for fructose-6-phosphate aldolase can be a DNA which hybridizes with a complementary sequence of the nucleotide sequence of SEQ ID NO: 68 or 70 or a probe which can be prepared from the complementary sequence under stringent conditions, and codes for a protein having the fructose-6-phosphate aldolase activity. Examples also include a DNA coding for the protein of SEQ ID NO: 69 or 71. The protein may be a protein showing a homology of 80% or more, in another example 90% or more, in another example 95% or more, and in another example 98% or more, to the total amino acid sequence of SEQ ID NO: 69 or 71, so long as it shows increased fructose-6-phosphate aldolase activity in a microorganism belonging to the family Enterobacteriaceae, when it is introduced into the microorganism.

Moreover, the gene may be a DNA coding for a protein having an amino acid sequence of SEQ ID NO: 69 or 71, but which can include substitution, deletion, insertion, addition or the like of one or several amino acid residues, so long as the fructose-6-phosphate aldolase activity is not reduced.

The fructose-6-phosphate aldolase activity can be measured by using the method of Schurmann M., Sprenger G. A. et al. (J. Biol. Chem., 2001 Apr. 6, 276 (14): 11055-61). The activity can be increased by methods similar to the aforementioned methods for enhancing glycerol dehydrogenase and dihydroxyacetone kinase.

The microorganism can be modified to reduce glycerol kinase and/or membrane-binding type glycerol-3-phosphate dehydrogenase activity, in addition to the enhancement of glycerol dehydrogenase and dihydroxyacetone kinase, the enhancement of the glycerol uptake activity, and the enhancement of activities of one or more kinds of enzymes including triosephosphate isomerase, fructose bisphosphate aldolase, fructose-1,6-bisphosphatase and fructose-6-phosphate aldolase.

"Glycerol kinase" can mean an enzyme which reversibly catalyzes the following reaction that generates glycerol-3-phosphate and ADP from glycerol and ATP (EC2.7.1.30)

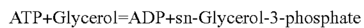

ATP+Glycerol=ADP+sn-Glycerol-3-phosphate

The phrase "being modified to reduce the glycerol kinase activity" can mean that the number of the glycerol kinase molecules per cell can be decreased compared with that of a wild-type strain or non-modified strain, or a state that the activity of the glycerol kinase per molecule can be reduced compared with that of a wild-type strain or non-modified strain. The modification can be performed so that the glycerol kinase activity per cell can be reduced to 70% or less, in another example 50% or less, in another example 30% or less, in another example 20% or less, of the activity of a wild-type strain or non-modified strain, and the enzymatic activity can be deleted. The enzymatic activity can be decreased by reducing the expression amount of the gene coding for the enzyme. Reduction of the expression amount of the gene includes reduction of the transcription amount of mRNA transcribed from the gene and reduction of translation amount of this mRNA.

Complete elimination of the production of the enzyme protein molecule or reduction or deletion of the activity per enzyme protein molecule is attained by disrupting the gene coding for the enzyme. Examples of wild-type strains of the microorganism belonging to the family Enterobacteriaceae which can serve as a reference for comparison include the *Escherichia coli* MG1655 strain (ATCC No. 47076) and W3110 strain (ATCC No. 27325), *Pantoea ananatis* AJ13335 strain (FERM BP-6615), and so forth.

Examples of the gene coding for glycerol kinase include the glpK gene (SEQ ID NO: 24, complementary strand of the nucleotide numbers 4113737..4115245 of GenBank Accession No. NC_000913) derived from *Escherichia coli*. The enzymatic activity of glycerol kinase can be measured by the method of Thorner & Paulus (The Enzymes, 3rd ed., 8, 487-508).

"Membrane-binding type glycerol-3-phosphate dehydrogenase" is an enzyme which catalyzes the oxidation reaction converting glycerol-3-phosphate to dihydroxyacetone phosphate, and is an enzyme which reversibly catalyzes the following reaction.

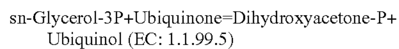
sn-Glycerol-3P+Ubiquinone=Dihydroxyacetone-P+Ubiquinol (EC: 1.1.99.5)

The phrase "being modified to reduce the membrane-binding type glycerol-3-phosphate dehydrogenase activity" can mean that the number of the membrane-binding type glycerol-3-phosphate dehydrogenase molecules per cell is decreased compared with that of a wild-type strain or non-modified strain, or a state that the activity of the membrane-binding type glycerol-3-phosphate dehydrogenase per molecule is reduced compared with that of a wild-type strain or non-modified strain. The modification can be performed so that the membrane-binding type glycerol-3-phosphate dehydrogenase activity per cell is reduced to 70% or less, in another example 50% or less, in another example 30% or less, of the activity of a wild-type strain or non-modified strain, and the enzymatic activity may be deleted. The enzymatic activity can be decreased by reducing the expression amount of the gene coding for the enzyme. Examples of wild-type strains of the microorganism belonging to the family Enterobacteriaceae which can serve as a reference for comparison include the *Escherichia coli* MG1655 strain (ATCC No. 47076) and W3110 strain (ATCC No. 27325), *Pantoea ananatis* AJ13335 strain (FERM BP-6615), and so forth.

The membrane-binding type glycerol-3-phosphate dehydrogenase is encoded by the glpABC operon and the glpD gene, and examples of the glpA gene of *Escherichia coli* include the sequence of SEQ ID NO: 26 (the nucleotide numbers 2350669..2352297 of GenBank Accession No. NC_000913), examples of the glpB gene of *Escherichia coli* include the sequence of SEQ ID NO: 28 (the nucleotide numbers 2352287..2353546 of GenBank Accession No. NC_000913), examples of the glpC gene of *Escherichia coli* include the sequence of SEQ ID NO: 30 (the nucleotide numbers 2353543..2354733 of GenBank Accession No. NC_000913), and examples of the glpD gene of *Escherichia coli* include the sequence of SEQ ID NO: 32 (the nucleotide numbers 3560036..3561541 of GenBank Accession No. NC_000913).

Reduction of activity of an objective enzyme such as glycerol kinase and glycerol-3-phosphate dehydrogenase mentioned above can be attained by (1) reduction or deletion of the enzymatic activity by introduction of a mutation into a coding region of a gene coding for the objective enzyme, or (2) reduction or deletion of the enzymatic activity by modification of an expression control sequence of a gene coding for the objective enzyme.

(1) Reduction or Deletion of Enzymatic Activity by Introduction of Mutation into Coding Region of Gene Coding for Objective Enzyme Introduction of a mutation into a coding region of a gene coding for an objective enzyme can be attained by introducing a mutation for an amino acid substitution (missense mutation), a stop codon (nonsense mutation), or a frame shift mutation which adds or deletes one or two nucleotides into a region of the objective gene coding for the enzyme on a chromosome by genetic recombination (Journal of Biological Chemistry, 272:8611-8617 (1997); Proceedings of the National Academy of Sciences, USA, 95 5511-5515 (1998); Journal of Biological Chemistry, 266, 20833-20839 (1991)). It can also be attained by deleting a part or all of the gene in the coding region. Specifically, it can be attained by introducing a mutation into a part of DNA of SEQ ID NO: 24, 26, 28, 30 or 32, or deleting a part or all of such DNA.

As for the introduction of mutation, the enzymatic activity can also be reduced or deleted by constructing a gene coding for a mutant enzyme of which the coding region is deleted or introduced with a mutation, and substituting the constructed gene for the normal gene on a chromosome by homologous recombination or the like, or by introducing a transposon or IS factor into the gene.

For introduction of such mutations for reducing or deleting activity of an enzyme as described above into a gene by genetic recombination, for example, the following methods are used. By modifying a partial sequence of an objective gene to prepare a mutant gene designed so that it does not produce an enzyme that functions normally, and transforming a microorganism belonging to the family Enterobacteriaceae with a DNA containing the gene to cause recombination of the mutant gene and the corresponding gene on a chromosome, the objective gene on a chromosome can be replaced with the mutant gene. For such gene substitution utilizing homologous recombination, there can be utilized a method called Red-driven integration (Datsenko, K. A, and Wanner, B. L., Proc. Natl. Acad. Sci. USA, 97:6640-6645 (2000)), a method of using a linear DNA such as a method utilizing the Red driven integration in combination with an excisive system derived from λ phage (Cho, E. H., Gumport, R. I., Gardner, J. F., J. Bacteriol., 184:5200-5203 (2002)), a method of using a plasmid containing a temperature sensitive replication origin (Datsenko, K. A, and Wanner, B. L., Proc. Natl. Acad. Sci. USA, 97:6640-6645 (2000), U.S. Pat. No. 6,303,383, Japanese Patent Laid-open No. 05-007491), and so forth. Moreover, such site-specific mutagenesis based on gene substitution utilizing homologous recombination as described above can also be performed by using a plasmid which is not able to replicate in a host. Moreover, reduction or deletion of the enzymatic activity can also be attained by modification for introducing a mutation into a coding region of an objective gene caused by a usual mutation treatment based on X-ray or ultraviolet irradiation or use of a mutation agent such as N-methyl-N'-nitro-N-nitrosoguanidine.

(2) Reduction or Deletion of Enzymatic Activity by Modification of Expression Control Sequence of Gene Coding for Objective Enzyme Reduction or deletion of an enzymatic activity by modification of an expression control sequence of a gene coding for an objective enzyme can also be attained by reducing the expression amount by introducing a mutation into an expression control sequence such as a promoter and SD sequence on a chromosomal DNA, by amplifying a gene coding for a regulator which reduces expression of the gene, or by deleting or attenuating a gene coding for an activator which improves expression of the gene. Methods for evaluating potency of promoters and examples of potent promoters are described in the paper of Goldstein et al. (Prokaryotic promoters in biotechnology, Biotechnol. Annu. Rev., 1995, 1, 105-128), and so forth. Furthermore, it is known that by replacing several nucleotides in the spacer region between the ribosome binding site (RBS) and the start codon, in particular, in the region immediately upstream from the start codon, the translation efficiency of mRNA can be significantly affected, and such a region can also be modified. In particular, the glpA, B and C genes take an operon structure, and therefore the expression amount thereof can be reduced by introducing a mutation into an expression control region such as a promoter region locating upstream of glpA.

<2> Production Method

An exemplary production method of the present invention is a method for producing an L-amino acid, which includes culturing a microorganism belonging to the family Enterobacteriaceae, having an L-amino acid-producing ability and modified to increase glycerol dehydrogenase and dihydroxyacetone kinase activities in a medium containing glycerol as a carbon source to produce and accumulate an L-amino acid in the medium or cells, and collecting the L-amino acid from the medium or the cells. Any batch culture, fed-batch culture, or continuous culture may be used. Glycerol contained in the medium can be contained in the starting medium, feed medium, or both.

The aforementioned fed-batch culture refers to a culture method in which the medium is continuously or intermittently fed into the culture vessel, and the medium is not extracted until the end of the culture. The continuous culture can mean a method in which the medium is continuously or intermittently fed into the culture vessel, and the medium is extracted from the vessel (usually in a volume equal to the volume of the fed medium) at the same time. The starting medium can mean a medium used in batch culture before feeding the feed medium in the fed-batch culture or continuous culture (medium used at the start of the culture). The feed medium can mean a medium which is supplied to the fermentation tank in the fed-batch culture or continuous culture. The batch culture can mean a method in which fresh medium is prepared for every culture, a strain is inoculated into the fresh medium, and medium is not added thereafter until harvest.

The glycerol present in the medium can be the sole carbon source, or a mixed medium can be used which contains other carbon sources in addition to glycerol. Saccharides can be used such as glucose, fructose, sucrose, lactose, galactose, blackstrap molasses, and a sugar solution obtained by hydrolysis of starch hydrolysate or biomass, alcohols such as ethanol, and organic acids such as fumaric acid, citric acid, and succinic acid. When a mixed medium is used, glycerol can be present in the medium at a ratio of 50% or more, in another example 60% or more, in another example 70% or more, in another example 80% or more, in another example 90% or more. Glycerol obtained as a by-product of biodiesel fuel production can also be used (Mu Y, et al, Biotechnol Lett., 28, 1755-91759 (2006); Haas M. J., et al., Bioresour. Technol., 97, 4, 671-8678 (2006)).

As for other components which can be added to the medium, a typical medium can contain, besides the carbon source, a nitrogen source, inorganic ions, and other organic components as required can be used. As the nitrogen source, ammonia, ammonium salts such as ammonium sulfate, ammonium carbonate, ammonium chloride, ammonium phosphate, ammonium acetate and urea, nitrates, and so forth can be used. Ammonia gas and aqueous ammonia used to adjust the pH can also be utilized as the nitrogen source. Furthermore, peptone, yeast extract, meat extract, malt extract, corn steep liquor, soybean hydrolysate, and so forth can also be utilized. The medium can contain one or more of these nitrogen sources. These nitrogen sources can also be used for both the starting medium and the feed medium. Furthermore, the same nitrogen source can be used for both the starting medium and the feed medium, or the nitrogen source of the feed medium may be different from that of the starting medium.

The medium can contain a phosphoric acid source and a sulfur source in addition to the carbon source, the nitrogen source and sulfur. As the phosphoric acid source, potassium dihydrogenphosphate, dipotassium hydrogenphosphate, phosphate polymers such as pyrophosphoric acid and so forth can be utilized. The sulfur source may be any sulfur source so long as it contains a sulfur atom, and salts of sulfuric acid such as sulfates, thiosulfates and sulfites and sulfur-containing amino acids such as cysteine, cystine and glutathione are examples. Among these, ammonium sulfate is another example.

Furthermore, the medium can contain a growth promoting factor (nutrient having a growth promoting effect) in addition to the carbon source, the nitrogen source and sulfur. As the growth promoting factor, trace metals, amino acids, vitamins, nucleic acids as well as peptone, casamino acid, yeast extract, soybean protein degradation product and so forth containing the foregoing substances can be used. Examples of the trace metals include iron, manganese, magnesium, calcium and so forth. Examples of the vitamins include vitamin $B_1$, vitamin $B_2$, vitamin $B_6$, nicotinic acid, nicotinic acid amide, vitamin $B_{12}$ and so forth. These growth promoting factors may be contained in the starting medium or the feed medium.

When an auxotrophic mutant that requires an amino acid or the like for growth thereof is used, the required nutrient should be supplemented to the medium. In particular, since L-lysine biosynthetic pathway is enhanced and L-lysine degrading ability is attenuated in many of L-lysine-producing bacteria as described below, one or more types of substances, such as L-threonine, L-homoserine, L-isoleucine and L-methionine can be added.

The starting medium and the feed medium can have the same or different compositions. Furthermore, the starting medium and the feed medium may have the same or different sulfur concentrations. Furthermore, when the feed medium is fed at multiple stages, the compositions of the feed media may be the same or different.

The culture is preferably performed as an aeration culture at a fermentation temperature of 20 to 45° C., particularly preferably at 30 to 42° C. The oxygen concentration is adjusted to 5 to 50%, desirably about 10%. Furthermore, the aeration culture is preferably performed with pH adjusted to 5 to 9. If pH drops during the culture, for example, calcium carbonate or an alkali such as ammonia gas and aqueous ammonia can be added to neutralize the culture. When the culture is performed for about 10 to 120 hours, a marked amount of L-amino acid accumulates in the culture medium. Although the concentration of L-amino acid which accumulates is not limited so long as it is higher than that observed with wild-type strains, and the L-amino acid can be isolated and collected from the medium, it may be 50 g/L or higher, in another example 75 g/L or higher, and in another example 100 g/L or higher.

The L-amino acid can be collected by a known collection method from the culture medium after the culture. For example, by removing cells from the culture medium by centrifugation or the like, and then crystallizing the L-amino acid by concentration, the L-amino acid can be collected.

The culture of the microorganism can be performed as a seed culture and main culture in order to ensure accumulation of the L-amino acid higher than a certain level. The seed culture can be performed as a shaking culture using a flask or the like, or batch culture, and the main culture can be performed as fed-batch culture or continuous culture. Alternatively, both the seed culture and the main culture can be performed as batch culture.

When fed-batch culture or continuous culture is performed, the feed medium can be intermittently fed so that the supply of glycerol and other carbon sources is temporarily stopped. The supply of the feed medium can be stopped for, at maximum, 30% or less, in another example 20% or less, and in another example 10% or less, of the feeding time. When the feed medium is intermittently fed, the feed medium can be initially added over a predetermined time, and the second and following additions can be controlled so that they are started when an elevation of pH or dissolved oxygen concentration is detected by a computer upon depletion of the carbon source in the fermentation medium. This usually occurs during the period when no medium is being fed, and prior to when the medium is fed, and thus the substrate concentration in the culture tank is always automatically maintained at a low level (U.S. Pat. No. 5,912,113).

The feed medium used for the fed-batch culture can be a medium containing glycerol or another carbon source and a nutrient having a growth promoting effect (growth promoting factor), and the glycerol concentration and the other carbon source concentration in the fermentation medium can be controlled to be at predetermined concentrations or lower. As the other carbon source, glucose, sucrose and fructose are examples. As the growth promoting factor, nitrogen source, phosphoric acid, amino acids and so forth are examples. As the nitrogen source, ammonia, ammonium salts such as ammonium sulfate, ammonium carbonate, ammonium chloride, ammonium phosphate, ammonium acetate and urea, nitrates and so forth can be used. Further, as the phosphoric acid source, potassium dihydrogenphosphate and dipotassium hydrogenphosphate can be used. As for the amino acids, when an auxotrophic mutant strain is used, the required nutrients can be added. Further, the feed medium can include one type of medium, or a mixture of two or more types of media. When two or more types of feed media are used, the media may be mixed and fed by using one feed tin or fed by using two or more feed tins.

When the continuous culture method is used, the medium may be extracted and fed simultaneously, or a part of the medium may be extracted, and then the medium may be fed. Further, the method may also be a continuous culture method which includes extracting the culture medium containing the L-amino acid and bacterial cells and returning only the cells to the fermenter to reuse the cells (French Patent No. 2669935). As the method of continuously or intermittently feeding a nutrient source, the same method as used in the fed-batch culture can be used.

The continuous culture method of reusing bacterial cells is a method of intermittently or continuously extracting the fermentation medium when the amino acid concentration reaches a predetermined level, extracting only the L-amino acid and re-circulating filtration residues containing bacterial cells into the fermenter, and it can be performed by referring to, for example, French Patent No. 2669935.

When the culture medium is intermittently extracted, a portion of the amount of L-amino acid can be extracted when the L-amino acid concentration reaches a predetermined level, and fresh medium is fed to continue the culture. Further, as for the volume of the medium to be added, the culture can be performed so that the final volume of the medium after the addition of the medium is equal to the volume of the culture medium before the extraction. The term "equal" can mean that the volume corresponds to about 93 to 107% of the volume of the culture medium before the extraction.

When the culture medium is continuously extracted, the extraction can be started at the same time as or after the feeding of the nutrient medium. For example, the starting time of the extraction is, at maximum, 5 hours, in another example 3 hours, and in another example 1 hour, after the start of the feeding. Further, the extraction volume of the culture medium is preferably equal to the volume of the medium fed.

<3> Microorganisms which can be Used as Parent Strains to Derive Exemplary Microorganisms of the Present Invention A bacterium belonging to the family Enterobacteriaceae and having an L-amino acid-producing ability, which can metabolize glycerol as a carbon source, can be used as a parent strain, and the desired property can be imparted by the aforementioned methods.

The family Enterobacteriaceae encompasses bacteria belonging to the genera of *Escherichia, Enterobacter, Erwinia, Klebsiella, Pantoea, Photorhabdus, Providencia, Salmonella, Serratia, Shigella, Morganella, Yersinia*, and so forth. In particular, bacteria classified into the family Enterobacteriaceae according to the taxonomy used by the NCBI (National Center for Biotechnology Information) database (www.ncbi.nlm.nih.gov/Taxonomy/Browser/wwwtax.cgi?id=91347) are examples.

The expression of "a bacterium belonging to the genus *Escherichia*" can mean that the bacterium is classified into the genus *Escherichia* according to classification known to a person skilled in the art of microbiology, although the bacterium is not particularly limited. Examples of the bacterium belonging to the genus *Escherichia* include, but are not limited to, *Escherichia coli* (*E. coli*).

The bacterium belonging to the genus *Escherichia* is not particularly limited. However, examples include, for example, the bacteria of the phyletic groups described in the work of Bachmann et al., Table 1 (Bachmann, B. J., 1996, pp. 2460-2488, In F. D. Neidhardt (ed.), *Escherichia coli* and *Salmonella*: Cellular and Molecular Biology/Second Edition, American Society for Microbiology Press, Washington, D.C.). Specific examples include the *Escherichia coli* W3110 (ATCC 27325), *Escherichia coli* MG1655 (ATCC 47076) and so forth derived from the prototype wild-type strain, K12 strain.

These strains are available from, for example, American Type Culture Collection (Address: P.O. Box 1549, Manassas, Va. 20108, United States of America). That is, accession numbers are given to each of the strains, and the strains can be ordered by using these numbers. The accession numbers of the strains are listed in the catalogue of the American Type Culture Collection.

The expression "bacterium belonging to the genus *Pantoea*" can mean that the bacterium is classified into the genus *Pantoea* according to classification known to a person skilled in the art of microbiology. Some strains of *Enterobacter agglomerans* have been recently re-classified into *Pantoea agglomerans, Pantoea ananatis, Pantoea stewartii* or the like based on the nucleotide sequence analysis of 16S rRNA etc. (Int. J. Syst. Bacteriol., 43, 162-173 (1993)). Bacteria belonging to the genus *Pantoea* can encompass such bacteria re-classified into the genus *Pantoea* as described above.

A bacterium having an L-amino acid-producing ability (an ability to produce an L-amino acid) can mean a bacterium which can produce and secrete an L-amino acid in a medium when it is cultured in the medium. It can also mean a bacterium which can accumulate an objective L-amino acid in the medium in an amount not less than 0.5 g/L, and in another example not less than 1.0 g/L. The term "L-amino acid" encompasses L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine.

As a parent strain which can be used, any of the L-amino acid-producing bacteria reported so far can be used, so long as a strain that can assimilate glycerol is chosen. Hereafter, L-amino acid-producing bacteria are described.

L-Threonine-Producing Bacteria

Examples of L-threonine-producing bacteria and parent strains which can be used to derive such bacteria include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A) and so forth.

The strain TDH-6 is deficient in the thrC gene, as well as being sucrose-assimilative, and the ilvA gene has a leaky mutation. This strain also has a mutation in the rhtA gene, which imparts resistance to high concentration of threonine or homoserine. The B-3996 strain harbors the plasmid pVIC40 obtained by inserting a thrA*BC operon containing a mutant thrA gene into a RSF1010-derived vector. This mutant thrA gene encodes aspartokinase homoserine dehydrogenase I which is substantially desensitized to feedback inhibition by threonine. The B-3996 strain was deposited on Nov. 19, 1987 at the All-Union Scientific Center of Antibiotics (Nagatinskaya Street 3-A, 117105 Moscow, Russia) under the accession number RIA 1867. The strain was also deposited at the Russian National Collection of Industrial Microorganisms (VKPM) (1 Dorozhny proezd., 1 Moscow 117545, Russia) on Apr. 7, 1987 under the accession number VKPM B-3996.

*E. coli* VKPM B-5318 (EP 0593792 B) can also be used. The B-5318 strain is prototrophic with regard to isoleucine, and in this strain, a temperature-sensitive lambda-phage Cl repressor and PR promoter replace the regulatory region of the threonine operon in the plasmid pVIC40. The strain VKPM B-5318 was deposited at the Russian National Collection of Industrial Microorganisms (VKPM) (1 Dorozhny proezd., 1 Moscow 117545, Russia) on May 3, 1990 under the accession number of VKPM B-5318.

The bacterium can be additionally modified so that expression of one or more of the following genes is increased:

- the mutant thrA gene which codes for aspartokinase-homoserine dehydrogenase I resistant to feed back inhibition by threonine;
- the thrB gene which codes for homoserine kinase;
- the thrC gene which codes for threonine synthase;
- the rhtA gene which codes for a putative transmembrane protein;
- the asd gene which codes for aspartate-β-semialdehyde dehydrogenase; and
- the aspC gene which codes for aspartate aminotransferase (aspartate transaminase).

The thrA gene which encodes aspartokinase-homoserine dehydrogenase I of *Escherichia coli* has been elucidated (nucleotide numbers 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide numbers 2801 to 3733, GenBank accession NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide numbers 3734 to 5020, GenBank accession NC_000913.2, gi: 49175990). The thrC gene is located between the thrB gene and the yaaX open reading frame on the chromosome of *E. coli* K-12. All three of these genes function as a single threonine operon. To increase expression of the threonine operon, the attenuator region which affects the transcription is desirably removed from the operon (WO2005/049808, WO2003/097839).

The mutant thrA gene which codes for aspartokinase-homoserine dehydrogenase I resistant to feed back inhibition by threonine as well as the thrB and thrC genes can be obtained as one operon from the well-known plasmid pVIC40 which is present in the threonine-producing *E. coli* strain VKPM B-3996. The plasmid pVIC40 is described in detail in U.S. Pat. No. 5,705,371.

The rhtA gene is present at 18 min on the *E. coli* chromosome close to the glnHPQ operon, which encodes components of the glutamine transport system. The rhtA gene is identical to ORF1 (ybiF gene, nucleotide numbers 764 to 1651, GenBank accession number AAA218541, gi:440181) and is located between the pexB and ompX genes. The unit expressing a protein encoded by the ORF1 has been designated rhtA gene (rht: resistance to homoserine and threonine). It has also been revealed that the rhtA23 mutation is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide numbers 3572511 to 3571408, GenBank Accession NC_000913.1, gi:16131307), and can be obtained by PCR (refer to White, T. J., Arnheim, N., and Erlich, H. A., Trends Genet., 5, 185-189 (1989)) utilizing primers prepared based on the nucleotide sequence of the gene. The asd genes of other microorganisms can be obtained in a similar manner.

The aspC gene of *E. coli* has also already been elucidated (nucleotide numbers 983742 to 984932, GenBank Accession NC_000913.1, gi:16128895), and can be obtained by PCR. The aspC genes of other microorganisms can be obtained in a similar manner.

L-Lysine-Producing Bacteria

Examples of L-lysine-producing bacteria belonging to the genus *Escherichia* include mutants having resistance to an L-lysine analogue. L-Lysine analogues inhibit growth of bacteria belonging to the genus *Escherichia*, but this inhibition is fully or partially desensitized when L-lysine is present in a medium. Examples of the L-lysine analogue include, but are not limited to, oxalysine, lysine hydroxamate, S-(2-aminoethyl)-L-cysteine (AEC), γ-methyllysine, α-chlorocaprolactam and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The WC196 strain can be used as an L-lysine-producing bacterium of *Escherichia coli*. This bacterial strain was bred by conferring AEC resistance to the W3110 strain, which was derived from *Escherichia coli* K-12. This strain was designated *Escherichia coli* AJ13069 and was deposited at the National Institute of Bioscience and Human-Technology, Agency of Industrial Science and Technology (currently National Institute of Advanced Industrial Science and Technology, International Patent Organism Depositary, Central 6, 1-1, Higashi 1-Chome, Tsukuba-shi, Ibaraki-ken, 305-8566, Japan) on Dec. 6, 1994 and assigned an accession number of FERM P-14690. Then, it was converted to an international deposit under the provisions of the Budapest Treaty on Sep. 29, 1995, and assigned an accession number of FERM BP-5252 (U.S. Pat. No. 5,827,698).

Examples of L-lysine-producing bacteria and parent strains which can be used to derive such bacteria also include strains in which expression of one or more genes encoding an L-lysine biosynthetic enzyme can be increased. Examples of such genes include, but are not limited to, dihydrodipicolinate synthase gene (dapA), aspartokinase gene (lysC), dihydrodipicolinate reductase gene (dapB), diaminopimelate decarboxylase gene (lysA), diaminopimelate dehydrogenase gene (ddh) (U.S. Pat. No. 6,040,160), phosphoenolpyrvate carboxylase gene (ppc), aspartate semialdehyde dehydrogenease gene (asd), and aspartase gene (aspA) (EP 1253195 A). In addition, the parent strains can have an increased level of expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), the gene coding for glutamate dehydrogenase (gdhA, Gene, 23:199-209 (1983)), or combinations thereof. Abbreviations of the genes are indicated in the parentheses.

It is known that wild-type dihydrodipicolinate synthetase derived from *Escherichia coli* suffers from feedback inhibition by L-lysine, while wild-type aspartokinase from *Escherichia coli* suffers from suppression and feedback inhibition by L-lysine. Therefore, when the dapA and lysC genes are used, these genes are preferably mutant genes coding the enzymes that do not suffer from the feedback inhibition by L-lysine.

Examples of DNA encoding a mutant dihydrodipicolinate synthetase desensitized to feedback inhibition by L-lysine include a DNA encoding a protein which has the amino acid sequence of the enzyme in which the histidine at position 118 is replaced by tyrosine. Examples of DNA encoding a mutant aspartokinase desensitized to feedback inhibition by L-lysine include a DNA encoding an AKIII having the amino acid sequence in which the threonine at position 352, the glycine at position 323, and the methionine at position 318 are replaced by isoleucine, asparagine and isoleucine, respectively (U.S. Pat. No. 5,661,012 and U.S. Pat. No. 6,040,160). Such mutant DNAs can be obtained by site-specific mutagenesis using PCR or the like.

Wide host-range plasmids RSFD80, pCAB1, and pCABD2 are known as plasmids containing a mutant dapA gene encoding a mutant dihydrodipicolinate synthetase and a mutant lysC gene encoding a mutant aspartokinase (U.S. Pat. No. 6,040,160). *Escherichia coli* JM109 strain transformed with RSFD80 was named AJ12396 (U.S. Pat. No. 6,040,160), and the strain was deposited at the National Institute of Bioscience and Human-Technology, Agency of Industrial Science and Technology, Ministry of International Trade and Industry (currently, International Patent Organism Depositary, National Institute of Advanced Industrial Science and Technology Central 6, 1-1, Higashi 1-Chome, Tsukuba-shi, Ibaraki-ken, 305-8566, Japan) on Oct. 28, 1993 and assigned an accession number of FERM P-13936, and the deposit was then converted to an international deposit under the provisions of Budapest Treaty on Nov. 1, 1994 and assigned an accession number of FERM BP-4859. RSFD80 can be obtained from the AJ12396 strain by a known method.

Examples of L-lysine-producing bacteria and parent strains which can be used to derive such bacteria also include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine include homoserine dehydrogenase, lysine decarboxylase (U.S. Pat. No. 5,827,698), and the malic enzyme (WO2005/010175). In order to reduce or delete the lysine decarboxylase activity, it is preferable to reduce expression of both the cadA gene and ldcC gene coding for lysine decarboxylase (International Publication WO2006/038695).

L-Cysteine-Producing Bacteria

Examples of L-cysteine-producing bacteria and parent strains which can be used to derive such bacteria include, but are not limited to, strains belonging to the genus *Escherichia*, such as *E. coli* JM15 which is transformed with different cysE alleles coding for feedback-resistant serine acetyltransferases (U.S. Pat. No. 6,218,168, Russian Patent Application No. 2003121601); *E. coli* W3110 having over-expressed genes which encode proteins suitable for secreting substances toxic for cells (U.S. Pat. No. 5,972,663); *E. coli* strains having lowered cysteine desulfohydrase activity (Japanese Patent Laid-open No. 11-155571); and *E. coli* W3110 with increased activity of a positive transcriptional regulator for cysteine regulon encoded by the cysB gene (WO01/27307).

L-Leucine-Producing Bacteria

Examples of L-leucine-producing bacteria and parent strains which can be used to derive such bacteria include, but are not limited to, strains belonging to the genus *Escherichia*, such as *E. coli* strains resistant to leucine (for example, the strain 57 (VKPM B-7386, U.S. Pat. No. 6,124,121)) or leucine analogues including β-2-thienylalanine, 3-hydroxyleucine, 4-azaleucine and 5,5,5-trifluoroleucine (Japanese Patent Publication (Kokoku) No. 62-34397 and Japanese Patent Laid-open No. 8-70879); *E. coli* strains obtained by a gene engineering method described in WO96/06926; and *E. coli* H-9068 (Japanese Patent Laid-open No. 8-70879).

The bacterium can be improved by enhancing expression of one or more genes involved in L-leucine biosynthesis. Examples of such genes include genes of the leuABCD operon, of which typical example is a mutant leuA gene coding for isopropyl malate synthase desensitized to feedback inhibition by L-leucine (U.S. Pat. No. 6,403,342). In addition, the bacterium can be improved by increasing expression of one or more genes coding for proteins which excrete L-amino acid from bacterial cells. Examples of such genes include the b2682 and b2683 genes (ygaZH genes) (EP 1239041 A2).

L-Histidine-Producing Bacteria

Examples of L-histidine-producing bacteria and parent strains which can be used to derive such bacteria include, but are not limited to, strains belonging to the genus *Escherichia*, such as *E. coli* strain 24 (VKPM B-5945, RU 2003677); *E. coli* strain 80 (VKPM B-7270, RU 2119536); *E. coli* NRRL B-12116 to B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP 1085087); and *E. coli* A180/pFM201 (U.S. Pat. No. 6,258, 554).

Examples of L-histidine-producing bacteria and parent strains which can be used to derive such bacteria also include strains in which expression of one or more genes encoding an L-histidine biosynthetic enzyme can be increased. Examples of such genes include ATP phosphoribosyl transferase gene (hisG), phosphoribosyl AMP cyclohydrolase gene (hisI), phosphoribosyl-ATP pyrophosphohydrolase gene (hisI), phosphoribosylformimino-5-aminoimidazole carboxamide ribotide isomerase gene (hisA), amidotransferase gene (hisH), histidinol phosphate aminotransferase gene (hisC), histidinol phosphatase gene (hisB), histidinol dehydrogenase gene (hisD), and so forth.

It is known that the L-histidine biosynthetic enzymes encoded by hisG and hisBHAFI are inhibited by L-histidine, and therefore L-histidine-producing ability can also be efficiently enhanced by introducing a mutation which confers resistance to the feedback inhibition into the ATP phosphoribosyl transferase gene (hisG) (Russian Patent Nos. 2003677 and 2119536).

Specific examples of strains having L-histidine-producing ability include *E. coli* FERM-P 5038 and 5048 which are introduced with a vector carrying a DNA encoding an L-histidine biosynthetic enzyme (Japanese Patent Laid-open No. 56-005099), *E. coli* strains introduced with a gene for amino acid-export (EP 1016710 A), *E. coli* 80 strain imparted with sulfaguanidine, DL-1,2,4-triazole-3-alanine, and streptomycin resistance (VKPM B-7270, Russian Patent No. 2119536), and so forth.

L-Glutamic Acid-Producing Bacteria

Examples of L-glutamic acid-producing bacteria and parent strains which can be used to derive such bacteria include, but are not limited to, strains belonging to the genus *Escherichia*, such as *E. coli* VL334thrC$^+$ (EP 1172433). *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* K12 strain (VKPM B-7) cells. As a result, an L-isoleucine auxotrophic L-glutamic acid-producing strain VL334thrC$^+$ (VKPM B-8961) was obtained.

Examples of L-glutamic acid-producing bacteria and parent strains which can be used to derive such bacteria include, but are not limited to, strains in which expression of one or more genes encoding an L-glutamic acid biosynthetic enzyme can be increased. Examples of such genes include genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phosphate dehydrogenase (gapA), triose phosphate isomerase (tpiA), fructose bisphosphate aldolase (fbp), phosphofructokinase (pfkA, pfkB), glucose phosphate isomerase (pgi), and so forth.

Examples of strains modified to increase expression of the citrate synthetase gene, the phosphoenolpyruvate carboxylase gene, and/or the glutamate dehydrogenase gene include those disclosed in EP 1078989 A, EP 955368 A and EP 952221 A.

Examples of L-glutamic acid-producing bacteria and parent strains which can be used to derive such bacteria also include strains having decreased or eliminated activity of an enzyme that catalyzes synthesis of a compound other than L-glutamic acid by branching off from an L-glutamic acid biosynthesis pathway. Examples of such enzymes include isocitrate lyase (aceA), α-ketoglutarate dehydrogenase (sucA), phosphotransacetylase (pta), acetate kinase (ack), acetohydroxy acid synthase (ilvG), acetolactate synthase (ilvI), formate acetyltransferase (pfl), lactate dehydrogenase (ldh), glutamate decarboxylase (gadAB), and so forth. Bacteria belonging to the genus *Escherichia* deficient in α-ketoglutarate dehydrogenase activity or having reduced α-ketoglutarate dehydrogenase activity and methods for obtaining them are described in U.S. Pat. Nos. 5,378,616 and 5,573, 945.

Specific examples of such strains include the following:

*E. coli* W3110sucA::Km$^r$

*E. coli* AJ12624 (FERM BP-3853)

*E. coli* AJ12628 (FERM BP-3854)

*E. coli* AJ12949 (FERM BP-4881)

*E. coli* W3110sucA::Km$^r$ is a strain obtained by disrupting the α-ketoglutarate dehydrogenase gene (hereinafter also referred to as "sucA gene") of *E. coli* W3110. This strain is completely deficient in α-ketoglutarate dehydrogenase.

Other examples of L-glutamic acid-producing bacteria include those which belong to the genus *Escherichia* and have resistance to an aspartic acid antimetabolite. These strains may also be deficient in α-ketoglutarate dehydrogenase, and examples include, for example, *E. coli* AJ13199 (FERM BP-5807) (U.S. Pat. No. 5,908,768), FFRM P-12379) which additionally has a lowered L-glutamic acid decomposing ability (U.S. Pat. No. 5,393,671); AJ13138 (FERM BP-5565) (U.S. Pat. No. 6,110,714), and so forth.

Examples of L-glutamic acid-producing bacteria include mutant strains belonging to the genus *Pantoea* which are deficient in α-ketoglutarate dehydrogenase activity or have a decreased α-ketoglutarate dehydrogenase activity, and they can be obtained as described above. Such strains include *Pantoea ananatis* AJ13356 (U.S. Pat. No. 6,331,419). *Pantoea ananatis* AJ13356 was deposited at the National Institute of Bioscience and Human-Technology, Agency of Industrial Science and Technology (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of Budapest Treaty on Jan. 11, 1999 and assigned an accession number of FERM BP-6616. *Pantoea ananatis* AJ13356 is deficient in α-ketoglutarate dehydrogenase activity as a result of disruption of the αKGDH-E1 subunit gene (sucA). This strain was identified as *Enterobacter agglomerans* when it was isolated and deposited as the *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, it is described as *Pantoea ananatis* in this specification.

L-Phenylalanine-Producing Bacteria

Examples of L-phenylalanine-producing bacteria and parent strains which can be used to derive such bacteria include, but are not limited to, strains belonging to the genus *Escherichia*, such as *E. coli* AJ12739 (tyrA::Tn10, tyrR) (VKPM B-8197); *E. coli* HW1089 (ATCC 55371) harboring the mutant pheA34 gene (U.S. Pat. No. 5,354,672); *E. coli* MWEC101-b (KR 8903681); *E. coli* NRRL B-12141, NRRL B-12145, NRRL B-12146 and NRRL B-12147 (U.S. Pat. No. 4,407,952). As parent strains, *E. coli* K-12 [W3110 (tyrA)/pPHAB] (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ12604 (FERM BP-3579) may also be used (EP 488424 B1). Furthermore, L-phenylalanine-producing bacteria belonging to the genus *Escherichia* with an enhanced activity of the protein encoded by the yedA gene or the yddG gene can also be used (U.S. Patent Published Application Nos. 2003/0148473 A1 and 2003/0157667 A1).

L-Tryptophan-Producing Bacteria

Examples of tryptophan-producing bacteria and parent strains which can be used to derive such bacteria, but are not limited to, strains belonging to the genus *Escherichia*, such as *E. coli* JP4735/pMU3028 (DSM10122) and JP6015/pMU91 (DSM10123) which are deficient in the tryptophanyl-tRNA synthetase encoded by mutant trpS gene (U.S. Pat. No. 5,756,345); *E. coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180,373); *E. coli* AGX17(pGX44) (NRRL B-12263) and AGX6(pGX50)aroP (NRRL B-12264) deficient in tryptophanase (U.S. Pat. No. 4,371,614); and *E. coli* AGX17/pGX50, pACKG4-pps in which phosphoenolpyruvate-producing ability is enhanced (WO97/08333, U.S. Pat. No. 6,319,696). L-Tryptophan-producing bacteria belonging to the genus *Escherichia* with an enhanced activity of the protein encoded by the yedA gene or the yddG gene may also be used (U.S. Patent Published Application Nos. 2003/0148473 A1 and 2003/0157667 A1).

Examples of L-tryptophan-producing bacteria and parent strains which can be used to derive such bacteria also include strains in which one or more activities of the enzymes anthranilate synthase (trpE), phosphoglycerate dehydrogenase (serA), and tryptophan synthase (trpAB) are increased. The anthranilate synthase and phosphoglycerate dehydrogenase both suffer from feedback inhibition by L-tryptophan and L-serine, and therefore a mutation desensitizing them to the feedback inhibition may be introduced into these enzymes. Specific examples of strains having such a mutation include *E. coli* SV164 which harbors desensitized anthranilate synthase and a transformant strain obtained by introducing the plasmid pGH5 (WO94/08031), which contains a mutant serA gene encoding feedback inhibition-desensitized phosphoglycerate dehydrogenase, into the *E. coli* SV164.

Examples of L-tryptophan-producing bacteria and parent strains which can be used to derive such bacteria also include strains into which the tryptophan operon containing a gene encoding inhibition-desensitized anthranilate synthase is introduced (Japanese Patent Laid-open Nos. 57-71397, 62-244382, U.S. Pat. No. 4,371,614). Moreover, L-tryptophan-producing ability may be imparted by increasing expression of a gene which encodes tryptophan synthase in the tryptophan operon (trpBA). The tryptophan synthase consists of $\alpha$ and $\beta$ subunits which are encoded by the trpA and trpB genes, respectively. In addition, L-tryptophan-producing ability can also be improved by increasing expression of the isocitrate lyase-malate synthase operon (WO2005/103275).

L-Proline-Producing Bacteria

Examples of L-proline-producing bacteria and parent strains which can be used to derive such bacteria include, but are not limited to, strains belonging to the genus *Escherichia*, such as *E. coli* 702ilvA (VKPM B-8012) which is deficient in the ilvA gene and is able to produce L-proline (EP 1172433).

The bacterium can be improved by increasing expression of one or more genes involved in L-proline biosynthesis. Examples of such genes include the proB gene coding for glutamate kinase desensitized to feedback inhibition by L-proline (DE 3127361). In addition, the bacterium can be improved by increasing expression of one or more genes coding for proteins excreting L-amino acid from bacterial cells. Examples of such genes include the b2682 and b2683 genes (ygaZH genes) (EP 1239041 A2).

Examples of bacteria belonging to the genus *Escherichia* and having L-proline-producing ability include the following *E. coli* strains: NRRL B-12403 and NRRL B-12404 (British Patent No. 2075056), VKPM B-8012 (Russian Patent Application No. 2000124295), plasmid mutants described in German Patent No. 3127361, plasmid mutants described by Bloom F. R. et al. (The 15th Miami winter symposium, 1983, p. 34), and so forth.

L-Arginine-Producing Bacteria

Examples of L-arginine-producing bacteria and parent strains which can be used to derive such bacteria include, but are not limited to, strains belonging to the genus *Escherichia*, such as *E. coli* strain 237 (VKPM B-7925) (U.S. Patent Published Application 2002/058315A1) and its derivative strains harboring mutant N-acetylglutamate synthase (Russian Patent Application No. 2001112869), *E. coli* strain 382 (VKPM B-7926) (EP 1170358 A1), and an arginine-producing strain into which argA gene encoding N-acetylglutamate synthetase is introduced (EP 1170361 A1).

Examples of L-arginine-producing bacteria and parent strains which can be used to derive such bacteria also include strains in which expression of one or more genes encoding an L-arginine biosynthetic enzyme can be increased. Examples of such genes include N-acetylglutamyl phosphate reductase gene (argC), ornithine acetyl transferase gene (argJ), N-acetylglutamate kinase gene (argB), acetylornithine transaminase gene (argD), ornithine carbamoyl transferase gene (argF), argininosuccinic acid synthetase gene (argG), argininosuccinic acid lyase gene (argH), and carbamoyl phosphate synthetase gene (carAB).

L-Valine-Producing Bacteria

Example of L-valine-producing bacteria and parent strains which can be used to derive such bacteria include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by produced L-valine. Further, the ilvA gene in the operon is desirably disrupted so that threonine deaminase activity is decreased.

Examples of L-valine-producing bacteria and parent strains which can be used to derive such bacteria also include mutants having a mutation of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 was deposited at the Russian National Collection of Industrial Microorganisms (VKPM) (1 Dorozhny Proezd, 1 Moscow 117545, Russia) on Jun. 24, 1988 under the accession number of VKPM B-4411.

Furthermore, mutants requiring lipoic acid for growth and/or lacking $H^+$-ATPase (WO96/06926) can also be used as the parent strains.

L-Isoleucine-Producing Bacteria

Examples of L-isoleucine-producing bacteria and parent strains include, but are not limited to, mutants having resistance to 6-dimethylaminopurine (Japanese Patent Laid-open No. 5-304969 A), mutants having resistance to an isoleucine analogue such as thiaisoleucine and isoleucine hydroxamate, and such mutants further having resistance to DL-ethionine and/or arginine hydroxamate (Japanese Patent Laid-open No. 5-130882). In addition, recombinant strains transformed with genes encoding proteins involved in L-isoleucine biosynthesis, such as threonine deaminase and acetohydroxate synthase, can also be used as the parent strains (Japanese Patent Laid-open No. 2-458, FR 0356739, and U.S. Pat. No. 5,998,178).

EXAMPLES

Example 1

Construction of L-Lysine-Producing Bacterium with Enhanced Fructose-6-Phosphate Aldolase, Glycerol Dehydrogenase and Dihydroxyacetone Kinase Activities <1-1> Construction of Plasmid for dak1 Gene Expression The total nucleotide sequence of *Saccharomyces cerevisiae* chromosome has already been elucidated (Science, 25 (1996)). On the basis of the nucleotide sequence of the dak1 gene reported in this literature, the synthetic oligonucleotide of SEQ ID NO: 14 was prepared as a 5' primer, and the synthetic oligonucleotide of SEQ ID NO: 15 was prepared as a 3' primer. PCR was performed by using these synthetic oligonucleotides and the chromosomal DNA of the *Saccharomyces cerevisiae* JCM7255 strain as a template. The PCR product was purified and ligated with the vector pMW119 (Takara Bio) digested with HindIII and SalI to construct a dak1 expression plasmid pMW-dak1. The JCM7255 strain is stored in the independent administrative agency, RIKEN, "Japan Collection of Microorganisms", 2-1, Hirosawa, Wako-shi, Saitama-ken.

<1-2> Construction of Glycerol Dehydrogenase Activity-Improved Strain

A WC196ΔcadAΔldcC strain modified to have the structure shown in SEQ ID NO: 11 was constructed. For the construction of the strain having this structure, the sequence of SEQ ID NO: 9 (PCR product) was used. In the sequence of SEQ ID NO: 9, the sequence of the nucleotide numbers 1 to 172 is the attR sequence of λ phage, the sequence of the nucleotide numbers 324 to 983 is a chloramphenicol resistance gene (cat), the sequence of the nucleotide numbers 1540 to 1653 is the attL sequence of λ phage, and the sequence of the nucleotide numbers 1654 to 1733 is the tacM promoter.

The tacM promoter (SEQ ID NO: 10) can be constructed by replacing the TTGACA sequence of the tac promoter (Gene, 25 (2-3), 167-178 (1983)) at the −35 region with TTCACA. The sequence of SEQ ID NO: 9 can be constructed by referring to the construction of pMW118-attL-Cm-attR (WO2005/010175).

The sequence of SEQ ID NO: 9 as a template was amplified by PCR using the primers of SEQ ID NOS: 12 and 13, and this amplification product was inserted into chromosome of the WC196ΔcadAΔldcC strain (refer to International Publication WO2006/038695) by the λ-RED method (WO2005/010175) to construct a strain in which the promoter sequence upstream of the gldA was replaced. In this way, a strain with improved glycerol dehydrogenase activity, WC196ΔcadAΔldcCPtacMgldA::Cm strain, was obtained.

<1-3> Construction of L-Lysine-Producing Bacterium with Enhanced Fructose-6-Phosphate Aldolase and Glycerol Dehydrogenase Activities A WC196ΔcadAΔldcC strain modified to have the structure shown in SEQ ID NO: 92 was constructed. For construction of the strain having this structure, the sequence of SEQ ID NO: 9 (PCR product) was used. In the sequence of SEQ ID NO: 9, the sequence of the nucleotide numbers 1 to 172 is the attR sequence of λ phage, the sequence of the nucleotide numbers 324 to 983 is a chloramphenicol resistance gene (cat), the sequence of the nucleotide numbers 1540 to 1653 is the attL sequence of λ phage, and the sequence of the nucleotide numbers 1654 to 1733 is the tacM promoter.

The tacM promoter (SEQ ID NO: 10) can be constructed by replacing the TTGACA sequence of the tac promoter (Gene, 25 (2-3), 167-178 (1983)) at the −35 region with TTCACA. The sequence of SEQ ID NO: 9 can be constructed by referring to the construction of pMW118-attL-Cm-attR (WO2005/010175).

The sequence of SEQ ID NO: 9 as a template was amplified by PCR using the primers of SEQ ID NOS: 93 and 94, and this amplification product was inserted into chromosome of the WC196ΔcadAΔldcC strain (refer to International Publication WO2006/038695) by the λ-RED method (WO2005/010175) to construct a strain in which the promoter sequence upstream of the fsaB-gldA operon was replaced. In this way, a strain with improved fructose-6-phosphate aldolase and glycerol dehydrogenase activities, WC196ΔcadAΔldcCPtacM fsaB-gldA::Cm strain, was obtained.

<1-4> Construction of L-Lysine-Producing Bacteria with Enhanced Fructose-6-Phosphate Aldolase, Glycerol Dehydrogenase and Dihydroxyacetone Kinase Activities The WC196ΔcadAΔldcC strain (refer to International Publication WO2006/038695), the WC196ΔcadAΔldcCPtacMgldA::Cm strain and the WC196ΔcadAΔldcCPtacM fsaB-gldA::Cm strain were transformed with the plasmid pCABD2 for Lys production carrying dapA, dapB and lysC genes (International Publication WO01/53459) in a conventional manner to obtain WC196ΔcadAΔldcC/pCABD2 strain, WC196ΔcadAΔldcCPtacMgldA::Cm/pCABD2 strain, and WC196ΔcadAΔldcCPtacM fsaB-gldA::Cm/pCABD2 strain. Furthermore, the WC196ΔcadAΔldcC/pCABD2 strain, the WC196ΔcadAΔldcCPtacMgldA::Cm/pCABD2 strain and the WC196ΔcadAΔldcCPtacM fsaB-gldA::Cm/pCABD2 strain were transformed with the dak1 expression plasmid pMW-dak1 in a conventional manner to obtain WC196ΔcadAΔldcC/pCABD2,pMW-dak1 strain, WC196ΔcadAΔldcCPtacMgldA::Cm/pCABD2,pMW-dak1 strain and WC196ΔcadAΔldcCPtacM fsaB-gldA::Cm/pCABD2,pMW-dak1 strain.

These strains were each cultured in L medium containing 20 mg/L of streptomycin or 20 mg/L of streptomycin and 50 mg/L of ampicillin at 37° C. until the final OD600 became about 0.6, then a 40% glycerol solution in a volume equal to the culture medium was added to each culture medium, and the mixture was stirred, then divided into appropriate volumes, and stored at −80° C. These are called glycerol stocks.

Example 2

Evaluation of L-Lysine-Producing Bacteria with Enhanced Fructose-6-Phosphate Aldolase, Glycerol Dehydrogenase and Dihydroxyacetone Kinase Activities The aforementioned glycerol stocks of the strains were thawed, 100 μL of each stock was uniformly applied to an L plate containing 20 mg/L of streptomycin or 20 mg/L of streptomycin and 50 mg/L of ampicillin, and culture was performed at 37° C. for 24 hours. The obtained cells on the plate were suspended in 1 ml of physiological saline, the suspension was inoculated in a volume V obtained by dividing a constant 50 with absorbance at 600 nm (n) of the suspension diluted 101 times (V=50/n) into 20 mL of a fermentation medium containing 20 mg/L of streptomycin or 20 mg/L of streptomycin and 50 mg/L of ampicillin contained in a 500-mL Sakaguchi flask, and culture was performed at 37° C. for 48 hours on a reciprocally shaking culture machine. After the culture, amount of lysine accumulated in the medium was measured by a known method (Biotec Analyzer AS210, SAKURA SEIKI).

The composition of the fermentation medium is shown below (unit: g/L).

| | |
|---|---|
| Glycerol | 40 |
| $(NH_4)_2SO_4$ | 24 |
| $K_2HPO_4$ | 1.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Yeast extract | 2.0 |
| | To final volume of 1 L |

The medium was adjusted to pH 7.0 with KOH, and autoclaved at 115° C. for 10 minutes, provided that glycerol and $MgSO_4 \cdot 7H_2O$ were separately sterilized, and 30 g/L of $CaCO_3$ of Japanese Pharmacopoeia subjected to hot air sterilization at 180° C. for 2 hours was added.

As antibiotics, 20 mg/L of streptomycin or 20 mg/L of streptomycin and 50 mg/L of ampicillin were added. The culture was performed under the conditions of a temperature of 37° C. and stirring at 115 rpm for 48 hours.

The results are shown in Table 5 (OD means absorbance at 600 nm representing cell amount, Lys (g/L) means the amount of L-lysine accumulated in flask, and yield (%) means yield of L-lysine based on the substrate). Whereas the strain in which only glycerol dehydrogenase was enhanced, the strain in which only dihydroxyacetone kinase was enhanced, and the strain in which fructose-6-phosphate aldolase and glycerol dehydrogenase were enhanced did not show change of yield and productivity compared with the non-modified strain, the WC196ΔcadAΔldcCPtacMgldA::Cm/pCABD2, pMW-dak1 strain in which both glycerol dehydrogenase and dihydroxyacetone kinase using ATP as a phosphate donor were enhanced accumulated a larger amount of L-lysine compared with the other strains. Further, the WC196ΔcadAΔldcCPtacM fsaB-gldA::Cm/pCABD2, pMW-dak1 strain in which fructose-6-phosphate aldolase, glycerol dehydrogenase and dihydroxyacetone kinase using ATP as a phosphate donor were enhanced accumulated a further larger amount of L-lysine.

TABLE 5

Table 5: L-Lysine accumulation of strains with enhanced fructose-6-phosphate aldolase (fsaB), glycerol dehydrogenase (gldA) and dihydroxyacetone kinase (dak1) activities

| | | | OD | Lys (g/L) | Yield (%) |
|---|---|---|---|---|---|
| WC196LC | pCABD2 | — | 16.7 | 14.7 | 36.8 |
| WC196LC | pCABD2 | pMW-dak1 | 14.3 | 14.8 | 36.9 |
| WC196LCPtacMgldA | pCABD2 | — | 18.1 | 14.7 | 36.8 |
| WC196LCPtacMfsaB-gldA | pCABD2 | — | 18.5 | 14.3 | 35.8 |
| WC196LCPtacMgldA | pCABD2 | pMW-dak1 | 15.3 | 15.3 | 38.1 |
| WC196LCPtacMfsaB-gldA | pCABD2 | pMW-dak1 | 14.0 | 16.9 | 42.1 |

In the names of strains mentioned in the table, "LC" is an abbreviation of "ΔcadAΔldcC", and "::Cm" is omitted.

Example 3

Construction of L-Threonine-Producing Bacteria with Enhanced Glycerol Dehydrogenase and Dihydroxyacetone Kinase Activities <3-1> Construction of Glycerol Dehydrogenase Activity-Improved Strain B5318 strains modified to have the structures shown in SEQ ID NOS: 90 and 91 were constructed. For construction of the strains having these structures, sequences of SEQ ID NOS: 88 and 89 (PCR products) were used. In the sequences of SEQ ID NOS: 88 and 89, the sequences of the nucleotide numbers 1 to 72 are the attR sequences of λ phage, the sequences of the nucleotide numbers 324 to 983 are chloramphenicol resistance genes (cat), the sequences of the nucleotide numbers 1540 to 1653 are the attL sequences of λ phage, and the sequences of the nucleotide numbers 1654 to 1733 are the tacM2 and tacM3 promoters.

The tacM2 and tacM3 promoters are constitutive promoters which can be constructed by replacing the TTGACA sequence of the tac promoter (Gene, 25 (2-3), 167-178 (1983)) at the −35 region with TGTACA and TTGGCA (Molecular Biology 39 (5) 719-726 (2005)). The sequences of SEQ ID NOS: 88 and 89 can be constructed by referring to the construction of pMW118-attL-Cm-attR (WO2005/010175).

The sequences of SEQ ID NOS: 88 and 89 as templates were amplified by PCR using the primers of SEQ ID NOS: 12 and 13, and these amplification products were each inserted into chromosome of the B5318 strain (VKPM B-5318) by the λ-RED method (WO2005/010175) to obtain strains in which the promoter sequence upstream of the gldA was replaced. In this way, strains with improved glycerol dehydrogenase activity, B5318PtacM2gldA::Cm strain and B5318PtacM3gldA::Cm strain, were obtained.

<1-3> Construction of L-Threonine-Producing Bacteria with Enhanced Glycerol Dehydrogenase and Dihydroxyacetone Kinase Activities The B5318PtacM2gldA::Cm strain and the B5318PtacM3gldA::Cm strain were transformed with the dak1 expression plasmid pMW-dak1 in a conventional manner to obtain B5318PtacM2gldA::Cm/pMW-dak1 strain and B5318PtacM3gldA::Cm/pMW-dak1 strain.

These strains were each cultured in L medium containing 20 mg/L of streptomycin or 20 mg/L of streptomycin and 50 mg/L of ampicillin at 37° C. until the final OD600 became about 0.6, then a 40% glycerol solution in a volume equal to the culture medium was added to each culture medium, and the mixture was stirred, then divided into appropriate volumes, and stored at −80° C. These are called glycerol stocks.

Example 4

Evaluation of L-Threonine-Producing Bacteria with Enhanced Glycerol Dehydrogenase and Dihydroxyacetone Kinase Activities The aforementioned glycerol stocks of the strains were thawed, 100 μL of each stock was uniformly applied to an L plate containing 20 mg/L of streptomycin or 20 mg/L of streptomycin and 50 mg/L of ampicillin, and culture was performed at 37° C. for 24 hours. The obtained cells on the plate were suspended in 1 ml of physiological saline, the suspension was inoculated in a volume (V) obtained by dividing a constant 50 with absorbance at 600 nm (n) of the suspension diluted 101 times (V=50/n) into 20 mL of a fermentation medium containing 20 mg/L of streptomycin or 20 mg/L of streptomycin and 50 mg/L of ampicillin contained in a 500-mL conical flask with baffle, and culture was performed at 40° C. for 24 hours on a rotary culture machine. After the culture, amount of threonine accumulated in the medium was measured by a known method (Hitachi Liquid Chromatography ODS-2 Column).

The composition of the fermentation medium is shown below (unit: g/L).

| | |
|---|---|
| Glycerol | 40 |
| $(NH_4)_2SO_4$ | 24 |
| $K_2HPO_4$ | 1.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Yeast extract | 2.0 |
| | To final volume of 1 L |

The medium was adjusted to pH 7.0 with KOH, and autoclaved at 115° C. for 10 minutes, provided that glycerol and $MgSO_4.7H_2O$ were separately sterilized, and 30 g/L of $CaCO_3$ of Japanese Pharmacopoeia subjected to hot air sterilization at 180° C. for 2 hours was added.

As antibiotics, 20 mg/L of streptomycin or 20 mg/L of streptomycin and 50 mg/L of ampicillin were added. The culture was performed under the conditions of a temperature of 40° C. and stirring at 144 rpm for 24 hours.

The results are shown in Table 6 (OD means absorbance at 600 nm representing cell amount, Thr (g/L) means amount of L-threonine accumulated in flask, and yield (%) means yield of L-threonine based on the substrate). Whereas the strain in which only glycerol dehydrogenase was enhanced did not show change of yield and productivity compared with the non-modified strain, the B5318PtacM2gldA::Cm/pMW-dak1 strain and the B5318PtacM3gldA::Cm/pMW-dak1 strain in which both glycerol dehydrogenase and dihydroxyacetone kinase using ATP as a phosphate donor were enhanced accumulated a larger amount of L-threonine compared with the other strains.

TABLE 6

Table 6: L-Threonine accumulation of strains with enhanced glycerol dehydrogenase (gldA) and dihydroxyacetone kinase (dak1) activities

| | | | OD600 | Thr (g/L) | Yield (%) |
|---|---|---|---|---|---|
| B5318 | — | — | 22.5 | 12.5 | 30.9 |
| B5318 | Ptac M2 gldA | — | 21.5 | 11.9 | 29.4 |
| B5318 | Ptac M2 gldA | pMW-dak | 21.1 | 13.2 | 32.6 |
| B5318 | Ptac M3 gldA | — | 23.1 | 12.3 | 30.4 |
| B5318 | Ptac M3 gldA | pMW-dak | 22.3 | 13.3 | 32.9 |

In the names of strains mentioned in the table, "pMW-dak1" is abbreviated as "pMW-dak", and "::Cm" is omitted.

Explanation of Sequence Listing:

SEQ ID NO: 1: gldA gene sequence of *Escherichia coli* (1104 bp)

SEQ ID NO: 2: GldA amino acid sequence of *Escherichia coli* (367 AA)

SEQ ID NO: 3: dakA1 gene sequence of *Saccharomyces cerevisiae* (1755 bp)

SEQ ID NO: 4: DakA amino acid sequence of *Saccharomyces cerevisiae* (584 AA)

SEQ ID NO: 5: dhbK1 gene sequence of *Agrobacterium tumefaciens* (1695 bp)

SEQ ID NO: 6: Dhbk1 amino acid sequence of *Agrobacterium tumefaciens* (564 AA)

SEQ ID NO: 7: dhaK gene sequence of *Citrobacter freundii* (1659 bp)

SEQ ID NO: 8: DhaK amino acid sequence of *Citrobacter freundii* (552 AA)

SEQ ID NO: 9: attR-cat-attL-ptacM-SD-spacer sequence (1740 bp)

SEQ ID NO: 10: tacM promoter (80 bp)

SEQ ID NO: 1: PtacMgldA::Cm sequence

SEQ ID NO: 12: atL-Ptac-gldA (PCR primer for enhancing gldA on chromosome)

SEQ ID NO: 13: atR-Ptac-fsaB1 (PCR primer for enhancing gldA on chromosome)

SEQ ID NO: 14: pMW-dak1F (primer for dakA cloning)

SEQ ID NO: 15: pMW-dak1R (primer for dak4 cloning)

SEQ ID NO: 16: glpF gene sequence of *Escherichia coli* (846 bp)

SEQ ID NO: 17: GlpF amino acid sequence of *Escherichia coli* (281 AA)

SEQ ID NO: 18: tpiA gene sequence of *Escherichia coli* (768 bp)

SEQ ID NO: 19: TpiA amino acid sequence of *Escherichia coli* (255 AA)

SEQ ID NO: 20: fbaA gene sequence of *Escherichia coli* (1080 bp)

SEQ ID NO: 21: FbaA amino acid sequence of *Escherichia coli* (359 AA)

SEQ ID NO: 22: glpX gene sequence of *Escherichia coli* (1011 bp)

SEQ ID NO: 23: GlpX amino acid sequence of *Escherichia coli* (336 AA)

SEQ ID NO: 24: glpK gene sequence of *Escherichia coli* (1509 bp)

SEQ ID NO: 25: GlpK amino acid sequence of *Escherichia coli* (502 AA)

SEQ ID NO: 26: glpA gene sequence of *Escherichia coli* (1629 bp)

SEQ ID NO: 27: GlpA amino acid sequence of *Escherichia coli* (542 AA)

SEQ ID NO: 28: glpB gene sequence of *Escherichia coli* (1260 bp)

SEQ ID NO: 29: GlpB amino acid sequence of *Escherichia coli* (419 AA)

SEQ ID NO: 30: glpC gene sequence of *Escherichia coli* (1191 bp)

SEQ ID NO: 31: GlpC amino acid sequence of *Escherichia coli* (396 AA)

SEQ ID NO: 32: glpD gene sequence of *Escherichia coli* (1506 bp)

SEQ ID NO: 33: GlpD amino acid sequence of *Escherichia coli* (501 AA)

SEQ ID NO: 34: dhaK gene sequence of *Escherichia coli* (1071 bp)

SEQ ID NO: 35: DhaK amino acid sequence of *Escherichia coli* (356 AA)

SEQ ID NO: 36: dhaL gene sequence of *Escherichia coli* (633 bp)

SEQ ID NO: 37: DhaL amino acid sequence of *Escherichia coli* (210 AA)

SEQ ID NO: 38: dhaM gene sequence of *Escherichia coli* (1419 bp)

SEQ ID NO: 39: DhaM amino acid sequence of *Escherichia coli* (472 AA)

SEQ ID NO: 40: Dihydroxyacetone kinase gene of *Schizosaccharomyces pombe* (1776 bp)

SEQ ID NO: 41: Dihydroxyacetone kinase of *Schizosaccharomyces pombe* (591 AA)

SEQ ID NO: 42: Dihydroxyacetone kinase gene of *Pichia angusta* (1830 bp)

SEQ ID NO: 43: Dihydroxyacetone kinase of *Pichia angusta* (609 AA)

SEQ ID NO: 44: Dihydroxyacetone kinase gene of *Pichia pastoris* (1827 bp)

SEQ ID NO: 45: Dihydroxyacetone kinase of *Pichia pastoris* (608 AA)

SEQ ID NO: 46: Dihydroxyacetone kinase gene of *Debaryomyces hansenii* (1824 bp)

SEQ ID NO: 47: Dihydroxyacetone kinase of *Debaryomyces hansenii* (607 AA)

SEQ ID NO: 48: Dihydroxyacetone kinase gene of *Escherichia blattae* (1752 bp)

SEQ ID NO: 49: Dihydroxyacetone kinase of *Escherichia blattae* (583 AA)

SEQ ID NO: 50: Dihydroxyacetone kinase gene of *Enterobacter* sp. 638 (1647 bp)

SEQ ID NO: 51: Dihydroxyacetone kinase of *Enterobacter* sp. 638 (548 AA)

SEQ ID NO: 52: Dihydroxyacetone kinase gene of *Psychromonas* sp. CNPT3 (1695 bp)

SEQ ID NO: 53: Dihydroxyacetone kinase of *Psychromonas* sp. CNPT3 (564 AA)

SEQ ID NO: 54: Dihydroxyacetone kinase gene of *Stappia aggregata* (1647 bp)

SEQ ID NO: 55: Dihydroxyacetone kinase of *Stappia aggregata* (548 AA)

SEQ ID NO: 56: Dihydroxyacetone kinase gene of *Rhizobium leguminosarum* bv. *viciae* 3841 (1641 bp)

SEQ ID NO: 57: Dihydroxyacetone kinase of *Rhizobium leguminosarum* bv. *viciae* 3841 (546 AA)

SEQ ID NO: 58: Dihydroxyacetone kinase gene of *Myxococcus xanthus* DK 1622 (1701 bp)

SEQ ID NO: 59: Dihydroxyacetone kinase of *Myxococcus xanthus* DK 1622 (566 AA)

SEQ ID NO: 60: Dihydroxyacetone kinase gene of *Burkholderia* sp. 383 (1701 bp)

SEQ ID NO: 61: Dihydroxyacetone kinase of *Burkholderia* sp. 383 (566 AA)

SEQ ID NO: 62: Dihydroxyacetone kinase gene of *Burkholderia thailandensis* E264 (1704 bp)

SEQ ID NO: 63: Dihydroxyacetone kinase of *Burkholderia thailandensis* E264 (567 AA)

SEQ ID NO: 64: Dihydroxyacetone kinase gene of *Burkholderia multivorans* ATCC 17616 (1851 bp)

SEQ ID NO: 65: Dihydroxyacetone kinase of *Burkholderia multivorans* ATCC 17616 (616 AA)

SEQ ID NO: 66: dhaR gene of *Escherichia coli* (1920 bp)

SEQ ID NO: 67: DhaR amino acid sequence of *Escherichia coli* (639 AA)

SEQ ID NO: 68: fsaA gene of *Escherichia coli* (663 bp)

SEQ ID NO: 69: FsaA amino acid sequence of *Escherichia coli* (220 AA)

SEQ ID NO: 70: fsaB gene of *Escherichia coli* (663 bp)

SEQ ID NO: 71: FsaB amino acid sequence of *Escherichia coli* (220 AA)

SEQ ID NO: 72: fbaB gene of *Escherichia coli* (1053 bp)

SEQ ID NO: 73: FbaB amino acid sequence of *Escherichia coli* (350 AA)

SEQ ID NO: 74: gldA gene of *Shigella dysenteriae* Sd197 (1143 bp)

SEQ ID NO: 75: GldA amino acid sequence of *Shigella dysenteriae* Sd197 (380 AA)

SEQ ID NO: 76: gldA gene of *Salmonella typhimurium* LT2 (1104 bp)

SEQ ID NO: 77: GldA amino acid sequence of *Salmonella typhimurium* LT2 (367 AA)

SEQ ID NO: 78: gldA gene of *Pseudomonas putida* (1098 bp)

SEQ ID NO: 79: GldA amino acid sequence of *Pseudomonas putida* (365 AA)

SEQ ID NO: 80: gldA gene of *Bacillus coagulans* 36D1 (1104 bp)

SEQ ID NO: 81: GldA amino acid sequence of *Bacillus coagulans* 36D1 (367 AA)

SEQ ID NO: 82: fbp gene of *Escherichia coli* (999 bp)

SEQ ID NO: 83: Fbp amino acid sequence of *Escherichia coli* (322 AA)

SEQ ID NO: 84: ybhA gene of *Escherichia coli* (819 bp)

SEQ ID NO: 85: YbhA amino acid sequence of *Escherichia coli* (272 AA)

SEQ ID NO: 86: ptsI gene of *Escherichia coli* (1782 bp)

SEQ ID NO: 87: PtsI amino acid sequence of *Escherichia coli* (575 AA)

SEQ ID NO: 88: attR-cat-attL-PtacM2-SD-spacer sequence

SEQ ID NO: 89: attR-cat-attL-PtacM3-SD-spacer sequence

SEQ ID NO: 90: PtacM2gldA::Cm sequence

SEQ ID NO: 91: PtacM3gldA::Cm sequence

SEQ ID NO: 92: PtacM fsaB-gldA::Cm sequence

SEQ ID NO: 93: atL-Ptac-fsaB (PCR primer for enhancing fsaB+gldA on chromosome)

SEQ ID NO: 94: atR-Ptac-fsaB (PCR primer for enhancing fsaB+gldA on chromosome)

INDUSTRIAL APPLICABILITY

By using the microorganism of the present invention, efficient production of an L-amino acid from glycerol by fermentation is enabled.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing an L-amino acid, comprising:

(A) providing an *Escherichia coli* having an L-amino acid-producing ability and modified to increase glycerol dehydrogenase and dihydroxyacetone kinase activities, (B) culturing said *Escherichia coli* in a medium containing glycerol as a carbon source to produce and accumulate an L-amino acid in the medium or cells, and (C) collecting the L-amino acid from the medium or the cells, wherein said *Escherichia coli* is modified to increase the glycerol dehydrogenase and dihydroxyacetone kinase activities by increasing copy numbers of a glycerol dehydrogenase gene and dihydroxyacetone kinase gene, and/or by replacing a promoter for the genes with a stronger promoter, and wherein the dihydroxyacetone kinase uses ATP as a phosphate donor.

2. The method of claim 1, wherein the copy numbers of the genes are increased by transformation of the *Escherichia coli* with a multi-copy vector containing the genes and/or by introduction of the genes into the chromosome of the *Escherichia coli*.

3. The method of claim 1, wherein the *Escherichia coli* is further modified to increase glycerol uptake activity by increasing copy number of a gene encoding for a glycerol facilitator, and/or by replacing a promoter for the gene for a glycerol facilitator with a stronger promoter.

4. The method of claim 1, wherein the *Escherichia coli* is further modified to increase at least one activity of an enzyme selected from the group consisting of triosephosphate isomerase, fructose bisphosphate aldolase, fructose-1,6-bisphosphatase, fructose-6-phosphate aldolase, and combinations thereof, wherein the at least one activity of the enzyme is increased by increasing the copy number of a gene coding for the enzyme, and/or by replacing a promoter for the gene with a stronger promoter.

5. The method of claim 1, wherein the *Escherichia coli* is further modified to reduce at least one activity of glycerol kinase and/or membrane-binding type glycerol-3-phosphate dehydrogenase.

6. The method of claim 1, wherein the L-amino acid is selected from the group consisting of L-glutamic acid, L-lysine, L-leucine, L-isoleucine, L-valine, L-tryptophan, L-phenylalanine, L-tyrosine, L-threonine, L-methionine, L-cysteine, L-arginine, L-serine, L-proline, L-asparatic acid, L-asparagine, L-glutamine, L-histidine, and combinations thereof.

7. The method of claim 4, wherein the copy number of a gene coding for the enzyme is increased by transformation of the *Escherichia coli* with a multi-copy vector containing the gene and/or introduction of the gene into the chromosome of the *Escherichia coli*.

8. The method of claim 1, wherein the glycerol dehydrogenase gene is obtained from *Escherichia coli*.

9. The method of claim 8, wherein the glycerol dehydrogenase gene encodes a protein selected from the group consisting of:

(a) a protein comprising the amino acid sequence of SEQ ID NO: 2; and (b) a protein comprising the amino acid sequence which is not less than 95% identical to the amino acid sequence of SEQ ID NO: 2 and the protein has glycerol dehydrogenase activity.

10. The method of claim 1, wherein the promoter under which the glycerol dehydrogenase gene is placed is a promoter obtained from tac promoter.

11. The method of claim 1, wherein the dihydroxyacetone kinase gene is obtained from *Saccharomyces cerevisiae*.

12. The method of claim 11, wherein the dihydroxyacetone kinase gene encodes a protein selected from the group consisting of:

(c) a protein comprising the amino acid sequence of SEQ ID NO: 4; and (d) a protein comprising the amino acid sequence which is not less than 95% identical to the amino acid sequence of SEQ ID NO: 4, and the protein has dihydroxyacetone kinase activity.

13. The method of claim 1, wherein the promoter under which dihydroxyacetone kinase gene is placed is a promoter obtained from tac promoter.

* * * * *